US009139564B2

(12) United States Patent
Kim et al.

(10) Patent No.: US 9,139,564 B2
(45) Date of Patent: *Sep. 22, 2015

(54) 2-BENZYL, 3-(PYRIMIDIN-2-YL) SUBSTITUTED PYRAZOLES USEFUL AS SGC STIMULATORS

(71) Applicant: IRONWOOD PHARMACEUTICALS, INC., Cambridge, MA (US)

(72) Inventors: Charles Kim, Cambridge, MA (US); Takashi Nakai, Newton, MA (US); Joel Moore, Lexington, MA (US); Nicholas Robert Perl, Brookline, MA (US); G-yoon Jamie Im, Cambridge, MA (US); Timothy Claude Barden, Salem, MA (US); Rajesh R. Iyengar, West Newton, MA (US); Daniel P. Zimmer, Somerville, MA (US); Angelika Fretzen, Somerville, MA (US); Paul Allan Renhowe, Sudbury, MA (US)

(73) Assignee: IRONWOOD PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/368,064

(22) PCT Filed: Dec. 26, 2012

(86) PCT No.: PCT/US2012/071654
§ 371 (c)(1),
(2) Date: Jun. 23, 2014

(87) PCT Pub. No.: WO2013/101830
PCT Pub. Date: Jul. 4, 2013

(65) Prior Publication Data
US 2015/0018353 A1 Jan. 15, 2015

Related U.S. Application Data

(60) Provisional application No. 61/654,580, filed on Jun. 1, 2012, provisional application No. 61/580,439, filed on Dec. 27, 2011.

(51) Int. Cl.
| | |
|---|---|
| A61K 31/506 | (2006.01) |
| C07D 403/04 | (2006.01) |
| C07D 413/14 | (2006.01) |
| C07D 417/14 | (2006.01) |
| A61K 31/4439 | (2006.01) |
| A61K 31/513 | (2006.01) |
| A61K 31/519 | (2006.01) |
| A61K 31/52 | (2006.01) |
| A61K 45/06 | (2006.01) |
| C07D 473/00 | (2006.01) |
| C07D 487/04 | (2006.01) |
| C07D 513/22 | (2006.01) |

(52) U.S. Cl.
CPC .......... *C07D 403/04* (2013.01); *A61K 31/4439* (2013.01); *A61K 31/506* (2013.01); *A61K 31/513* (2013.01); *A61K 31/519* (2013.01); *A61K 31/52* (2013.01); *A61K 45/06* (2013.01); *C07D 413/14* (2013.01); *C07D 417/14* (2013.01); *C07D 473/00* (2013.01); *C07D 487/04* (2013.01); *C07D 513/22* (2013.01)

(58) Field of Classification Search
CPC .. C07D 413/14; C07D 403/04; C07D 417/14; C07D 473/00; C07D 487/04; C07D 513/22; A61K 45/06; A61K 31/513; A61K 31/519; A61K 31/506; A61K 31/4439; A61K 31/52
See application file for complete search history.

(56) References Cited

U.S. PATENT DOCUMENTS

| | | | |
|---|---|---|---|
| 3,169,966 A | 2/1965 | Schmidt et al. | |
| 3,228,946 A | 1/1966 | Schmidt et al. | |
| 3,228,997 A | 1/1966 | Schmidt et al. | |
| 3,250,761 A | 5/1966 | Schmidt et al. | |
| 5,470,862 A | 11/1995 | Lin et al. | |
| 6,028,072 A | 2/2000 | Lee et al. | |
| 8,748,442 B2 * | 6/2014 | Kim et al. | 514/269 |
| 2003/0105336 A1 | 6/2003 | Schindler et al. | |
| 2006/0079542 A1 * | 4/2006 | Nestor | 514/269 |
| 2010/0075964 A1 | 3/2010 | Busch et al. | |
| 2012/0184515 A1 * | 7/2012 | Klar et al. | 514/170 |

(Continued)

FOREIGN PATENT DOCUMENTS

| | | |
|---|---|---|
| BE | 612971 | 7/1962 |
| BE | 627392 | 1/1963 |
| BE | 627394 | 1/1963 |

(Continued)

OTHER PUBLICATIONS

Structures of Some Compounds Found in STN Substructure Searches in File Registry with Dates of STN Entries Shown with Each of the Compound Records. (Date Unknown).
Skinner, Philip J. et al., Fluorinated Pyrazole Acids are Agonists of the High Affinity Niacin Receptor GPR109a, Bioorganic & Medical Chemistry Letters (2007), 17(20), 5620-5623, Elsevier Ltd. ISSN: 0960-894X.
Yonetoku, Yasuhiro et al., Novel Potent and Selective Calcium-Release-Activated Calcium (CRAC) Channel Inhibitors. Synthesis and Inhibitory Activity of Aryl-3-trifluoromethylpyrazoles, Bioorganic & Medicinal Chemistry (2006), 14(15), 5370-5383, Elsevier B.V.
Zhang, Jidong et al., Potent Nonpeptide Endothelin Antagonists: Synthesis and Structure-Activity Relationships of Pyrazole-5-carboxylic Acids, Medicinal Chemistry, Hoechst Marion Roussel, Bioorganic & Medicinal Chemistry Letters (2000), 10(22), 2575-2578, Elsevier Science Ltd., ISSN: 0960-894X.

(Continued)

*Primary Examiner* — Alexander R Pagano
(74) *Attorney, Agent, or Firm* — Heslin Rothenberg Farley & Mesiti, P.C.

(57) ABSTRACT

Compound of Table I are described. They are useful as stimulators of sGC, particularly NO-independent, heme-dependent stimulators. These compounds may be useful for treating, preventing or managing various disorders that are herein disclosed.

6 Claims, No Drawings

(56) References Cited

U.S. PATENT DOCUMENTS

| 2014/0315934 | A1* | 10/2014 | Hitchcock et al. | 514/269 |
|---|---|---|---|---|
| 2014/0323448 | A1* | 10/2014 | Kim et al. | 514/171 |

FOREIGN PATENT DOCUMENTS

| DE | 1197088 | | 9/1962 |
|---|---|---|---|
| DE | 19744026 | | 10/1997 |
| DE | 19744027 | | 10/1997 |
| DE | 19649460 | | 5/1998 |
| EP | 0908456 | A1 | 4/1999 |
| EP | 1433788 | | 12/2002 |
| EP | 1479678 | | 11/2004 |
| EP | 2006288 | A1 | 12/2008 |
| FR | 1403372 | | 7/1964 |
| WO | 9307138 | | 4/1993 |
| WO | 9715570 | | 5/1997 |
| WO | 9827091 | | 6/1998 |
| WO | 9856785 | | 12/1998 |
| WO | 0009500 | | 2/2000 |
| WO | 0027394 | A1 | 5/2000 |
| WO | 0039083 | | 7/2000 |
| WO | 2007014054 | | 2/2001 |
| WO | 0187287 | | 11/2001 |
| WO | 0218350 | | 3/2002 |
| WO | 03000659 | | 1/2003 |
| WO | 03026649 | | 4/2003 |
| WO | 03039539 | | 5/2003 |
| WO | 2004013135 | | 2/2004 |
| WO | 2004016606 | | 2/2004 |
| WO | 2004069158 | | 8/2004 |
| WO | 2006104141 | | 10/2006 |
| WO | 2006114313 | | 11/2006 |
| WO | 2007002559 | | 1/2007 |
| WO | 2008004096 | | 1/2008 |
| WO | 2008024390 | | 2/2008 |
| WO | 2008141731 | | 11/2008 |
| WO | 2009076454 | | 6/2009 |
| WO | 2009143039 | | 11/2009 |
| WO | 2010015656 | | 2/2010 |
| WO | 2010015657 | | 2/2010 |
| WO | 2010020366 | A1 | 2/2010 |
| WO | 2010054762 | | 5/2010 |
| WO | 2010054763 | | 5/2010 |
| WO | 2011119518 | A1 | 9/2011 |
| WO | 2011147810 | A1 | 12/2011 |
| WO | 2012003405 | A1 | 1/2012 |
| WO | 2012064559 | A1 | 5/2012 |
| WO | 2012075678 | A1 | 6/2012 |

OTHER PUBLICATIONS

Takahashi, Masahiko et al., Ring Transformation of 1, 2, 4, 5-Tetrazines to 4-Aminopyrazoles by Cyanotrimethysilane, Faculty English, Ibaraki University, Hitachi, 316, Japan Tetrahedron Letters (1987), 28(19), 2139-42, TELEAY: ISSN: 0040-4039.
Zabel, Dirk et al., Iron and Cobalt Complexes of Tridentate N-Donor Ligands in Ethylene Polymerization: Efficient Shielding of the Active Sites by Simple Phenyl Groups, Fachbereich Chemie, Technische Universitaet Kaiserlautern, European Journal of Inorganic Chemistry (2008), (23), 3648-3654, ISSN: 1434-1948, Wiley-VCH Verlag GmbH Co.
Bouabdallah, Ibrahim et al., Catecholase Activities of Two C-C Linked Bipyrazole N-donor Ligands with Copper (II) Salts, Laboratory of Organic Chemistry, Macromolecular and Natural Products, Dept. of Chemistry, Faculty of Sciences, University Mohammed the First, Oujda, 60000, Morocco, Journal Marocain de Chimie Heterocyclique (2007), 6(1), 21-25.
Bouabdallah, Ibrahim et al., 1, 1'-Dibenzy1-5, 5'-Dipeheny1-3, 3'-Bipyrazole, Laboratorie de Chimie Organique Physique, Dept. de Chimi, Faculte des Sciences, Universite Mohammed First, Oujda, 6000, Morocco (2006), ISSN: 1422-8599.
Kalluraya, Balakrishna et al., Reactions of Aryl/arylozyacet Hydrazides with Acetylenic Ketones, Dept. of Studies in Chemistry, Mangalore University, Mangalagangothri, 574 199, India, Indian Journal of Heterocyclic Chemistry (1999), 8(4), 309-314. Abstract.
Jaehnisch, K. et al., Furylvinyl Halides. X. Reactions of β-Fur-2-yl-β-Chloro-α-cyanoacrylic Acid Derivative with Hydrazines, Zentralinst. Organic Chemical, Akad. Wiss. DDR, Berlin-Adlershof, DDR-1199, Ger. Dem. Rep., Journal fuer Praktische Chemie (Leipzig) (1989), 331(4), 552-8. ISSN: 0021-8383.
Kost, A.N. et al., Condensation of 1-Acylpyrazolines, Mosk. Gos. University im. Lomonosova, Moscow, USSR Khimiya Geterotsiklicheskikh Soedinenii (1974), (9), 1268-70. ISSN: 0132-6244.
Kost, A.N. et al., The Effect of Phosphoryl Chloride on 1-Acetyl-3, 5, 5-Trimethylpyrazoline. A New Synthesis of Bipyrazoles, Mosk. Gos. University im. Lomonosova, Moscow, USSR, Doklady Akademii Nauk SSSR (1968), 179(2) 337-40. ISSN: 0002-3264.
Khalil, A. et al., Phase-Transfer Catalyzed Alkylation and 3-Substituted-1H-Pyrazol-2-in-5-ones in the Absence or Presence of Carbon Disulphide, Phosphorus, Sulfur Silicon Relat, Elem. (2005), 180(2), 479-496.
Tarrago, Georges et al., Orientation de la Reaction D'alkylation des Pyrazoles dans des Conditions Neuters et an Catalyse Par Transfer de Phase, J. Heterocycl. Chemical (1980), 17(1), 137-142.
Bouabdallah, Ibrahim et al., Regioselective Synthesis and Crystal Structure of 1, 1'-dibenzyl-5, 5'-diisopropyl-3, 3'-bipyrazole, Journal Marocain de Chimie Heterocyclique (2004), 3(1), pp. 39-44.
Goodell, John R. et al., Identification of Compounds with Anti-West Nile Virus Activity, Journal of Medicinal Chemistry (2006), 49(6), pp. 2127-2137.
Rostom, Sherif A.F., Poylsubstituted Pyrazoles, Part 6, Synthesis of Some 1-(4-Chlorophenyl)-4-Hydroxy-1H-Pyrazol-3-Carbonl Derivatives Linked to Nitrogenous Heterocyclic Ring Systems as Potential Antitumor Agents, Bioorganic & Medicinal Chemistry (2010), 18(7), pp. 2767-2776.
Ye, Long et al., Pyrazolylthiazole as ΔF508-Cystic Fibrosis Transmembrane Conoductance Regulator Correctors with Improved Hysrophilicity Compared to Bithiazoles, Journal of Medicinal Chemistry (2010), 53(9), 3772-3781.
Bonacorso, Helio G. et al., Synthesis of New Trihalomethylated and Non-Symmetrical Substituted 2-)1-H-Pyrazole)-5-(1H-Pyrazolycaronyl)pyridines, Journal of the Brazilian Chemical Society (2009), 20(3), 509-517.
Sakya, Subas M. et al., Facile Microwave Assisted Decarbonylation of 4-Formyl Group in 5-Alkyl Amino Substituted Pyrazoles, Tetrahedron Letters (2008), 49(14), 2280-2282, CODEN: TELEAY; ISSN: 0040-4039.
Suen, Yat Fan et al., A Novel Route to Fully Substituted 1H-Pyrazoles, Journal of Organic Chemistry (2005), 70(21), 8468-8471, CODEN: JOCEAH; ISSN: 0022-3263.
Amer, Fathy A. et al., Synthesis of 4,4'-Aryldihydrazono-3-(3'-Pyridyl)-2-Pyrazolin-4,5-Diones and 1-Aryl-3-(3'-Pyridyl)-4,4'-Arylbizazo-5-Aryliminopyrazoles and Their Application as Disazo Disperse Dyes, Journal of Chemical Technology and Biotechnology (1979-1982) (1980), 30(2), 78-84, CODEN, JCTBDC, ISSN: 0142-0356.
Sawyer et al., Journal of Medicinal Chemistry, 2003, American Chemical Society, vol. 46, No. 19, pp. 3953-3956.
International Preliminary Report on Patentability for PCT/US2011/058902, issued May 14, 2013.
Chemical Abstracts Service, Columbus, Ohio, US;1978, Ivashchenko, A.V. et al:"Synthesis and study of 2-(1-pyrazolyl)purine derivatives", XP002718743, retrieved from STN; Database accession No. 1978:50805 abstract & Ivashchenko, A.V. et al: "Synthesis and study of 2-(1-pyrazolyl)purine derivatives" Khimiya Geterotsiklicheskikh Soedinenii, (10), 1404-6 CODEN: KGSSAQ; ISSN: 0132-6244,1977, Database CA [Online].
Chemical Abstracts Service, Columbus, Ohio, US;1978, Ivashchenko, A.V. et al:"Synthesis and study of derivatives of 2-(1-pyrazolyl)pyrimidine", XP002718744, retrieved from STN; Database accession No. 1978:22825 abstract & Ivashchenko, A.V. et al:

(56) References Cited

OTHER PUBLICATIONS

"Synthesis andstudyof derivatives of 2-(1-pyrazolyl)pyrimidine" Khimiya Geterotsiklicheskikh Soedinenii, (9), 1255-7 CODEN:KGSSAQ; ISSN: 0132-6244, 1977.
International Search Report for PCT/US2012/071654 dated Apr. 16, 2013.

Selwood D L et al; "Synthesis and Biological Evaluation of Novel Pyrazoles and Indazoles as Activators of the Nitric Oxide Receptor, Soluble Guanylate Cyclase," Journal of Medicinal Chemistry, American Chemical Society, US, vol. 44., No. 1, Nov. 22, 2001.

* cited by examiner

2-BENZYL, 3-(PYRIMIDIN-2-YL) SUBSTITUTED PYRAZOLES USEFUL AS SGC STIMULATORS

CROSS REFERENCE TO RELATED APPLICATIONS

This application is a 371 filing of PCT/US2012/071654, filed Dec. 26, 2012, which claims priority to U.S. Provisional Application Nos. 61/580,439 filed 27 Dec. 2011 and 61/654,580 filed 1 Jun. 2012, the disclosures of which are herein incorporated by reference.

FIELD OF THE INVENTION

The present disclosure relates to stimulators of soluble guanylate cyclase (sGC), pharmaceutical formulations thereof and their use, alone or in combination with one or more additional agents, for treating and/or preventing various diseases, wherein an increase in the concentration of nitric oxide (NO) or an increase in the concentration of cyclic Guanosine Monophosphate (cGMP) might be desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts GTP into the secondary messenger cyclic GMP (cGMP). The increased level of cGMP, in turn, modulates the activity of downstream effectors including protein kinases, phosphodiesterases (PDEs), and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure.

Experimental and clinical evidence indicates that reduced bioavailability and/or responsiveness to endogenously produced NO contributes to the development of cardiovascular, endothelial, renal and hepatic disease, as well as erectile dysfunction and other sexual disorders (e.g. female sexual disorder or vaginal atrophy). In particular, the NO signaling pathway is altered in cardiovascular diseases, including, for instance, systemic and pulmonary hypertension, heart failure, angina, stroke, thrombosis and other thromboembolic diseases, peripheral arterial disease, fibrosis of the liver, lung or kidney and atherosclerosis.

sGC stimulators are also useful in the treatment of lipid related disorders such as e.g., dyslipidemia, hypercholesterolemia, hypertriglyceridemia, sitosterolemia, fatty liver disease, and hepatitis.

Pulmonary hypertension (PH) is a disease characterized by sustained elevation of blood pressure in the pulmonary vasculature (pulmonary artery, pulmonary vein and pulmonary capillaries), which results in right heart hypertrophy, eventually leading to right heart failure and death. In PH, the bioactivity of NO and other vasodilators such as prostacyclin is reduced, whereas the production of endogenous vasoconstrictors such as endothelin is increased, resulting in excessive pulmonary vasoconstriction. sGC stimulators have been used to treat PH because they promote smooth muscle relaxation, which leads to vasodilation.

Treatment with NO-independent sGC stimulators also promoted smooth muscle relaxation in the corpus cavernosum of healthy rabbits, rats and humans, causing penile erection, indicating that sGC stimulators are useful for treating erectile dysfunction.

NO-independent, heme-dependent, sGC stimulators, such as those disclosed herein, have several important differentiating characteristics, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed. These compounds have been shown to produce anti-aggregatory, anti-proliferative and vasodilatory effects.

Since compounds that stimulate sGC in an NO-independent manner offer considerable advantages over other current alternative therapies, there is a need to develop novel stimulators of sGC. They are potentially useful in the prevention, management and treatment of disorders such as pulmonary hypertension, arterial hypertension, heart failure, atherosclerosis, inflammation, thrombosis, renal fibrosis and failure, liver cirrhosis, lung fibrosis, erectile dysfunction, female sexual arousal disorder and vaginal atrophy and other cardiovascular disorders; they are also potentially useful for the prevention, management and treatment of lipid related disorders.

SUMMARY OF THE INVENTION

The present invention is directed to the compounds depicted in Table I and their pharmaceutically acceptable salts thereof

TABLE I

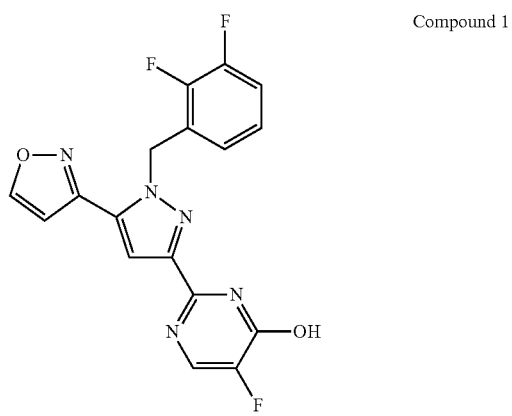

Compound 1

TABLE I-continued
Compound 2
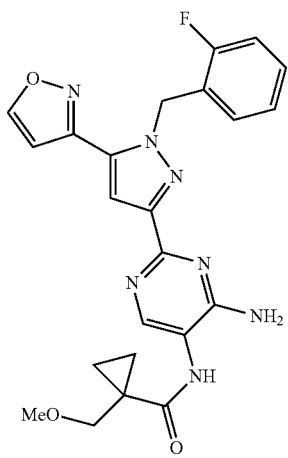 [SMILES: COCC1(C(=O)Nc2cnc(-c3cc(-c4ccon4)n(Cc4ccccc4F)n3)nc2N)CC1]
Compound 3
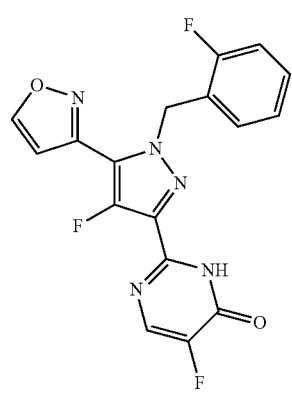 [SMILES: O=c1[nH]c(-c2nn(Cc3ccccc3F)c(-c3ccon3)c2F)ncc1F]
Compound 4
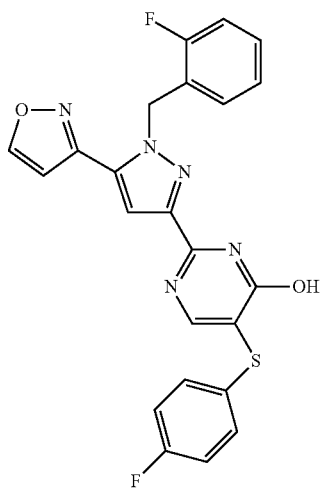 [SMILES: Oc1nc(-c2cc(-c3ccon3)n(Cc3ccccc3F)n2)ncc1Sc1ccc(F)cc1]
TABLE I-continued
Compound 5
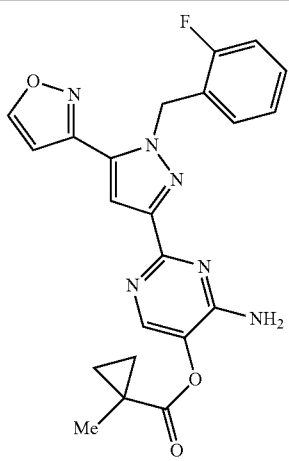 [SMILES: CC1(C(=O)Oc2cnc(-c3cc(-c4ccon4)n(Cc4ccccc4F)n3)nc2N)CC1]
Compound 6
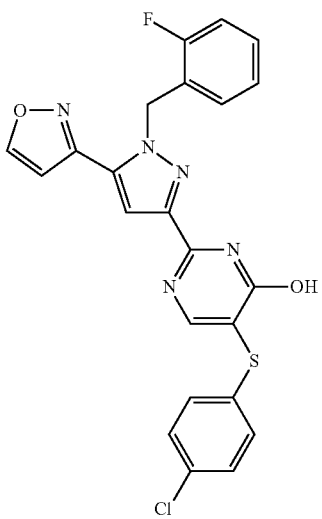
Compound 7
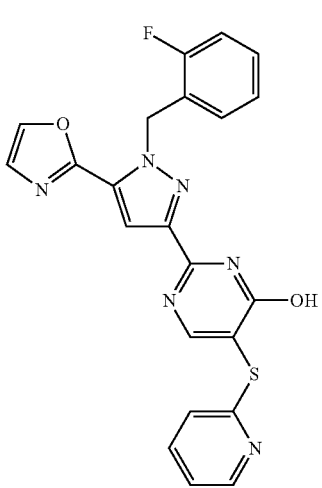 [SMILES: Oc1nc(-c2cc(-c3ncco3)n(Cc3ccccc3F)n2)ncc1Sc1ccccn1]

TABLE I-continued
Compound 8
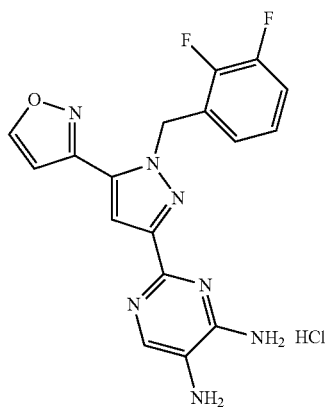 [SMILES: Nc1cnc(-c2cc(-c3ccon3)n(Cc3cccc(F)c3F)n2)nc1N ; Cl]
Compound 9
Compound 10
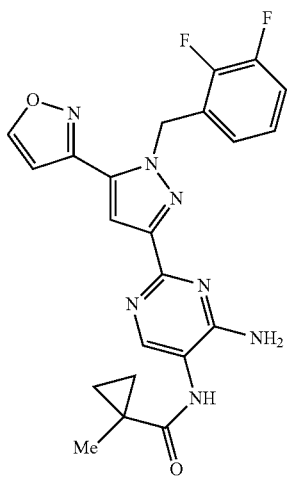
TABLE I-continued
Compound 11
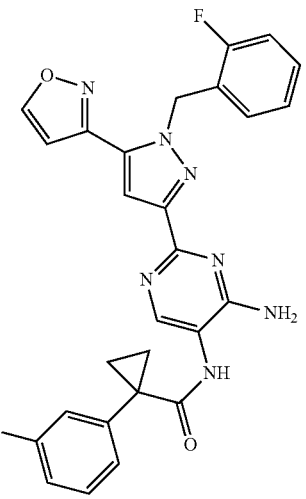
Compound 12
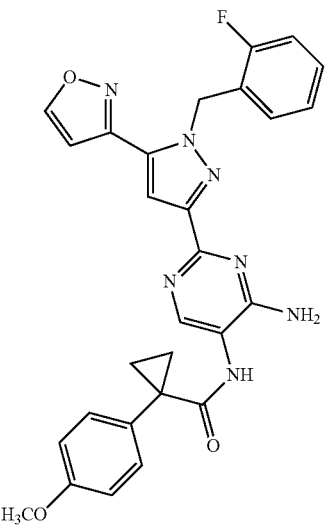
Compound 13

TABLE I-continued
Compound 14
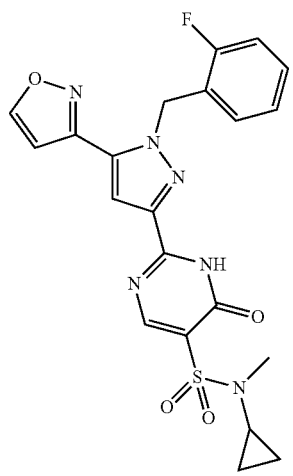
Compound 17
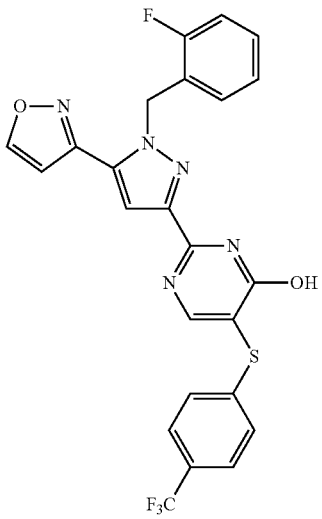
Compound 15
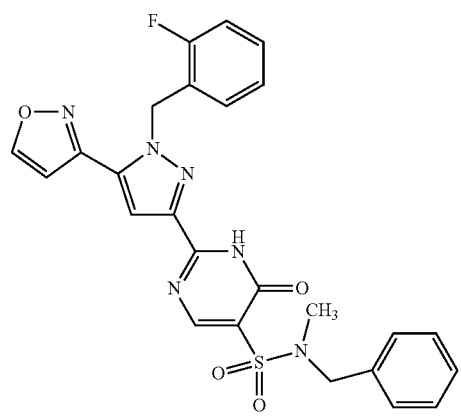
Compound 18
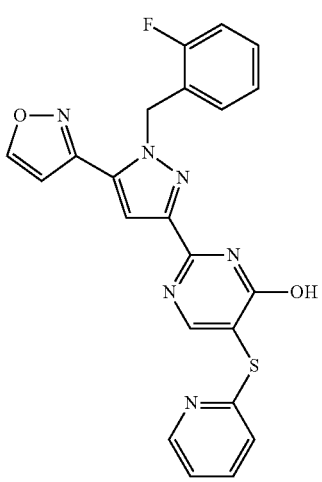
Compound 16
Compound 19
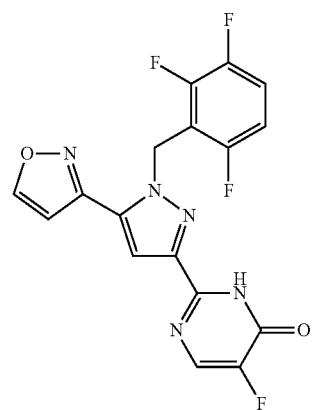

TABLE I-continued
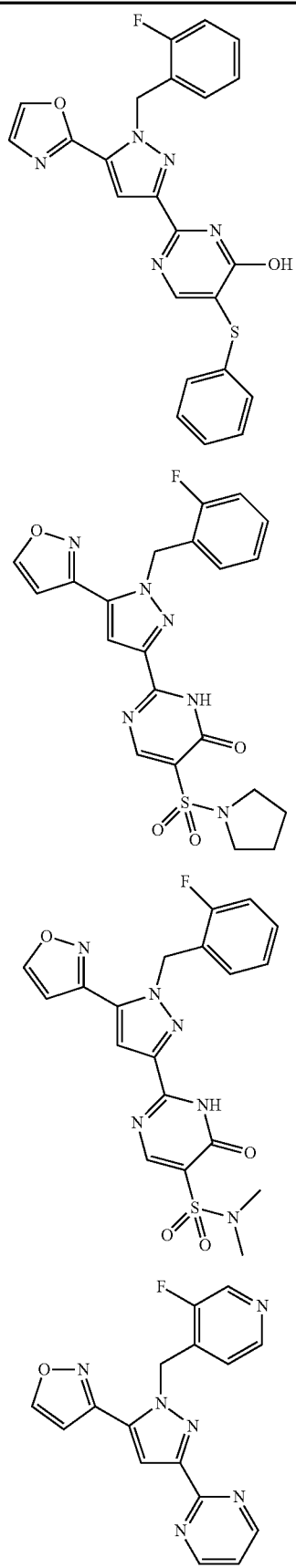
Compound 20
Compound 21
Compound 22
Compound 23
TABLE I-continued
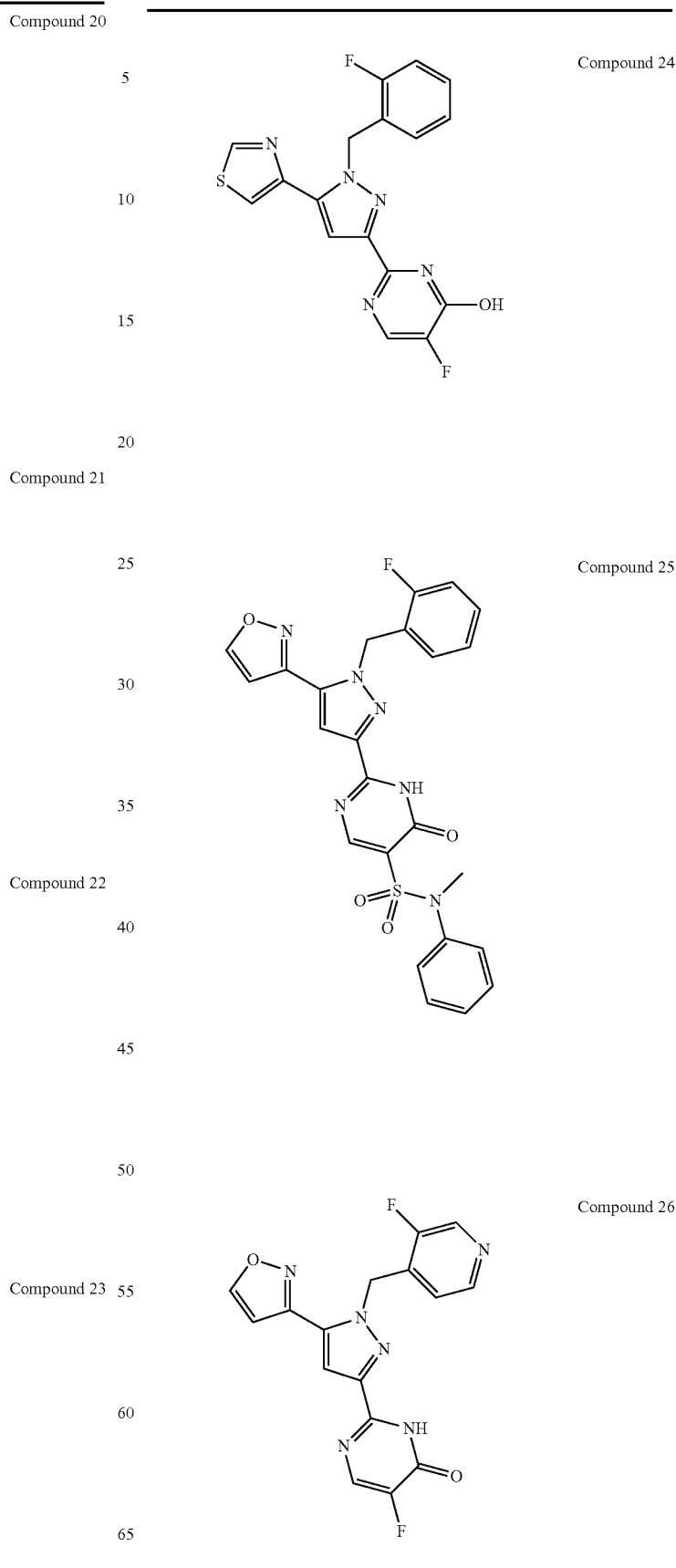
Compound 24
Compound 25
Compound 26

TABLE I-continued
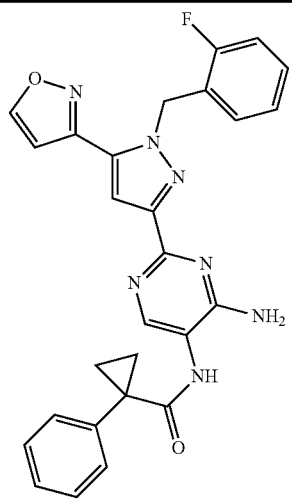
Compound 27
Compound 28
Compound 29
Compound 30
TABLE I-continued
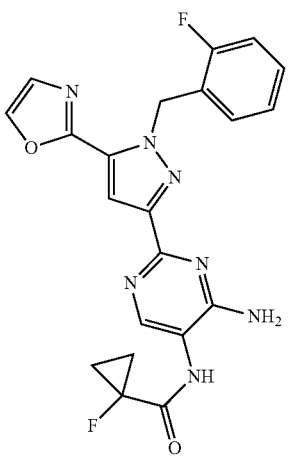
Compound 31
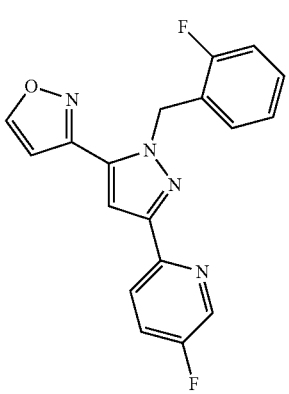
Compound 32
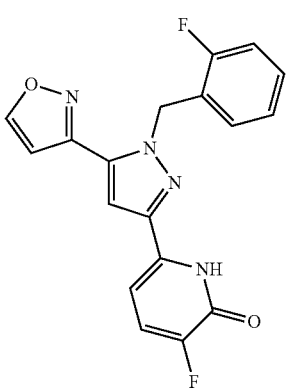
Compound 33
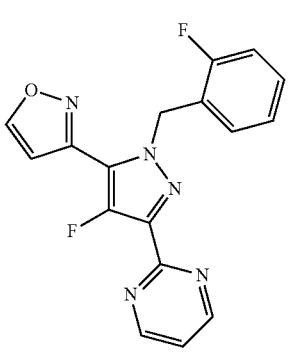
Compound 34

TABLE I-continued
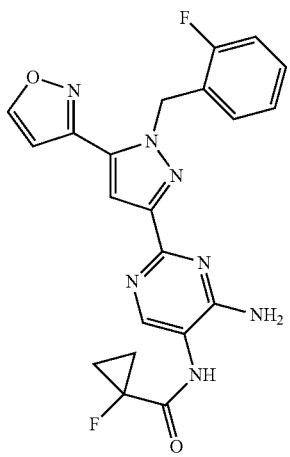
Compound 35
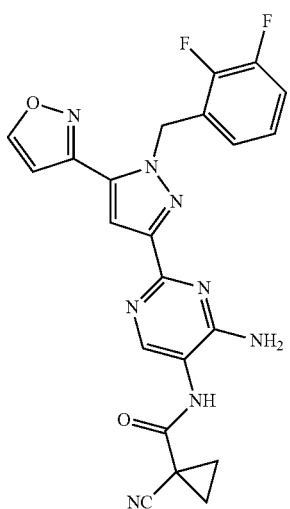
Compound 36
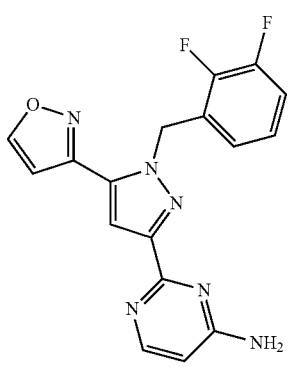
Compound 37
TABLE I-continued
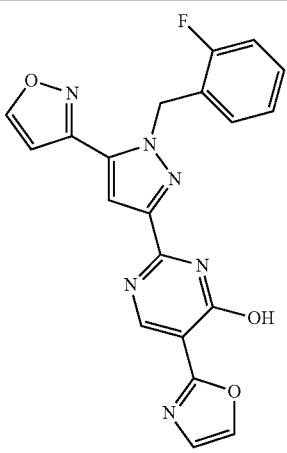
Compound 38
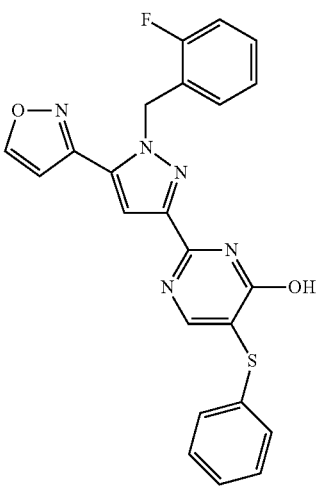
Compound 39
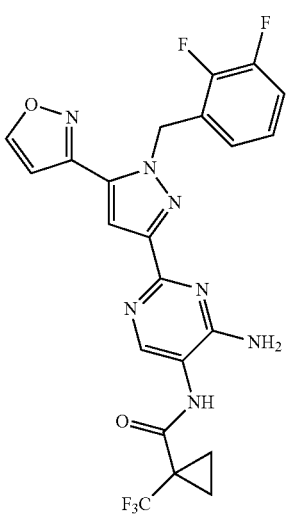
Compound 40

TABLE I-continued
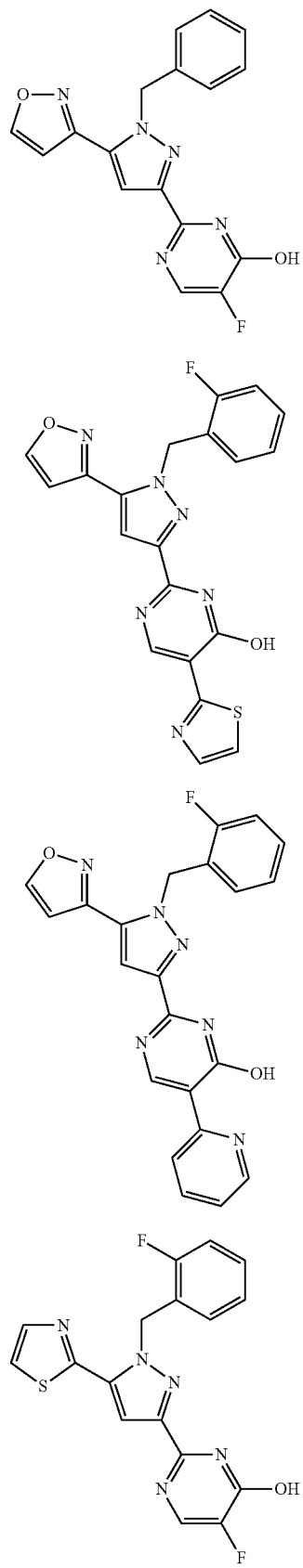
Compound 41
Compound 42
Compound 43
Compound 44
TABLE I-continued
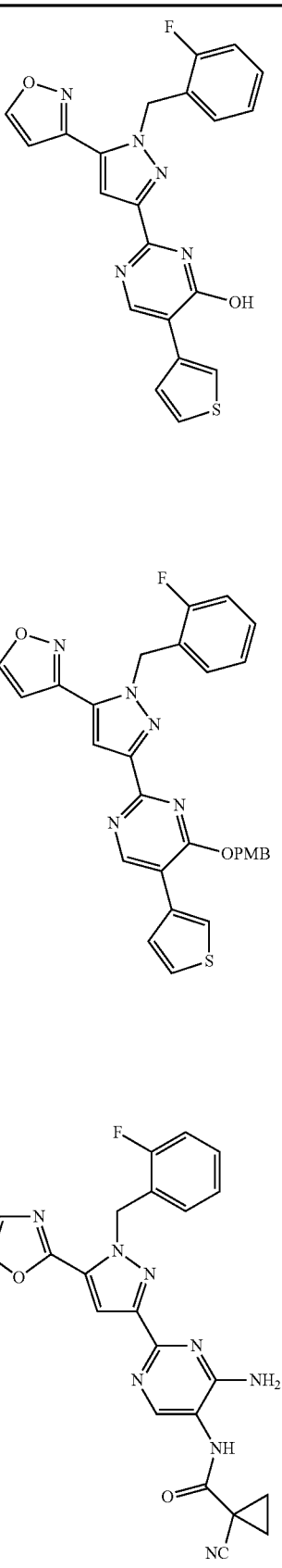
Compound 45
Compound 46
Compound 47

TABLE I-continued
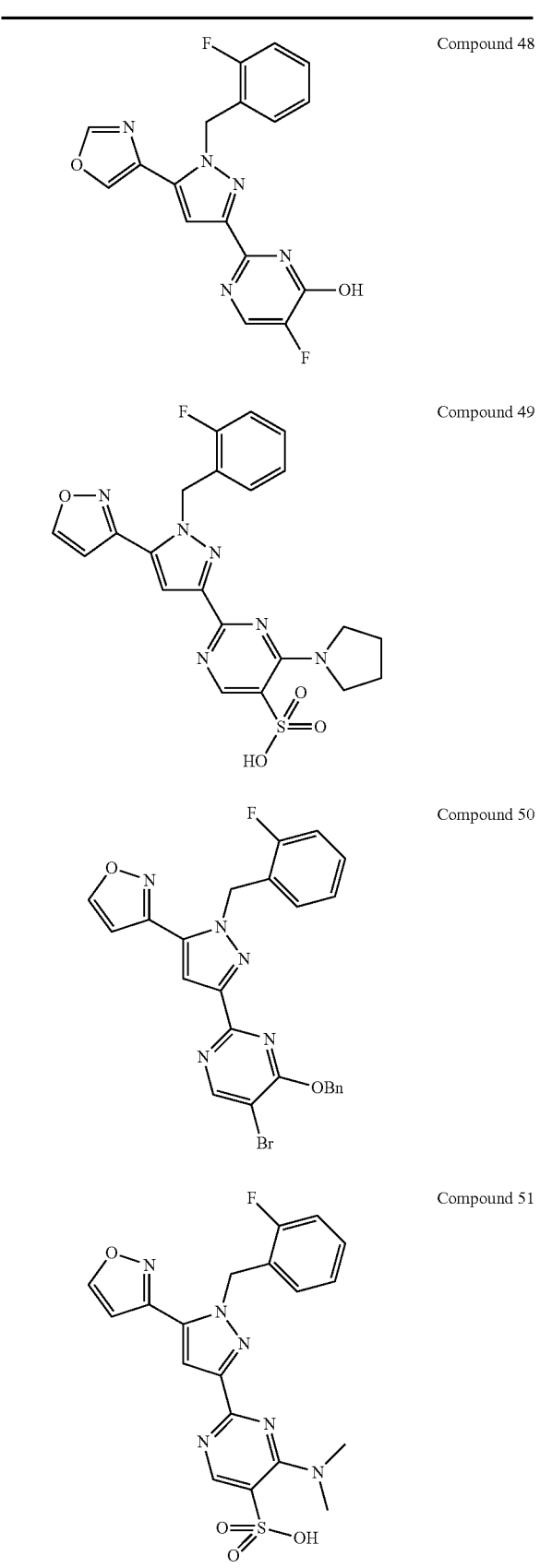
Compound 48
Compound 49
Compound 50
Compound 51
TABLE I-continued
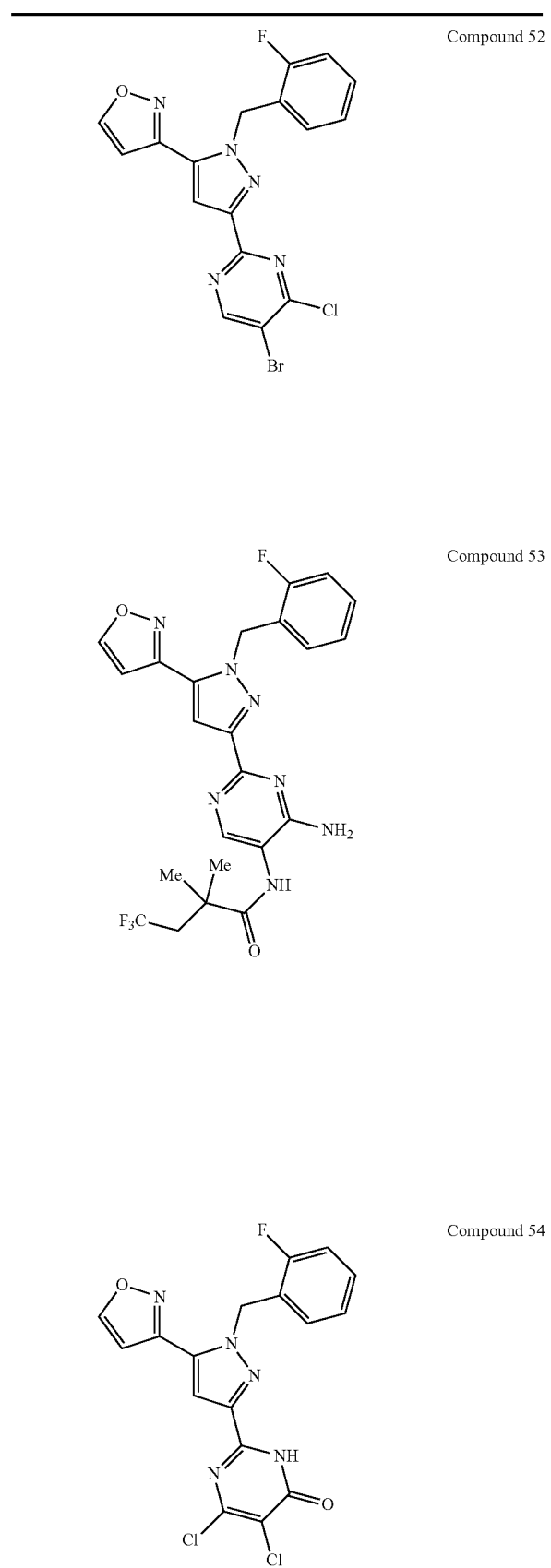
Compound 52
Compound 53
Compound 54

TABLE I-continued
Compound 55
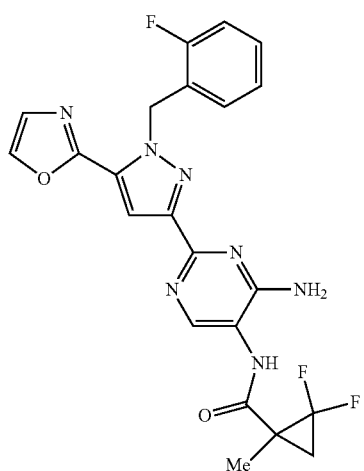
Compound 56
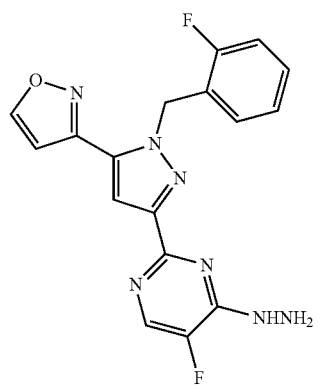
Compound 57
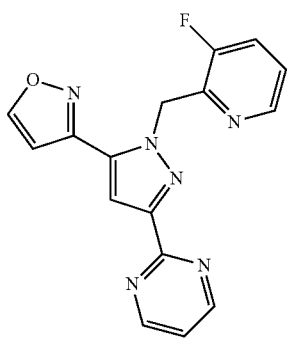
TABLE I-continued
Compound 58
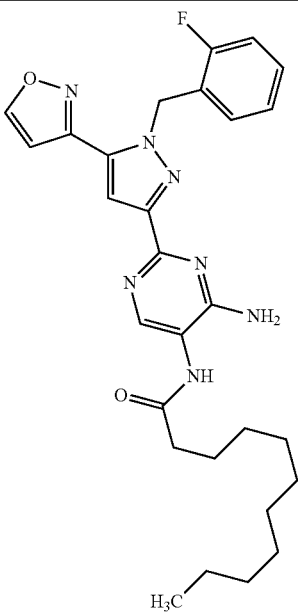
Compound 59
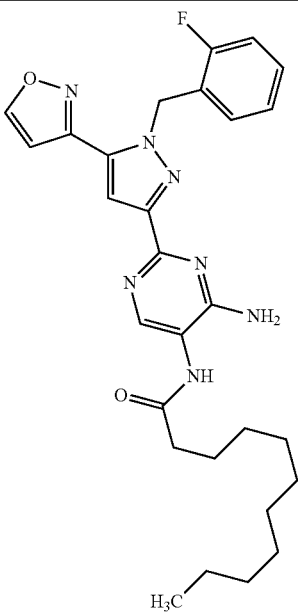
Compound 60
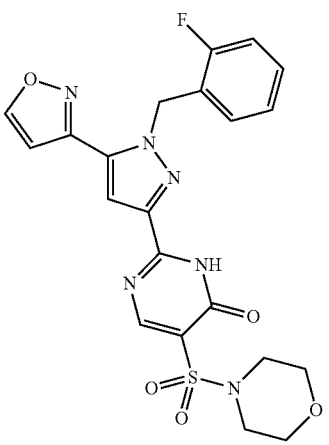

TABLE I-continued
Compound 61
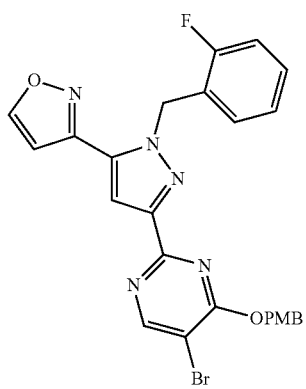
Compound 62
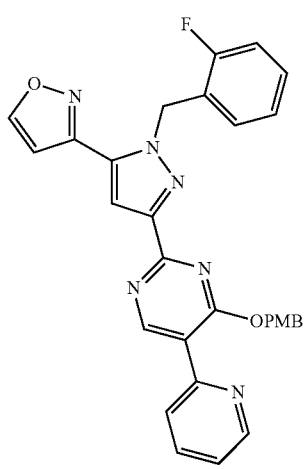
Compound 63
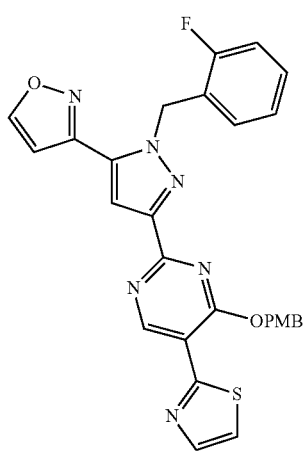
TABLE I-continued
Compound 64
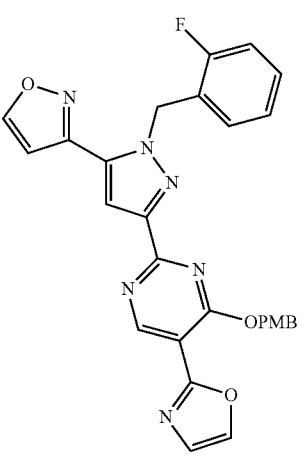
Compound 65
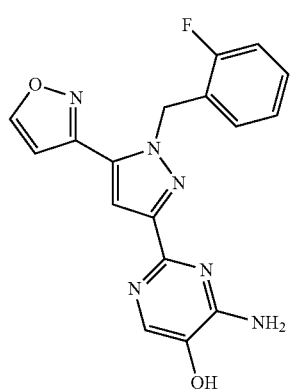
Compound 66
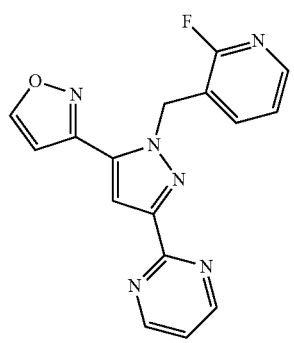
Compound 67
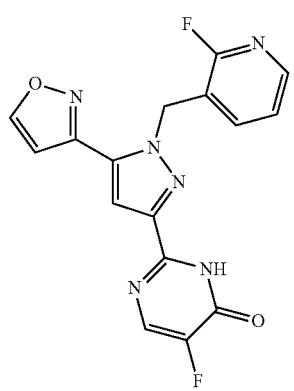

TABLE I-continued
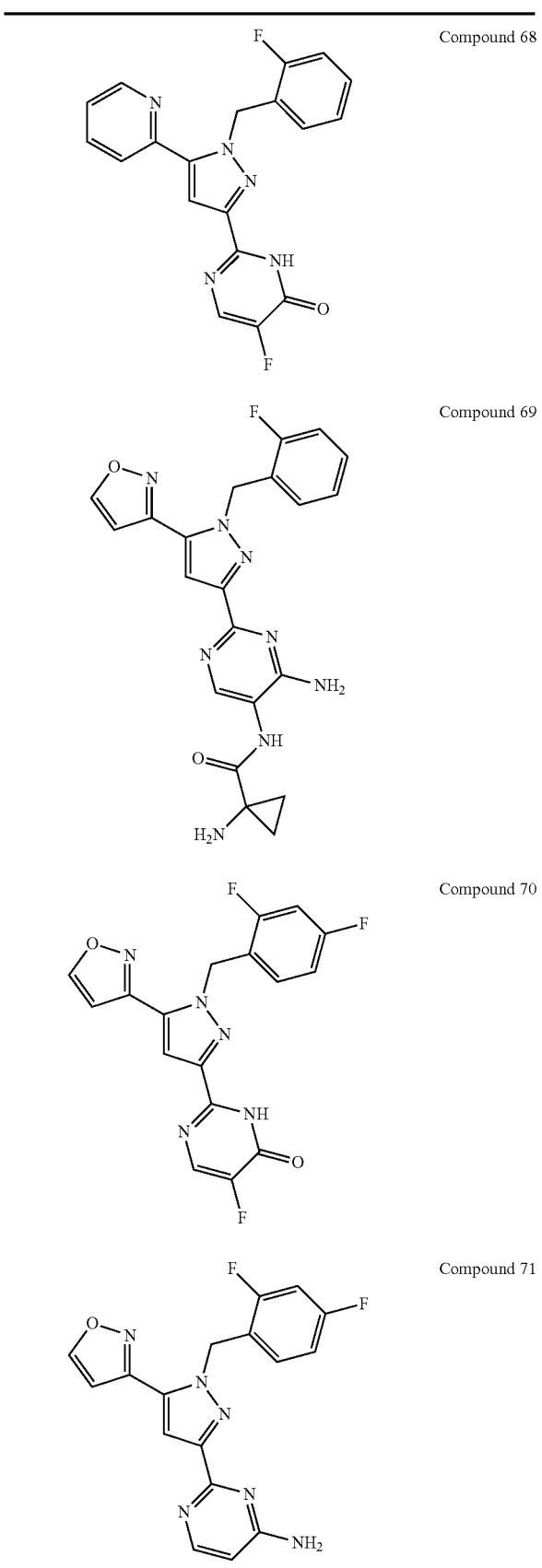
Compound 68
Compound 69
Compound 70
Compound 71
TABLE I-continued
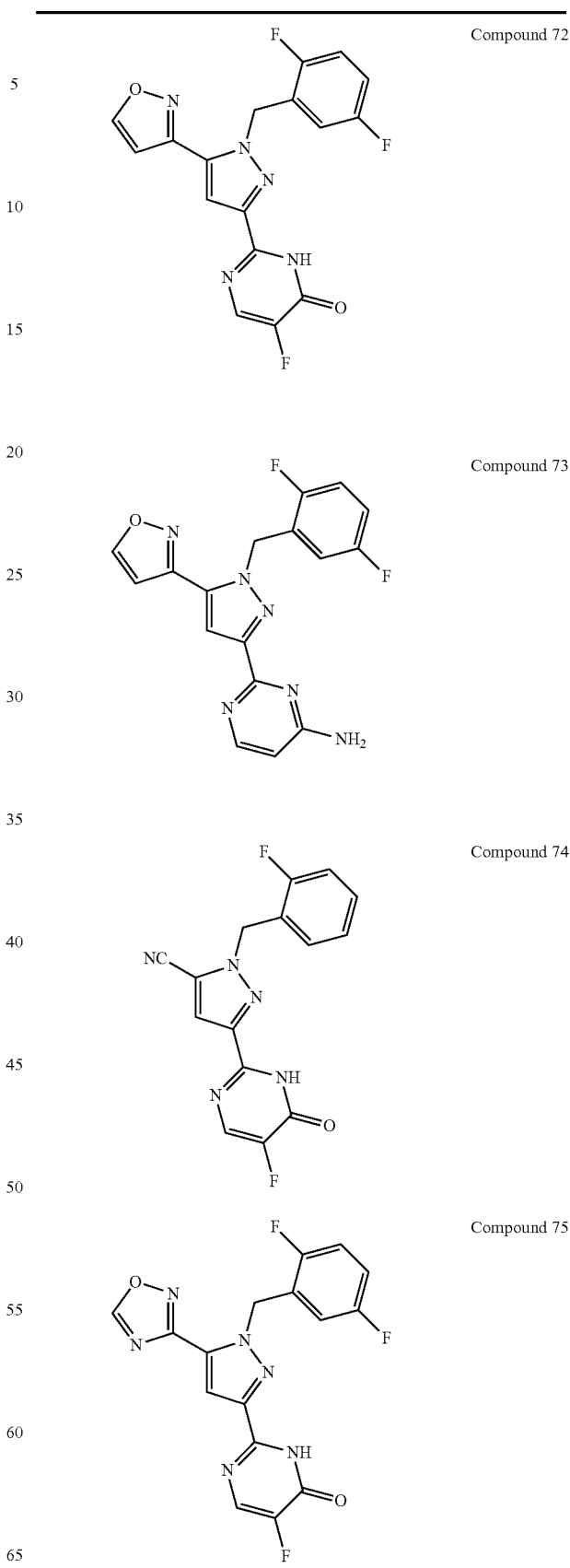
Compound 72
Compound 73
Compound 74
Compound 75

TABLE I-continued
Compound 76
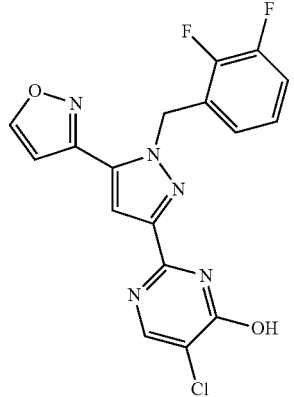
Compound 77
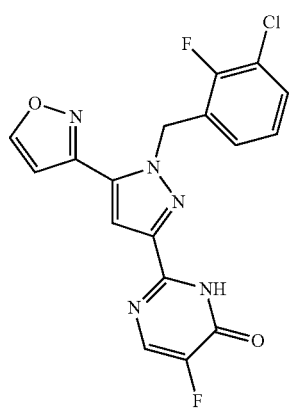
Compound 78
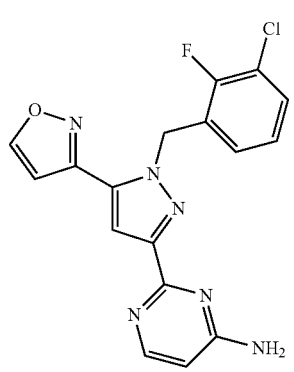
Compound 79
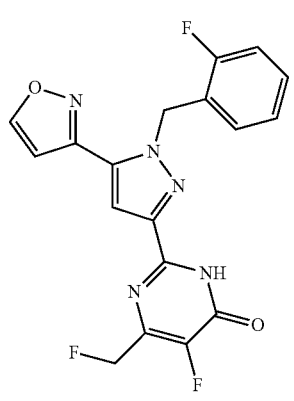
TABLE I-continued
Compound 80
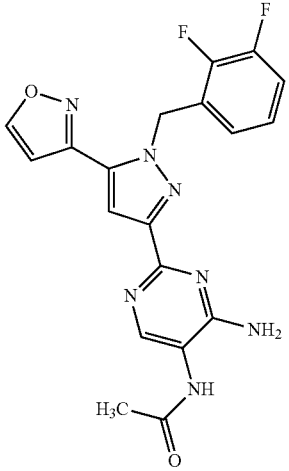
Compound 81
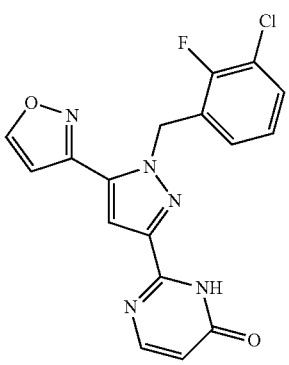
Compound 82
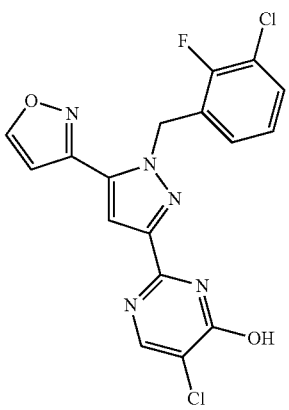

TABLE I-continued
Compound 83
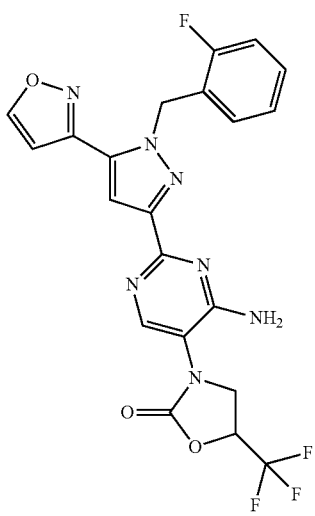
Compound 84
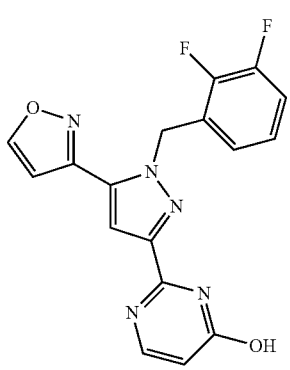
Compound 85
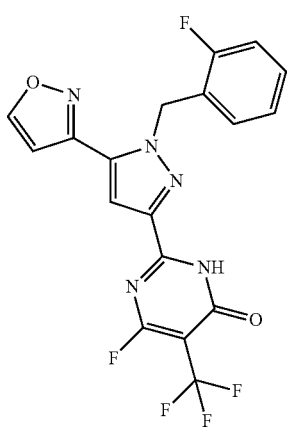
TABLE I-continued
Compound 86
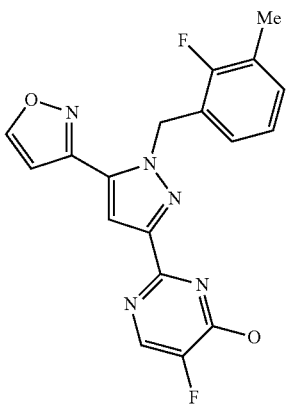
Compound 87
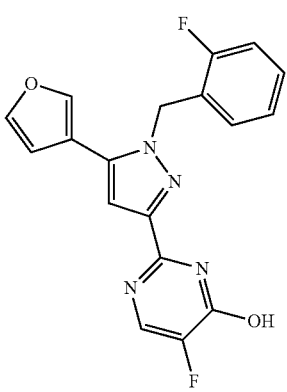
Compound 88
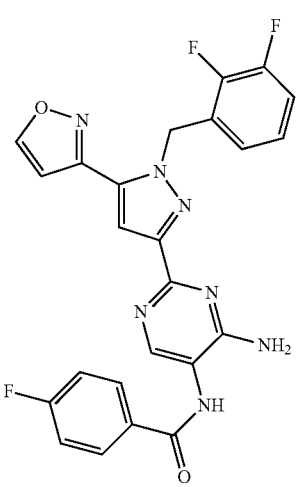
Compound 89
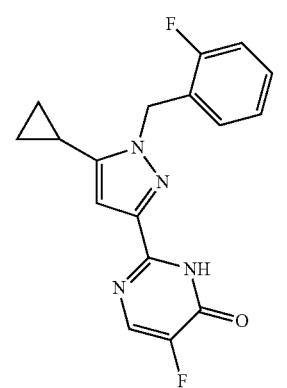

TABLE I-continued
Compound 90
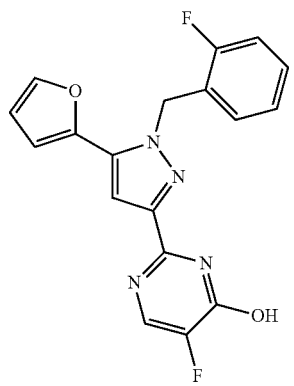
Compound 91
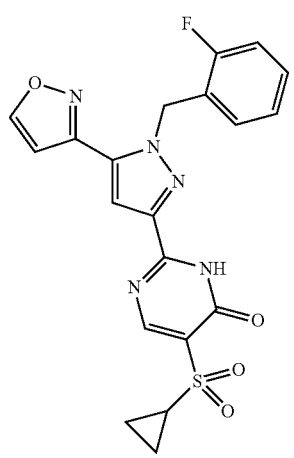
Compound 92
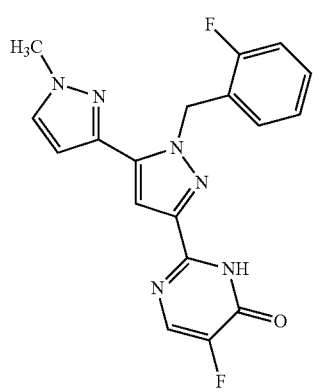
Compound 93
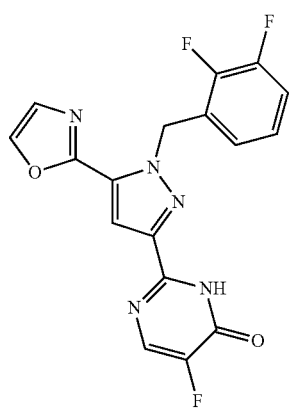
TABLE I-continued
Compound 94
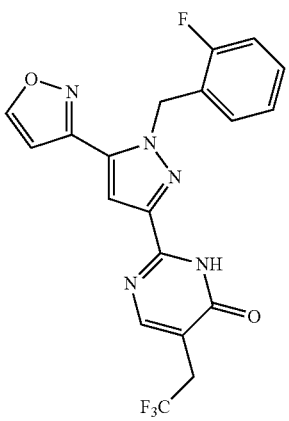
Compound 95
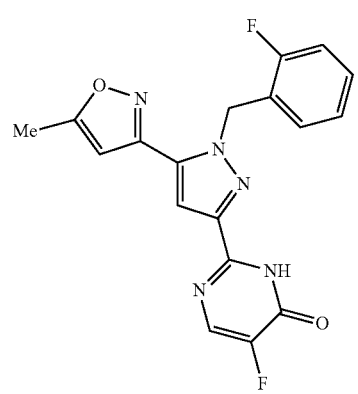
Compound 96
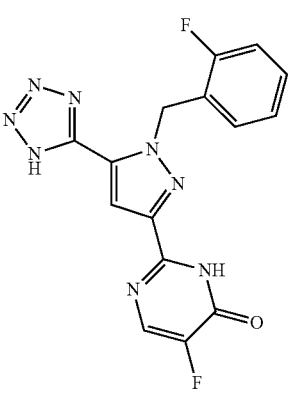
Compound 97
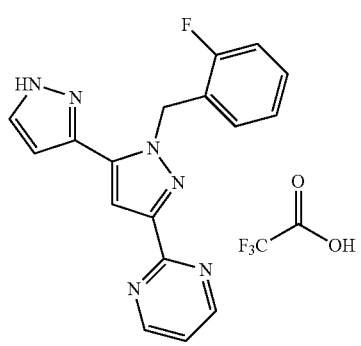

TABLE I-continued
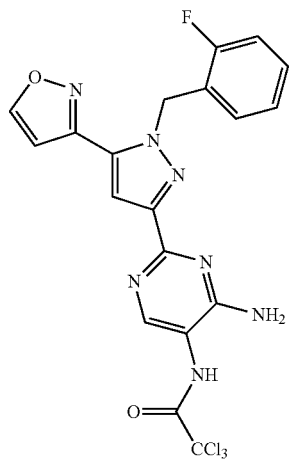
Compound 98
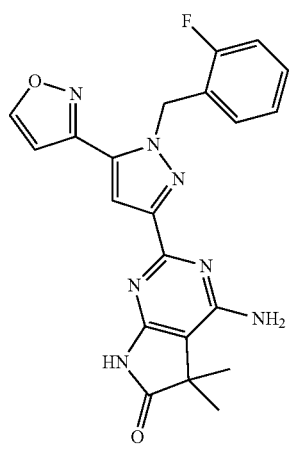
Compound 99
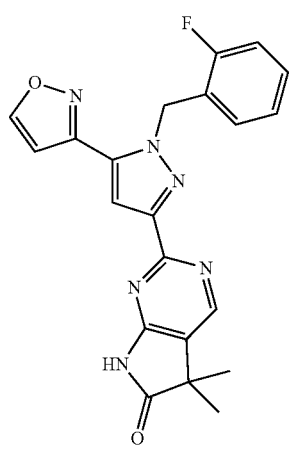
Compound 100
TABLE I-continued
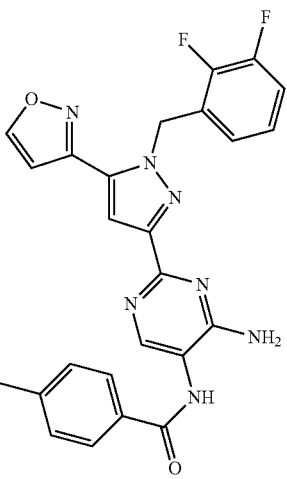
Compound 101
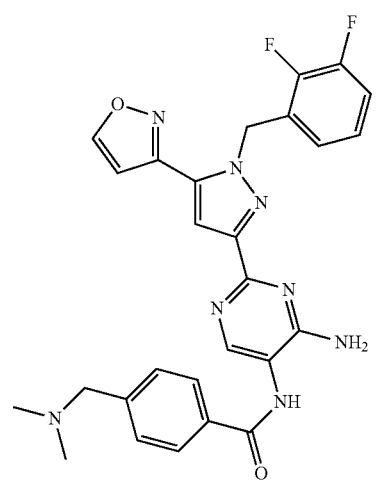
Compound 102
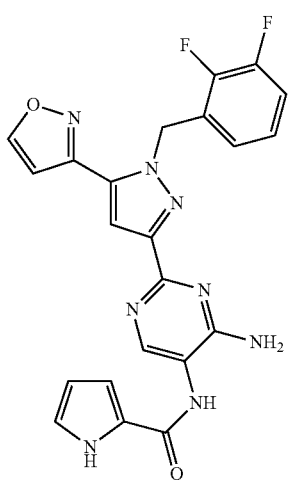
Compound 103

TABLE I-continued
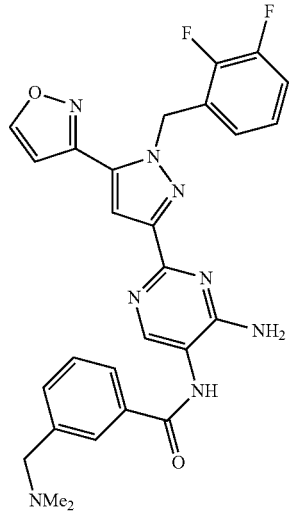
Compound 104
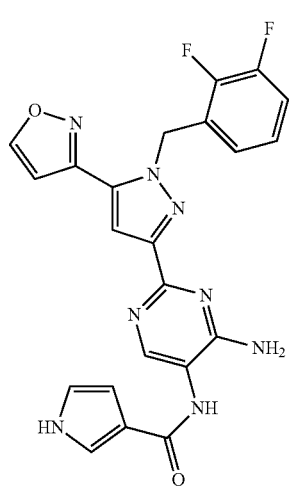
Compound 105
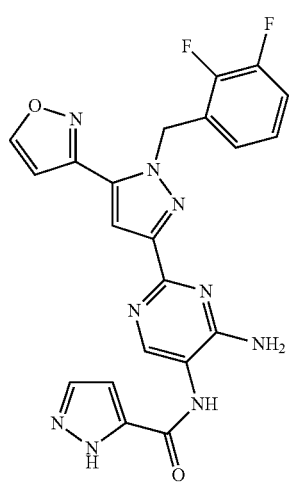
Compound 106
TABLE I-continued
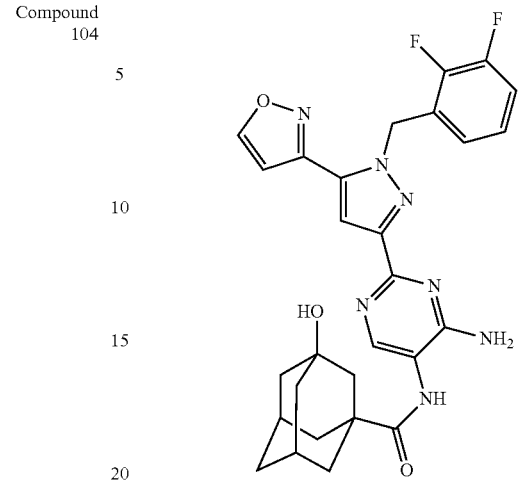
Compound 107
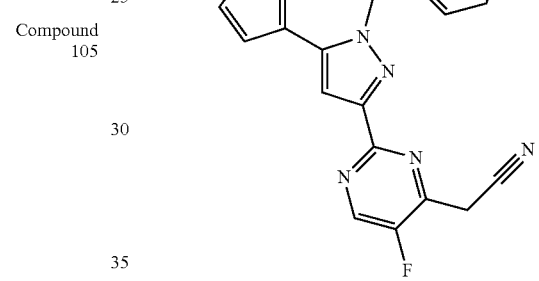
Compound 108
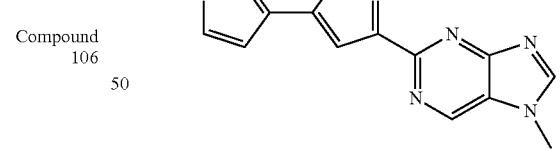
Compound 109
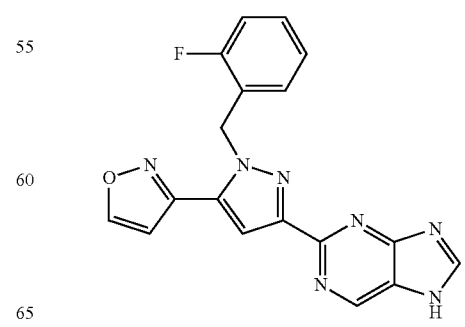
Compound 110

TABLE I-continued
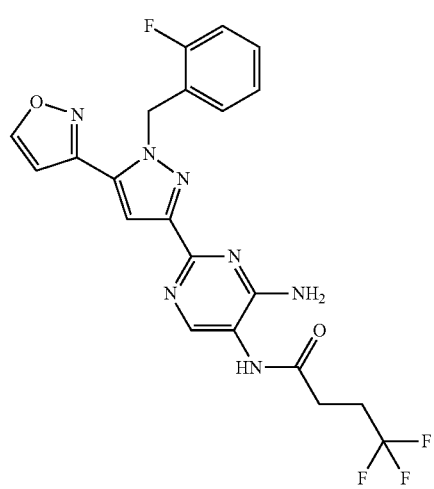
Compound 111
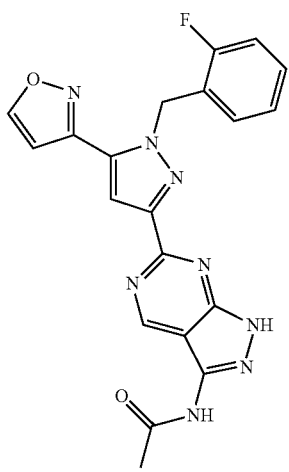
Compound 114
Compound 112
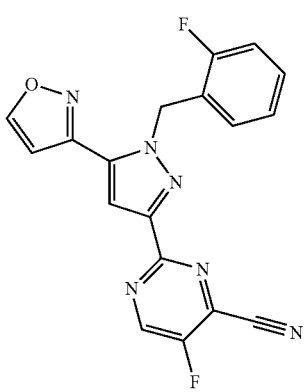
Compound 115
Compound 113
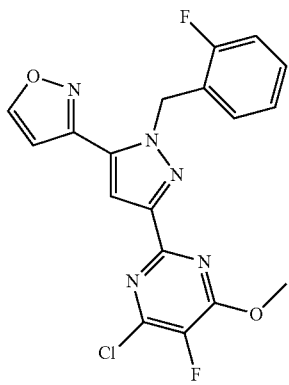
Compound 116
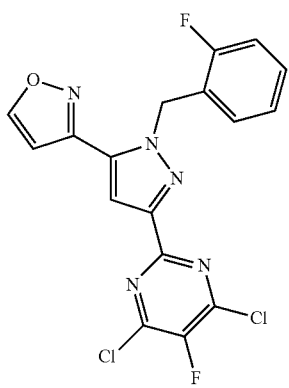
Compound 117

TABLE I-continued

| | |
|---|---|
| 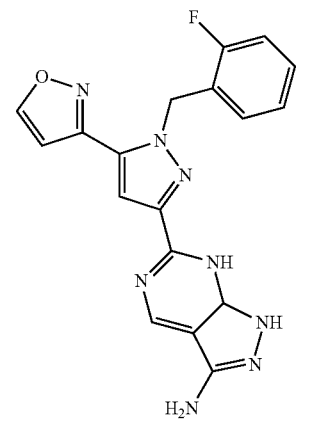 | Compound 118 |
| 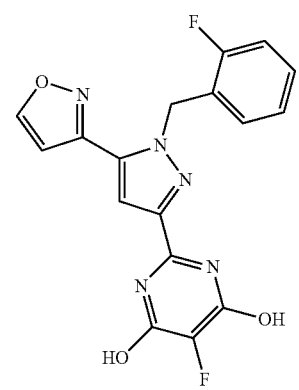 | Compound 119 |
| 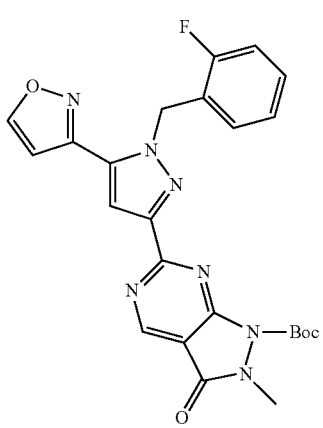 | Compound 120 |
| 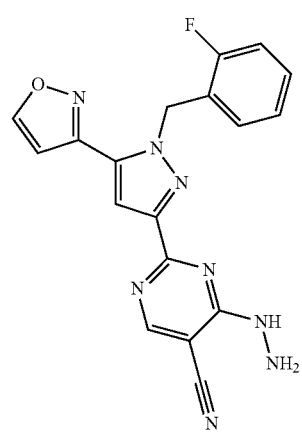 | Compound 121 |
| 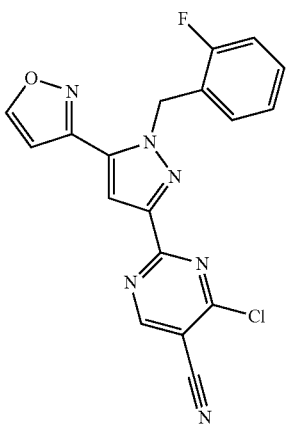 | Compound 122 |

The invention also provides a method of treating or preventing a disease, health condition or disorder in a subject in need thereof, comprising administering, alone or in combination therapy, a therapeutically or prophylactically effective amount of a compound from Table I or a pharmaceutically acceptable salt thereof to the subject; wherein the disease, health condition or disorder is a peripheral, pulmonary, hepatic, liver, cardiac or cerebral vascular/endothelial disorders or conditions, a urogenital-gynecological disorder or condition, a thromboembolic disease, a fibrotic disorder, a pulmonary or respiratory disorder, a renal or hepatic disorder, a metabolic disorder, atherosclerosis or a lipid related disorder that can benefit from sGC stimulation or from an increase in the concentration of cGMP.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

DEFINITIONS AND GENERAL TERMINOLOGY

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

The phrase "up to", as used herein, refers to zero or any integer number that is equal or less than the number following the phrase. For example, "up to 3" means any one of 0, 1, 2, or 3.

A compound, such as the compounds of Table I or other compounds herein disclosed, may be present in its free form (e.g. an amorphous form, or a crystalline form or polymorphs). Under certain conditions, compounds may also form salts. As used herein, the term co-form is synonymous with the term multi-component crystalline form. When one of the components in the co-form has clearly transferred a proton to the other component, the resulting co-form is referred to as a "salt". The formation of a salt is determined by how large the difference is in the pKas between the partners that form the mixture.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are within the scope of the disclosure.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W. et al., "Protective Groups in Organic Synthesis", Third Edition, John Wiley & Sons, New York: 1999, the entire contents of which is hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-ethyl-3-(3-dimethylaminopropyl)carbodiimide), DCC (dicyclohexylcarbodiimide), BOP (benzotriazol-1-yloxy-tris (dimethylamino)-phosphonium hexafluorophosphate), pyBOP ((benzotriazol-1-yloxy)tripyrrolidinophosphonium hexafluorophosphate), etc.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The present invention includes compounds depicted in Table I and their pharmaceutically acceptable salts.

Methods of Preparing the Compounds

The compounds of Table I may be prepared according to the schemes and examples depicted and described below. Unless otherwise specified, the starting materials and various intermediates may be obtained from commercial sources, prepared from commercially available compounds or prepared using well-known synthetic methods. Another aspect of the present invention is a process for preparing the compounds of Table I as disclosed herein.

General synthetic procedures for the compounds of this invention are described below. The synthetic schemes are presented as examples and do not limit the scope of the invention in any way.

General Procedure A-I (Most General Version)

General Procedure A-I

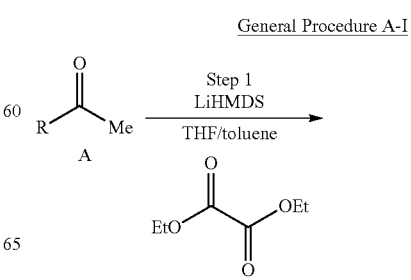

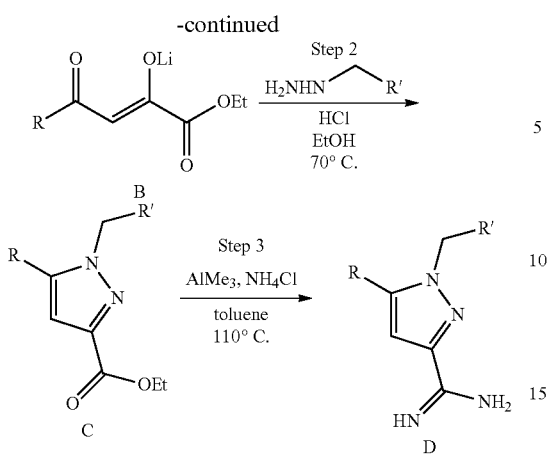

Step 1: Dione Enolate Formation:

To a solution of ketone A in THF cooled to −78° C., LiHMDS (e.g., 0.9 eq, 1.0 M in toluene) is added dropwise, for example, via a syringe. The reaction mixture is then allowed to warm to about 0° C., then charged with diethyl oxalate (1.2 eq). At this time, the reaction mixture is warmed to room temperature and stirred at that temperature until judged complete (e.g., using either TLC or LC/MS analysis). Once the reaction is complete (reaction time typically about 45 minutes), the product dione enolate B is used as-is in Step 2, i.e., the cyclization step, without any further purification.

Step 2: Pyrazole Formation:

Dione enolate B is diluted with ethanol and consecutively charged with HCl (e.g., 3 eq, 1.25M solution in ethanol) and arylhydrazine hydrate (e.g., 1.15 eq). The reaction mixture is heated to about 70° C. and stirred at this temperature until cyclization is deemed complete (e.g., by LC/MS analysis, typically about 30 minutes). Once complete, the reaction mixture is treated carefully with solid sodium bicarbonate (e.g., 4 eq) and diluted with dichloromethane and water. The organic layer is separated, and the aqueous layer is further diluted with water before extraction with dichloromethane (3 times). The combined organics are washed with brine, dried over $MgSO_4$, filtered, and concentrated in vacuo. The resulting pyrazole C is then purified by $SiO_2$ chromatography using an appropriate gradient of EtOAc/hexanes.

Step 3: Amidine Formation:

To a suspension of $NH_4Cl$ (e.g., 5 eq) in toluene cooled to about 0° C. is added $AlMe_3$ (e.g., 5 eq, 2.0M solution in toluene) dropwise, for example, via a syringe. The reaction mixture is allowed to warm to room temperature, and stirred until no more bubbling is observed. Pyrazole C is added in 1 portion to the reaction mixture. The reaction mixture is then heated to about 110° C., and stirred at this temperature until the reaction is judged complete (e.g., using either TLC or LC/MS analysis). Once complete, the reaction mixture is cooled, treated with excess methanol, and stirred vigorously for about 1 hour at room temperature. The thick slurry is filtered, and the resulting solid cake is washed with methanol. The filtrate is concentrated in vacuo, and the resulting solids are re-suspended in an ethyl acetate:isopropyl alcohol, 5:1 v:v, solvent mixture. The reaction mixture is further treated with a saturated sodium carbonate solution, and stirred for about 10 minutes before the layers are separated. The aqueous layer is extracted with the ethyl acetate:isopropyl alcohol, 5:1 v:v, solvent mixture (3×), and the combined organics are washed with brine. The organics are further dried over MgSO4, filtered, and the solvent is removed in vacuo. The product amidine D is used as-is in subsequent steps without further purification.

General Procedure A-II:

This general procedure is exemplified for a compound containing an isoxazole attached to the 5-position of the 1,2-diazolyl core in Formula I below, but it can also be applied using analogous procedures to the preparation of intermediates of general Formula I (wherein $R°$ is halogen or alkyl and n=0, 1 or 2). Specific details for a number of embodiments of Formula I are described in the experimental section.

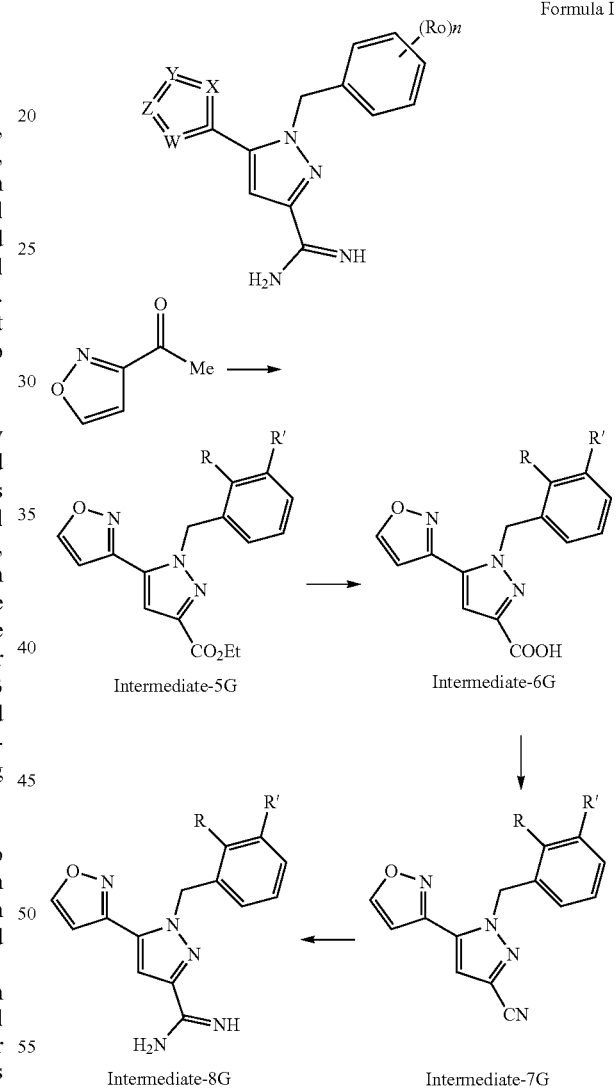

To a −78° C. solution of 1-(isoxazol-3-yl)ethanone (1.0 equiv) in tetrahydrofuran (0.2 M), lithium hexamethyldisilazide (1 M solution in toluene, 0.88 equiv) was added dropwise. The solution was immediately warmed to 0° C. and stirred for 30 minutes at this temperature. Diethyl oxalate (1.2 equiv) was then added, e.g., via a syringe, over the course of 5 minutes. After stirring for 15 more minutes at 0° C., the solution was warmed to room temperature and stirred for 30 minutes at this temperature Anhydrous ethanol was added to make the solution 0.1 M. The appropriate hydrazine hydrochloride (1.3 equiv), and acetic acid (8.3 equiv) were added. The solution was stirred at 75° C. until LC/MS indicated complete consumption of the β-ketoester intermediate. After removing the solvent in vacuo, water and dichloromethane were added. The layers were separated and the aqueous layer was extracted with dichloromethane. The organics were combined, dried over magnesium sulfate, filtered, and the solvent was removed under vacuum. The crude product was purified by silica gel chromatography to provide Intermediate-5G.

To a solution of Intermediate-5G (1 equiv) in a mixture of tetrahydrofuran, methanol, and water (3:1:1, volume ratio, 0.15 M), lithium hydroxide hydrate (1.2 equiv) was added. The reaction was monitored by LC/MS, and additional base was added until complete consumption of the starting ester was observed. The solution was then acidified to pH~2 using aqueous 1 N hydrochloric acid. Ethyl acetate and water were added and the layers were separated. The aqueous layer was extracted with ethyl acetate and the organics were combined, dried over magnesium sulfate, filtered, and the solvent was removed under vacuum to give the crude Intermediate-6G that was carried onto the next step without further purification.

To a slurry of Intermediate-6G (1 equiv), 2-methylpropan-2-amine (2 equiv), and triethylamine (2 equiv) in ethyl acetate (0.3 M) were added T3P (3 equiv) as a 50% solution in ethyl acetate. The solution was heated at 65° C. until LC/MS showed complete consumption of the starting acid. The solvent was removed under vacuum, phosphoryl trichloride (8 equiv) was added, and the reaction mixture was stirred at 70° C. until LC/MS indicated complete conversion to the desired nitrile. The crude mixture was poured into ice water and dichloromethane. The layers were separated and the aqueous layer was extracted with dichloromethane. The organics were combined, dried over magnesium sulfate, filtered and the solvent was removed under vacuum. Purification by silica gel chromatography provided Intermediate-7G.

To a stirred 0° C. solution of Intermediate-7G (1 equiv) in methanol (0.2 M), sodium hydride (60% dispersion in mineral oil, 2 equiv) was added portion-wise. The solution was immediately warmed to room temperature and then heated at 60° C. until LC/MS showed only a small amount of starting material. Ammonium chloride (5 equiv) and acetic acid (1 equiv) were added and the reaction mixture heated at 70° C. until LC/MS indicated complete conversion to the desired amidine. The solution was diluted with ethyl acetate and saturated aqueous sodium carbonate. The layers were separated and the aqueous layer was extracted with ethyl acetate. The organics were combined, washed with brine, dried over magnesium sulfate, filtered, and the solvent was removed under vacuum. After adding diethyl ether, the resulting suspension was filtered to provide Intermediate-8G as a solid.

General Procedure B:

This procedure is exemplified below starting with a compound of Formula I wherein X=N, Y=O and W, Z=C and n is 0, but it can also be used to make other compounds of Formula II, wherein the ring attached to the 5-position of the 1,2-diazolyl core is, for instance, any oxazole, isoxazole, thiazole or isothiazole; n is 0, 1 or 2 and R° is a halogen or alkyl, with slight modifications. The specific details for a number of embodiments of Formula I and Formula II are described in the experimental section.

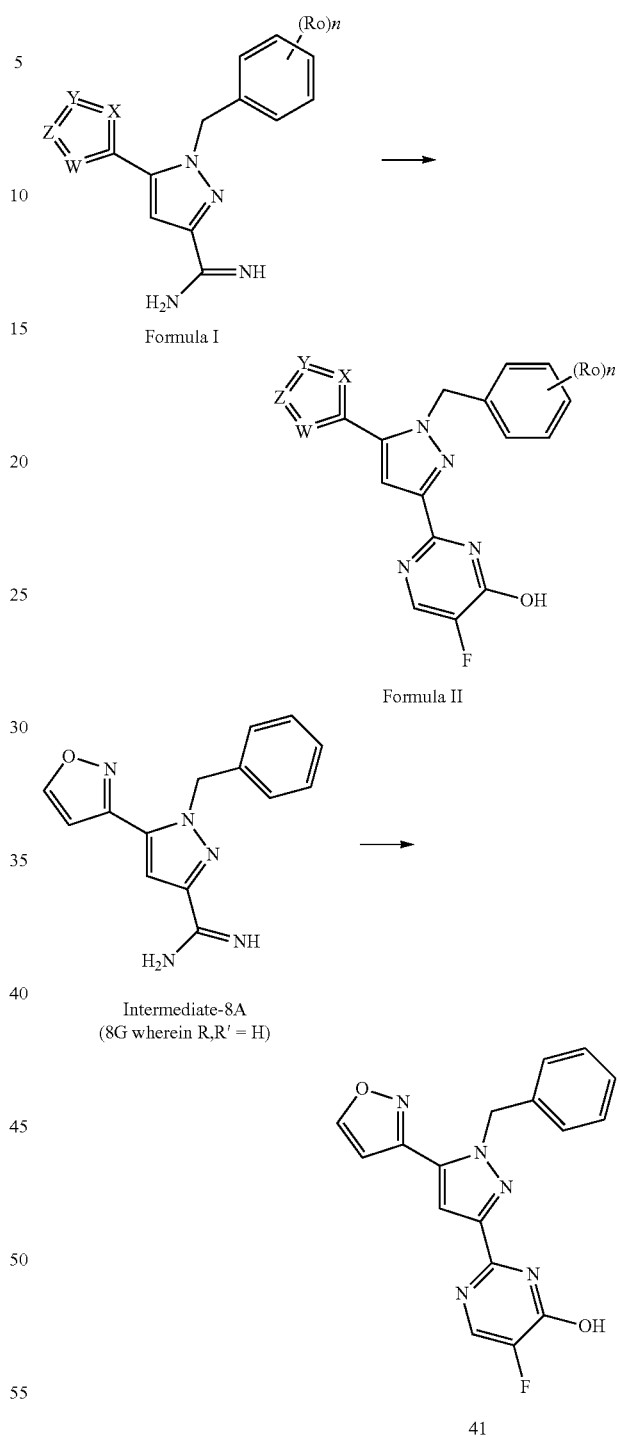

Intermediate-8A (75 mg, 0.281 mmol) and ethyl 3-(dimethylamino)-2-fluoroacrylate (256 mg, 0.842 mmol) were combined and heated neat at 85° C. for 16 hours. An additional 2 equiv of ester was added and the reaction mixture stirred for another 24 hours. The solvent was removed in vacuo and purification of the resulting residue by silica gel chromatography (0-10% methanol in dichloromethane) provided impure solid that was triturated with diethyl ether (5 mL) to give Compound 41 (19 mg, 20%) as a pale pink solid.

General Procedure C

This procedure is exemplified below for the preparation of Compound 8 and an exemplar subsequent amidation product (Compound 10), however analogous procedures can be used for the preparation of any diamine hydrochloride of Formula III and subsequent amidation products. The specific details for the preparation of several embodiments of Formula III are described in the experimental section.

General Procedure C

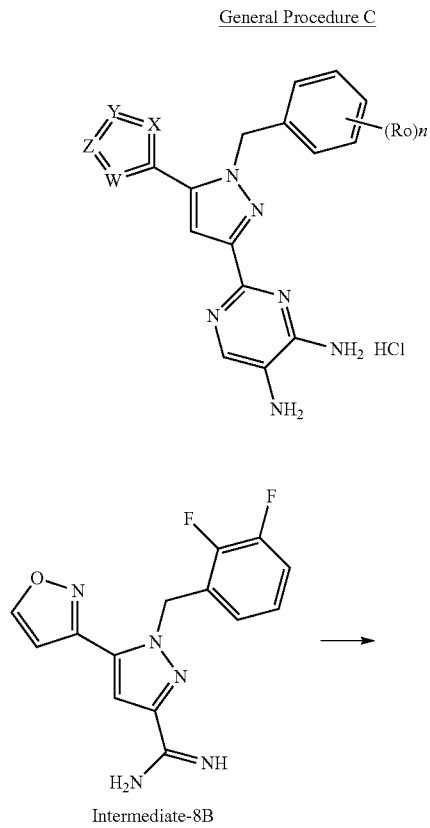

Formula III

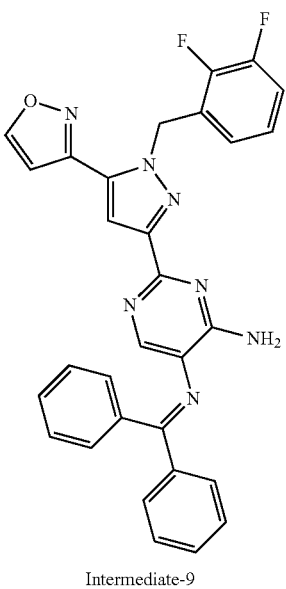

Intermediate-9

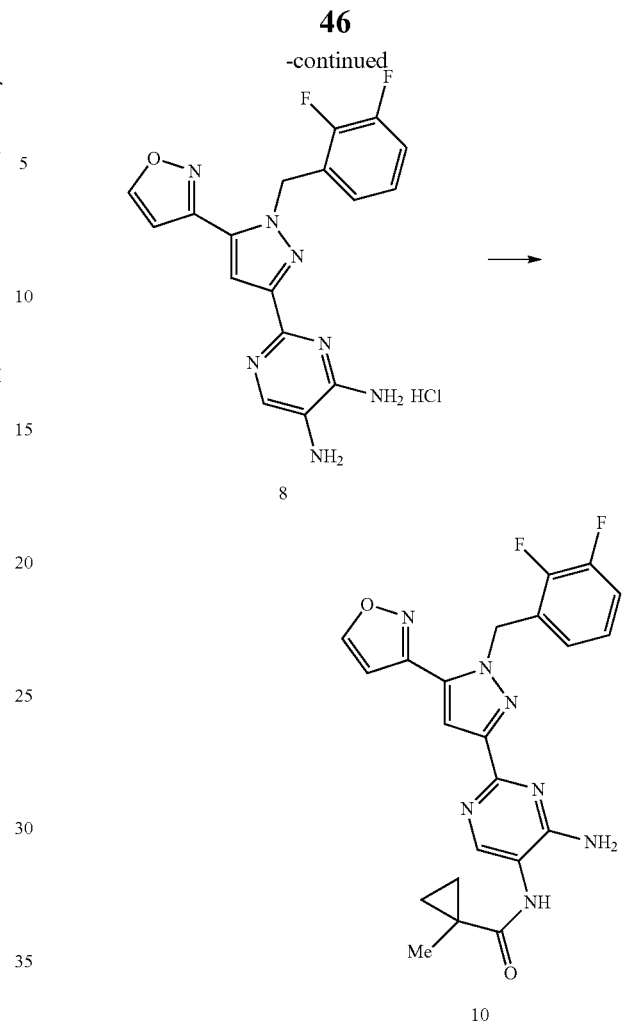

Intermediate-8B (300 mg, 0.99 mmol) and 3-(dimethylamino)-2-(diphenylmethyleneamino)acrylonitrile (681 mg, 2.47 mmol) were dissolved in pyridine (5.5 mL). 1,8-Diazabicycloundec-7-ene (300 µl, 2.0 mmol) was added, and the solution was heated at 110° C. for 16 hours. The solvent was removed in vacuum and purification by silica gel chromatography (10-100% ethyl acetate in hexanes) provided Intermediate-9 (96 mg, 18%) as a yellow solid.

To a solution of Intermediate-9 (96 mg, 0.180 mmol) in tetrahydrofuran (1.8 mL) was added aqueous 3N hydrochloric acid (1.4 mL). After stirring for 15 minutes at room temperature, the solvent was removed in vacuo. Diethyl ether (15 mL) was added, and after stirring for 20 minutes, the solids were filtered off to give Compound 8 (60 mg, 82%) as a brown solid.

To a solution of 1-methylcyclopropanecarboxylic acid (25 equiv) in dichloromethane was added oxalyl chloride (22.1 equiv) and catalytic N,N-dimethylformamide. Once gas evolution ceased, this crude reaction mixture was added portionwise to a suspension of Compound 8 (1 equiv) in dichloromethane/pyridine (3:1) until complete consumption of starting material was observed by LC/MS. After an aqueous ammonium chloride and dichloromethane workup, column chromatography (0-10% methanol in dichloromethane) provided the desired compound (Compound 10) as a light brown solid (59%).

General Procedure D

This procedure is exemplified below for the preparation of Compound 45, but can be used for the synthesis of other analogues of general Formulae IV, wherein Het indicates an aromatic heterocycle, with slight modifications. The specific details for a number of embodiments of Formula IV, are described in the experimental section.
General Procedure D
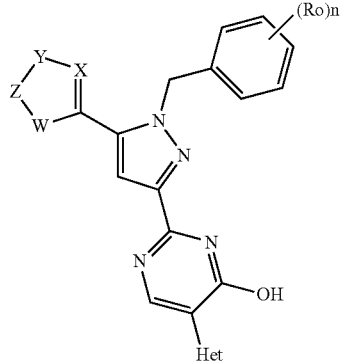
Formula IV
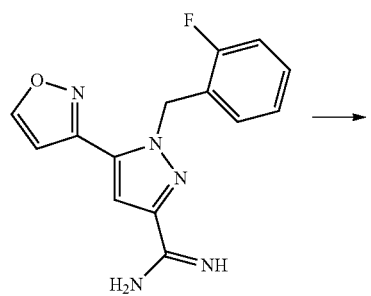
Intermediate-8C
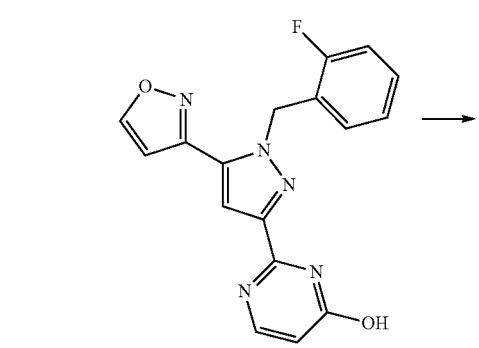
Intermediate-11
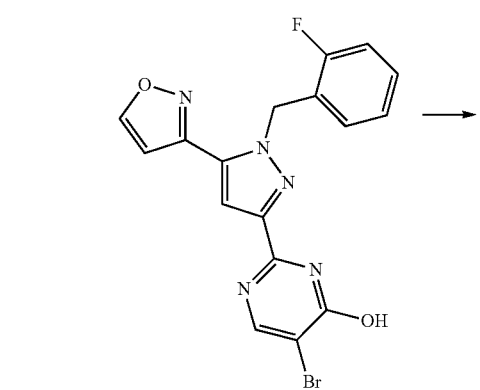
Intermediate-1
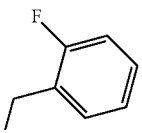
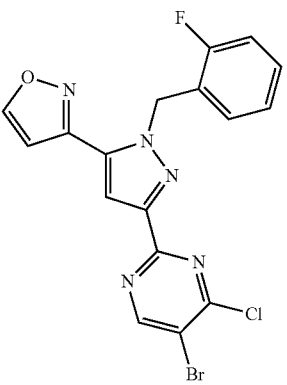
52
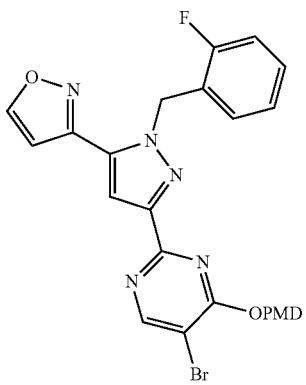
61
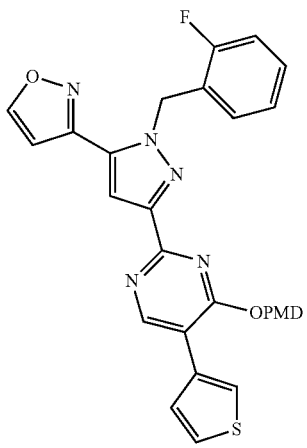
46

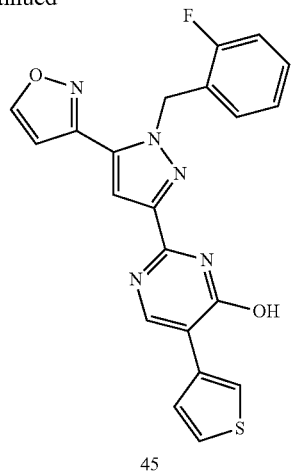

A mixture of Intermediate-8C (1 equiv) and methyl 3-methoxyacrylate (3 equiv) was stirred at 90° C. for 6 h. The solvent was removed in vacuo and purification by silica gel chromatography (0-7% methanol/dicloromethane) delivered the desired compound as a colorless solid (41%).

To a solution of 2-(1-(2-fluorobenzyl)-5-(isoxazol-3-yl)-1H-pyrazol-3-yl)pyrimidin-4-ol (Intermediate-11, 276 mg, 1 equiv) in acetic acid (4 ml) at 0° C., was added bromine (59 μl, 1.4 equiv). The mixture was removed from the ice bath and stirred at 25° C. for 3 h. The mixture was concentrated under vacuum. The resulting residue was rinsed with a minimal amount of methanol and acetone. The precipitate was collected by filtration to give a mixture of the starting material as well as the desired 2-(1-(2-fluorobenzyl)-5-(isoxazol-3-yl)-1H-pyrazol-3-yl)pyrimidin-4-ol. Repeating the reaction and subjecting the solid to the bromination conditions gave 202 mg (59%) of the desired product (Intermediate-1) as a white solid.

To a suspension of Intermediate-1 (711 mg, 1.71 mmol) in toluene (10 mL) was added phosphoryl chloride (0.48 mL, 5.1 mmol). The resulting solution was heated at 110° C. for 15 hours, at which point the crude reaction mixture was diluted with dichloromethane (75 mL) and saturated aqueous sodium bicarbonate. The layers were separated and the aqueous layer was extracted with dichloromethane (2×50 mL). The organics were dried over magnesium sulfate, filtered, and the solvent was removed in vacuo to give the crude product as a solid. Purification by silica gel chromatography (10-100% ethyl acetate in hexanes) provided Compound 52 (645 mg, 87%) as a pale yellow solid.

To a suspension of 60% sodium hydride in mineral oil (12 mg, 0.31 mmol) in tetrahydrofuran (2 mL) at 0° C. was added p-methoxybenzyl alcohol (38 μl, 0.31 mmol) dropwise over the course of 1 minute. After stirring for 15 minutes, the solution was warmed to room temperature and stirred for an additional 5 minutes. The solution was then cooled to 0° C. and Compound 52 (102 mg, 0.23 mmol) was added in a single portion. The solution was immediately warmed to room temperature and stirred for an additional 45 minutes. Saturated aqueous ammonium chloride (50 mL) and dichloromethane (50 mL) were added. The layers were separated and the aqueous layer was extracted with dichloromethane (2×50 mL). The organics were dried over magnesium sulfate, filtered, and the solvent was removed in vacuo. The crude residue was purified by silica gel chromatography (10-30% ethyl acetate in hexanes) to give Compound 61 as a white solid.

A suspension of cesium carbonate (71 mg, 0.22 mmol), potassium fluoride (23 mg, 0.39 mmol), thiophen-3-ylboronic acid (30 mg, 0.23 mmol), and Compound 61 (25 mg, 0.047 mmol) in dimethoxyethane (1 mL) was degassed with a stream of nitrogen for 10 min. Palladium tetrakistriphenylphosphine (16 mg, 0.014 mmol) was added and the solution was heated to 90° C. After 1.5 h, the solution was diluted with ethyl acetate (75 mL) and water (50 mL). The layers were separated and the aqueous layer was extracted with ethyl acetate (2×50 mL). The organics were dried over magnesium sulfate, filtered, and the solvent was removed under vacuum. The crude product was purified by silica gel chromatography (10-40% ethyl acetate in hexanes) to provide Compound 46 (16 mg, 66%) as a brown oily solid.

A mixture of Compound 46 (13 mg, 0.024 mmol) and trifluoroacetic acid (300 μl, 3.89 mmol) was stirred at room temperature for 20 minutes. The solution was diluted with dichloromethane (40 mL) and saturated aqueous sodium bicarbonate. The layers were separated and the aqueous layer was extracted with dichloromethane (2×50 mL). The organics were combined, dried over magnesium sulfate, filtered, and the solvent was removed under vacuum. Purification by silica gel chromatography (0-50% ethyl acetate in hexanes) provided Compound 45 (12 mg, quantitative yield) as a white solid.

General Procedure E

This general procedure is exemplified by the preparation of Compound 51 as depicted below but it can be used for the synthesis of other compounds of general Formula V. The specific details for the preparation of various embodiments of Formula IV are described in the experimental section.

General Procedure E

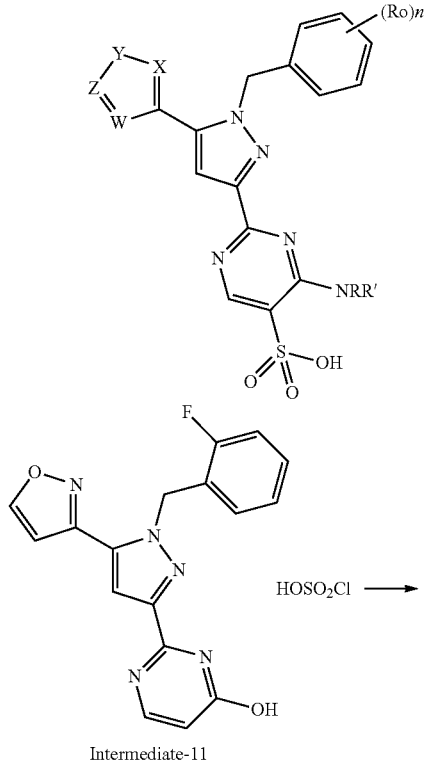

-continued

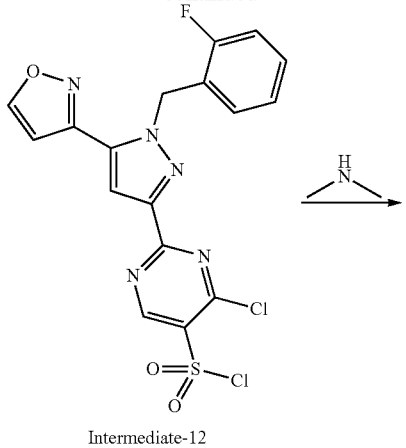

Intermediate-12

51

A solution of 2-(1-(2-fluorobenzyl)-5-(isoxazol-3-yl)-1H-pyrazol-3-yl)pyrimidin-4-ol (Intermediate-11, 200 mg, 1 equiv) and sulfurochloridic acid (1.9 ml) was heated at 100° C. for 30 min in a sealed vial. The mixture was diluted in ethyl acetate (50 ml) and washed with water (50 ml). The organic layer was dried, filtered and evaporated to give 239 mg of crude 4-chloro-2-(1-(2-fluorobenzyl)-5-(isoxazol-3-yl)-1H-pyrazol-3-yl)pyrimidine-5-sulfonyl chloride as a cream colored solid (Intermediate-12) that was taken directly onto the next step without further purification.

A portion of the solid product (100 mg) was combined with dimethyl amine (2.0 M in THF, 2.2 ml, 20 equiv) and stirred at 25° C. for 30 min. The mixture was diluted in ethyl acetate (100 ml) and washed with water (50 ml). The organic layer was dried, filtered and evaporated to give a crude oil. Purification of the oil by column chromatography (0 to 10% methanol in dichloromethane) and re-crystallization from a hexanes/ethyl acetate mixture gave the desired product as a white solid (Compound 51, 18% overall yield over two steps).

General Procedure F:

This general procedure is exemplified below for the preparation of Compound 60, however it can also be used for the preparation of other compounds of general Formula VI. Specific details of the preparation of several embodiments of Formula VI are described in the experimental section.

General Procedure F

Formula VI

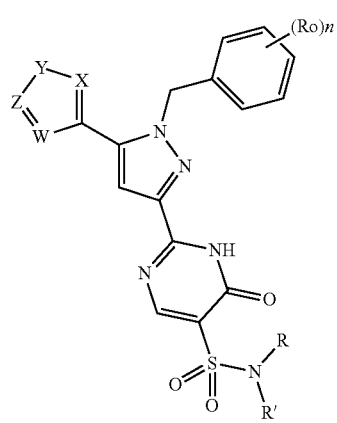

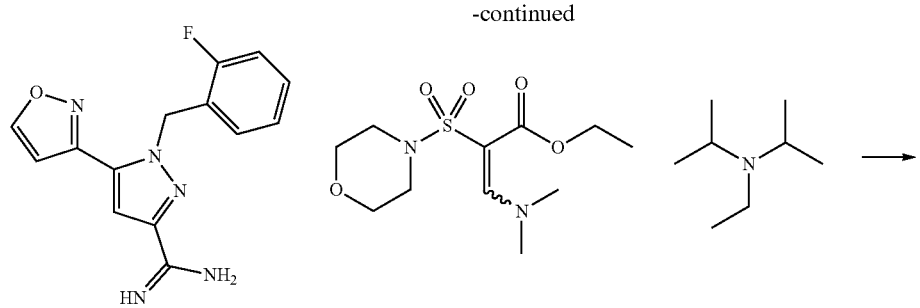

Intermediate 8C

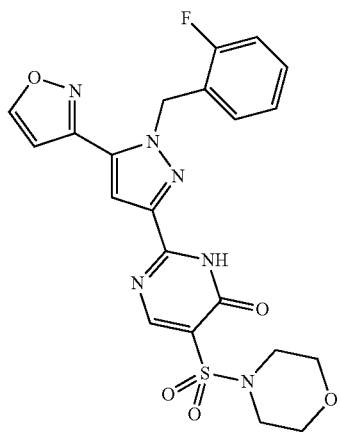

60

A solution of Intermediate 8C, ethyl 3-(dimethylamino)-2-(morpholinosulfonyl)acrylate (2 equiv.) and Hunig's base (1 equiv.) was stirred at 85° C. for 2 days in ethanol. The solvent was removed under vacuum and purification by silica gel chromatography (0 to 40% ethyl acetate in hexanes) followed by rinsing with a minimal amount of methanol gave the desired product as a white solid (Compound 60, 3% yield).

General Procedure G

This general procedure is exemplified below for the preparation of Compound 4, however it can also be used for the preparation of other compounds of general Formula VII. Specific details of the preparation of several embodiments of Formula VII are described in the experimental section.

General Procedure G

Formula VII

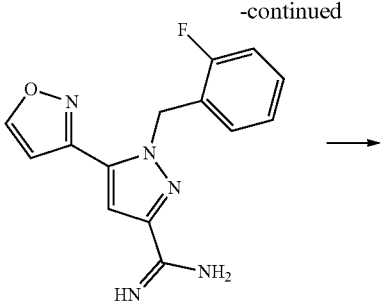

Intermediate 8C

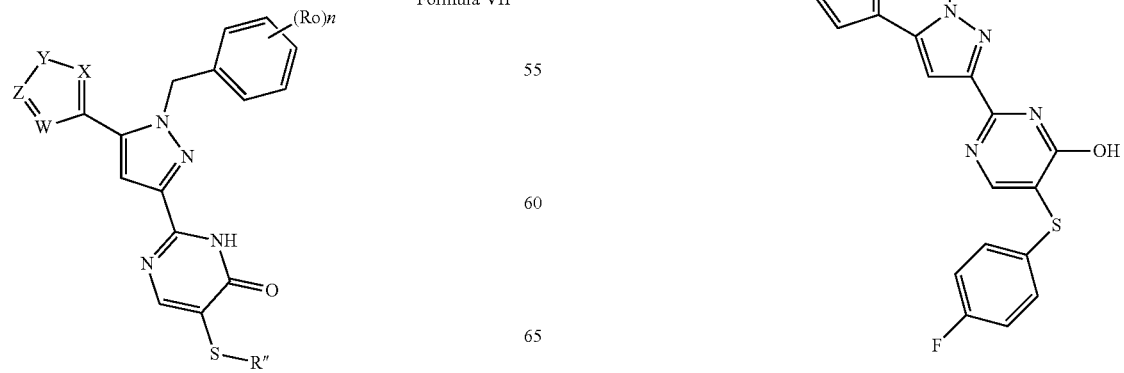

4

A solution of Intermediate 8C (1 equiv) and ethyl 3-(dimethylamino)-2-(4-fluorophenylthio)acrylate (4 equiv) was stirred neat at 100° C. for 14 hours. Purification by silica gel chromatography (0-50% 7:1 acetonitrile:methanol in diclomethane) delivered the desired product 2-(1-(2-fluorobenzyl)-5-(isoxazol-3-yl)-1H-pyrazol-3-yl)-5-(4-fluorophenylthio)pyrimidin-4-ol as a solid (Compound 4, 8%).

General Procedure H

This general procedure is exemplified below for the preparation of Compound 24, however it can also be used for the preparation of other compounds of general Formula VIII. Specific details of the preparation of several embodiments of Formula VIII are described in the experimental section.

General Procedure H

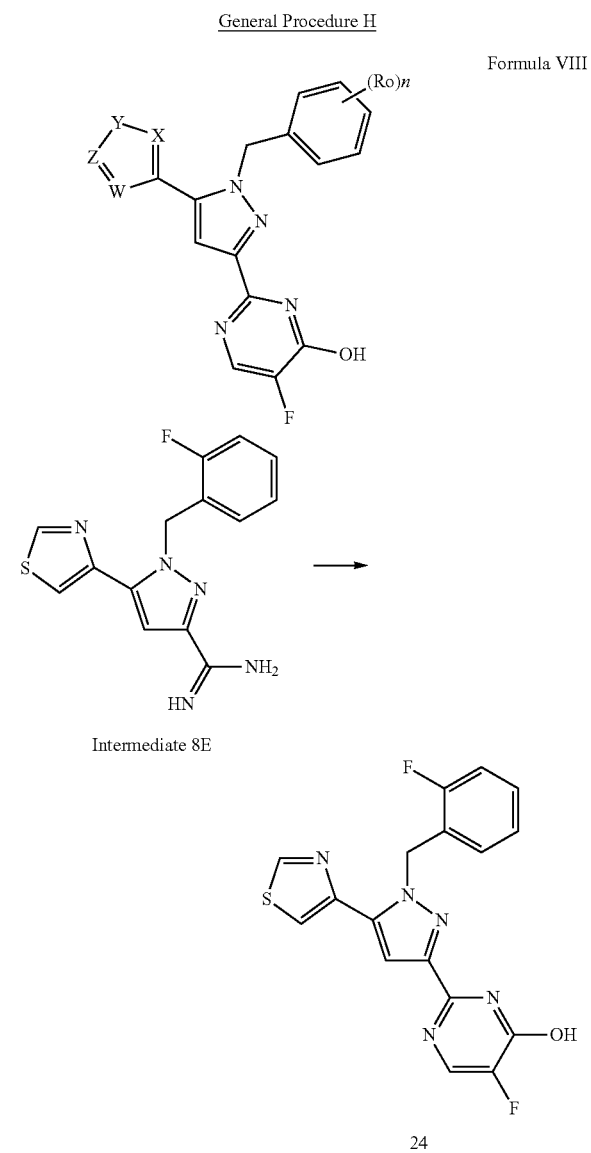

A solution of Intermediate 8E (1 equiv) and (Z)-ethyl 3-(dimethylamino)-2-fluoroacrylate (4 equiv) was stirred neat at 100° C. for 14 hours. Purification by silica gel chromatography (0-50% 7:1 acetonitrile:methanol in diclomethane) delivered desired product 5-fluoro-2-(1-(2-fluorobenzyl)-5-(thiazol-4-yl)-1H-pyrazol-3-yl)pyrimidin-4-amine as a solid (Compound 24, 5%).

Pharmaceutically Acceptable Salts of the Invention.

The phrase "pharmaceutically acceptable salt," as used herein, refers to pharmaceutically acceptable organic or inorganic salts of a compound of Table I. For use in medicine, the salts of a compound of Table I will be pharmaceutically acceptable salts. Other salts may, however, may be useful in the preparation of a compound of Table I or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a compound of Table I is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N.sup.1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of Table I is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.
Pharmaceutical Compositions and Methods of Administration.

The compounds herein disclosed, and their pharmaceutically acceptable salts thereof may be formulated as pharmaceutical compositions or "formulations".

A typical formulation is prepared by mixing a compound of Table I, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Table I is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Table I or pharmaceutical composition thereof) or aid in the manufacturing of the pharmaceutical product (i.e., medicament).

The formulations may be prepared using conventional dissolution and mixing procedures. For example, the bulk drug substance (i.e., a compound of Table I, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Table I or a pharmaceutically acceptable salt thereof is typically formulated into pharmaceutical dosage forms to provide an easily controllable dosage of the drug and to enable patient compliance with the prescribed regimen. Pharmaceutical formulations of a compound of Table I, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula I will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, tretralose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semi-permeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolat. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e.g., Explotab™ CLV), microcrystalline cellulose (e.g., Avicel™), microcrystalline silicified cellulose (e.g., ProSolv™) and croscarmellose sodium (e.g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multi-layered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. No. 6,419,952, U.S. Pat. No. 6,342,249, U.S. Pat. No. 5,324,280, U.S. Pat. No. 4,672,850, U.S. Pat. No. 4,627,850, U.S. Pat. No. 4,203,440, and U.S. Pat. No. 3,995,631.

As further noted above, the agents described herein may be provided in the form of microparticulates, generally ranging in size from about 10 µm to about 2 mm (including, for example, from about 100 µm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet and dry-granulation processes, extrusion/spheronization, roller-compaction, melt-congealing, or by spray-coating seed cores. For example, in wet and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 µm) can be designed using polymers able to be degraded in vivo (e.g. biodegradable poly-alkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304, 121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Table I that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound of Table I in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of a compound of Table I contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Table I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Table I include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Table I or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Therapeutic Methods

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO or an increase in the concentration of cGMP might be desirable. The diseases that can be treated include as pulmonary hypertension, arterial hypertension, heart failure, atherosclerosis, inflammation, thrombosis, renal fibrosis and failure, liver cirrhosis, erectile dysfunction and other related cardiovascular disorders.

Increased concentration of cGMP leads to vasodilation, inhibition of platelet aggregation and adhesion, anti-hypertensive effects, anti-remodeling effects, anti-apoptotic effects, anti-inflammatory effects and neuronal signal transmission effects. Thus, sGC stimulators may be used to treat and/or prevent a range of diseases and disorders, including but not limited to a peripheral, pulmonary, hepatic, liver, cardiac or cerebralvascular/endothelial disorders or conditions, a urogenital-gynecological disorder or condition, a thromboembolic disease, a fibrotic disorder, a pulmonary or respiratory disorder, a renal or hepatic disorder, a metabolic disorder, atherosclerosis, or a lipid related disorder.

In other embodiments, the compounds here disclosed are sGC stimulators that may be useful in the prevention and/or treatment of diseases and disorders characterized by undesirable reduced bioavailability of and/or sensitivity to NO, such as those associated with conditions of oxidative stress or nitrosative stress.

Throughout this disclosure, the terms "hypertension", "arterial hypertension" or "high blood pressure (HBP)" are used interchangeable and refer to an extremely common and highly preventable chronic condition in which blood pressure (BP) in the arteries is higher than normal. If not properly controlled, it represents a significant risk factor for several serious cardiovascular and renal conditions. Hypertension may be a primary disease, called "essential hypertension" or "idiopathic hypertension", or it may be caused by other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension.

Hypertension is an extremely common comorbid condition in diabetes, affecting ~20-60% of patients with diabetes, depending on obesity, ethnicity, and age. This type of hypertension is herein referred to as "diabetic hypertension". In type 2 diabetes, hypertension is often present as part of the metabolic syndrome of insulin resistance also including central obesity and dyslipidemia. In type 1 diabetes, hypertension may reflect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

As used herein "heart failure" is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neurohormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness, edema of the feet, ankles and legs, rapid weight gain, chronic cough, including that producing mucus or blood. Depending on its clinical presentation, heart failure is classified as de novo, transient or chronic. Acute heart failure, i.e. the rapid or gradual onset of symptoms requiring urgent therapy, may develop de novo or as a result of chronic heart failure becoming decompensated. Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease (COPD), peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, nonvoluntary loss of at least 6% of body weight over a period of six months.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertriglyceridemia" involves elevated levels of triglycerides). "Hyperlipoproteinemia" refers to elevated levels of lipoproteins (usually LDL unless otherwise specified).

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or brain. PVD can result from atherosclerosis, inflammatory processes leading to stenosis, an embolism, or thrombus formation. It causes either acute or chronic "ischemia (lack of blood supply)". Often PVD is a term used to refer to atherosclerotic blockages found in the lower extremity. PVD also includes a subset of diseases classified as microvascular diseases resulting from episodal narrowing of the arteries (e.g., "Raynaud's phenomenon"), or widening thereof (erythromelalgia), i.e. vascular spasms.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen, and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin.

A "stroke", or cerebrovascular accident (CVA), is the rapid loss of brain function(s) due to disturbance in the blood supply to the brain. This can be due to "ischemia" (lack of blood flow) caused by blockage (thrombosis, arterial embolism), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Ischemia", is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism).

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

Specific diseases of disorders which may be treated and/or prevented by administering an sGC stimulator of the invention, include but are not limited to: hypertension (e.g., diabetic hypertension, arterial hypertension, pulmonary hypertension, resistant hypertension, peripheral artery disease, etc), heart failure (e.g., left ventricular diastolic dysfunction (LVDD) and left ventricular systolic dysfunction (LVSD), sleep apnea associated with heart failure), arteriosclerotic disease (e.g., atherosclerosis) thromboembolic disorders (e.g., chronic thromboembolic pulmonary hypertension, thrombosis, stroke, embolism, pulmonary embolism), renal diseases (e.g., renal fibrosis, ischemic renal disease, renal failure, renal insufficiency, chronic kidney disease), hepatic disease (e.g., liver fibrosis or cirrhosis), respiratory disease (e.g., pulmonary fibrosis, asthma, chronic obstructive pulmonary disease, interstitial lung disease), sexual disorders (e.g., erectile dysfunction, male and female sexual dysfunction, vaginal atrophy), sickle cell anemia, neuro inflammatory diseases or disorders and metabolic disorders (e.g., lipid related disorders).

The compounds of Table I as well as pharmaceutically acceptable salts thereof, as stimulators of sGC, are useful in the prevention and/or treatment of the following types of diseases, conditions and disorders which can benefit from sGC stimulation:

(1) Peripheral, pulmonary, hepatic, liver, cardiac or cerebral vascular/endothelial disorders/conditions:

disorders related to high blood pressure and decreased coronary blood flow such as increased acute and chronic coronary blood pressure, arterial hypertension and vascular disorder resulting from cardiac and renal complications (e.g. heart disease, stroke, cerebral ischemia, renal failure); resistant hypertension, diabetic hypertension, congestive heart failure; diastolic or sistolic dysfunction; coronary insufficiency; arrhythmias.

thromboembolic disorders and ischemias such as myocardial infarction, stroke, transient ischemic attacks (TIAs); stable or unstable angina pectoris;

peripheral arterial disease, peripheral occlusive arterial disease;

pulmonary/respiratory conditions such as pulmonary hypertension, pulmonary arterial hypertension, and associated pulmonary vascular remodeling (e.g. localized thrombosis and right heart hypertrophy); pulmonary hypertonia; primary pulmonary hypertension, secondary pulmonary hypertension, familial pulmonary hypertension, sporadic pulmonary hypertension, precapillary pulmonary hypertension, idiopathic pulmonary hypertension, thrombotic pulmonary arteriopathy, plexogenic pulmonary arteriopathy;

pulmonary hypertension associated with or related to: left ventricular dysfunction, hypoxemia, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), connective tissue disease, lupus, schitosomiasis, sarcoidosis, chronic obstructive pulmonary disease, asthma, emphysema, chronic bronchitis, pulmonary capillary hemangiomatosis; histiocytosis X, lymphangiomatosis and compressed pulmonary vessels (such as due to adenopathy, tumor or fibrosing mediastinitis);

arteresclerotic diseases or conditions such as atherosclerosis (e.g., associated with endothelial injury, platelet and monocyte adhesion and aggregation, smooth muscle proliferation and migration); restenosis (e.g. developed after thrombolysis therapies, percutaneous transluminal angioplasties (PTAs), percutaneous transluminal coronary angioplasties (PTCAs) and bypass); inflammation;

cardiovascular disease associated with metabolic syndrome (e.g., obesity, dyslipidemia, diabetis, high blood pressure); lipid related disorders such as dyslipidemia, hypercholesterolemia, hypertriglyceridemia, sitosterolemia, fatty liver disease, and hepatitis;

liver cirrhosis, associated with chronic liver disease, hepatic fibrosis, hepatic stellate cell activation, hepatic fibrous collagen and total collagen accumulation; liver disease of necro-inflammatory and/or of immunological origin; andurogenital system disorders, such as renal fibrosis and renal failure resulting from chronic kidney diseases or insufficiency (e.g. due to accumulation/deposition and tissue injury, progressive sclerosis, glomerunephritis); prostate hypertrophy;

(2) sexual disorders of conditions: erectile dysfunction; female sexual dysfunction (e.g., female sexual arousal dysfunction), vaginal atrophyand incontinence.

In some embodiments of the invention, the compounds of Table I as well as pharmaceutically acceptable salts thereof are also useful in the prevention and/or treatment of the following types of diseases, conditions and disorders which can benefit from sGC stimulation:

In other embodiments of the invention, the compounds of Table I as well as pharmaceutically acceptable salts thereof are useful in the prevention and/or treatment of the following types of diseases, conditions and disorders which can benefit from sGC stimulation: hypertension, resistant hypertension, diabetic hypertension, pulmonary hypertension (PH), pulmonary arterial hypertension, PH associated with COPD, chronic airflow obstruction, asthma or pulmonary fibrosis, thrombosis, embolism, thromboembolic disorders, atherosclerosis, right heart hypertrophy, heart failure, diastolic dysfunction, systolic dysfunction, sleep apnea associated with heart failure, liver cirrhosis, renal fibrosis, renal failure resulting from chronic kidney diseases or insufficiency, metabolic disorder, dyslipidemia, hypercholesterolemia, hypertriglyceridemia, sitosterolemia, fatty liver disease, hepatitis, erectile dysfunction, female sexual dysfunction, female sexual arousal dysfunction and vaginal atrophy.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound of Table I, or a pharmaceutically acceptable salt thereof, to the subject in need of the treatment. Alternatively, the invention provides the use of a compound of Table I, or a pharmaceutically acceptable salt thereof, in the treatment of one of these diseases, conditions and disorders in a subject in need of the treatment. The invention further provides a method of making or manufacturing a medicament useful for treating one of these diseases, conditions and disorders comprising using a compound of Table I, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof blood, saliva, urine, faeces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernable symptoms) of said condition (i.e. "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of an sGC, cGMP and/or NO mediated condition. In other embodiments the terms "treat", "treatment" and "treating" refer to the inhibition of the progression of an sGC, cGMP and/or NO mediated condition, either physically by, e.g., stabilization of a discernable symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g. a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Table I or a pharmaceutically acceptable salt thereof and a second amount of an additional suitable therapeutic agent.

In one embodiment of this invention, a compound of Table I and the additional therapeutic agent are each administered in an effective amount (i.e., each in an amount which would be therapeutically effective if administered alone). In another embodiment, the compound of Table I and the additional therapeutic agent are each administered in an amount which alone does not provide a therapeutic effect (a sub-therapeutic dose). In yet another embodiment, the compound of Table I can be administered in an effective amount, while the additional therapeutic agent is administered in a sub-therapeutic dose. In still another embodiment, the compound of Table I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Table I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Table I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of this disclosure, either administered separately or in the same pharmaceutical composition, include, but are not limited to:

(1) Endothelium-derived releasing factor (EDRF);

(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatrate®-SR, Imdur®, Ismo®, Isordil®, Isordil®, Titradose®, Monoket®), FK 409 (NOR-3); FR 144420 (NOR-4); 3-morpholinosydnonimine; Linsidomine chlorohydrate ("SIN-1"); S-nitroso-N-acetylpenicillamine ("SNAP"); AZD3582 (CI-NOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), S-nitrosoglutathione (GSNO), Sodium Nitroprusside, S-nitrosoglutathione monoethyl-ester (GSNO-ester), 6-(2-hydroxy-1-methyl-nitrosohydrazino)-N-methyl-1-hexanamine (NOC-9) or diethylamine NONOate. Nitric oxide donors are also as disclosed in U.S. Pat. Nos. 5,155,137, 5,366,997, 5,405,919, 5,650,442, 5,700,830, 5,632,981, 6,290,981, 5,691,423 5,721,365, 5,714,511, 6,511,911, and U.S. Pat. No. 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;

(3) Other substances that enhance cGMP concentrations such as protoporphyrin IX, arachidonic acid and phenyl hydrazine derivatives;

(4) Nitric Oxide Synthase substrates: for example, n-hydroxyguanidine based analogs, such as N[G]-hydroxy-L-arginine (NOHA), 1-(3,4-dimethoxy-2-chlorobenzylideneamino)-3-hydroxyguanidine, and PR5 (1-(3,4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluormethyl) propylguanidine; and others reviewed in Cali et al. (2005, Current Topics in Medicinal Chemistry 5:721-736) and disclosed in the references cited therein;

(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g. 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schäfer et al., Journal of Thrombosis and Homeostasis 2005; Volume 3, Supplement 1: abstract number P1487);

(6) NO independent heme-independent sGC activators, including, but not limited to:BAY 58-2667 (see patent publication DE19943635)

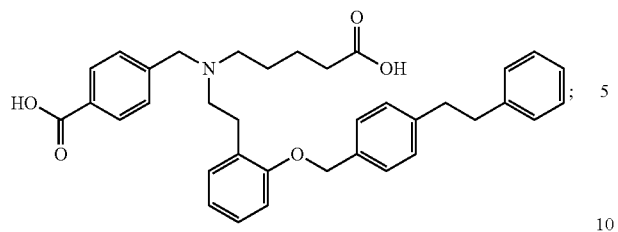

HMR-1766 (ataciguat sodium, see patent publication WO2000002851)

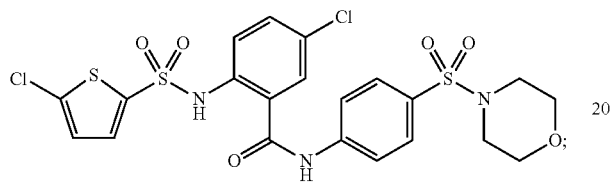

S 3448 (2-(4-chloro-phenylsulfonylamino)-4,5-dimethoxy-N-(4-(thiomorpholine-4-sulfonyl)-phenyl)-benzamide (see patent publications DE19830430 and WO2000002851)

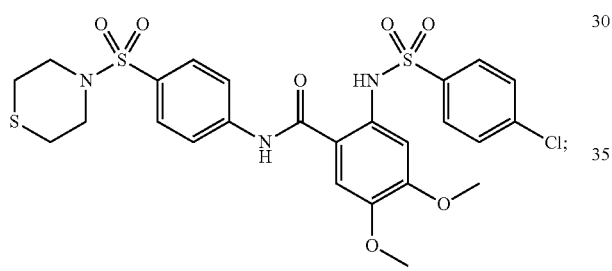

and
HMR-1069 (Sanofi-Aventis).

(7) Heme-dependent sGC stimulators including, but not limited to:

YC-1 (see patent publications EP667345 and DE19744026)

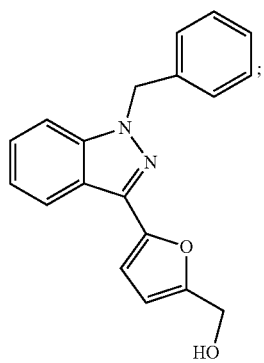

BAY 41-2272 (see patent publications DE19834047 and DE19942809)

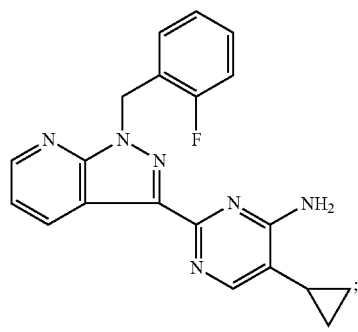

BAY 41-8543 (see patent publication DE19834044)

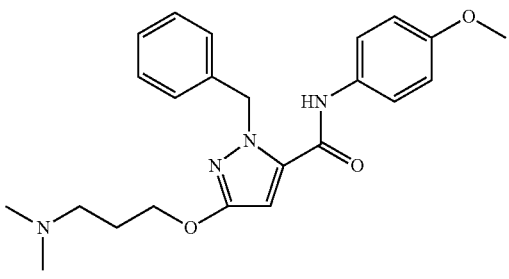

BAY 63-2521 (see patent publication DE19834044)
CFM-1571 (see patent publication WO2000027394)

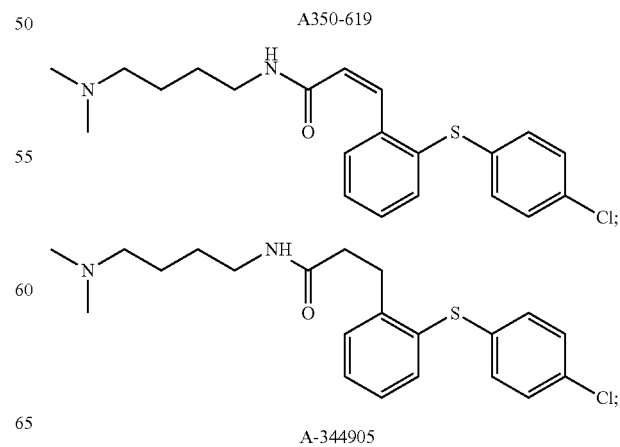

A350-619

A-344905

-continued

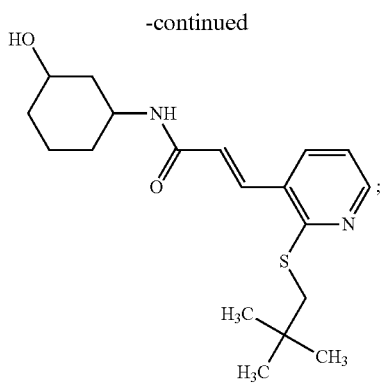

A-778935 and other compounds disclosed in Tetrahedron Letters (2003), 44(48): 8661-8663.

(8) Compounds that inhibit the degradation of cGMP, such as: PDE5 inhibitors, such as, for example, Sildenafil (Viagra®) and other related agents such as Avanafil, Lodenafil, Mirodenafil, Sildenafil citrate (Revatio®), Tadalafil (Cialis® or Adcirca®), Vardenafil (Levitra®) and Udenafil; Alprostadil; and Dipyridamole;

(9) Calcium channel blockers such as:
Dihydropyridine calcium channel blockers: Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Diltiazem, Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas), Isradipine (Lomir);
Phenylalkylamine calcium channel blockers: Verapamil (Calan, Isoptin)

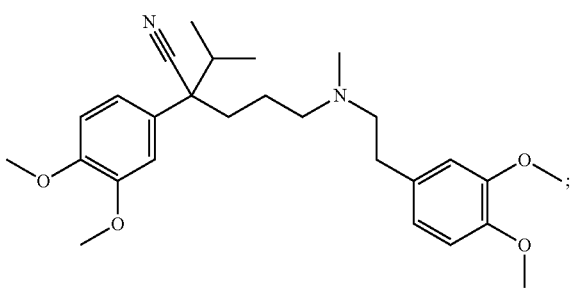

Gallopamil (Procorum, D600);
Benzothiazepines: Diltiazem (Cardizem);

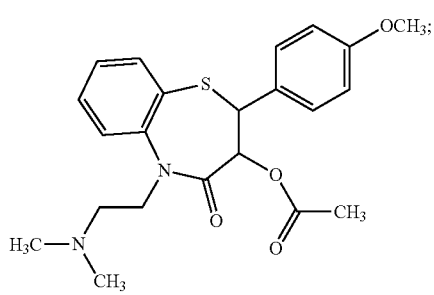

Nonselective calcium channel inhibitors such as: mibefradil, bepridil and fluspirilene, fendiline

(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S; dual/nonselective endothelin antagonist Actelion-1, that entered clinical trials in 2008;

(11) Prostacyclin derivatives or analogues: for instance prostacyclin (prostaglandin $I_2$), Epoprostenol (synthetic prostacyclin, marketed as Flolan®); Treprostinil (Remodulin®), Iloprost (Ilomedin®), Iloprost (marketed as Ventavis®); oral and inhaled forms of Remodulin® that are under development; Beraprost, an oral prostanoid available in Japan and South Korea;

(12) Antihyperlipidemics such as: bile acid sequestrants (e.g., Cholestyramine, Colestipol, Colestilan and Colesevelam); statins such as Atorvastatin, Simvastatin, Lovastatin, Fluvastatin, Pitavastatin, Rosuvastatin and Pravastatin; cholesterol absorption inhibitors such as Ezetimibe; other lipid lowering agents such as Icosapent ethyl ester, Omega-3-acid ethyl esters, Reducol; fabric acid derivatives such as Clofibrate, Bezafibrate, Clinofibrate, Gemfibrozil, Ronifibrate, Binifibrate, Fenofirate, Ciprofibrate, Choline fenofibrate; nicotinic acid derivatives such as Acipimox and Niacin; also combinations of statins, niacin, intestinal cholesterol absorption-inhibiting supplements (ezetimibe and others) and fibrates; antiplatelet therapies such as Clopidogrel bisulfate;

(13) Anticoagulants, such as the following types:
Coumarines (Vitamin K antagonists): Warfarin® (Coumadin) mostly used in the US and UK; Acenocoumarol® and Phenprocoumon®, mainly used in other countries; Phenindione®;
Heparin and derivative substances such as: Heparin; low molecular weight heparin, Fondaparinux and Idraparinux;
Direct thrombin inhibitors such as: Argatroban, Lepirudin, Bivalirudin and Dabigatran; Ximelagatran (Exanta®), not approved in the US;
Tissue plasminogen activators, used to dissolve clots and unblock arteries, such as Alteplase;

(14) Antiplatelet drugs: for instance thienopyridines such as Lopidogrel and Ticlopidine; Dipyridamole; Aspirin;

(15) ACE inhibitors, for example the following types:
Sulfhydryl-containing agents such as Captopril (trade name Capoten®), the first ACE inhibitor and Zofenopril;
Dicarboxylate-containing agents such as Enalapril (Vasotec/Renitec®); Ramipril (Altace/Tritace/Ramace/Ramiwin®); Quinapril (Accupril®), Perindopril (Coversyl/Aceon®); Lisinopril (Lisodur/Lopril/Novatec/Prinivil/Zestril®) and Benazepril (Lotensin®);
Phosphonate-containing agents such as: Fosinopril;
Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;
Other ACE inhibitors such as Alacepril, Delapril, Cilazapril, Imidapril, Trandolapril, Temocapril, Moexipril, Spirapril,

(16) Supplemental oxygen therapy;

(17) Beta blockers, such as the following types:
Non-selective agents: Alprenolol®, Bucindolol®, Carteolol®, Carvedilol® (has additional α-blocking activity), Labetalol® (has additional α-blocking activity), Nadolol®, Penbutolol® (has intrinsic sympathomimetic activity), Pindolol® (has intrinsic sympathomimetic activity), Oxprenonol, Acebutolol, Sotalol, Mepindolol, Celiprolol, Arotinolol, Tertatolol, Amosulalol, Nipradilol, Propranolol® and Timolol®;

β$_1$-Selective agents: Acebutolol® (has intrinsic sympathomimetic activity), Atenolol®, Betaxolol®, Bisoprolol®, Celiprolol®, Dobutamine hydrochloride, Irsogladine maleate, Carvedilol, Talinolol, Esmolol®, Metoprolol® and Nebivolol®;

β$_2$-Selective agents: Butaxamine® (weak α-adrenergic agonist activity);

(18) Antiarrhythmic agents such as the following types:
Type I (sodium channel blockers): Quinidine, Lidocaine, Phenytoin, Propafenone
Type III (potassium channel blockers): Amiodarone, Dofetilide, Sotalol
Type V: Adenosine, Digoxin

(19) Diuretics such as: Thiazide diuretics, e.g., Chlorothiazide, Chlorthalidone, and Hydrochlorothiazide, Bendroflumethiazide, Cyclopenthiazide, Methyclothiazide, Polythiazide, Quinethazone, Xipamide, Metolazone, Indapamide, Cicletanine; Loop diuretics, such as Furosemide and Toresamide; potassium-sparing diuretics such as Amiloride, Spironolactone, Canrenoate potassium, Eplerenone and Triamterene; combinations of these agents; other diuretics such as Acetazolamid and Carperitide (20a) Direct acting vasodilators such as Hydralazine hydrochloride, Diazoxide, Sodium nitroprusside, Cadralazine; other vasodilators such as Isosorbide dinitrate and Isosorbide 5-mononitrate;

(20b) Exogenous vasodilators such as:
Adenocard®, an adenosine agonist, primarily used as an anti-arrhythmic;
Alpha blockers (which block the vasoconstricting effect of adrenaline):
Alpha-1-adrenoceptor antagonists such as Prazosin, Indoramin, Urapidil, Bunazosin, Terazosin, Doxazosin
Atrial natriuretic peptide (ANP);
Ethanol;
Histamine-inducers, which complement proteins C3a, C4a and C5a work by triggering histamine release from mast cells and basophil granulocytes;
Tetrahydrocannabinol (THC), major active chemical in marijuana which has minor vasodilatory effects;
Papaverine, an alkaloid found in the opium poppy *papaver somniferum*;b

(21) Bronchodilators: there are two major types of bronchodilator, β$_2$ agonists and anticholinergics, exemplified below:
β$_2$ agonists: Salbutamol® or albuterol (common brand name: Ventolin) and Terbutaline® are short acting β$_2$ agonists for rapid relief of COPD symptoms. Long acting β$_2$ agonists (LABAs) such as Salmeterol® and Formoterol®;
anticholinergics: Ipratropium® is the most widely prescribed short acting anticholinergic drug. Tiotropium® is the most commonly prescribed long-acting anticholinergic drug in COPD;
Theophylline®, a bronchodilator and phosphodiesterase inhibitor;

(22) Corticosteroids: such as beclomethasone, methylprednisolone, betamethasone, prednisone, prenisolone, triamcinolone, dexamethasone, fluticasone, flunisolide and hydrocortisone, and corticosteroid analogs such as budesonide

(23) Dietary supplements such as, for example: omega-3 oils; folid acid, niacin, zinc, copper, Korean red *ginseng* root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Testosterone transdermal patch; Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;

(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WO0178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

(25) Immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

(26) Non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);

(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

(28) Cyclooxygenase-2 (COX-2) inhibitors such as celecoxib (Celebrex®), rofecoxib (Vioxx®), valdecoxib, etoricoxib, parecoxib and lumiracoxib; (opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and

(29) Anti-diabetic agents such as insulin and insulin mimetics, sulfonylureas (e.g., Glyburide, Glybenclamide, Glipizide, Gliclazide, Gliquidone, Glimepiride, Meglinatide, Tolbutamide, Chlorpropamide, Acetohexamide, Tolazamide), biguanides, e.g., metformin (Glucophage®), α-glucosidase inhibitors (such as Acarbose, Epalrestat, Voglibose, Miglitol), thiazolidinone compounds, e.g., rosiglitazone (Avandia®), troglitazone (Rezulin®), ciglitazone, pioglitazone (Actos®) and englitazone; insulin sensitizers such as Pioglitazone and Rosiglitazone; Insulin secretagogues such as Repaglinide, Nateglinide and Mitiglinide; Incretin mimetics such as Exanatide and Liraglutide; Amylin analogues such as Pramlintide; glucose lowering agents such as Chromiumm picolinate (optinally combined with biotin); dipeptidyl peptidase IV inhibitors such as Sitagliptin, Vildagliptin, Saxagliptin, Alogliptin and Linagliptin; vaccines currently being developed for the treatment of diabetes; AVE-0277, Alum-GAD, BHT-3021, IBC-VS01; cytokine targeted therapies in development for the treatment of diabetes such as Anakinra, Canakinumab, Diacerein, Gevokizumab, LY-2189102, MABP-1, GIT-027; drugs in development for the treatment of diabetes:

| Drugs in development for the treatment of diabetes | | | |
|---|---|---|---|
| Drug Name | Organization | Mechanism of Action | Status |
| Dapagliflozin | AstraZeneca/Bristol-Myers Squibb | SGLT-2 Inhibitors | Recommended Approval |
| Alogliptin benzoate/metformin hydrochloride | Takeda | Insulin Sensitizers/Dipeptidyl Peptidase IV (CD26; DPP-IV; DP-IV) Inhibitors | Pre-Registered |
| Anagliptin | Kowa/Sanwa | Dipeptidyl Peptidase IV (CD26; DPP-IV; DP-IV) Inhibitors | Pre-Registered |
| Insulin degludec | Novo Nordisk | | Pre-Registered |
| Insulin degludec/insulin aspart | Novo Nordisk | | Pre-Registered |
| Insulin human (rDNA origin) inhalation powder | MannKind | | Pre-Registered |
| Lixisenatide | Sanofi | Insulin Secretagogues/GLP-1 Receptor Agonists | Pre-Registered |
| Recombinant human insulin | Biodel | | Pre-Registered |
| Teneligliptin | Mitsubishi Tanabe Pharma | Dipeptidyl Peptidase IV (CD26; DPP-IV; DP-IV) Inhibitors | Pre-Registered |
| AVE-0277 | Andromeda Biotech/Teva | | Phase III |
| Albiglutide | GlaxoSmithKline | GLP-1 Receptor Agonists | Phase III |
| Aleglitazar | Roche | PPARalpha Agonists/PPARgamma Agonists | Phase III |
| Atorvastatin calcium/glimepiride | GlaxoSmithKline | K(ATP) Channel Blockers/Dipeptidyl Peptidase IV (CD26; DPP-IV; DP-IV) Inhibitors/HMG-CoA Reductase Inhibitors/TNFSF6 Expression Inhibitors | Phase III |
| BYK-324677 | Nycomed | | Phase III |
| Balaglitazone | Dr. Reddy's Laboratories | Insulin Sensitizers/PPARgamma Partial Agonists | Phase III |
| CSG-452 | Chugai Pharmaceutical | SGLT-2 Inhibitors | Phase III |
| Canagliflozin | Johnson & Johnson/Mitsubishi Tanabe Pharma | SGLT-2 Inhibitors | Phase III |
| Canagliflozin/metformin hydrochloride | Johnson & Johnson | SGLT-2 Inhibitors/Insulin Sensitizers | Phase III |
| Dapagliflozin/Metformin hydrochloride | AstraZeneca/Bristol-Myers Squibb | SGLT-2 Inhibitors/Insulin Sensitizers | Phase III |
| Dulaglutide | Lilly | Insulin Secretagogues/GLP-1 Receptor Agonists | Phase III |
| Empagliflozin | Boehringer Ingelheim/Lilly | SGLT-2 Inhibitors | Phase III |
| Empagliflozin/linagliptin | Boehringer Ingelheim/Lilly | SGLT-2 Inhibitors/Dipeptidyl Peptidase IV (CD26; DPP-IV; DP-IV) Inhibitors | Phase III |
| Gemigliptin | LG Life Sciences | Dipeptidyl Peptidase IV (CD26; DPP-IV; DP-IV) Inhibitors | Phase III |
| Hepatic-directed vesicle insulin | Diasome Pharmaceuticals | | Phase III |
| Human isophane insulin | Wockhardt | | Phase III |
| IN-105 | Biocon | | Phase III |

Drugs in development for the treatment of diabetes

| Drug Name | Organization | Mechanism of Action | Status |
|---|---|---|---|
| Insulin degludec/liraglutide | Novo Nordisk | Insulin Secretagogues/GLP-1 Receptor Agonists | Phase III |
| Insulin glargine | Sanofi | | Phase III |
| Ipragliflozin L-proline | Astellas Pharma/ Kotobuki | SGLT-2 Inhibitors | Phase III |
| LY-2605541 | Lilly | | Phase III |
| LY-2963016 | Lilly | | Phase III |
| Lixisenatide/Insulin glargine | Sanofi | Insulin Secretagogues/GLP-1 Receptor Agonists | Phase III |
| Lobeglitazone sulfate | Chong Kun Dang Pharm (CKD Pharm) | PPARalpha Agonists/ PPARgamma Agonists/Insulin Sensitizers | Phase III |
| Luseogliflozin | Taisho | SGLT-2 Inhibitors | Phase III |
| Otelixizumab | Tolerx | Anti-CD3 | Phase III |
| Ranolazine | Gilead | Sodium Channel Blockers | Phase III |
| Recombinant human insulin | National Institute of Health Sciences | | Phase III |
| Sitagliptin phosphate monohydrate/pioglitazone hydrochloride | Merck & Co. | PPARgamma Agonists/Insulin Sensitizers/ Dipeptidyl Peptidase IV (CD26; DPP-IV; DP-IV) Inhibitors | Phase III |
| Sitagliptin/atorvastatin calcium | Merck & Co. | Dipeptidyl Peptidase IV (CD26; DPP-IV; DP-IV) Inhibitors/ HMG-CoA Reductase Inhibitors/TNFSF6 Expression Inhibitors | Phase III |
| TAK-875 | Takeda | Free Fatty Acid Receptor 1 (FFAR1; GPR40) Agonists/ Insulin Secretagogues | Phase III |
| TT-401 | 7TM Pharma | Cannabinoid CB1 Antagonists | Phase I |
| TT-401 | Transition Therapeutics | | Phase I |
| ZYH-2 | Cadila Healthcare (d/b/a Zydus Cadila) | PPARalpha Ligands/ PPARgamma Ligands | Phase I |
| ZYO-1 | Cadila Healthcare (d/b/a Zydus Cadila) | Cannabinoid CB1 Antagonists | Phase I |
| 701645 | Cellonis Biotechnologies | | Phase I |
| 701499 | Cellonis Biotechnologies | | Phase I |
| 743300 | University of California, San Francisco | | Phase I |
| 448661 | University of Pittsburgh | | Phase I |
| AD-1 | National Institute Pharma Res Dev | | Clinical |
| Colesevelam hydrochloride | Daiichi Sankyo | Bile Acid Sequestrants | Clinical |
| DBPR-108 | National Health Research Institutes/ ScinoPharm | | IND Filed |
| Nodlin | Biolaxy | | IND Filed |
| PSN-491 | Prosidion | Glucose-Dependent Insulinotropic Receptor (GDIR, GPR119) Agonists/ Dipeptidyl Peptidase IV (CD26; DPP-IV; DP-IV) Inhibitors | IND Filed |
| Tolimidone | Melior Discovery | Lyn Kinase Activators | IND Filed |
| ZYD-1 | Cadila Healthcare (d/b/a Zydus Cadila) | GLP-1 Receptor Agonists | IND Filed |

| Drug Name | Organization | Mechanism of Action | Status |
|---|---|---|---|
| ZYOG-1 | Cadila Healthcare (d/b/a Zydus Cadila) | GLP-1 Receptor Agonists | IND Filed |

Drugs in development for the treatment of diabetes

(30) HDL cholesterol-increasing agents such as Anacetrapib, MK-524A, CER-001, DRL-17822, Dalcetrapib, JTT-302, RVX-000222, TA-8995;

(31) Antiobesity drugs such as Methamphetamine hydrochloride, Amfepramone hydrochloride (Tenuate®), Phentermine (Ionamin®), Benzfetamine hydrochloride (Didrex®), Phendimetrazine tartrate (Bontril®, Prelu-2 ®, Plegine®), Mazindol (Sanorex®), Orlistat (Xenical®), Sibutramine hydrochloride monohydrate (Meridia®, Reductil®), Rimonabant (Acomplia®), Amfepramone, Chromium picolinate, RM-493, TZP-301; combination such as Phentermine/Topiramate, Bupropion/Naltrexone, Sibutramine/Metformin, Bupropion SR/Zonisamide SR, Salmeterol, xinafoate/fluticasone propionate; Lorcaserin hydrochloride, Phentermine/topiramate, Bupropion/naltrexone, Cetilistat, Exenatide, KI-0803, Liraglutide, Metformin hydrochloride, Sibutramine/Metformin, 876167, ALS-L-1023, Bupropion SR/Zonisamide SR, CORT-108297, Canagliflozin, Chromium picolinate, GSK-1521498, LY-377604, Metreleptin, Obinepitide, P-57AS3, PSN-821, Salmeterol xinafoate/fluticasone propionate, Sodium tungstate, Somatropin (recombinant), TM-30339, TTP-435, Tesamorelin, Tesofensine, Velneperit, Zonisamide, BMS-830216, ALB-127158, AP-1030, ATHX-105, AZD-2820, AZD-8329, Beloranib hemioxalate, CP-404, HPP-404, ISIS-FGFR4Rx, Insulinotropin, KD-3010PF, 05212389, PP-1420, PSN-842, Peptide YY3-36, Resveratrol, S-234462; S-234462, Sobetirome, TM-38837, Tetrahydrocannabivarin, ZYO-1, beta-Lapachone;

(32) Angiotensin receptor blockers such as Losartan, Valsartan, Candesartan cilexetil, Eprosaran, Irbesartan, Telmisartan, Olmesartran medoxomil, Azilsartan medoxomil;

(33) Renin inhibitors such as Aliskiren hemifumirate;

(34) Centrally acting alpha-2-adrenoceptor agonists such as Methyldopa, Clonidine, Guanfacine;

(35) Adrenergic neuron blockers such as Guanethidine, Guanadrel;

(36) Imidazoline I-1 receptor agonists such as Rimenidine dihydrogen phosphate and Moxonidine hydrochloride hydrate;

(37) Aldosterone antagonists such as Spironolactone and Eplerenone

(38) Potassium channel activators such as Pinacidil

(39) Dopamine D1 agonists such as Fenoldopam mesilate; Other dopamine agonists such as Ibopamine, Dopexamine and Docarpamine;

(40) 5-HT2 antagonists such as Ketanserin;

(41) Drugs that are currently being developed for the treatment of arterial hypertension:

| Drug Name | Organization | Mechanism of Action | Status |
|---|---|---|---|
| Azilsartan | Takeda | Angiotensin AT1 Antagonists/ Angiotensin AT2 Antagonists/ Insulin Sensitizers | Registered |
| Amlodipine besylate/irbesartan | Dainippon Sumitomo Pharma | Angiotensin AT1 Antagonists/ Calcium Channel Blockers | Pre-Registered |
| Azilsartan/amlodipine besilate | Takeda | Angiotensin AT1 Antagonists/ Insulin Sensitizers/ Calcium Channel Blockers | Phase III |
| Clinidipine/valsartan | Ajinomoto/Mochida | Angiotensin AT1 Antagonists/ Calcium Channel Blockers | Phase III |
| Fimasartan | Boryung | Angiotensin AT1 Antagonists | Phase III |
| Irbesartan/atorvastatin | Hanmi | Angiotensin AT1 Antagonists/ Dipeptidyl Peptidase IV (CD26; DPP-IV; DP-IV) Inhibitors/HMG-CoA Reductase Inhibitors/ TNFSF6 Expression Inhibitors | Phase III |

| Drug Name | Organization | Mechanism of Action | Status |
|---|---|---|---|
| Irbesartan/trichlormethiazide | Shionogi | Angiotensin AT1 Antagonists | Phase III |
| Losartan potassium/hydrochlorothiazide/amlodipine besylate | Merck & Co. | Angiotensin AT1 Antagonists/ Calcium Channel Blockers | Phase III |
| Pratosartan | Boryung | Angiotensin AT1 Antagonists | Phase III |
| ACT-28078 | Actelion | | Phase II |
| Amiloride hydrochloride/spironolactone | Hemodynamic Therapeutics | Mineralocorticoid Receptor (MR) Antagonists/ Na+/H+ Exchanger (NHE) Inhibitors/ Epithelial Sodium Channels (ENaC) Blockers/ K(V)1.5 Channel Blockers/ K(V)4.3 Channel Blockers | Phase II |
| Angiotensin vaccine/CoVaccine HT | BTG | | Phase II |
| CYT006-AngQb | Cytos Biotechnology | Anti-Angiotensin II | Phase II |
| Cholecalciferol | Emory University | | Phase II |
| Cobiprostone | Sucampo Pharmaceuticals | ClC-2 Channel Activators | Phase II |
| INT-001 | IntelGenx | | Phase II |
| LCZ-696 | Novartis | Angiotensin AT1 Antagonists/ Neprilysin (Enkephalinase, Neutral Endopeptidase, NEP) Inhibitors | Phase II |
| LFF-269 | Novartis | | Phase II |
| Octreotide acetate | Chiasma | Growth Hormone Release Inhibitors/ Somatostatin Agonists | Phase II |
| PL-3994 | Palatin Technologies | Atrial Natriuretic Peptide A (NPR1; Guanylate Cyclase A) Receptor Agonists | Phase II |
| Rostafuroxine | Sigma-Tau | | Phase II |
| SLx-2101 | NT Life Sciences | Phosphodiesterase V (PDE5A) Inhibitors | Phase II |
| TBC-3711 | Encysive Pharmaceuticals | Endothelin ETA Receptor Antagonists | Phase II |
| Udenafil | Dong-A/Falk Pharma | Phosphodiesterase V (PDE5A) Inhibitors | Phase II |
| Atorvastatin calciuum/losartan potassium | HanAll BioPharma | Angiotensin AT1 Antagonists/ Dipeptidyl Peptidase IV (CD26; DPP-IV; DP-IV) Inhibitors/HMG-CoA Reductase Inhibitors/ TNFSF6 Expression Inhibitors | Phase I |
| BIA-5-1058 | BIAL | Dopamine beta-monooxygenase Inhibitors | Phase I |
| CS-3150 | Daiichi Sankyo | | Phase I |
| DSP-9599 | Dainippon Sumitomo Pharma | Renin Inhibitors | Phase I |

-continued

| Drug Name | Organization | Mechanism of Action | Status |
|---|---|---|---|
| MK-1597 | Actelion/Merck & Co. | Renin Inhibitors | Phase I |
| MK-4618 | Merck & Co. | | Phase I |
| MK-5478 | Merck & Co. | | Phase I |
| MK-7145 | Merck & Co. | | Phase I |
| MK-8266 | Merck & Co. | | Phase I |
| MK-8457 | Merck & Co. | | Phase I |
| MP-157 | Mitsubishi Tanabe Pharma | Angiotensin AT2 Agonists | Phase I |
| MT-3995 | Mitsubishi Tanabe Pharma | Mineralocorticoid Receptor (MR) Antagonists | Phase I |
| Mirodenafil hydrochloride | SK Chemicals | Phosphodiesterase V (PDE5A) Inhibitors | Phase I |
| NV-04 | Novogen | Antioxidants | Phase I |
| Nifedipine/Candesartan cilexetil | Bayer | Angiotensin AT1 Antagonists/ Calcium Channel Blockers/ Antioxidants | Phase I |
| QGC-001 | Quantum Genomics | Glutamyl Aminopeptidase (Aminopeptidase A) Inhibitors | Phase I |
| RDX-5791 | Ardelyx | Na+/H+ Exchanger type 3 (NHE-3) Inhibitors | Phase I |
| TAK-272 | Takeda | Renin Inhibitors | Phase I |
| TAK-591 | Takeda | Angiotensin AT2 Antagonists | Phase I |
| VTP-27999 | Vitae Pharmaceuticals | Renin Inhibitors | Phase I |
| Vasomera | PhaseBio | VPAC2 (VIP2) Agonists | Phase I |
| Tylerdipine hydrochloride | Sihuan Pharmaceutical | Calcium Channel Blockers | IND Filed |

(42) Vasopressin antagonists such as Tolvaptan;
(43) Calcium channel sensitizers such as Levosimendan or activators such as Nicorandil;
(44) PDE-3 inhibitors such as Amrinone, Milrinone, Enoximone, Vesnarinone, Pimobendan, Olprinone;
(45) Adenylate cyclase activators such as Colforsin dapropate hydrochloride;
(46) Positive inotropic agents such as Digoxin and Metildigoxin; metabolic cardiotonic agents such as Ubidecarenone; brain naturetic peptides such as Nesiritide;

(47) Drugs that are currently in development for the treatment of heart failure:

| Drugs in development for the treatment of heart failure | | | |
|---|---|---|---|
| Drug Name | Organization | Mechanism of Action | Status |
| Bucindolol hydrochloride | ARCA | beta-Adrenoceptor Antagonists | Pre-Registered |
| Aliskiren hemifumarate | Novartis | Renin Inhibitors | Phase III |
| Ferric carboxymaltose | Vifor | | Phase III |
| LCZ-696 | Novartis | Angiotensin AT1 Antagonists/Neprilysin (Enkephalinase, Neutral Endopeptidase, NEP) Inhibitors | Phase III |
| Neuregulin-1 | Zensun | | Phase III |
| Olmesartan medoxomil | Tohoku University | Angiotensin AT1 Antagonists | Phase III |
| C3BS-CQR-1 | Cardio3 BioSciences | | Phase II/III |
| MyoCell | Bioheart | | Phase II/III |
| Serelaxin | Novartis | | Phase II/III |
| AAV1/SERCA2a | AmpliPhi Biosciences/ Celladon/Mount Sinai School of Medicine | | Phase II |
| Albiglutide | GlaxoSmithKline | GLP-1 Receptor Agonists | Phase II |

| Drugs in development for the treatment of heart failure | | | |
|---|---|---|---|
| Drug Name | Organization | Mechanism of Action | Status |
| Allogeneic mesenchymal precursor cells | Mesoblast | | Phase II |
| AlsterMACS | Miltenyi Biotec | | Phase II |
| BAY-94-8862 | Bayer | Mineralocorticoid Receptor (MR) Antagonists | Phase II |
| COR-1 | Corimmun | | Phase II |
| CXL-1020 | Cardioxyl Pharmaceuticals | Nitric Oxide Donors | Phase II |
| Cenderitide | Nile Therapeutics | Guanylate Cyclase Activators | Phase II |
| Endometrial regenerative cells | ERCell/Medistem | | Phase II |
| JNJ-39588146 | Johnson & Johnson | | Phase II |
| Omecamtiv mecarbil | Amgen/Cytokinetics | Cardiac Myosin Activators | Phase II |
| PL-3994 | Palatin Technologies | Atrial Natriuretic Peptide A (NPR1; Guanylate Cyclase A) Receptor Agonists | Phase II |
| Remestemcel-L | Osiris | | Phase II |
| TRV-120027 | Trevena | Angiotensin AT1 Receptor Ligands | Phase II |
| Urocortin 2 | Neurocrine Biosciences | CRF2 Agonists | Phase II |
| AAV6-CMV-SERCA2a | Imperial College | | Phase I/II |
| Anakinra | National Institutes of Health (NIH) | IL-1 Receptor Antagonists | Phase I/II |
| LipiCell | Bioheart/Instituto de Medicina Regenerativa | | Phase I/II |
| ALD-201 | Cytomedix/Texas Heart Institute | | Phase I |
| BAY-1021189 | Bayer | | Phase I |
| BAY-1067197 | Bayer | Adenine Receptor Agonists | Phase I |
| BAY-86-8050 | Bayer | Drugs Acting on Vasopressin (AVP) Receptors | Phase I |
| BIA-5-1058 | BIAL | Dopamine beta-monooxygenase Inhibitors | Phase I |
| CSCs | University of Louisville | | Phase I |
| Calcitonin gene related peptide | VasoGenix | | Phase I |
| JVS-100 | Juventas Therapeutics | | Phase I |
| MyoCell SDF-1 | Bioheart | | Phase I |
| Myoblast | Advanced Cell Technology (ACT) | | Phase I |
| RO-1160367 | Serodus | 5-HT4 Antagonists | Phase I |
| Recombinant human glial growth factor 2 | Acorda/Vanderbilt University | | Phase I |
| [18F]LMI-1195 | Lantheus Medical Imaging | | Phase I |
| 677950 | Kyoto Prefectural University of Medicine | | Phase I |

(48) Drugs currently in development for the treatment of pulmonary hypertension:

Drugs in development for the treatment of pulmonary hypertension

| Drug Name | Organization | Mechanism of Action | Status |
|---|---|---|---|
| Imatinib mesylate | Novartis | Breast Cancer-Resistant Protein (BCRP; ABCG2) Inhibitors/Abl Kinase Inhibitors/Angiogenesis Inhibitors/Bcr-Abl Kinase Inhibitors/CSF1R (c-FMS) Inhibitors/KIT (C-KIT) Inhibitors/Apoptosis Inducers/PDGFRalpha Inhibitors/PDGFRbeta Inhibitors/Inhibitors of Signal Transduction Pathways | Pre-Registered |
| Treprostinil diethanolamine | United Therapeutics | Prostacyclin Analogs | Pre-Registered |
| GSK-1325760A | GlaxoSmithKline | | Phase III |
| Macitentan | Actelion | Endothelin ETA Receptor Antagonists/Endothelin ETB Receptor Antagonists | Phase III |
| Riociguat | Bayer | Guanylate Cyclase Activators | Phase III |
| Selexipag | Actelion/Nippon Shinyaku | Prostanoid IP Agonists | Phase III |
| Udenafil | Dong-A | Phosphodiesterase V (PDE5A) Inhibitors | Phase III |
| L-Citrulline | Nat Heart, Lung, and Blood Institute/Vanderbilt University | | Phase II/III |
| BQ-123 | Brigham & Women's Hospital | Endothelin ETA Receptor Antagonists | Phase II |
| Cicletanine | Gilead | | Phase II |
| Fasudil hydrochloride | Asahi Kasei | Rho Kinase Inhibitors/Calcium Sensitizers | Phase II |
| Nilotinib hydrochloride monohydrate | Novartis | Bcr-Abl Kinase Inhibitors/Apoptosis Inducers/Inhibitors of Signal Transduction Pathways | Phase II |
| PRX-08066 | Clinical Data | 5-HT2B Antagonists | Phase II |
| Terguride | ErgoNex Pharma | 5-HT2A Antagonists/5-HT2B Antagonists/Dopamine Autoreceptor Agonists/Dopamine D2 Receptor Partial Agonists/Prolactin Secretion Inhibitors | Phase II |
| Tezosentan disodium | Actelion | Endothelin ETA Receptor Antagonists/Endothelin ETB Receptor Antagonists | Phase II |
| Anakinra | Virginia Commonwealth University (VCU) | IL-1 Receptor Antagonists | Phase I/II |
| Simvastatin | Imperial College | HDL-Cholesterol Increasing Agents/HMG-CoA Reductase Inhibitors | Phase I/II |
| 99mTC-PulmoBind | Montreal Heart Institute (MHI) | | Phase I |
| APD-811 | Arena | Prostanoid IP Agonists | Phase I |
| Sorafenib | Bayer | Raf kinase B Inhibitors/Raf kinase C Inhibitors/Angiogenesis Inhibitors/Flt3 (FLK2/STK1) Inhibitors/VEGFR-1 (Flt-1) Inhibitors/KIT (C-KIT) Inhibitors/VEGFR-2 (FLK-1/KDR) Inhibitors/VEGFR-3 (FLT4) Inhibitors/PDGFRbeta Inhibitors/RET Inhibitors/Inhibitors of Signal Transduction Pathways | Phase I |
| Triplelastat | Proteo Biotech | Elastase Inhibitors | Phase I |
| 2586881 | Apeiron Biologics | | Preclinical |
| C-122 | Corridor Pharmaceuticals | Caspase 3 Activators/Dopamine D1 Antagonists/5-HT2B Antagonists/5-HT7 Antagonists/Caspase 8 Activators/Dopamine D2 Antagonists/Dopamine D3 Antagonists/Histamine H1 Receptor Antagonists/Caspase 9 Activators/Apoptosis Inducers | Preclinical |
| PLX-I | United Therapeutics | Angiogenesis Inducers | Preclinical |

(49) Drugs in current development for the treatment of female sexual dysfunction:

Drugs in active development for the treatment of female sexual dysfunction

| Drug Name | Organization | Mechanism of Action | Status |
|---|---|---|---|
| Alprostadil | Apricus Biosciences/VIVUS | | Phase III |
| Prasterone | EndoCeutics/Monash University | HSD11B1 Expression Inhibitors | Phase III |
| Testosterone transdermal gel | BioSante | Androgen Receptor Agonists | Phase III |
| Bremelanotide | Palatin Technologies | Melanocortin MC3 Receptor Agonists/Melanocortin MC4 Receptor Agonists | Phase II |
| Pill-Plus | Pantarhei Bioscience | | Phase II |
| Testosterone MDTS | Acrux | Androgen Receptor Agonists | Phase II |
| Estradiol/testosterone | BioSante | Estrogen Receptor (ER) Agonists/Androgen Receptor Agonists | Phase I |
| LGD-2941 | Ligand | Selective Androgen Receptor Modulators (SARM) | Phase I |
| Lidocaine/heparin | Urigen | | Phase I |
| OnabotulinumtoxinA | Allergan | | Phase I |
| S1P-104 | S1 Biopharma | | IND Filed |
| PL-6983 | Palatin Technologies | | Preclinical |
| S1P-401 | S1 Biopharma | | Preclinical |

(50) Drugs used for the treatment of erectile dysfunction such as Alprostadil, Aviptadil, Phentolamine mesilate, Weige, Alprostadil;

(51) Drugs currently in development for the treatment of male sexual dysfunction:

Drugs in active development for the treatment of erectile dysfunction

| Drug Name | Organization | Mechanism of Action | Status |
|---|---|---|---|
| Fluvastatin sodium | Novartis | Apoptosis Inducers/HMG-CoA Reductase Inhibitors | Phase III |
| Lodenafil carbonate | Cristalia | Phosphodiesterase V (PDE5A) Inhibitors | Phase III |
| EFLA-400 | Chonbuk National University Hospital | | Phase II/III |
| Apomorphine hydrochloride | Vectura | Dopamine D2 Agonists | Phase II |
| LY-900010 | Lilly | Phosphodiesterase V (PDE5A) Inhibitors/Selective Androgen Receptor Modulators (SARM) | Phase II |
| Nitroglycerin | Futura Medical | | Phase II |
| RX-10100 | Rexahn | Drugs Acting on Dopaminergic Transmission/Drugs Acting on Serotonergic Transmission | Phase II |
| YHD-1023 | Yuhan | | Phase II |
| INT-007 | IntelGenx | | Phase I |
| LY-2452473 | Lilly | Selective Androgen Receptor Modulators (SARM) | Phase I |
| hMaxi-K | Albert Einstein College of Medicine/Ion Channel Innovations/Mount Sinai School of Medicine | | Phase I |
| KH-204 | KMSI | | Clinical |
| CKD-533 | Chong Kun Dang Pharm (CKD Pharm) | Phosphodiesterase V (PDE5A) Inhibitors | Preclinical |
| MP-52 | Biopharm | | Preclinical |
| TGHW01AP | Fabre-Kramer | Dopamine D1 Agonists/Dopamine D2 Agonists | Preclinical |

(51) Drugs in development for the treatment of sleep apnea:

Drugs in development for the treatment of sleep apnea

| Drug Name | Organization | Mechanism of Action | Status |
|---|---|---|---|
| CX-1739 | Cortex | AMPA Receptor Modulators | Phase II |
| Phentermine/topiramate | VIVUS | AMPA Antagonists/Kainate Antagonists/Sodium Channel Blockers/Carbonic Anhydrase Type II Inhibitors | Phase II |
| AVE-0118 | Sanofi | Potassium Channel Blockers | Phase I |
| Suvorexant | Merck & Co. | Orexin Receptor Antagonists | Phase I |
| COL-132 | Collegium Pharmaceutical | | Clinical |

(52) Drugs currently in development for the treatment of metabolic syndrome:

Antiobesity drugs under active development for the treatment of patients with metabolic syndrome

| Drug Name | Organization | Mechanism of Action | Status |
|---|---|---|---|
| Chromium picolinate | University of Pennsylvania | | Phase II |
| RM-493 | Ipsen | Melanocortin MC4 Receptor Agonists | Preclinical |
| TZP-301 | Tranzyme | GHS Receptor Antagonists | Preclinical |

Antihyperlipidemic drugs under active development for the treatment of patients with metabolic syndrome

| Drug Name | Organization | Mechanism of Action | Status |
|---|---|---|---|
| GFT-505 | Genfit | PPARalpha Agonists/ PPARdelta Agonists | Phase II |
| MBX-8025 | Metabolex | PPARdelta Agonists | Phase II |
| Pitavastatin calcium | Kowa | APOA1 Expression Enhancers/ HMG-CoA Reductase Inhibitors/ SPP1 (Osteopontin) Expression Inhibitors | Phase I |
| CDX-085 | Cardax Pharmaceuticals | Antioxidants | Preclinical |

(53) Antiobesity drugs:

Drugs marketed for the treatment of obesity

| Drug Name | Organization | Mechanism of Action | Year and country of first launch |
|---|---|---|---|
| Methamphetamine hydrochloride (Desoxyn) | Abbott | Noradrenergic, alpha- and beta- adrenoceptor agonist | 1943 (U.S.) |
| Amfepramone hydrochloride (Tenuate) | Sanofi | Noradrenergic release stimulant | 1959 (U.S.) |
| Phentermine (Ionamin) | UCB Celltech | Noradrenergic release stimulant | 1959 (U.S.) |
| Benzfetamine hydrochloride (Didrex) | Pfizer | Noradrenergic release stimulant | 1960 (U.S.) |
| Phendimetrazine tartrate (Bontril, Prelu-2, Plegine) | Pfizer | Noradrenergic release stimulant | 1961 (U.S.) |
| Mazindol (Sanorex) | Novartis | Noradrenergic reuptake inhibitor | 1973 (U.S.) |
| Orlistat (Xenical) | Roche | Pancreatic lipase inhibitor | 1998 (New Zealand) |
| Sibutramine hydrochloride monohydrate (Meridia, Reductil) | Abbott | Norepinephrine and 5-HT reuptake inhibitor | 1998 (U.S.) (withdrawn 2010) |
| Rimonabant (Acomplia) | Sanofi | Cannabinoid CB1 antagonist | 2006 (U.K.) (withdrawn 2008) |

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, 2$^{nd}$ Ed., Washington, D.C.: American Chemical Society, 1997, herein incorporated in its entirety by reference.

Example 1

Syntheses of the Compounds of Table I

General Procedure A-I (Most General Version)

General Procedure A-I

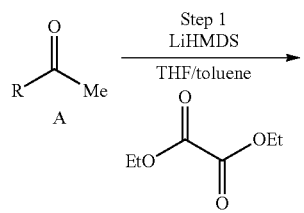

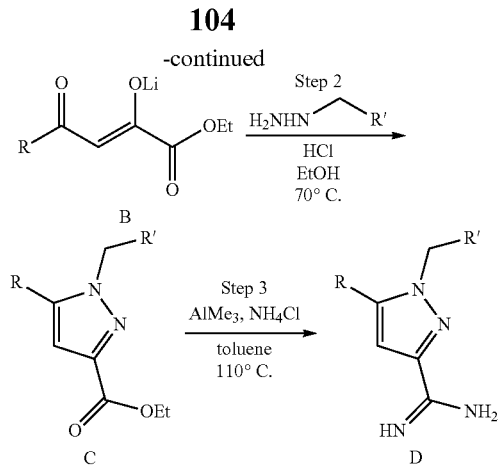

Step 1: Dione Enolate Formation:

To a solution of ketone A in THF cooled to −78° C., LiHMDS (e.g., 0.9 eq, 1.0 M in toluene) is added dropwise, for example using a syringe. The reaction mixture is then allowed to warm to about 0° C., then charged with diethyl oxalate (1.2 eq). At this time, the reaction mixture is warmed to room temperature and stirred at that temperature until judged complete (e.g., using either TLC or LC/MS analysis). Once the reaction is complete (reaction time typically about 45 minutes), the product dione enolate B is used as-is in Step 2, i.e., the cyclization step, without any further purification.

Step 2: Pyrazole Formation:

Dione enolate B is diluted with ethanol and consecutively charged with HCl (e.g., 3 eq, 1.25M solution in ethanol) and arylhydrazine hydrate (e.g., 1.15 eq). The reaction mixture is heated to about 70° C. and stirred at this temperature until cyclization is deemed complete (e.g., by LC/MS analysis, typically about 30 minutes). Once complete, the reaction mixture is treated carefully with solid sodium bicarbonate (e.g., 4 eq) and diluted with dichloromethane and water. The organic layer is separated, and the aqueous layer is further diluted with water before extraction with dichloromethane (3 times). The combined organics are washed with brine, dried over MgSO$_4$, filtered, and concentrated in vacuo. The resulting pyrazole C is then purified by SiO$_2$ chromatography using an appropriate gradient of EtOAc/hexanes.

Step 3: Amidine Formation:

To a suspension of NH$_4$Cl (e.g., 5 eq) in toluene cooled to about 0° C. is added AlMe$_3$ (e.g., 5 eq, 2.0M solution in toluene) dropwise, e.g., via a syringe. The reaction mixture is allowed to warm to room temperature, and stirred until no more bubbling is observed. Pyrazole C is added in 1 portion to the reaction mixture, heated to about 110° C., and stirred at this temperature until judged complete (e.g., using either TLC or LC/MS analysis). Once complete, the reaction mixture is cooled, treated with excess methanol, and stirred vigorously for about 1 hour at room temperature. The thick slurry is filtered, and the resulting solid cake is washed with methanol. The filtrate is concentrated in vacuo, and the resulting solids are re-suspended in an ethyl acetate:isopropyl alcohol, 5:1 v:v, solvent mixture. The reaction mixture is further treated with a saturated sodium carbonate solution, and stirred for about 10 minutes before the layers are separated. The aqueous layer is extracted with the ethyl acetate:isopropyl alcohol, 5:1 v:v, solvent mixture (3×), and the combined organics are washed with brine. The organics are further dried over MgSO4, filtered, and the solvent is removed in vacuo. The product amidine D is used as-is in subsequent steps without further purification.

Intermediate-5 (5G wherein R, R'=F)

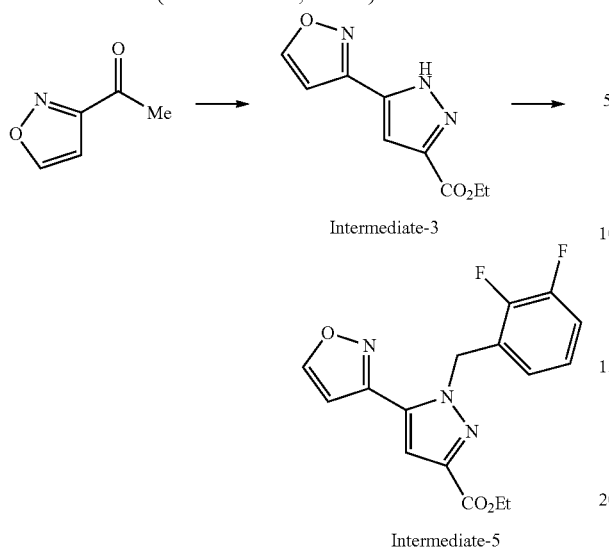

Intermediate-3

Intermediate-5

To a −78° C. solution of 1-(isoxazol-3-yl)ethanone (2.18 g, 19.62 mmol) in tetrahydrofuran (58 mL) was added lithium hexamethyldisilazide (1 M in toluene, 18 mL, 18 mmol) dropwise over the course of 20 minutes. The solution was warmed to 0° C. and stirred for 30 minutes, at which point diethyl oxalate (2.9 mL, 21.6 mmol) was added over the course of 5 minutes. The solution was warmed to room temperature and stirred for 45 minutes. Ethanol (58 mL), hydrazine hydrate (0.88 mL, 18 mmol), and acetic acid (5.8 mL) were sequentially added. The heterogeneous solution was heated to 70° C. After stirring for 2.25 hours at this temperature, the solvent was removed under vacuum. Water (300 mL) and dichloromethane (300 mL) were added, the layers were separated, and the aqueous layer was extracted with dichloromethane (5×150 mL). The organics were combined, dried over magnesium sulfate, filtered, and the solvent was removed under vacuum. Purification by silica gel chromatography (0-15% methanol in dichloromethane) and re-purification (ethyl acetate in dichloromethane) gave impure product. The resulting solid was triturated with diethyl ether to give Intermediate-3 (2.21 g, 59%) as a white solid.

To a 0° C. solution of Intermediate-3 (1.0 g, 4.8 mmol) in tetrahydrofuran (48 mL) was added sodium hydride (60% in mineral oil, 0.21 g, 5.3 mmol) in two portions. After stirring for 20 minutes at 0° C., 1-(bromomethyl)-2,3-difluorobenzene (0.92 ml, 7.2 mmol) was added in a single portion. The solution was immediately warmed to room temperature and maintained at that temperature for 18 hours. Saturated aqueous sodium bicarbonate (200 mL) and ethyl acetate (200 mL) were added, the layers were separated, and the aqueous layer was extracted with ethyl acetate (2×150 mL). The organics were combined, washed with saturated aqueous sodium chloride (200 mL), dried over magnesium sulfate, filtered, and the solvent removed under vacuum. Purification of the resulting crude residue by silica gel chromatography (0-40% ethyl acetate in hexanes) provided a first eluting isomer and Intermediate-5 (second eluting isomer) (889 mg, 55% yield) as white solids.

Intermediate-5:
$^1$H NMR (400 MHz, CDCl3) δ 8.46 (d, 1H), 7.18 (s, 1H), 7.04 (q, 1H), 6.94-6.89 (m, 1H), 6.59-6.55 (m, 2H), 5.97 (s, 2H), 4.42 (q, 2H), 1.40 (t, 3H).

Intermediate-5B

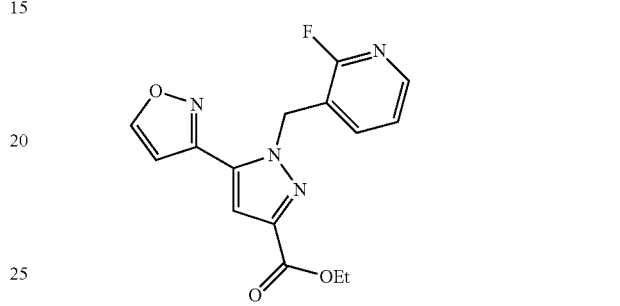

Intermediate-5B

To a −78° C. solution of 1-(isoxazol-3-yl)ethanone (155 mg, 1.40 mmol) in tetrahydrofuran (14 mL) was added lithium hexamethyldisilazide (1 M in toluene, 1.33 mL, 1.33 mmol) in a dropwise manner over the course of 5 minutes. The solution was immediately warmed to 0° C. for 30 minutes at which point diethyl oxalate (227 µL, 1.67 mmol) was added in a dropwise manner over the course of 5 minutes. After stirring for 10 min at 0° C., the solution was warmed to room temperature for 1 hour. Ethanol (14 mL) and 3-fluoro-4-(hydrazinylmethyl)pyridine trifluoroacetic acid (463 mg, 1.81 mmol) were added and the solution was heated to 40° C. until LCMS indicated consumption of intermediate dione. The solvent was removed in vacuo. Water (20 mL) and dichloromethane (20 mL) were added to the resulting residue. The layers were separated and the aqueous layer was extracted with dichloromethane (3×30 mL). The organics were washed with brine (10 mL), dried over magnesium sulfate, filtered, and the solvent was removed in vacuo. The crude residue was purified via silica gel chromatography (0-80% hexanes in ethyl acetate) to give Intermediate-5B (227 mg, 51% yield) as a white solid.

Intermediate-5B:
$^1$H-NMR (400 MHz, CDCl$_3$) δ 8.49 (d, 1H), 8.11 (d, 1H), 7.19-7.25 (m, 2H), 7.03-7.10 (m, 1H), 6.59 (d, 1H), 5.95 (s, 2H), 4.45 (q, 2H), 1.42 (t, 3H).

Intermediate 8C

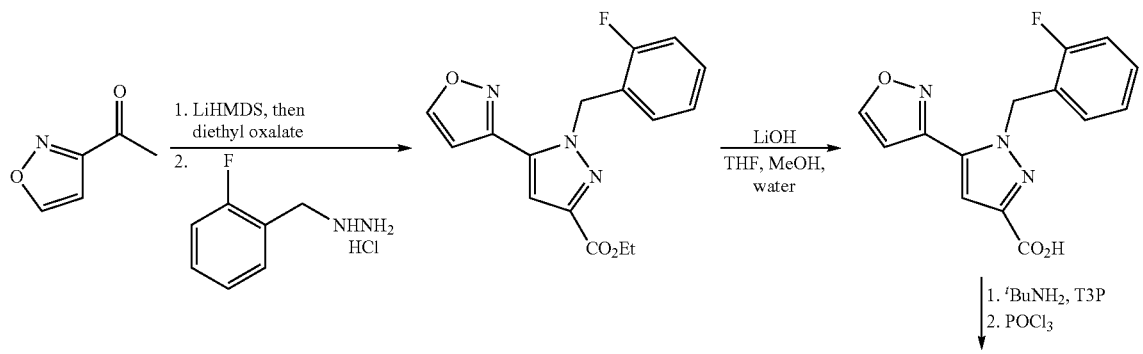

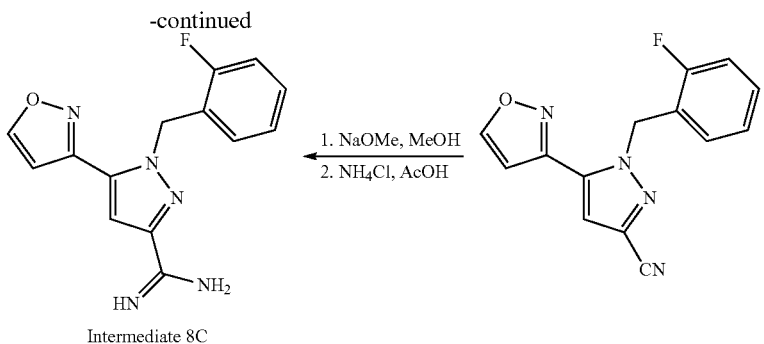

Intermediate 8C

Step 1: Pyrazole Formation:

To a cooled (−73° C.) solution of 1-(isoxazol-3-yl)ethanone (44.0 g, 356 mmol) in THF (1100 ml) was added LiHMDS (1M in toluene, 346 mL, drop-wise addition over 60 min). The reaction mixture was warmed to 0° C., the vessel was placed in an ice bath, and diethyl oxalate (58 mL, 428 mmol) was added. The bath was removed and reaction was stirred for 45 min. At this juncture, the reaction vessel was placed back in the ice bath and the reaction mixture was consecutively charged with (2-fluorobenzyl)hydrazine hydrochloride (79.0 g, 447 mmol, dissolved in 800 mL absolute EtOH) and acetic acid (110 mL). The ice bath was removed and the reaction was stirred overnight at rt, then at 60° C. for 3 h. The reaction was then cooled to 0° C., and then filtered through Celite. The filtrate was then concentrated and the crude material was purified via silica gel chromatography employing a hexane/ethyl acetate gradient (95:5-3:2) to afford the desired material (31.9 g, 28.4%).

Step 2: Hydrolysis:

The ester from above was dissolved in a 3:1 mixture of THF/MeOH (280 mL) then charged with an aqueous solution of LiOH hydrate (6.35 g in 70 mL water). After 30 minutes at rt, the volatiles were removed in vacuo. The crude material was diluted with 230 mL water and acidified to pH 2 via the addition of 70 mL 3N HCl. The resulting suspension was stirred for 2 h, filtered, then dried to give 27.2 g (94%) of the desired acid, which was used without further purification.

Step 3: Nitrite Formation:

To a slurry of the carboxylic acid (27.1 g, 94 mmol) in 300 mL EtOAc was added triethylamine (26.3 mL, 189 mmol) and $^t$BuNH$_2$ (drop-wise addition over 10 min). The reaction mixture was cooled to −15° C. then charged with T3P (50% wt in EtOAc, 167 mL). The ice bath was removed and the reaction was stirred for 30 min. At this time, an additional 2 mL $^t$BuNH$_2$ was added along with 5 mL triethylamine and 15 mL T3P solution. After 60 minutes of additional stirring, the volatiles were removed and the resulting paste was charged with 70 mL POCl$_3$ (755 mmol) and heated to 70° C. for 1 h. At this time, the mixture was slowly poured into ice water. The mixture was stirred for 30 min at rt, then filtered. The filter cake was washed with water (4×100 mL) then dried to yield 24.0 g (95%) of the desired nitrile, which was used without any further purification.

Step 4: Amidine Formation:

To a stirred, cooled (0° C.) mixture of the nitrile (24.0 g, 89 mmol) in methanol (300 mL) was added sodium methoxide (25% wt solution in MeOH, 20.46 mL). Once addition was complete, the ice bath was removed and the reaction mixture was heated to 60° C. for 4 h, at which time ammonium chloride (23.9 g, 447 mmol) and acetic acid (6.2 mL, 107 mmol) were added. The reaction was stirred at rt overnight. At this juncture, diethyl ether (700 mL) was added and the resulting precipitate was filtered, washed with additional diethyl ether (2×200 mL), and air dried. The filter cake was suspended in 100 mL water and charged with 200 mL saturated, aqueous sodium carbonate solution (1.2 equiv of base, based on ammonium chloride). The mixture was stirred for 1 h, and then filtered. The solid was washed with water (3×100 mL) and hexane (2×100 m), then dried to afford the desired amidine as a white solid (19.9 g, 78%).

Intermediate-8C:

$^1$H NMR (400 MHz, CD$_3$OD) δ 8.83 (d, 1H), 7.47 (s, 1H), 7.32-7.27 (m, 1H), 7.11-7.04 (m, 2H), 6.96 (ddd, 1H), 6.84 (d, 1H), 5.96 (s, 2H) ppm.

Compound 30

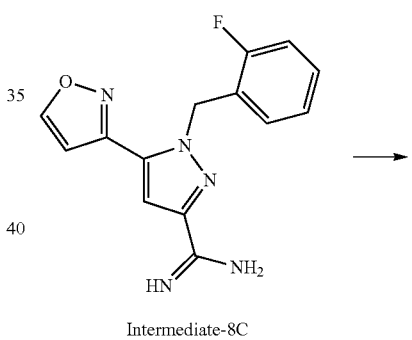

Intermediate-8C

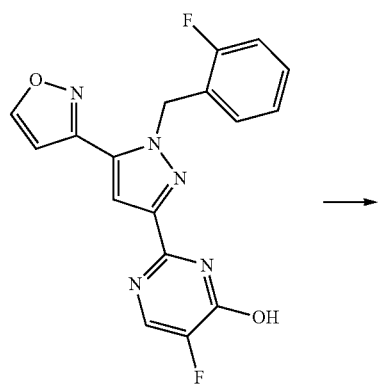

Intermediate-13

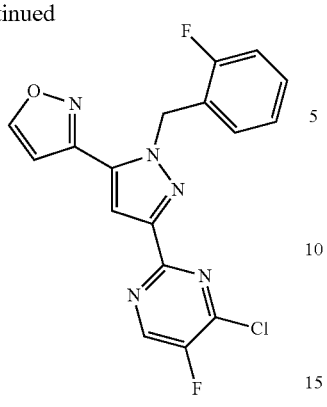

Compound 30

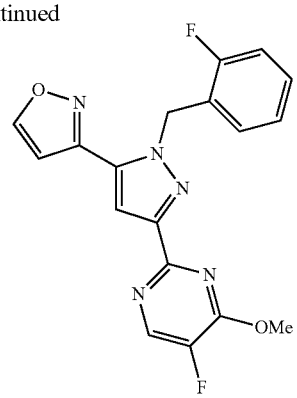

Compound-28

A solution of Intermediate 8C (1 equiv) and ethyl 3-(dimethylamino)-2-fluoroacrylate (3 equiv) was stirred at 85° C. in ethanol for 14 h. The solvent was removed in vacuo and purification by silica gel chromatography (0-50% 7:1 acetonitrile:methanol in dicloromathane) delivered the desired compound as a white solid (47.6%).
Intermediate 13:
$^1$H NMR (400 MHz, DMSO-d6) 13.28 (bs, 1H), 9.12 (d, 1H), 8.16 (bs, 1H), 7.65 (s, 1H), 7.37-7.32 (m, 1H), 7.25-7.20 (m, 2H), 7.12 (t, 1H), 7.02-6.96 (m, 1H), 5.92 (s, 2H) ppm.

5-fluoro-2-(1-(2-fluorobenzyl)-5-(isoxazol-3-yl)-1H-pyrazol-3-yl)pyrimidin-4-ol (Intermediate 13, 0.050 g, 0.141 mmol) was charged with phosphorus oxychloride (1.0 ml, 10.73 mmol) and the resulting mixture was stirred at 45° C. until the reaction was judged complete by LC/MS. Once complete, the reaction was diluted with 25 mL dichloromethane and carefully quenched with water. The two phases were separated, and the aqueous portion was then washed with an additional 25 mL dichloromethane. The organic portions were combined, dried with sodium sulfate, filtered, and then concentrated. Purification from the crude oil was carried out using silica gel chromatography employing a 0-75% ethyl acetate in hexane gradient and afforded the desired product as a white solid in 86% yield.
$^1$H NMR (400 MHz, CDCl$_3$) δ 8.65 (s, 1H), 8.47 (d, 1H), 7.43 (s, 1H), 7.23-7.17 (m, 1H), 7.03 (ddd, 1H), 6.97 (ddd, 1H), 6.85 (ddd, 1H), 6.60 (d, 1H), 6.02 (s, 2H) ppm.
Compound 28

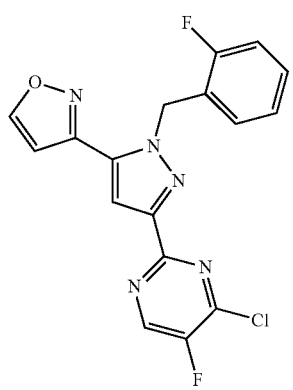

Compound-30

To a solution of 3-(3-(4-chloro-5-fluoropyrimidin-2-yl)-1-(2fluorobenzyl)-1H-pyrazol-5-yl)isoxazole (Compound 30, 0.040 g, 0.107 mmol) in 1 mL methanol was added sodium methoxide (0.024 ml, 0.107 mmol) as a 25% weight solution. The reaction was stirred at 40° C. until judged complete by LC/MS. Once complete, the reaction mixture was directly concentrated in vacuo, and the resulting crude oil was purified using silica gel chromatography employing a 0-100% ethyl acetate in hexane gradient to afford the desired compound as a white solid in 55% yield.
$^1$H NMR (400 MHz, CDCl$_3$) δ 8.46 (d, 1H), 8.41 (d, 1H), 7.36 (s, 1H), 7.23-7.17 (m, 1H), 7.03 (ddd, 1H), 6.86 (ddd, 1H), 6.60 (d, 1H), 5.98 (s, 2H), 4.20 (s, 3H) ppm.
Compound 56

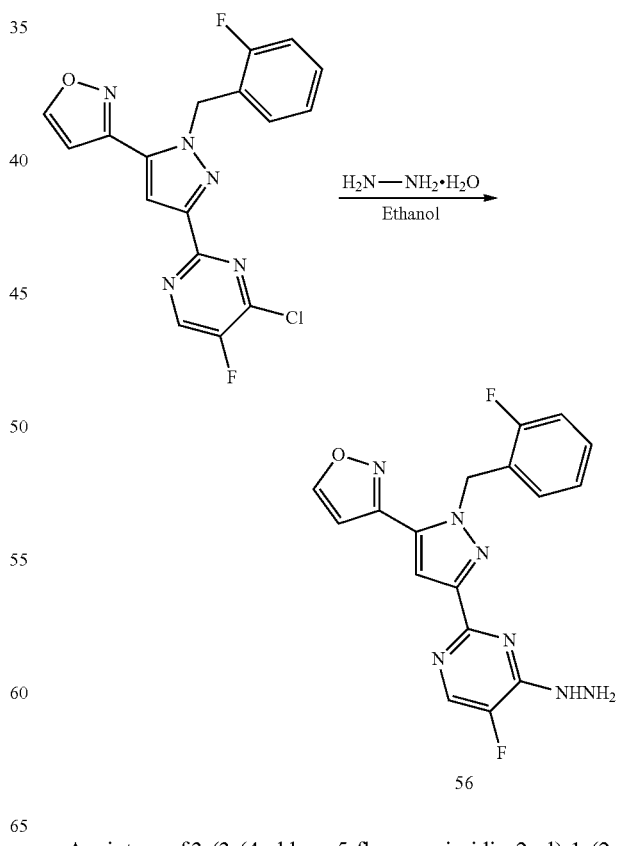

56

A mixture of 3-(3-(4-chloro-5-fluoropyrimidin-2-yl)-1-(2-fluorobenzyl)-1H-pyrazol-5-yl)isoxazole (Compound 30, 1 equiv) and hydrazine hydrate (2 equiv) in ethanol (1.9 ml) was stirred at 50° C. for 24 h. The mixture was cooled to 25° C. and the precipitate was collected by filtration to give Compound 56 as a white solid (79% yield).

Compound 56:

¹H NMR (400 MHz, DMSO-d₆) δ 9.10 (d, 1H) 9.00 (s, 1H) 8.14 (d, 1H) 7.63 (s, 1H) 7.33 (q, 1H) 7.19-7.26 (m, 2H) 7.11 (t, 1H) 6.81 (t, 1H) 5.90 (s, 2H) 4.57 (br. s., 2H).

Compound 85

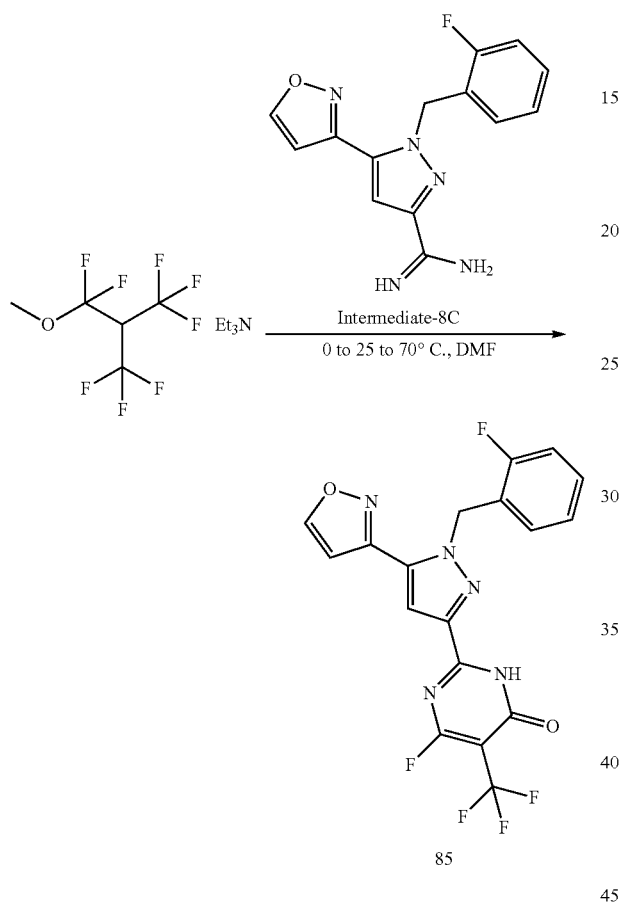

To a cold solution of 2-(difluoro(methoxy)methyl)-1,1,1,3,3,3-hexafluoropropane (81 mg, 1 equiv.) in DMF (876 µl) at 0° C., was added, slowly, trimethylamine (98 µl, 2 equiv.). The mixture was stirred at 0° C. for 1 h. To this mixture, was added a solution of 1-(2-fluorobenzyl)-5-(isoxazol-3-yl)-1H-pyrazole-3-carboximidamide (Intermediate 8C, 100 mg, 1 equiv.) in DMF (876 µl). The mixture was stirred at room temperature for 1 h and heated to 70° C. for an additional 1 h. The mixture was cooled to room temperature. It was diluted in ethyl acetate (100 ml) and washed with water (50 ml×3). The organic layer was dried, filtered and evaporated to give solid. The resulting solid was dissolved in methanol and absorbed onto silica gel. Purification by column chromatography (0 to 100% ethyl acetate in hexanes) gave 6-fluoro-2-(1-(2-fluorobenzyl)-5-(isoxazol-3-yl)-1H-pyrazol-3-yl)-5-(trifluoromethyl)pyrimidin-4(3H)-one (35 mg, 24% yield) as a yellow solid.

Compound 85:

¹H NMR (400 MHz, chloroform-d) δ ppm 5.88 (br s, 2H) 6.57 (s, 1H) 7.00 (br s, 3H) 7.21 (br s, 1H) 7.37 (s, 1H) 8.49 (s, 1H).

Intermediate-0

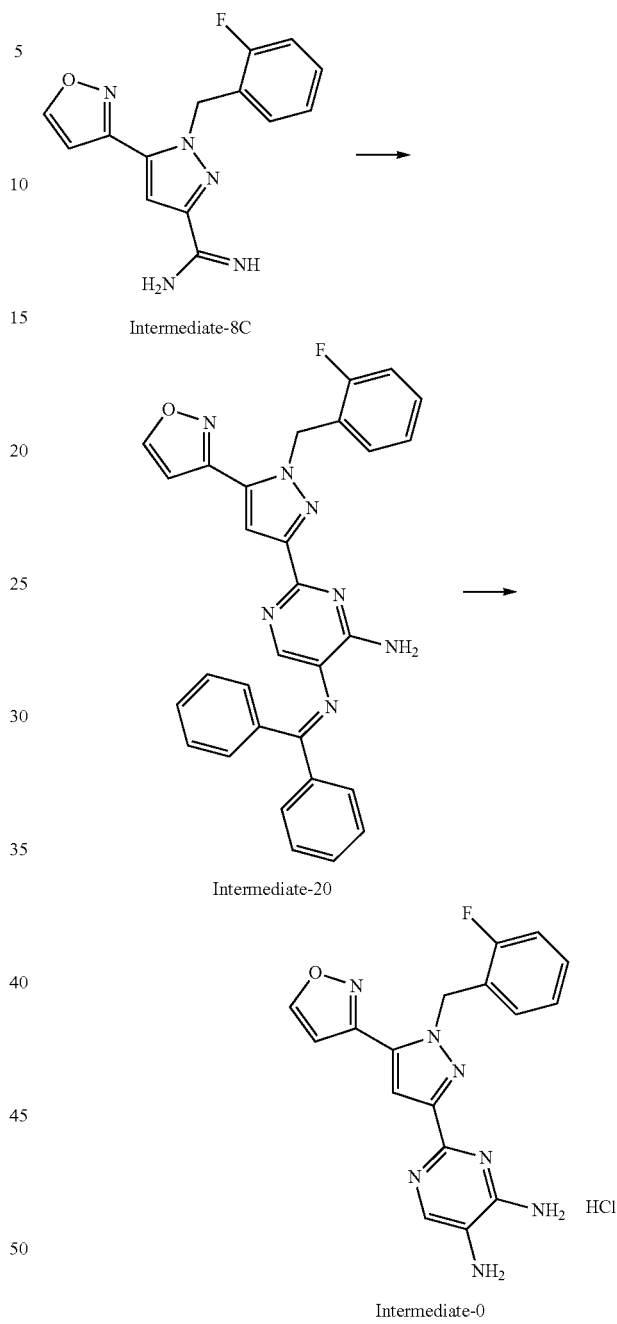

Intermediate-20 was synthesized as an orange glassy solid (15% yield over 4 steps) following General Procedure A followed by a reaction analogous to the one used for the preparation of Intermediate-9, using the corresponding mono fluorinated hydrazine. The cyclization reaction (from Intermediate 8C to Intermediate 20) was conducted in pyridine with two equivalents of 1,8-diazabicyclo[5.4.0]undec-7-ene.

Intermediate 20:

¹H NMR (400 MHz, CDCl₃) δ 8.39 (d, 1H), 7.79-7.76 (m, 2H), 7.53-7.49 (m, 1H), 7.44-7.40 (m, 2H), 7.37-7.31 (m, 5H), 7.19-7.12 (m, 3H), 7.01-6.96 (m, 1H), 6.94-6.90 (m, 1H), 6.77-6.73 (m, 1H), 6.53 (d, 1H), 5.98 (s, 2H), 5.53 (br s, 2H).

To a solution of N5-(diphenylmethylene)-2-(1-(2-fluorobenzyl)-5-(isoxazol-3-yl)-1H-pyrazol-3-yl)pyrimidine-4,5-diamine (Intermediate-20) (0.263 g, 0.510 mmol) in tetrahydrofuran (5.0 mL) was added aqueous 3N hydrochloric acid (1.0 ml, 3.00 mmol). After stirring for 20 minutes, the solvent was evaporated and the residual material was washed with a 5:1 mixture of diethyl ether and hexane to provide Intermediate-0 as a light brown solid (187 mg, 0.485 mmol, 95% yield).

Intermediate-0:
$^1$H NMR (400 MHz, CD$_3$OD) δ 8.82 (s, 1H), 7.46 (s, 2H), 7.32-7.27 (m, 1H), 7.13-7.06 (m, 2H), 6.98-6.94 (m, 1H), 6.90 (s, 1H), 5.98 (s, 2H).

Compound 9

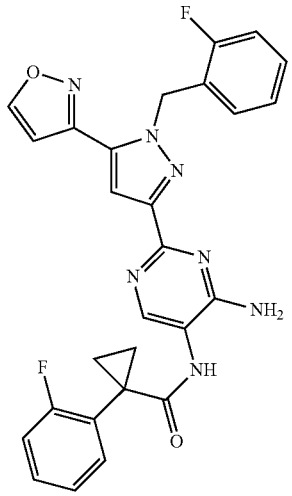 [SMILES: Nc1nc(-c2cc(-c3ccon3)n(Cc3ccccc3F)n2)ncc1NC(=O)C1(c2ccccc2F)CC1]

To a solution of 1-(2-fluorophenyl)cyclopropanecarboxylic acid (12 equiv) in dichloromethane was added oxalyl chloride (11 equiv), followed by catalytic N,N-dimethylformamide. Once gas evolution ceased, this crude reaction mixture was added portion-wise to a suspension of Intermediate-0 (1 equiv) in dichloromethane/pyridine (1:1) and the mixture stirred until complete consumption of starting material was observed by LS/MS. After an aqueous ammonium chloride and dichloromethane workup, column chromatography on silica (10-100% ethyl acetate in hexanes) provided the desired product as an off-white solid (63%).

Compound 9:
$^1$H NMR (400 MHz, CD$_3$OD) δ 8.74 (d, 1H), 7.96 (s, 1H), 7.55-7.50 (m, 1H), 7.42-7.36 (m, 2H), 7.26-7.14 (m, 3H), 7.09-7.04 (m, 1H), 7.00 (ddd, 1H), 6.85 (d, 1H), 6.80 (ddd, 1H), 5.93 (s, 2H), 1.68 (dd, 2H), 1.21 (dd, 2H) ppm.

Compound 11

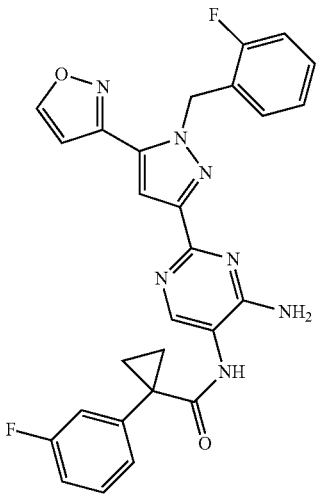 [SMILES: Nc1nc(-c2cc(-c3ccon3)n(Cc3ccccc3F)n2)ncc1NC(=O)C1(c2cccc(F)c2)CC1]

To a solution of 1-(3-fluorophenyl)cyclopropanecarboxylic acid (12 equiv) in dichloromethane was added oxalyl chloride (11 equiv), followed by catalytic N,N-dimethylformamide. Once gas evolution ceased, this crude reaction mixture was added portion-wise to a suspension of Intermediate-0 (1 equiv) in dichloromethane/pyridine (1:1) and the mixture stirred until complete consumption of starting material was observed by LS/MS. After an aqueous ammonium chloride and dichloromethane workup, column chromatography (10-100% ethyl acetate in hexanes) provided the desired product as an off-white solid (31%).

Compound 11:
$^1$H NMR (400 MHz, CD$_3$OD) δ 8.74 (d, 1H), 7.99 (s, 1H), 7.42-7.32 (m, 4H), 7.28-7.22 (m, 1H), 7.09-6.98 (m, 3H), 6.85 (d, 1H), 6.83-6.78 (m, 1H), 5.93 (s, 2H), 1.63 (dd, 2H), 1.21 (dd, 2H) ppm.

Compound 12

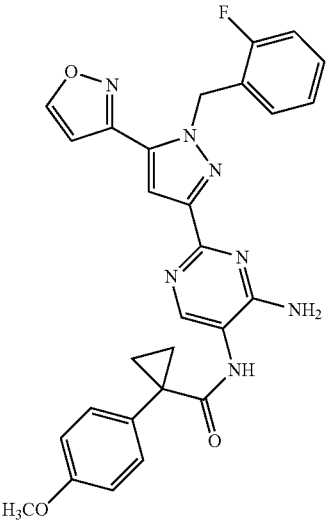 [SMILES: COc1ccc(C2(C(=O)Nc3cnc(-c4cc(-c5ccon5)n(Cc5ccccc5F)n4)nc3N)CC2)cc1]

To a solution of 1-(4-methoxyphenyl)cyclopropanecarboxylic acid (12 equiv) in dichloromethane was added oxalyl chloride (11 equiv), followed by catalytic N,N-dimethylformamide. Once gas evolution ceased, this crude reaction mixture was added portion-wise to a suspension of Intermediate-0 in dichloromethane/pyridine (1:1) until complete consumption of starting material was observed by LS/MS. After an aqueous ammonium chloride and dichloromethane workup, column chromatography (0-40% 7:1 acetonitrile/methanol in dichloromethane) provided the desired product as an off-white solid (58%).

Compound 12:
$^1$H NMR (400 MHz, CD$_3$OD) δ 8.66 (d, 1H), 7.91 (s, 1H), 7.40 (d, 2H), 7.32 (s, 1H), 7.19-7.12 (m, 1H), 7.00-6.96 (m, 1H), 6.94-6.90 (m, 1H), 6.87 (d, 1H), 6.82 (d, 1H), 6.77 (d, 1H), 6.76-6.71 (m, 1H), 5.85 (s, 2H), 3.71 (s, 3H), 1.51 (dd, 2H), 1.07 (dd, 2H) ppm.

Compound 13

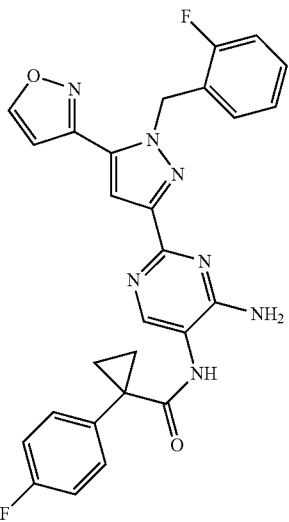 [SMILES: Nc1nc(-c2cc(-c3ccon3)n(Cc3ccccc3F)n2)ncc1NC(=O)C1(c2ccc(F)cc2)CC1]

To a solution of 1-(4-fluorophenyl)cyclopropanecarboxylic acid (12 equiv) in dichloromethane was added oxalyl chloride (11 equiv) and catalytic N,N-dimethylformamide. Once gas evolution ceased, this crude reaction mixture was added portion-wise to a suspension of Intermediate-0 (1 equiv) in dichloromethane/pyridine (1:1) until complete consumption of starting material was observed by LS/MS. After an aqueous ammonium chloride and dichloromethane workup, column chromatography (10-100% ethyl acetate in hexanes) provided the desired product as tan solid (60%).

Compound 13:
$^1$H NMR (400 MHz, CD$_3$OD) δ 8.74 (d, 1H), 7.97 (s, 1H), 7.59 (dd, 2H), 7.39 (s, 1H), 7.27-7.21 (m, 1H), 7.12 (t, 2H), 7.06 (ddd, 1H), 7.00 (ddd, 1H), 6.84 (d, 1H), 6.82-6.78 (m, 1H), 5.92 (s, 2H), 1.63 (dd, 2H), 1.17 (dd, 2H) ppm.

Compound 2

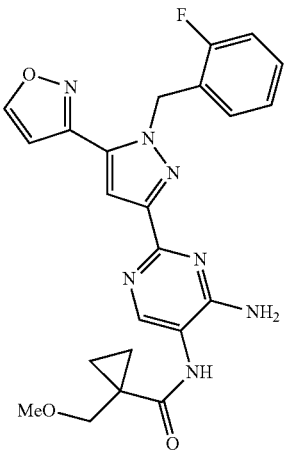

To a solution of 1-(methoxymethyl)cyclopropanecarboxylic acid (10 equiv) in dichloromethane was added oxalyl chloride (9 equiv) and catalytic N,N-dimethylformamide. Once gas evolution ceased, this crude reaction mixture was added portion-wise to a suspension of Intermediate-0 (1 equiv) in dichloromethane/pyridine (1:1) until complete consumption of starting material was observed by LS/MS. After an aqueous ammonium chloride and dichloromethane workup, column chromatography (0-40% 7:1 acetonitrile/methanol in dichloromethane) provided the desired product as an off-white solid (57%).

Compound 2:
$^1$H NMR (400 MHz, CD$_3$OD) δ 8.74 (d, 1H), 8.14 (s, 1H), 7.41 (s, 1H), 7.28-7.22 (m, 1H), 7.07 (ddd, 1H), 7.02 (ddd, 1H), 6.86 (d, 1H), 6.84-6.80 (m, 1H), 5.94 (s, 2H), 3.64 (s, 2H), 3.45 (s, 3H), 1.28 (dd, 2H), 0.89 (dd, 2H) ppm.

Compound 27

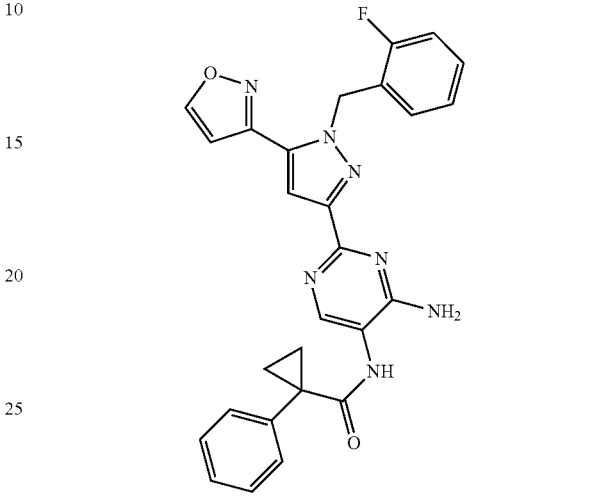

To a solution of 1-phenylcyclopropanecarboxylic acid (12 equiv) in dichloromethane was added oxalyl chloride (10.6 equiv) and catalytic N,N-dimethylformamide. Once gas evolution ceased, this crude reaction mixture was added portion-wise to a suspension of 2-(1-(2-fluorobenzyl)-5-(isoxazol-3-yl)-1H-pyrazol-3-yl)pyrimidine-4,5-diamine hydrochloride Intermediate-0 (1 equiv) in dichloromethane/pyridine (2:1) until complete consumption of starting material was observed by LS/MS. After an aqueous ammonium chloride and dichloromethane workup, column chromatography (30-90% ethyl acetate in hexanes) provided the desired compound as a tan solid (68%).

Compound 27:
$^1$H NMR (400 MHz, MeOD) δ 8.73 (s, 1H), 7.99 (s, 1H), 7.57-7.55 (m, 2H), 7.41-7.37 (m, 3H), 7.33-7.30 (m, 1H), 7.25-7.20 (m, 1H), 7.07-7.03 (m, 1H), 6.99 (t, 1H), 6.83-6.77 (m, 2H), 5.91 (s, 2H), 1.63-1.60 (m, 2H), 1.20-1.17 (m, 2H).

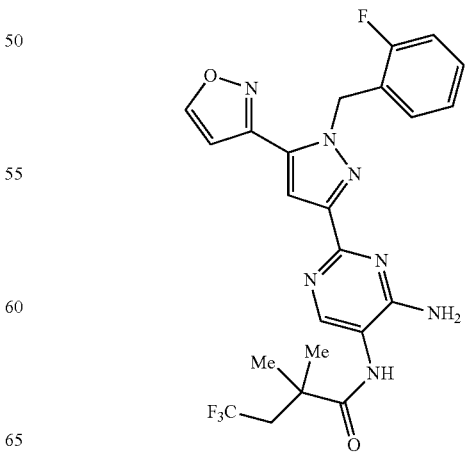

Compound 53

To a solution of 4,4,4-trifluoro-2,2-dimethylbutanoic acid (20 equiv) in dichloromethane was added oxalyl chloride (18 equiv) and catalytic N,N-dimethylformamide. Once gas evolution ceased, this crude reaction mixture was added portionwise to a suspension of 2-(1-(2-fluorobenzyl)-5-(isoxazol-3-yl)-1H-pyrazol-3-yl)pyrimidine-4,5-diamine hydrochloride Intermediate-0 (1 equiv) in dichloromethane/pyridine (2:1) until complete consumption of starting material was observed by LS/MS. After an aqueous ammonium chloride and dichloromethane workup, column chromatography (60-100% ethyl acetate in hexanes) provided the desired compound as a tan solid (66%).

Compound 53:
$^1$H NMR (400 MHz, MeOD) δ 8.75 (d, 1H), 8.08 (s, 1H), 7.43 (s, 1H), 7.28-7.23 (m, 1H), 7.11-7.01 (m, 2H), 6.86-6.82 (m, 2H), 5.95 (s, 2H), 2.65 (q, 2H), 1.46 (s, 6H).

Compound 35

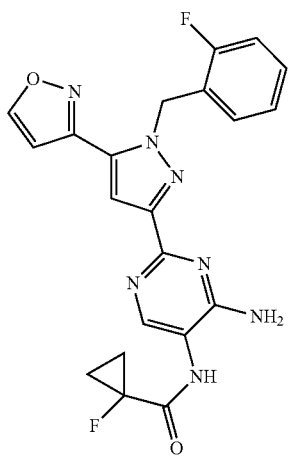

To a solution of 1-fluorocyclopropanecarboxylic acid (18 equiv) in dichloromethane was added oxalyl chloride (16 equiv) and catalytic N,N-dimethylformamide. Once gas evolution ceased, this crude reaction mixture was added portionwise to a suspension of 2-(1-(2-fluorobenzyl)-5-(isoxazol-3-yl)-1H-pyrazol-3-yl)pyrimidine-4,5-diamine hydrochloride Intermediate-0 (1 equiv) in dichloromethane/pyridine (2:1) until complete consumption of starting material was observed by LS/MS. After an aqueous ammonium chloride and dichloromethane workup, column chromatography (0-5% methanol in dichloromethane) provided the desired compound as a tan solid (69%).

Compound 35:
$^1$H-NMR (400 MHz, MeOD) δ 8.73 (d, 1H), 8.19 (s, 1H), 7.41 (s, 1H), 7.26-7.21 (m, 1H), 7.08-6.99 (m, 2H), 6.84-6.80 (m, 2H), 5.93 (s, 2H), 1.43-1.39 (m, 4H).

Compound 58

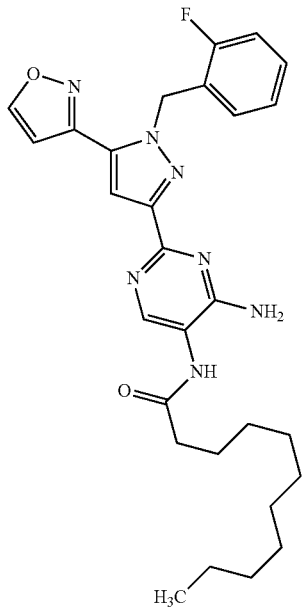

To a solution of 2-(1-(2-fluorobenzyl)-5-(isoxazol-3-yl)-1H-pyrazol-3-yl)pyrimidine-4,5-diamine hydrochloride (Intermediate-0, 1 equiv) in dichloromethane/pyridine (1:1) was added undecanoyl chloride until complete consumption of starting material was observed by LS/MS. After an aqueous ammonium chloride and dichloromethane workup, column chromatography (0-85% ethyl acetate in dichloromethane) provided the desired product as an off-white solid (70%).

Compound 58:
$^1$H NMR (400 MHz, CD$_3$OD) δ 8.66 (d, 1H), 8.20 (s, 1H), 7.33 (s, 1H), 7.20-7.14 (m, 1H), 6.99 (ddd, 1H), 6.94 (ddd, 1H), 6.78 (d, 1H), 6.74 (ddd, 1H), 5.86 (s, 2H), 2.35 (t, 2H), 1.66-1.59 (m, 2H), 1.35-1.17 (m, 14H), 0.80 (t, 3H) ppm.

Compound 69

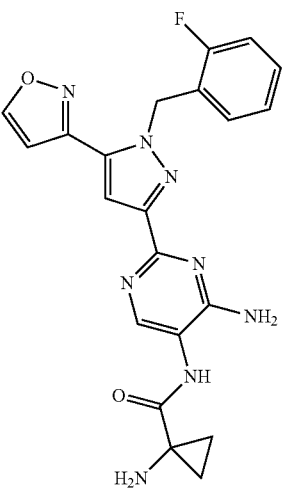

69

To a solution of 1-((((9H-fluoren-9-yl)methoxy)carbonylamino)cyclopropanecarboxylic acid (Intermediate-0, 500 mg, 1.55 mmol) in dichloromethane was added oxalyl chloride (180 mg, 1.42 mmol) and catalytic N,N-dimethylformamide. Once gas evolution ceased, this crude reaction mixture was added portion-wise to a suspension of 2-(1-(2-fluorobenzyl)-5-(isoxazol-3-yl)-1H-pyrazol-3-yl)pyrimidine-4,5-diamine hydrochloride (1 equiv) in dichloromethane/pyridine (1:1) until complete consumption of starting material was observed by LS/MS. After an aqueous ammonium chloride and dichloromethane workup, the layers were separated and the organic portion was dried (sodium sulfate, filtered, and concentrated. The crude material was then directly charged with a 4:1 mixture of acetonitrile and piperidine, and after deprotection was complete via LC/MS analysis, the reaction mixture was concentrated. The crude material was then purified via preparative HPLC chromatography to afford the desired compound in 13% yield. $^1$H-NMR (400 MHz, $CD_3OD$) δ 8.83 (d, 1H), 8.24 (s, 1H), 7.58 (s, 1H), 7.32-7.27 (m, 1H), 7.12-7.07 (m, 1H), 7.06 (t, 1H), 6.98 (ddd, 1H), 6.90 (d, 1H), 6.01 (s, 2H), 1.85 (t, 2H), 1.51 (t, 2H).

Compound 83

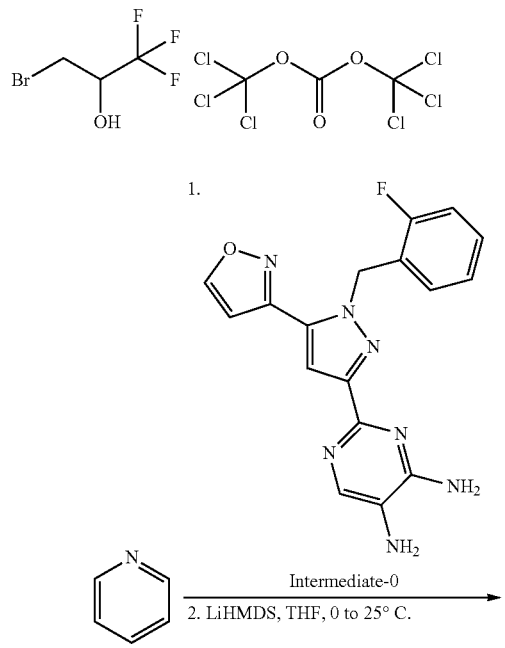

Step 1

To a cold mixture of bis(trichloromethyl)carbonate (63 mg, 0.75 equiv.) and 3-bromo-1,1,1-trifluoro-propan-2-ol (82 mg, 0.75 equiv) in dichloromethane (1.5 ml) under Argon and at 0° C., was added pyridine (0.035 ml, 1.5 equiv.). The mixture was stirred at 0° C. for 30 min. In a separate flask, a suspension of 2-(1-(2-fluorobenzyl)-5-(isoxazol-3-yl)-1H-pyrazol-3-yl)pyrimidine-4,5-diamine (100 mg, 1 equiv.) was cooled to 0° C. To this suspension, was added the mixture of containing the alkyl bromide via syringe. The mixture was removed from the ice bath and stirred at room temperature. The mixture was diluted in ethyl acetate (100 ml) and washed with 1N HCl (40 ml). The organic layer was dried, filtered and evaporated to give solid. The solid was purified by column chromatography (0 to 100% ethyl acetate in hexanes) to give 2-bromo-3,3,3-trifluoropropyl (4-amino-2-(1-(2-fluorobenzyl)-5-(isoxazol-3-yl)-1H-pyrazol-3-yl)pyrimidin-5-yl)carbamate (56 mg, 35% yield) as a solid.

$^1$H NMR (400 MHz, chloroform-d) δ ppm 8.45-8.38 (m, 2H) 7.78 (br. s., 1H) 7.38-7.32 (m, 1H) 7.25 (d, 1H) 7.18-7.10 (m, 1H) 6.99-6.87 (m, 2H) 6.79 (t, 1H) 6.57 (d, 1H), 5.93 (s, 2H), 5.77 (br. s., 1H), 5.45 (br. s., 1H), 3.55 (dd, 1H) 3.42-3.29 (m, 1H).

Step 2

To a cold solution of 2-bromo-3,3,3-trifluoropropyl (4-amino-2-(1-(2-fluorobenzyl)-5-(isoxazol-3-yl)-1H-pyrazol-3-yl)pyrimidin-5-yl)carbamate (56 mg, 1 equiv.) in THF (491 µl) at 0° C., was added 1.0 M solution LiHMDS in THF (118 µl, 1 equiv.). The mixture was removed from the ice bath and stirred for an additional 24 h at 25° C. The mixture was concentrated under vacuum. The resulting residue was diluted in ethyl acetate (100 ml), washed with water (50 ml), dried and concentrated under vacuum. The crude product was purified by column chromatography (0 to 100% ethyl acetate in hexanes, then 1% methanol in dichloromethane) and recrystallized from a diethyl ether:methanol mixture to give 3-(4-amino-2-(1-(2-fluorobenzyl)-5-(isoxazol-3-yl)-1H-pyrazol-3-yl)pyrimidin-5-yl)-5-(trifluoromethyl)oxazolidin-2-one (13 mg, 27% yield).

$^1$H NMR (400 MHz, DMSO-$d_6$) δ ppm 9.10 (d, 1H) 8.50 (s, 1H) 7.57 (s, 1H) 7.34 (d, 2H) 7.30 (s, 1H) 7.27-7.20 (m, 1H) 7.12 (t, 1H) 6.92 (t, 1H) 6.75 (d, 1H) 5.91 (s, 2H) 4.43 (br. s., 1H) 4.11-4.01 (m, 2H).

Compound 34

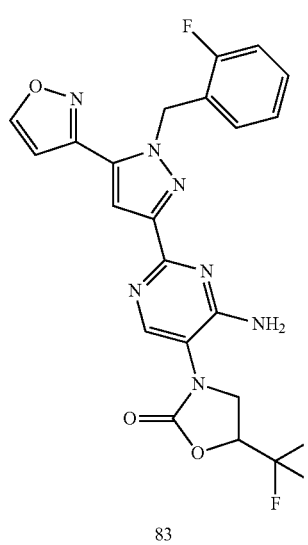

83

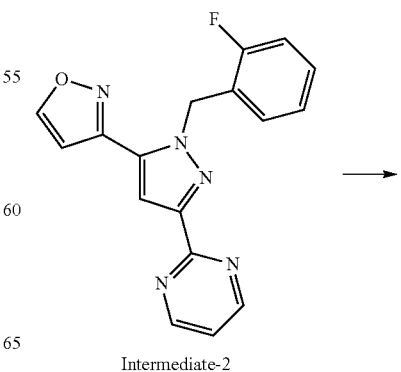

Intermediate-2

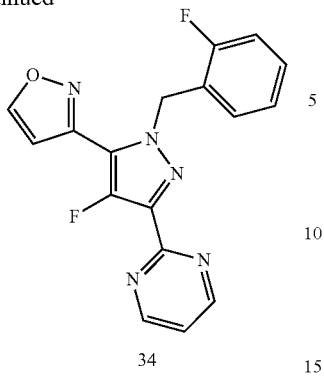

34

To a suspension of 3-(3-(pyrimidin-2-yl)-1H-pyrazol-5-yl) isoxazole (Intermediate 8C, 73.9 mg, 0.347 mmol) and cesium carbonate (181 mg, 0.555 mmol) in acetonitrile (2 mL) was added 1-(bromomethyl)-2-fluorobenzene (0.059 mL, 0.485 mmol). The suspension was heated at 60° C. for 1 h, at which point the solution had turned faint yellow. LCMS analysis indicated the absence of the starting material. The heterogenous solution was filtered, concentrated, and purified by silica gel chromatography (EtOAc/hex 10-100%). The compound above is the more polar isomer of the alkylation of the central pyrazole. The product was a colorless solid (23%). Intermediate-2:

$^1$H NMR (400 MHz, CDCl$_3$) δ 8.83 (d, 2H), 8.45 (d, 1H), 7.47 (s, 1H), 7.24 (t, 1H), 7.20-7.15 (m, 1H), 7.02 (td, 1H), 6.96 (td, 1H), 6.84 (td, 1H), 6.59 (d, 1H), 6.03 (s, 2H).

A solution of sodium bicarbonate (9 mg, 0.1 mmol), 1-chloromethyl-4-fluoro-1,4-diazoniabicyclo[2.2.2]octane bis(tetrafluoroborate) (40 mg, 0.1 mmol), and Intermediate-2 (18 mg, 0.056 mmol) in acetonitrile (1 ml) was stirred for 18 hours at 75° C. Additional 1-chloromethyl-4-fluoro-1,4-diazoniabicyclo[2.2.2]octane bis(tetrafluoroborate) (20 mg) was added, and after stirring for 2 h at 75° C. the solution was poured into dichloromethane (50 mL) and water (30 mL). The layers were separated and the aqueous layer was extracted with dichloromethane (2×20 mL). The organics were dried over magnesium sulfate, filtered, and the solvent was removed in vacuo. Purification by silica gel chromatography (ethyl acetate in dichloromethane) provided Compound 34 (4.9 mg, 26%) that was contaminated with ~20% chloropyrazole.

Compound 34:

$^1$H-NMR (400 MHz, CDCl$_3$) δ 8.88 (d, 2H), 8.50 (s, 1H), 7.30-7.17 (m, 2H), 7.04-6.94 (m, 2H), 6.92-6.85 (m, 1H), 6.81 (s, 1H), 5.98 (s, 2H).

Compound 4

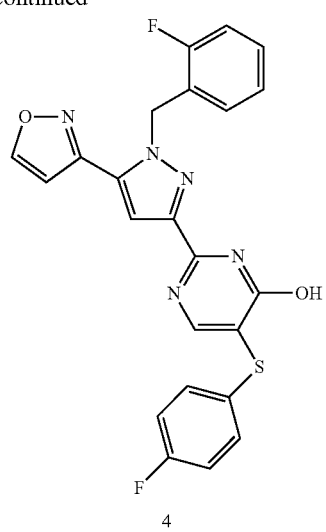

4

A solution of Intermediate 8C (1 equiv) and ethyl 3-(dimethylamino)-2-(4-fluorophenylthio)acrylate (4 equiv) was stirred neat at 100° C. for 14 hours. Purification by silica gel chromatography (0-50% 7:1 acetonitrile:methanol in dicloromethane) delivered the desired product 2-(1-(2-fluorobenzyl)-5-(isoxazol-3-yl)-1H-pyrazol-3-yl)-5-(4-fluorophenylthio)pyrimidin-4-ol as a solid (8%).

Compound 4:

$^1$H NMR (400 MHz, CDCl$_3$) δ 5.88 (s, 2H) 6.58 (d, 1H) 7.00-7.11 (m, 5H) 7.19-7.33 (m, 2H) 7.50 (dd, 2H) 7.61 (s, 1H) 8.51 (d, 1H) 10.24 (br. s., 1H).

Compound 6

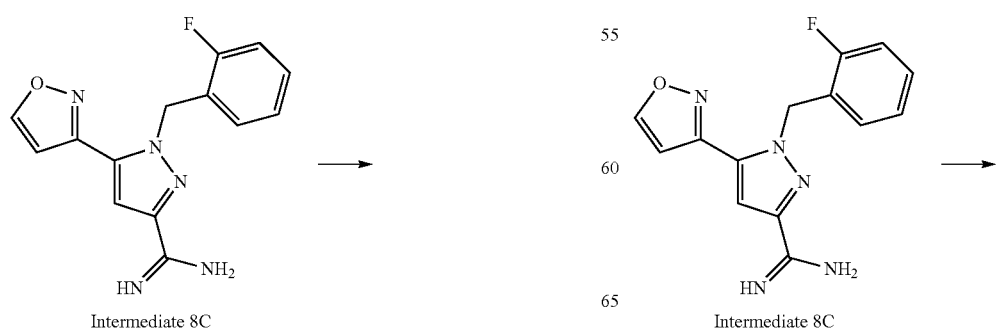

123
-continued

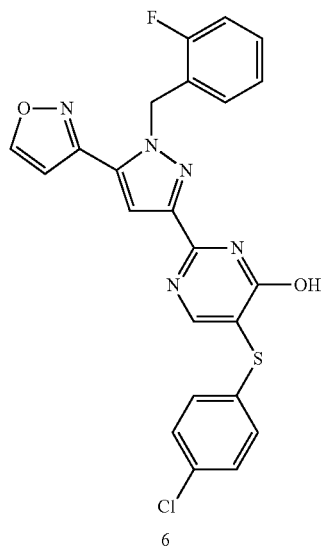

6

A solution of Intermediate 8C (1 equiv) and ethyl 2-(4-chlorophenylthio)-3-(dimethylamino)acrylate (4 equiv) was stirred neat at 100° C. for 14 hours. Purification by silica gel chromatography (0-50% 7:1 acetonitrile:methanol in diclo-romethane) delivered desired product 5-(4-chlorophenylthio)-2-(1-(2-fluorobenzyl)-5-(isoxazol-3-yl)-1H-pyrazol-3-yl)pyrimidin-4-ol as a solid (5%).

Compound 6:
$^1$H NMR (400 MHz, CDCl$_3$) δ 5.88 (s, 2H) 6.59 (d, 1H) 7.01-7.10 (m, 3H) 7.10-7.23 (m, 1H) 7.26-7.34 (m, 3H) 7.35-7.43 (m, 2H) 7.80 (s, 1H) 8.51 (d, 1H).

Compound 17

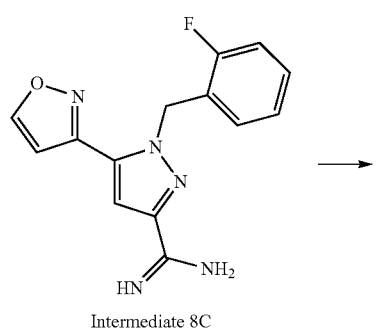

Intermediate 8C

124
-continued

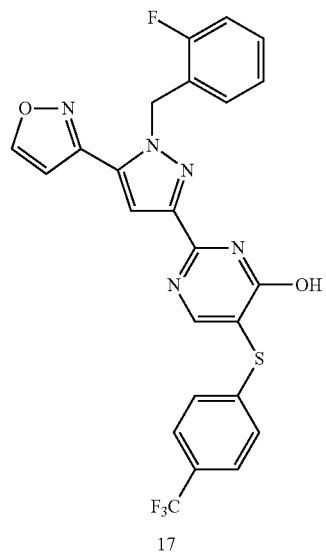

17

A solution of Intermediate-8C (1 equiv) and (E)-ethyl 3-(dimethylamino)-2-(4-(trifluoromethyl)phenylthio)acry-late (4 equiv) was stirred neat at 100° C. for 14 hours. Purification by silica gel chromatography (0-50% 7:1 acetonitrile:methanol in dicloromethane) delivered desired product 2-(1-(2-fluorobenzyl)-5-(isoxazol-3-yl)-1H-pyrazol-3-yl)-5-(4-(trifluoromethyl)phenylthio)pyrimidin-4-ol as a solid (20%).

Compound 17:
$^1$H NMR (400 MHz, CDCl$_3$) δ 5.92 (s, 2H) 6.62 (d, J=1.57 Hz, 1H) 7.03-7.13 (m, 3H) 7.26-7.36 (m, 2H) 7.67-7.74 (m, 2H) 7.75-7.82 (m, 2H) 8.18 (s, 1H) 8.53 (d, J=1.17 Hz, 1H)

Compound 18

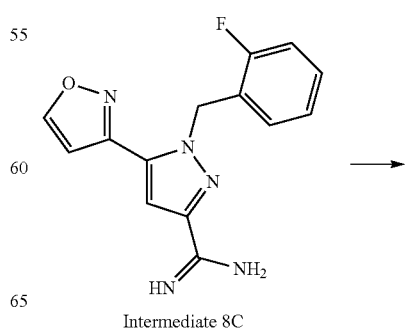

Intermediate 8C

-continued

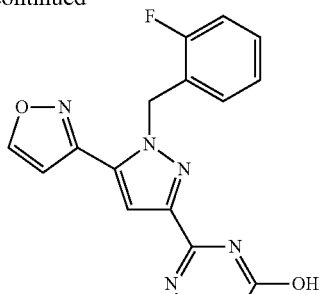

18

A solution of Intermediate-8C (1 equiv) and (E)-ethyl 3-(dimethylamino)-2-(pyridin-2-ylthio)acrylate (4 equiv) was stirred neat at 100° C. for 14 hours. Purification by silica gel chromatography (0-50% 7:1 acetonitrile:methanol in dicloromethane) delivered desired product 2-(1-(2-fluorobenzyl)-5-(isoxazol-3-yl)-1H-pyrazol-3-yl)-5-(pyridin-2-ylthio)pyrimidin-4-ol as a solid (7%).

Compound 18:
$^1$H NMR (400 MHz, CDCl$_3$) δ 5.85 (s, 2H) 6.56 (d, J=1.56 Hz, 1H) 6.91-7.08 (m, 4H) 7.14-7.26 (m, 3H) 7.47 (td, J=7.73, 1.76 Hz, 1H) 8.26-8.37 (m, 2H) 8.47 (d, J=1.57 Hz, 1H) 10.29 (br. s., 1H).

Compound 29

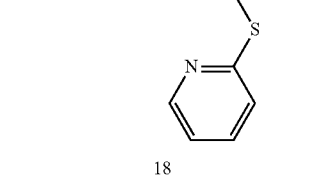

Intermediate 8C

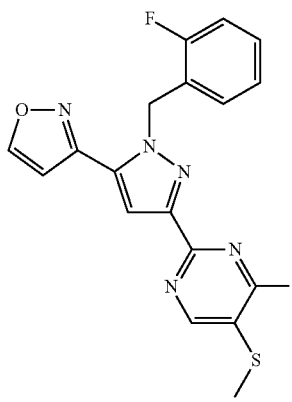

29

A solution of Intermediate 8C (1 equiv) and (E)-ethyl 3-(dimethylamino)-2-(methylthio)acrylate was stirred neat at 100° C. for 14 hours. Purification by silica gel chromatography (0-50% 7:1 acetonitrile:methanol in dicloromethane) delivered desired product 2-(1-(2-fluorobenzyl)-5-(isoxazol-3-yl)-1H-pyrazol-3-yl)-5-(methylthio)pyrimidin-4-ol as a solid (28%).

Compound 29:
$^1$H NMR (400 MHz, CDCl$_3$) δ 2.44 (s, 3H) 5.88 (s, 2H) 6.60 (d, J=1.57 Hz, 1H) 6.98-7.14 (m, 4H) 7.27 (br. s., 1H) 7.74 (s, 1H) 8.51 (d, J=1.57 Hz, 1H) 10.15 (br. s., 1H)

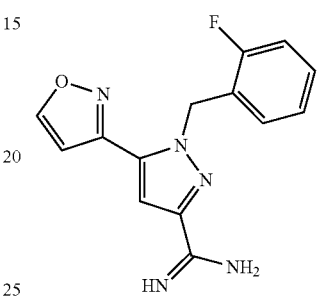

Intermediate 8C

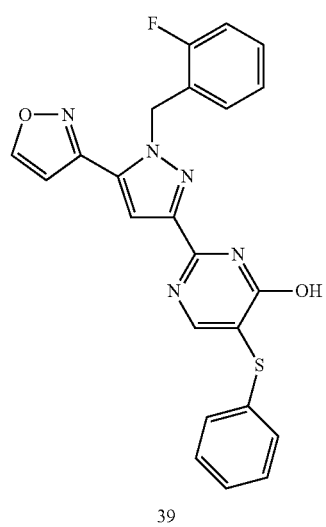

39

Compound 39

A solution of Intermediate 8C (1 equiv) and (E)-ethyl 3-(dimethylamino)-2-(phenylthio)acrylate was stirred neat at 100° C. for 14 hours. Purification by silica gel chromatography (0-50% 7:1 acetonitrile:methanol in dicloromethane) delivered desired product 2-(1-(2-fluorobenzyl)-5-(isoxazol-3-yl)-1H-pyrazol-3-yl)-5-(phenylthio)pyrimidin-4-ol as a solid (5%).

Compound 39:
$^1$H NMR (400 MHz, CDCl$_3$) δ 5.88 (s, 2H) 6.58 (d, J=1.57 Hz, 1H) 7.01-7.11 (m, 3H) 7.21 (s, 1H) 7.26-7.30 (m, 1H) 7.31-7.41 (m, 3H) 7.48 (d, J=6.65 Hz, 2H) 7.66 (s, 1H) 8.50 (d, J=1.57 Hz, 1H).

Compound 60

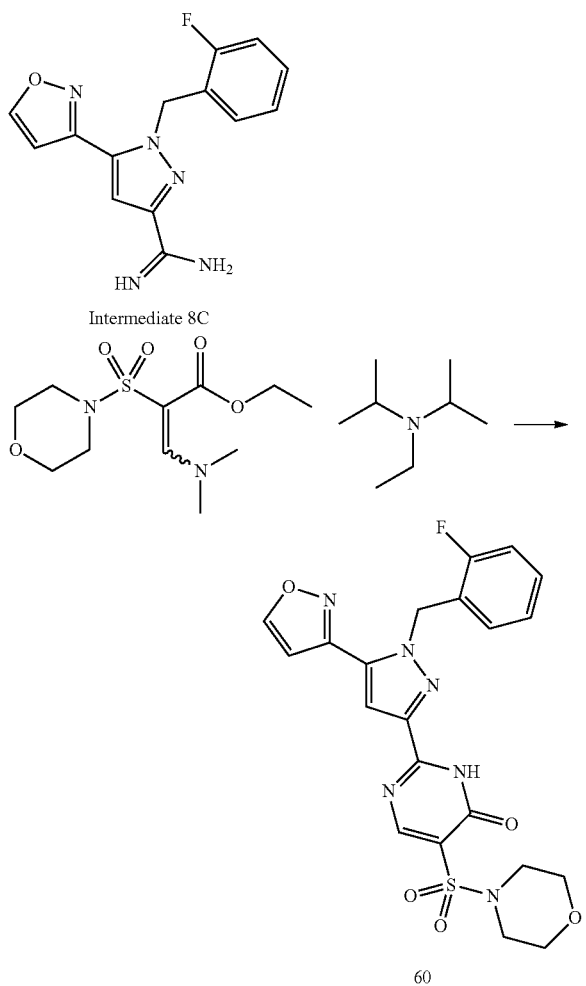

A solution of Intermediate 8C, ethyl 3-(dimethylamino)-2-(morpholinosulfonyl)acrylate (2 equiv.) and Hunig's base (1 equiv.) was stirred at 85° C. for 2 days in ethanol. The solvent was removed under vacuum and purification by silica gel chromatography (0 to 40% ethyl acetate in hexanes) followed by rinsing with a minimal amount of methanol gave the desired product as a white solid (3% yield).
Compound 60:
$^1$H NMR (400 MHz, DMSO-$d_6$) δ ppm 9.11 (d, 1H) 7.77 (s, 1H) 7.33 (q, 1H) 7.18-7.28 (m, 2H) 7.11 (t, 1H) 6.95 (br. s., 1H) 5.94 (s, 2H) 3.58 (d, 4H) 3.22 (d, 4H).
Compound 25

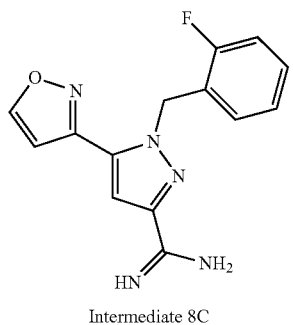

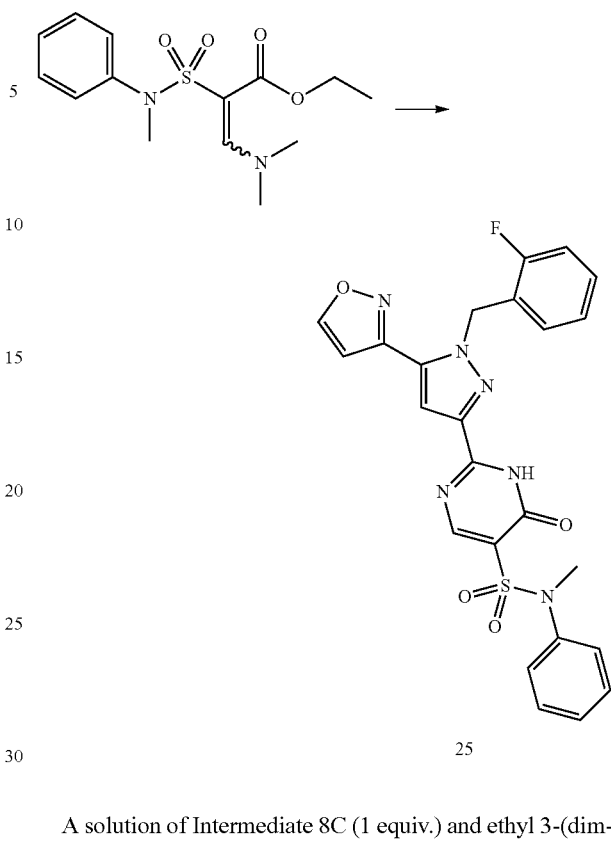

A solution of Intermediate 8C (1 equiv.) and ethyl 3-(dimethylamino)-2-(N-methyl-N-phenylsulfamoyl)acrylate (1 equiv.) was stirred at 85° C. for 24 h in ethanol. The solvent was removed under vacuum and purification by silica gel chromatography (5% methanol in dichloromethane) gave the desired product as a white solid (7% yield).

Compound 25:
$^1$H NMR (400 MHz, DMSO-$d_6$) δ 9.13 (d, 1H) 8.28 (br. s., 1H) 7.77 (s, 1H) 7.30-7.43 (m, 6H) 7.19-7.28 (m, 3H) 7.13 (t, 1H) 5.95 (s, 2H) 3.39-3.50 (m, 3H).

Compound 22

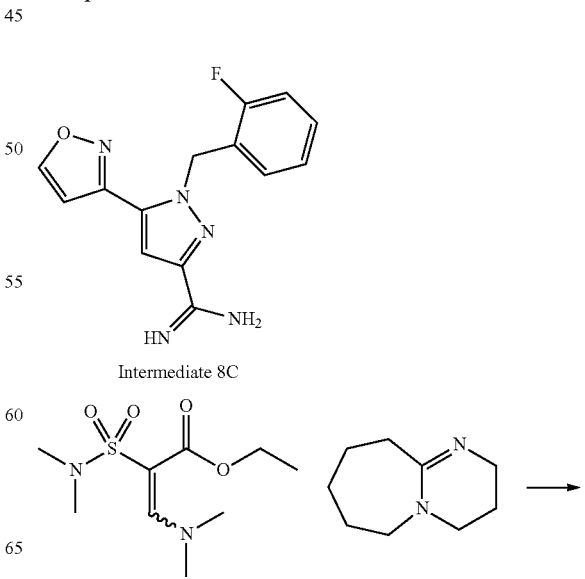

129

-continued

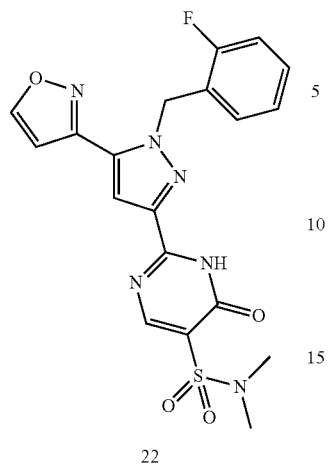

22

A solution of Intermediate 8C (1 equiv.), ethyl 3-(dimethylamino)-2-(N,N-dimethylsulfamoyl)acrylate (3 equiv.) and DBU (1 equiv.) was stirred at 85° C. for 2 h in ethanol. The solvent was removed under vacuum and purification by silica gel chromatography (0 to 10% methanol in dichloromethane) gave the desired compound as a white solid (29% yield).

Compound 22:

$^1$H NMR (400 MHz, DMSO-d$_6$) δ 9.14 (d, 1H) 8.49 (br. s., 1H) 7.79 (s, 1H) 7.31-7.40 (m, 1H) 7.28 (br. s., 1H) 7.20-7.26 (m, 1H) 7.13 (t, 1H) 6.97 (br. s., 1H) 5.96 (s, 2H) 2.72-2.95 (m, 6H).

Compound 21

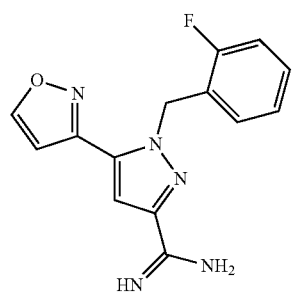

Intermediate 8C

130

-continued

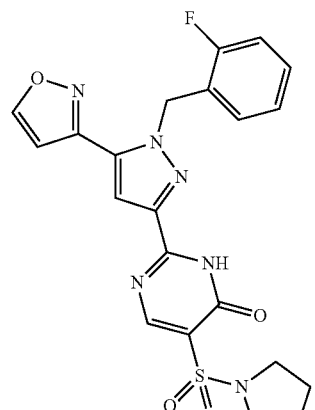

21

A solution of Intermediate 8C (1 equiv.), ethyl 3-(dimethylamino)-2-(pyrrolidin-1-ylsulfonyl)acrylate (2.5 equiv.) and DBU (1 equiv.) was stirred at 85° C. for 2 h in ethanol. The solvent was removed under vacuum and purification by silica gel chromatography (0 to 10% methanol in dichloromethane) gave the desired compound as a white solid (15% yield).

Compound 21:

$^1$H NMR (400 MHz, DMSO-d$_6$) δ 9.14 (d, 1H) 8.50 (br. s., 1H) 7.80 (s, 1H) 7.31-7.40 (m, 1H) 7.20-7.30 (m, 2H) 7.13 (t, 1H) 7.00 (br. s., 1H) 5.96 (br. s., 2H) 3.38 (t, 4H) 1.77 (t, 4H).

Compound 16

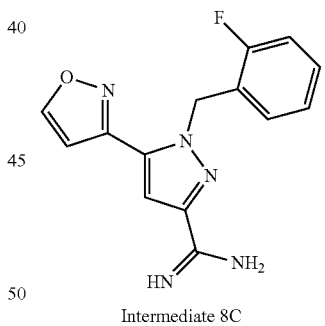

Intermediate 8C

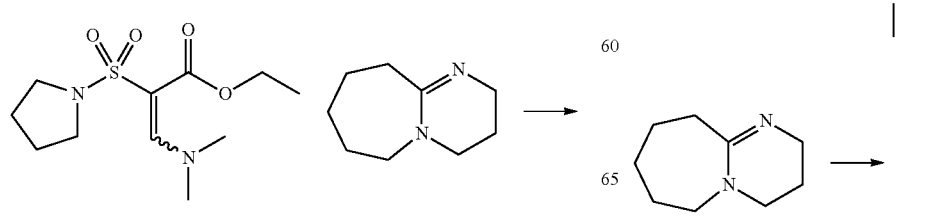

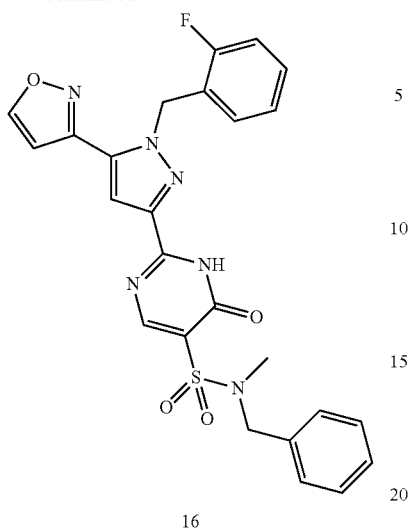

16

A solution of Intermediate 8C (1 equiv.), 2-(N-benzyl-N-methylsulfamoyl)-3-(dimethylamino)acrylate (2.5 equiv.) and DBU (1 equiv.) was stirred at 85° C. for 2 h in ethanol. The solvent was removed under vacuum and purification by silica gel chromatography (0 to 10% methanol in dichloromethane) gave the desired compound as a white solid (16% yield).

Compound 16:

$^1$H NMR (400 MHz, methanol-$d_4$) δ 8.78 (d, 1H) 8.51 (s, 1H) 7.88 (s, 1H) 7.56 (s, 1H) 7.23-7.37 (m, 7H) 7.02-7.13 (m, 2H) 6.89-6.97 (m, 2H) 6.01 (s, 2H) 2.78 (s, 3H).

Compound 14

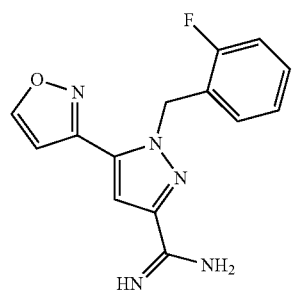

Intermediate 8C

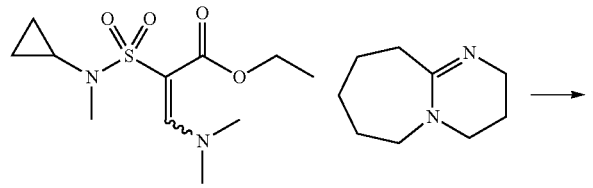

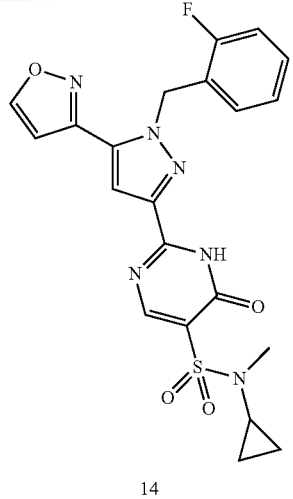

14

A solution of Intermediate 8C (1 equiv.), 2-(N-cyclopropyl-N-methylsulfamoyl)-3-(dimethylamino)acrylate (2.5 equiv.) and DBU (1 equiv.) was stirred at 85° C. for 2 h in ethanol. The solvent was removed under vacuum and purification by silica gel chromatography (0 to 10% methanol in dichloromethane) gave the desired compound as a white solid (5% yield).

Compound 14:

$^1$H NMR (400 MHz, DMSO-$d_6$) δ 9.14 (d, 1H) 8.53 (br. s., 1H) 7.81 (s, 1H) 7.31-7.40 (m, 1H) 7.19-7.30 (m, 2H) 7.13 (t, 1H) 7.01 (br. s., 1H) 5.97 (br. s., 2H) 3.35 (br. s., 1H) 2.90 (s, 3H) 0.72 (br. s., 2H) 0.63 (d, 2H).

Compound 79

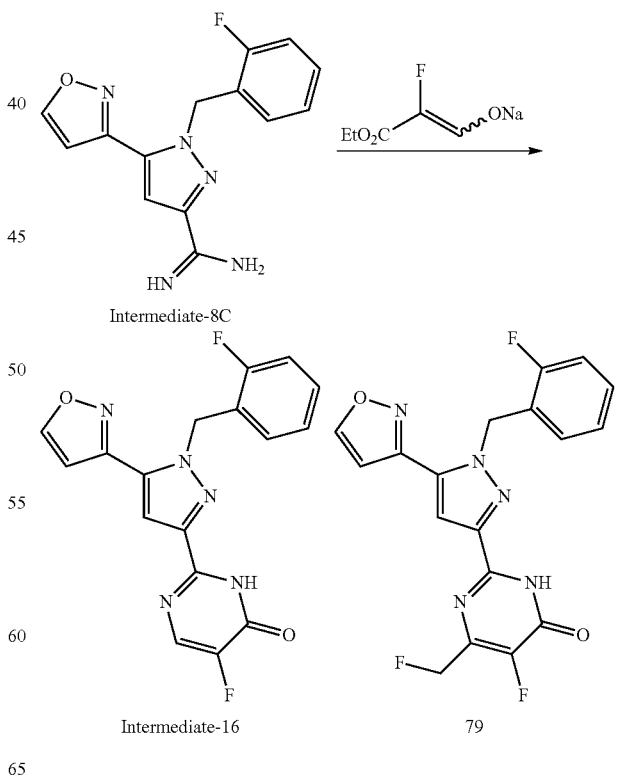

Intermediate-8C was accessed via General Procedure A from 1-(isoxazol-3-yl)ethanone using (2-fluorobenzyl)hydrazine hydrochloride in the first step. A suspension of sodium (E,Z)-3-ethoxy-2-fluoro-3-oxoprop-1-en-1-olate (364 mg, 2.33 mmol) and Intermediate-8C (250 mg, 0.77 mmol) in ethanol (7.77 mL) was stirred at 90° C. for 18 hours. The contents were diluted with ethyl acetate (20 mL) and water (20 mL). The mixture was treated carefully with HCl (1.24 mL, 1.55 mmol, 1.25M solution in ethanol). Layers were separated, and the aqueous layer was extracted with dichloromethane (3×10 mL). The organics were washed with brine (10 mL), dried over MgSO4, filtered, and the solvent was removed in vacuo. Purification by silica gel chromatography (0-30% 7:1=acetonitrile:methanol in dichloromethane) provided Intermediate-16. Compound 79 (45 mg, 15% yield) also was isolated as a white solid, as a result of a contaminant in the sodium (E,Z)-3-ethoxy-2-fluoro-3-oxoprop-1-en-1-olate reagent used.

Compound 79:

$^1$H-NMR (400 MHz, DMSO-d$_6$) δ 13.42 (br s, 1H), 9.12 (d, 1H), 7.66 (s, 1H), 7.38-7.30 (m, 1H), 7.28 (d, 1H), 7.26-7.19 (m, 1H), 7.14-7.09 (m, 1H), 6.96 (t, 1H), 5.93 (s, 2H), 5.46 (d, 1H), 5.34 (d, 1H).

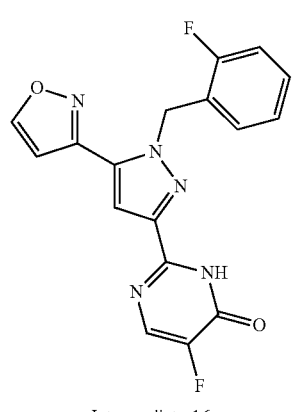

Intermediate-16

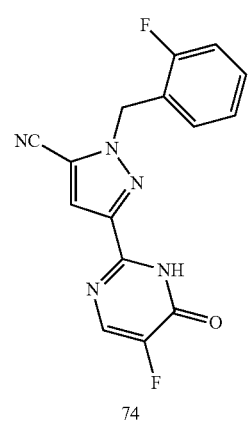

74

Compound 74

Intermediate-16 (1 g, 2.81 mmol) was directly charged with DBU (0.53 mL, 3.52 mmol) and subsequently heated to 110° C. Once the reaction was complete by LC/MS analysis, the mixture was diluted with dichloromethane (100 mL) and washed with 1N HCl. The layers were separated and the organic portion was dried (sodium sulfate), filtered, and concentrated. The crude material was purified via flash chromatography using a 0-10% methanol in dichloromethane gradient to afford Compound 74 in 45% yield.

Compound 74:

$^1$H-NMR (400 MHz, DMSO-d$_6$) δ 13.39 (bs, 1H), 8.15 (bs, 1H), 7.77 (s, 1H), 7.48-7.41 (m, 2H), 7.30-7.22 (m, 2H), 5.68 (s, 2H).

Compound 75

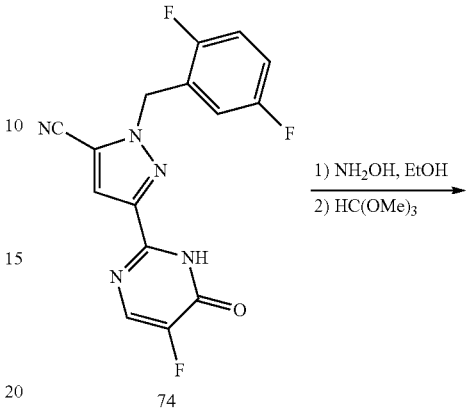

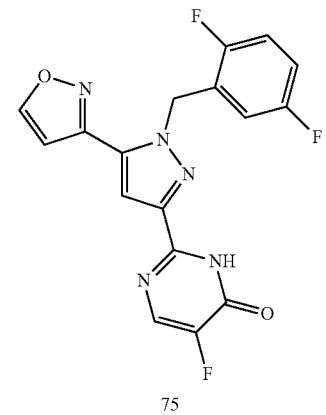

75

Compound 74, (described above, 260 mg, 0.830 mmol) was diluted with ethanol (10 mL) and consecutively charged with potassium carbonate (344 mg, 2.49 mmol) and hydroxylamine hydrochloride (72 mg, 1.04 mmol). After stirring overnight at rt, the reaction was diluted with EtOAc (50 mL) and filtered. The filtrate was concentrated and the crude material was charged with trimethylorthoformate (5 mL) and heated to 100° C. Once the cyclization was complete by LC/MS analysis, the reaction mixture was directly concentrated and the crude material was purified via flash chromatography using a 0-10% methanol in dichloromethane gradient to afford the desired material in 11% yield.

Compound 75:

$^1$H-NMR (400 MHz, DMSO-d$_6$) δ 13.37 (bs, 1H), 9.87 (s, 1H), 8.15 (bs, 1H), 7.62 (s, 1H), 7.31-7.34 (m, 1H), 7.23 (t, 1H), 7.14 (ddd, 1H), 7.04 (t, 1H), 5.95 (s, 2H).

Compound 5

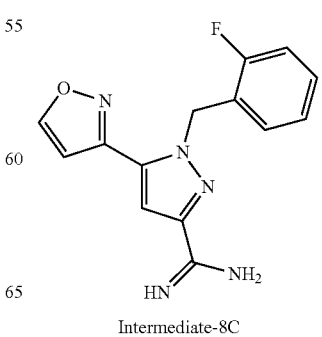

Intermediate-8C

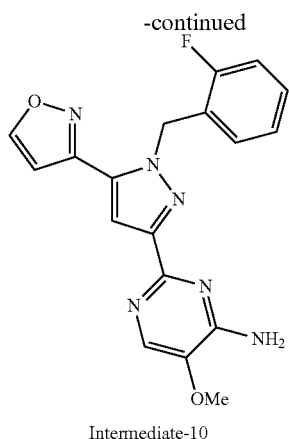

Intermediate-10

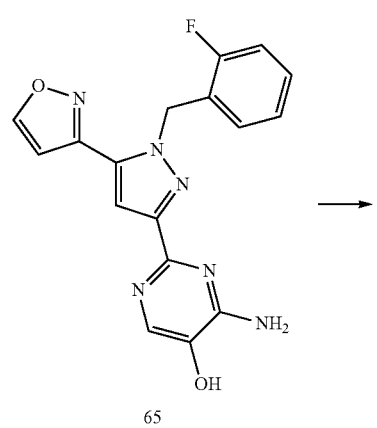

65

To a solution of Intermediate-10 (19 mg, 0.052 mmol) in dichloromethane (1 mL) at 0° C. was added boron tribrominde (0.104 mL, 0.104 mmol). The solution was warmed to room temperature immediately and maintained at that temperature for 26 hours. The solution was cooled to 0° C. and methanol (3 mL) was added. After warming to room temperature, saturated aqueous sodium carbonate (50 mL) was added. Saturated aqueous ammonium chloride was added, along with a 5:1 dichloromethane/2-propanol mixture (50 mL). The layers were separated and the aqueous was extracted with 5:1 dichloromethane/2-propanol (2×30 mL). The organics were combined, dried over magnesium sulfate, filtered, and the solvent was removed in vacuo to give crude Compound 65, which was used without further purification.

To a solution of 1-methylcyclopropanecarboxylic acid (25 equiv) in dichloromethane was added oxalyl chloride (22.1 equiv) and catalytic N, N-dimethylformamide. Once gas evolution ceased, this crude reaction mixture was added portionwise to a suspension of Compound 65 (1 equiv) in dichloromethane/pyridine (2:1) until complete consumption of starting material was observed by LS/MS. After an aqueous ammonium chloride and dichloromethane workup, column chromatography (0-10% methanol in dichloromethane) provided Compound-5 as a white film (7%, 2 steps).

Compound-5:

$^1$H-NMR (400 MHz, MeOD) δ 8.74 (d, 1H), 7.99 (s, 1H), 7.04 (s, 1H), 7.27-7.23 (m, 1H), 7.09-7.00 (m, 2H), 6.85-6.80 (m, 2H), 5.94 (s, 2H), 1.46-1.44 (m, 2H), 0.94-0.91 (m, 2H).

Compound 52

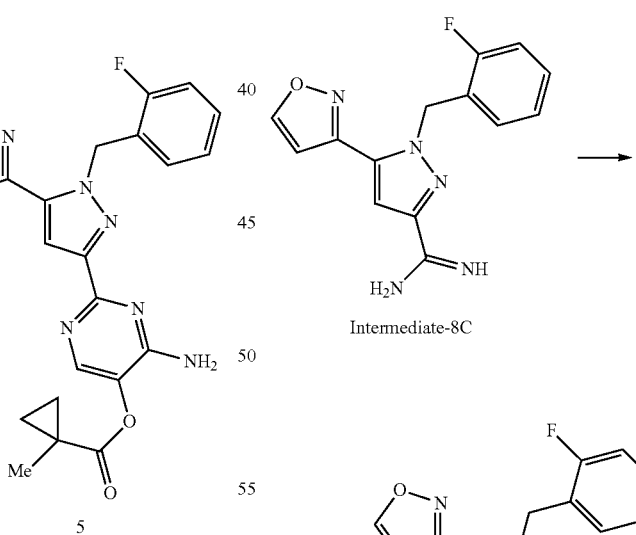

Intermediate-10 was prepared by the cyclization reaction of Intermediate-8C in ethanol in the presence of three equivalents of 3-(dimethylamino)-2-methoxyacrylonitrile and one equivalent of 1,8-diazabicyclo[5.4.0]undec-7-ene.

Intermediate-10:

$^1$H NMR (400 MHz, DMSO-d6) δ 9.08 (d, 1H), 7.88 (s, 1H), 7.43 (s, 1H), 7.36-7.28 (m, 1H), 7.25-7.18 (m, 2H), 7.14-7.08 (m, 1H), 6.84 (t, 1H), 6.97-6.69 (bs, 2H), 5.87 (s, 2H), 3.86 (s, 3H).

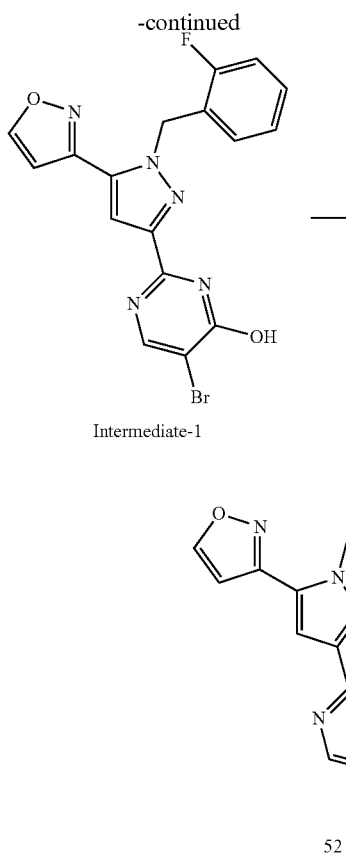

Intermediate-1

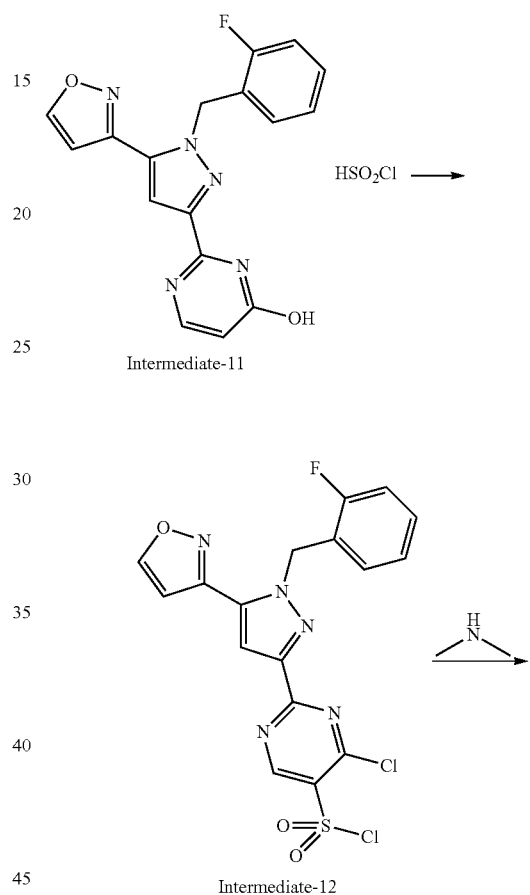

A mixture of Intermediate-8C (1 equiv) and methyl 3-methoxyacrylate (3 equiv) was stirred at 90° C. for 6 h. The solvent was removed in vacuo and purification by silica gel chromatography (0-7% methanol/dicloromethane) delivered the desired compound as a colorless solid (41%).
Intermediate-11:

$^1$H NMR (400 MHz, CDCl$_3$) δ 10.46 (br s, 1H), 8.51 (d, 1H), 7.96 (d, 1H), 7.31 (s, 1H), 7.31-7.24 (m, 1H), 7.07-7.02 (m, 3H), 6.60 (d, 1H), 6.38 (d, 1H), 5.89 (s, 2H).

To a solution of 2-(1-(2-fluorobenzyl)-5-(isoxazol-3-yl)-1H-pyrazol-3-yl)pyrimidin-4-ol Intermediate-11 (276 mg, 1 equiv) in acetic acid (4 ml) at 0° C., was added bromine (59 IA, 1.4 equiv). The mixture was removed from the ice bath and stirred at 25° C. for 3 h. The mixture was concentrated under vacuum. The resulting residue was rinsed with a minimal amount of methanol and acetone. The precipitate was collected by filtration to give a mixture of the starting material as well as the desired 2-(1-(2-fluorobenzyl)-5-(isoxazol-3-yl)-1H-pyrazol-3-yl)pyrimidin-4-ol. Repeating and subjecting the solid to the bromination conditions gave 202 mg (59%) of the desired product as a white solid.
Intermediate-1:

$^1$H NMR (400 MHz, DMSO-d6) 9.10 (d, 1H), 8.40 (bs, 1H), 7.67 (s, 1H), 7.36-7.29 (m, 1H), 7.24-7.17 (m, 1H), 7.13-7.08 (m, 1H), 7.02-6.96 (m, 1H), 5.90 (s, 2H). To a suspension of Intermediate-1 (711 mg, 1.71 mmol) in toluene (10 mL) was added phosphoryl chloride (0.48 mL, 5.1 mmol). The resulting solution was heated at 110° C. for 15 hours, at which point the crude reaction mixture was diluted with dichloromethane (75 mL) and saturated aqueous sodium bicarbonate. The layers were separated and the aqueous layer was extracted with dichloromethane (2×50 mL). The organics were dried over magnesium sulfate, filtered, and the solvent was removed in vacuo to give the crude product as a solid. Purification by silica gel chromatography (10-100% ethyl acetate in hexanes) provided Compound 52 (645 mg, 87%) as a pale yellow solid.

Compound 52:

$^1$H-NMR (400 MHz, CDCl$_3$) δ 8.86 (s, 1H), 8.46 (d, 1H), 7.45 (s, 1H), 7.22-7.17 (m, 1H), 7.04-6.94 (m, 2H), 6.84-6.80 (m, 1H), 6.58 (d, 1H), 6.01 (s, 2H).

Compound 51

A solution of 2-(1-(2-fluorobenzyl)-5-(isoxazol-3-yl)-1H-pyrazol-3-yl)pyrimidin-4-ol Intermediate-11 (200 mg, 1 equiv) and sulfurochloridic acid (1.9 ml) was heated at 100° C. for 30 min in a sealed vial. The mixture was diluted in ethyl acetate (50 ml) and washed with water (50 ml). The organic layer was dried, filtered and evaporated to give 239 mg of crude 4-chloro-2-(1-(2-fluorobenzyl)-5-(isoxazol-3-yl)-1H-pyrazol-3-yl)pyrimidine-5-sulfonyl chloride as a cream colored solid (Intermediate-12) that was taken directly onto the next step without further purification.

A portion of the solid product (100 mg) was combined with dimethyl amine (2.0 M in THF, 2.2 ml, 20 equiv) and stirred at 25° C. for 30 min. The mixture was diluted in ethyl acetate (100 ml) and washed with water (50 ml). The organic layer was dried, filtered and evaporated to give a crude oil. Purification of the oil by column chromatography (0 to 10% methanol in dichloromethane) and re-crystallization from a hexanes/ethyl acetate mixture gave the desired product as a white solid (18% overall yield over two steps).

Compound 51:

$^1$H NMR (400 MHz, METHANOL-d$_4$) δ ppm 8.80 (d, 1H) 8.06 (br. s., 1H) 7.70-7.78 (m, 1H) 7.53 (br. s., 1H) 7.37 (t, 1H) 7.31 (d, 1H) 6.96 (s, 1H) 6.40 (br. s., 1H) 6.08 (s, 2H) 2.49 (s, 6H).

Compound 49

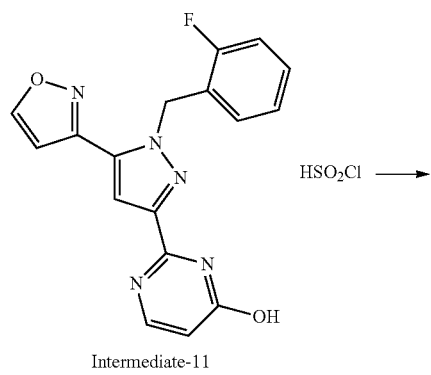

Intermediate-11

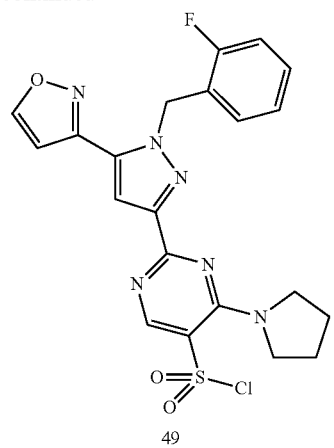

49

A portion of the solid Intermediate-12 obtained above (100 mg) was combined with pyrrolidine (91 μl, 5 equiv) and dichloromethane (1.1 ml). The mixture was stirred at 25° C. for 30 min. The mixture was diluted in ethyl acetate (100 ml) and washed with water (50 ml). The organic layer was dried, filtered and evaporated to give crude oil. Purification of the oil by column chromatography (0 to 10% methanol in dichloromethane) and recrystallization from a methanol/diethyl ether mixture gave the desired product as a cream colored solid (32% overall yield over two steps).

Compound 49:

$^1$H NMR (400 MHz, DMSO-d$_6$) δ ppm 12.62 (br. s., 1H) 9.09-9.20 (m, 1H) 7.77-7.83 (m, 1H) 7.71 (s, 1H) 7.51 (t, 1H) 7.35 (d, 1H) 7.26 (d, 1H) 6.37 (br. s., 1H) 5.99 (s, 2H) 2.96 (t, 4H) 1.44-1.51 (m, 4H).

Compound 59

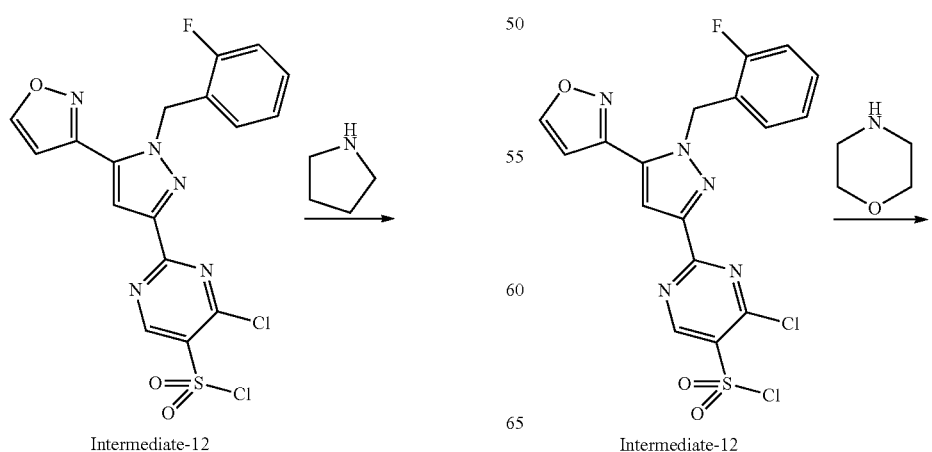

-continued

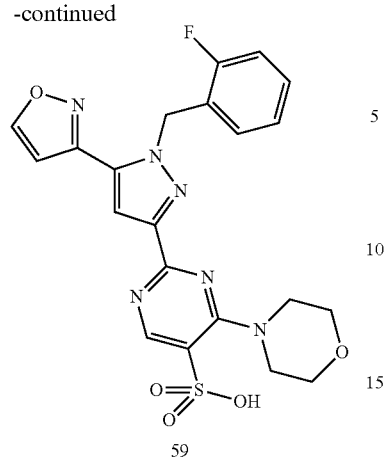

59

A solution of 2-(1-(2-fluorobenzyl)-5-(isoxazol-3-yl)-1H-pyrazol-3-yl)pyrimidin-4-ol Intermediate-11 (56 mg, 1 equiv) and sulfurochloridic acid (0.5 ml) in a sealed vial was heated to 100° C. for 30 min. The mixture was diluted in ethyl acetate (50 ml) and washed with water (50 ml). The organic layer was dried, filtered and evaporated to give 79 mg of crude 4-chloro-2-(1-(2-fluorobenzyl)-5-(isoxazol-3-yl)-1H-pyrazol-3-yl)pyrimidine-5-sulfonyl chloride as a oil (Intermediate-12).

The oil was combined with morpholine (45 μl, 3 equiv.) and the resulting mixture was stirred at 25° C. for 30 min. The mixture was diluted in ethyl acetate (100 ml) and washed with water (50 ml). The organic layer was dried, filtered and evaporated to give crude oil. Purification of the oil by column chromatography (0 to 10% methanol in dichloromethane) gave the desired product as a white solid (47% overall yield over two steps).

Compound 59:
$^1$H NMR (400 MHz, DMSO-$d_6$) δ 12.58 (br. s., 1H) 9.06-9.18 (m, 1H) 8.01 (br. s., 1H) 7.68-7.74 (m, 1H) 7.66 (s, 1H) 7.51 (t, 1H) 7.32 (d, 1H) 7.22 (s, 1H) 6.33 (br. s., 1H) 5.97 (s, 2H) 3.45-3.55 (m, 4H) 2.64 (br. s., 4H).

Compound 54

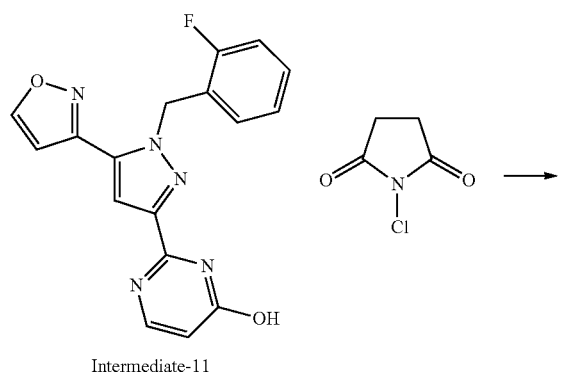

Intermediate-11

-continued

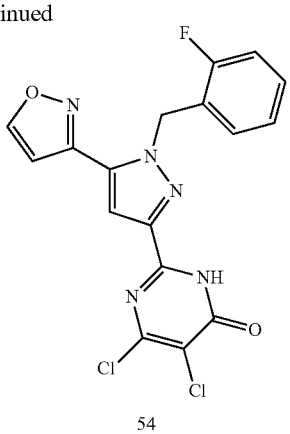

54

A mixture of 2-(1-(2-fluorobenzyl)-5-(isoxazol-3-yl)-1H-pyrazol-3-yl)pyrimidin-4-ol Intermediate-11 (50 mg, 1 equiv) and N-chlorosuccinimide (90 mg, 4.6 equiv) in acetic acid (741 μl) was stirred at 100° C. for 1 h. The mixture was then cooled to room temperature. The precipitate was collected by filtration and dried under vacuum to give the desired product as a white solid (65% yield).

Compound 54:
$^1$H NMR (400 MHz, DMSO-$d_6$) δ 9.27 (d, 1H) 8.38 (br. s., 1H) 7.30-7.42 (m, 1H) 7.12-7.23 (m, 4H) 5.74 (s, 2H).

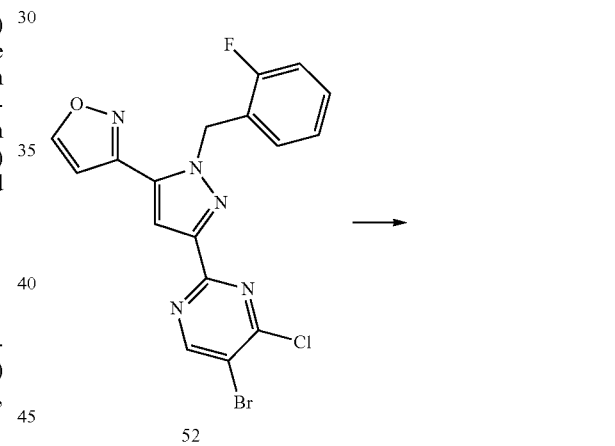

52

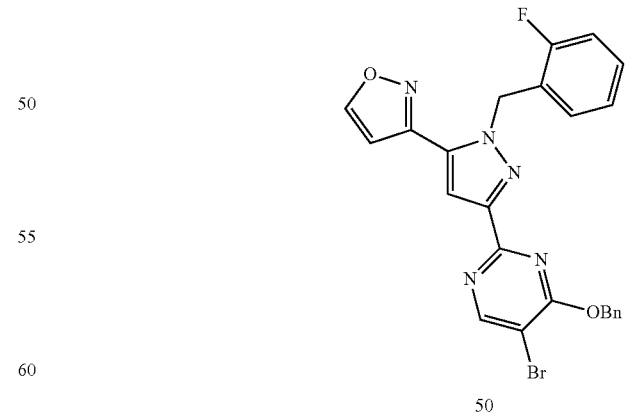

50

Compound 50
To a 0° C. suspension of 60% sodium hydride in mineral oil (12 mg, 0.30 mmol) in tetrahydrofuran (2 mL) was added benzyl alcohol (31 μl, 0.30 mmol) dropwise over the course of 1 minute. After stirring for 15 minutes, the solution was warmed to room temperature and stirred for an additional 5 minutes. The solution was then cooled to 0° C. and Compound 52 (100 mg, 0.23 mmol) was added in a single portion. The solution was immediately warmed to room temperature and stirred for an additional 45 minutes. Saturated aqueous ammonium chloride (50 mL) and dichloromethane (50 mL) were added. The layers were separated and the aqueous layer was extracted with dichloromethane (2×50 mL). The organics were combined, dried over magnesium sulfate, filtered, and the solvent was removed under vacuum. The crude residue was purified by silica gel chromatography (0-10% ethyl acetate in dichloromethane) to provide Compound 50 (112 mg, 96%) as a white solid.

Compound 50:

$^1$H-NMR (400 MHz, CDCl$_3$) δ 8.66 (s, 1H), 8.47 (d, 1H), 7.53-7.52 (m, 2H), 7.40-7.33 (m, 4H), 7.23-7.17 (m, 1H), 7.05-6.95 (m, 2H), 6.89-6.85 (m, 1H), 6.59 (s, 1H), 5.98 (s, 2H), 5.62 (s, 2H).

Compound 46

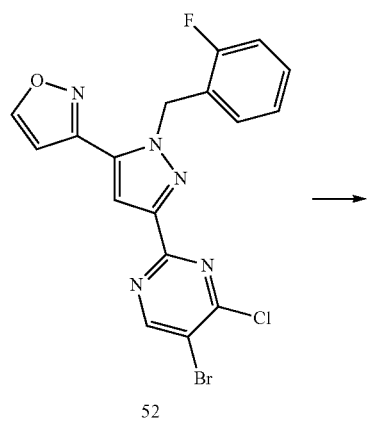

52

→

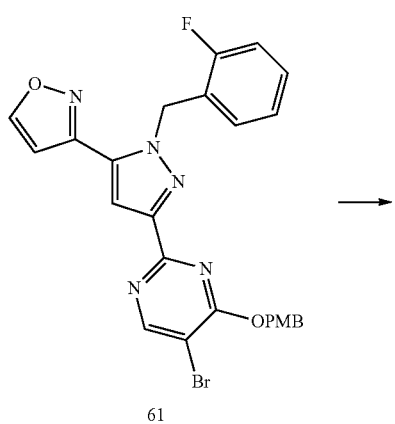

61

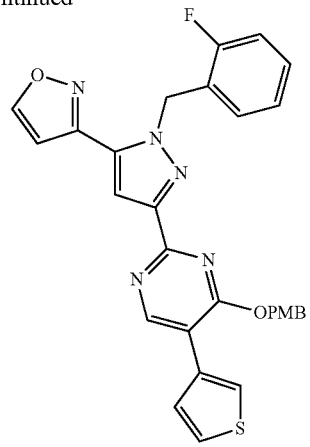

46

To a suspension of 60% sodium hydride in mineral oil (12 mg, 0.31 mmol) in tetrahydrofuran (2 mL) at 0° C. was added p-methoxybenzyl alcohol (38 μl, 0.31 mmol) dropwise over the course of 1 minute. After stirring for 15 minutes, the solution was warmed to room temperature and stirred for an additional 5 minutes. The solution was then cooled to 0° C. and Compound 52 (102 mg, 0.23 mmol) was added in a single portion. The solution was immediately warmed to room temperature and stirred for an additional 45 minutes. Saturated aqueous ammonium chloride (50 mL) and dichloromethane (50 mL) were added. The layers were separated and the aqueous layer was extracted with dichloromethane (2×50 mL). The organics were dried over magnesium sulfate, filtered, and the solvent was removed in vacuo. The crude residue was purified by silica gel chromatography (10-30% ethyl acetate in hexanes) to give Compound 61 as a white solid.

Compound 61:

$^1$H NMR (400 MHz, DMSO) δ 9.13 (d, 1H), 8.80 (s, 1H), 7.74 (s, 1H), 7.53 (d, 2H), 7.38-7.33 (m, 1H), 7.29 (d, 1H), 7.24-7.21 (m, 1H), 7.14 (t, 1H), 6.97-6.86 (m, 3H), 5.96 (s, 2H), 5.53 (s, 2H), 3.74 (s, 3H).

A suspension of cesium carbonate (71 mg, 0.22 mmol), potassium fluoride (23 mg, 0.39 mmol), thiophen-3-ylboronic acid (30 mg, 0.23 mmol), and Compound 61 (25 mg, 0.047 mmol) in dimethoxyethane (1 mL) was degassed with a stream of nitrogen for 10 min. Palladium tetrakistriphenylphosphine (16 mg, 0.014 mmol) was added and the solution was heated to 90° C. After 1.5 h, the solution was diluted with ethyl acetate (75 mL) and water (50 mL). The layers were separated and the aqueous layer was extracted with ethyl acetate (2×50 mL). The organics were dried over magnesium sulfate, filtered, and the solvent was removed under vacuum. The crude product was purified by silica gel chromatography (10-40% ethyl acetate in hexanes) to provide Compound 46 (16 mg, 66%) as a brown oily solid.

Compound 46:

$^1$H-NMR (400 MHz, CDCl$_3$) δ 8.80 (s, 1H), 8.46 (s, 1H), 7.78-7.77 (m, 1H), 7.50-7.44 (m, 4H), 7.37 (dd, 1H), 7.22-7.17 (m, 1H), 7.05-6.96 (m, 2H), 6.92-6.89 (m, 3H), 6.60 (d, 1H), 5.61 (s, 2H), 3.80 (s, 3H).

Compound 45

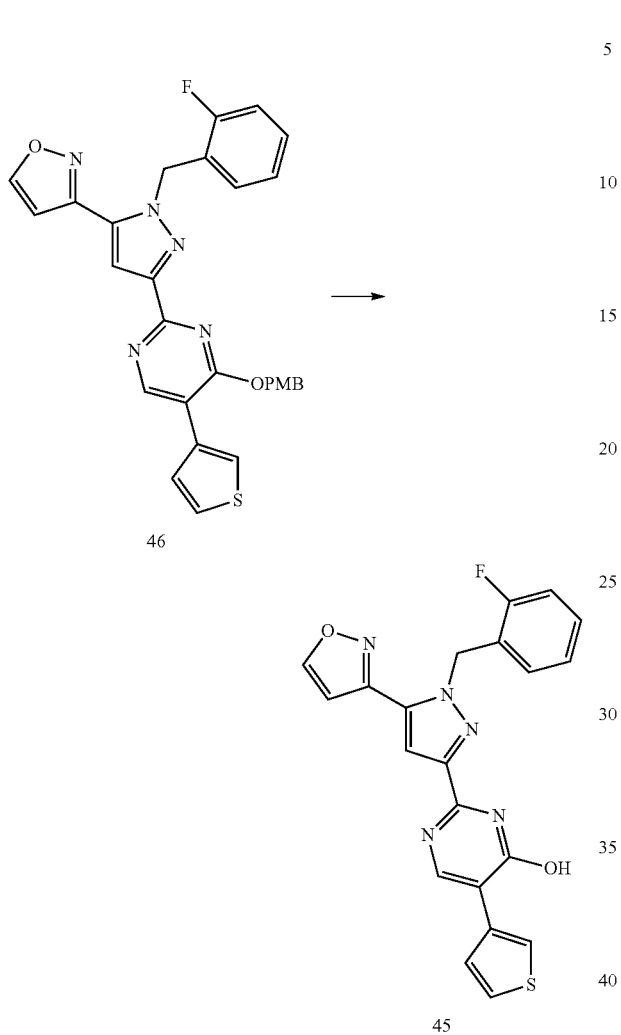

Compound 43

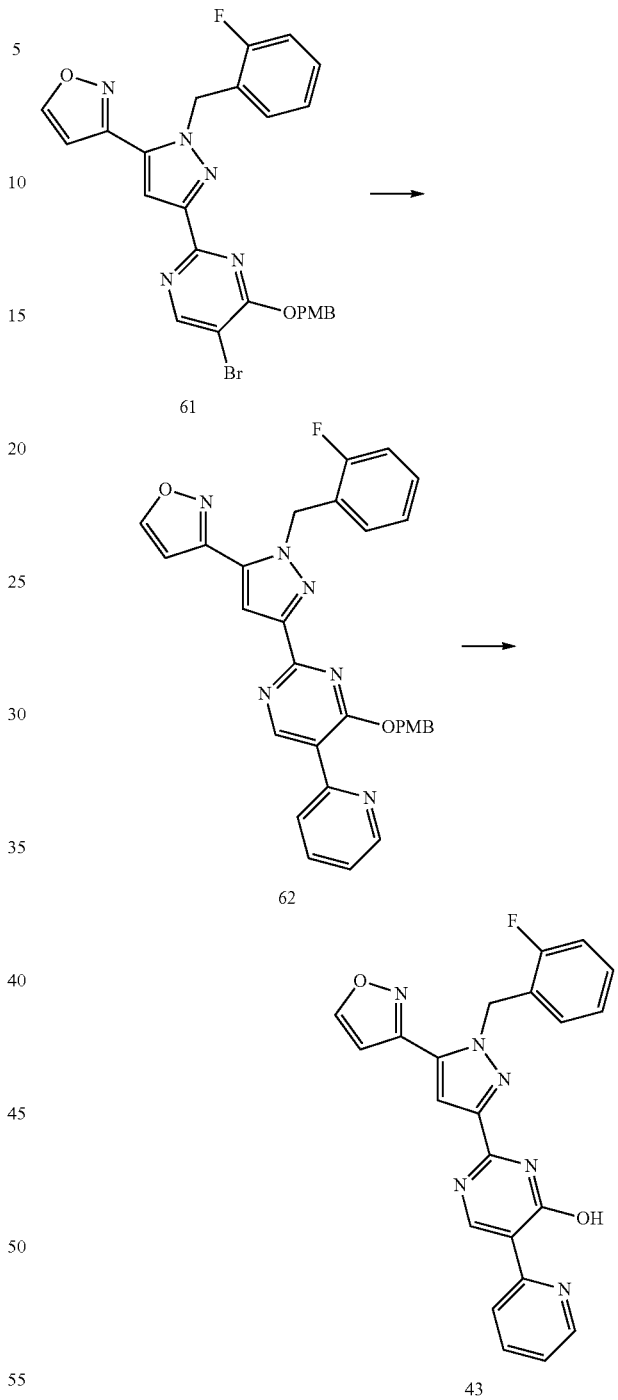

A mixture of Compound 46 (13 mg, 0.024 mmol) and trifluoroacetic acid (300 μl, 3.89 mmol) was stirred at room temperature for 20 minutes. The solution was diluted with dichloromethane (40 mL) and saturated aqueous sodium bicarbonate. The layers were separated and the aqueous layer was extracted with dichloromethane (2×50 mL). The organics were combined, dried over magnesium sulfate, filtered, and the solvent was removed under vacuum. Purification by silica gel chromatography (0-50% ethyl acetate in hexanes) provided Compound 45 (12 mg, quantitative yield) as a white solid.

Compound 45:

$^1$H-NMR (400 MHz, CDCl$_3$) δ 10.40 (s, 1H), 8.51 (d, 1H), 8.33 (s, 1H), 8.24 (d, 1H), 7.51-7.50 (m, 1H), 7.37 (dd, 1H), 7.32-7.26 (m, 2H), 7.09-7.04 (m, 3H), 6.60 (d, 1H), 5.91 (d, 2H).

A solution of 2-(tributylstannyl)pyridine (0.049 mL, 0.129 mmol), Compound 61 (46 mg, 0.086 mmol), and palladium tetrakistriphenylphosphine (30 mg, 0.026 mmol) was heated to 90° C. in dimethoxyethane (2 mL) for 1.5 hours. After removing the solvent in vacuo, purification by silica gel chromatography (0-65% ethyl acetate in hexanes) provided Compound 62. The intermediate was treated with trifluoroacetic acid (300 μl, 3.89 mmol) and stirred at room temperature for 20 minutes. The solution was then diluted with dichloromethane (40 mL) and saturated aqueous sodium bicarbonate. The layers were separated and the aqueous layer was extracted with dichloromethane (2×50 mL). The organics were combined, dried over magnesium sulfate, filtered, and the solvent was removed in vacuo. Purification by silica gel chromatography (0-5% methanol in dichloromethane) gave product contaminated with triphenyl phosphine byproducts. Further purification by trituration with diethyl ether (5 mL) provided Compound 43 (21 mg, 60%) as a tan solid.

Compound 43:

$^1$H-NMR (400 MHz, DMSO): δ 13.28 (br s, 1H), 9.43 (d, 1H), 9.21 (br s, 1H), 8.97-8.90 (m, 1H), 8.76 (br d, 1H), 8.20-8.12 (m, 1H), 8.08 (br s, 1H), 7.67-7.62 (m, 2H), 7.54-7.50 (m, 2H), 7.43 (t, 1H), 7.34-7.30 (m, 1H), 6.24 (s, 2H).

Compound 42

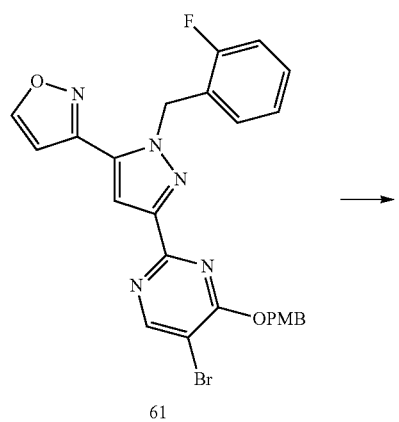

61

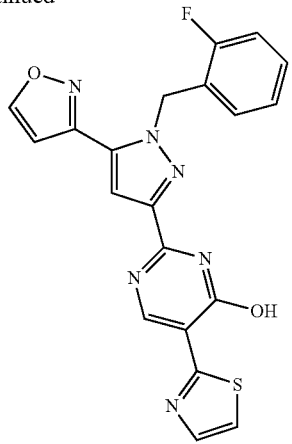

42

A solution of 2-(tributylstannyl)thiazole (21 mg, 0.056 mmol), Compound 61 (20 mg, 0.037 mmol), and palladium tetrakistriphenylphosphine (13 mg, 0.011 mmol) in dichloroethane (2 mL) was heated to 90° C. for 3.5 hours. The solvent was removed under vacuum, and purification by silica gel chromatography (0-60% ethyl acetate in hexanes) provided Compound 63 as a white solid.

Compound 63:

$^1$H NMR (400 MHz, CDCl$_3$) δ 9.56 (s, 1H), 8.47 (d, 1H), 7.93 (d, 1H), 7.52 (d, 2H), 7.48 (s, 1H), 7.42 (d, 1H), 7.22-7.18 (m, 1H), 7.06-6.97 (m, 2H), 6.93-6.90 (m, 3H), 6.61 (d, 1H), 6.02 (s, 2H), 5.71 (s, 2H), 3.81 (s, 3H).

Compound 63 (8 mg, 0.015 mmol) was treated with trifluoroacetic acid (300 µl, 3.89 mmol) and stirred at room temperature for 20 minutes. The solution was diluted with dichloromethane (40 mL) and saturated aqueous sodium bicarbonate. The layers were separated and the aqueous layer was extracted with dichloromethane (2×50 mL). The organics were combined, dried over magnesium sulfate, filtered, and the solvent was removed under vacuum. Purification by silica gel chromatography (0-5% methanol in dichloromethane) provided Compound 42 (2 mg, 16%) as a yellow solid.

Compound 42:

$^1$H-NMR (400 MHz, CDCl$_3$) δ 9.14 (s, 1H), 8.52 (s, 1H), 7.95 (d, 1H), 7.47 (d, 1H), 7.39 (s, 1H), 7.31-7.24 (m, 1H), 7.09-7.05 (m, 3H), 6.82 (s, 1H), 5.94 (s, 2H).

Compound 38

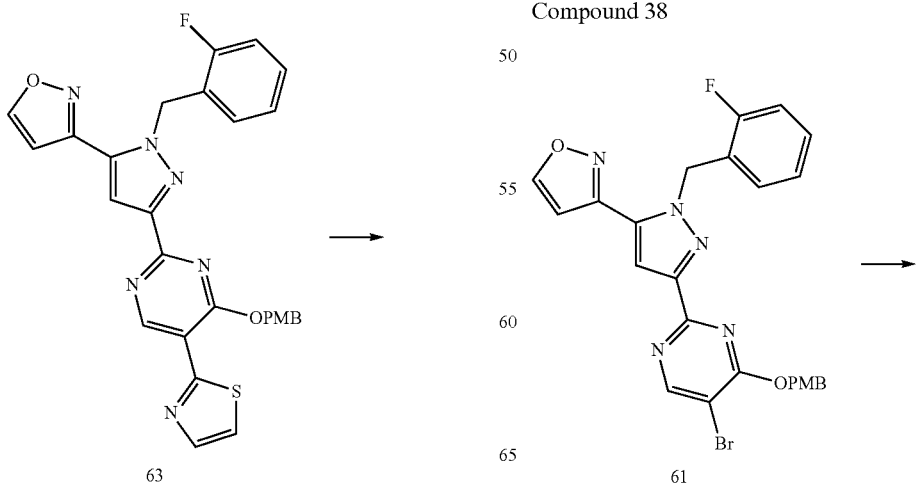

63    61

-continued

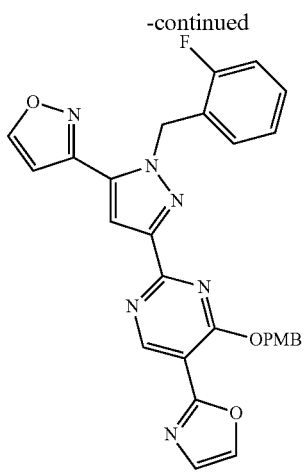

64

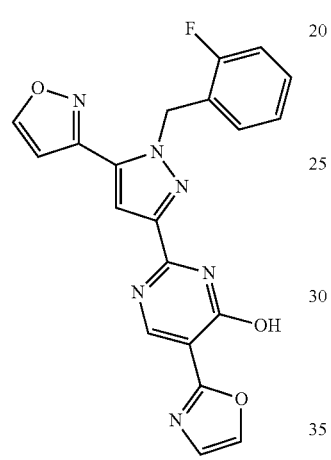

38

A solution of 2-(tributylstannyl)oxazole (20 mg, 0.056 mmol), Compound 61 (20 mg, 0.037 mmol), and palladium tetrakistriphenylphosphine (13 mg, 0.011 mmol) in dichloroethane (2 mL) was heated to 90° C. for 15 hours. The solvent was removed under vacuum and purification by silica gel chromatography (10-65% ethyl acetate in hexanes) provided Compound 64.

The residue was stirred at room temperature with trifluoroacetic acid (300 μl, 3.89 mmol) for 10 minutes and then diluted with dichloromethane (40 mL) and saturated aqueous sodium bicarbonate. The layers were separated and the aqueous layer was extracted with dichloromethane (2×50 mL). The organics were combined, dried over magnesium sulfate, filtered, and the solvent was removed in vacuo. The resulting white solid was triturated with diethyl ether (5 mL) to give Compound 38 (8 mg, 54%) as a white solid.

Compound 38:

$^1$H-NMR (400 MHz, MeOD) δ 8.86 (br s, 1H), 8.79 (s, 1H), 8.07 (s, 1H), 7.59 (s, 1H), 7.31-7.27 (m, 1H), 7.11-7.03 (m, 2H), 6.95-6.92 (m, 2H), 6.02 (s, 2H).

Intermediate 8F:

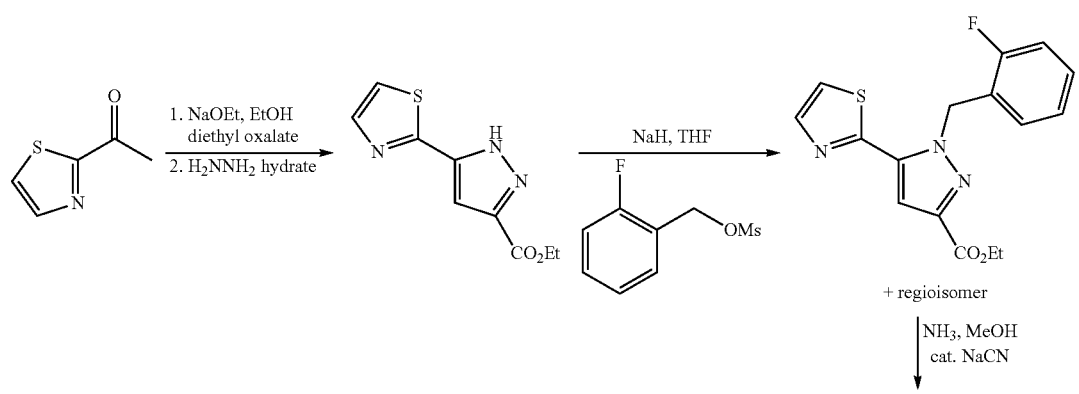

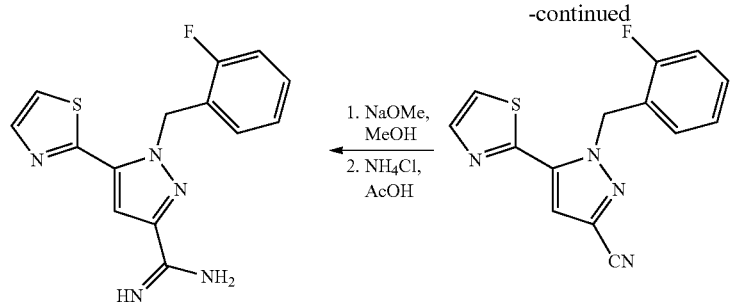 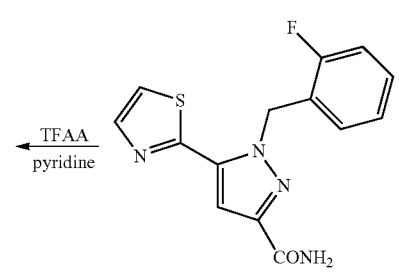

Step 1: Pyrazole Formation:

To a stirring solution of sodium ethoxide (10.70 g, 157 mmol) in EtOH (500 mL) was added diethyl oxalate (21.48 ml, 157 mmol) and 1-(thiazol-2-yl)ethanone (16.31 ml, 157 mmol). Reaction was stirred at rt overnight. At this time, hydrazine hydrate (7.71 ml, 157 mmol) followed by AcOH (9.00 ml, 157 mmol) were added and the reaction was heated to 50° C. and monitored by LC/MS. Once complete, reaction was concentrated almost to dryness (some residual EtOH remained). Addition of 300 mL water induced precipitation of the product (57% yield), which was filtered and dried overnight.

Step 2: Alkylation:

Ethyl 5-(thiazol-2-yl)-1H-pyrazole-3-carboxylate (from above, 11.0 g, 49.3 mmol) was dissolved in THF (100 mL) and consecutively treated with sodium hydride (1.97 g, 49.3 mmol) and 2-fluorobenzyl methanesulfonate (10.06 g, 49.3 mmol). Reaction was monitored by LC/MS. Once complete, the crude reaction was quenched with ammonium chloride and extracted with DCM (3×). The organic portions were combined, dried and filtered. The crude material was purified by flash chromatography using a 0-50% EtOAc/hexane gradient. The two regioisomers were not separated, therefore the mixture (total yield=98%) was carried on to the next step without any further purification or analysis.

Step 3: Amidation:

The regioisomeric mixture from above (20.00 g, 60.4 mmol) was transferred to a PARR reactor using 60 mL of a 7N ammonia in MeOH solution. The apparatus was sealed and placed in an oil bath heated to 125° C. The reaction was stirred over night. In the morning (~14 hours reaction time), the PARR reactor was removed from the oil bath and cooled to 0° C. before deconstructing the apparatus. Once opened, the contents were poured into a rb flask, where precipitation began to occur. This solid was deemed to be the undesired regioisomer by NMR analysis. Therefore, the desired was isolated via filtration followed by concentration. The material was carried on to the dehydration step without any further purification.

Step 4: Dehydration:

The crude amide from Step 3 was diluted with pyridine (40 mL) then charged with trifluoroacetic anhydride (2 equiv, drop-wise addition). The reaction progress was monitored closely by LC/MS analysis. Once complete, the reaction was diluted with 200 mL EtOAc then washed with a saturated aqueous solution of ammonium chloride. The organic portion was dried, filtered, and concentrated. The crude oil was then purified via normal phase chromatography employing a 0-75% EtOAc in hexane gradient to afford the desired product (5.2 g, 30% over three steps).

Step 5: Amidine Formation:

1-(2-fluorobenzyl)-5-(thiazol-2-yl)-1H-pyrazole-3-carbonitrile (5.2 g, 18.29 mmol) was diluted with MeOH (50 ml). Sodium hydride (1.317 g, 54.9 mmol) was carefully added, portion-wise (vigorous bubbling), and then the reaction was capped and heated to 65° C. After one hour, ammonium chloride (4.89 g, 91 mmol) and acetic acid (1.098 g, 18.29 mmol) were added and the reaction mixture was heated to 90° C. and stirred overnight. The reaction was then directly concentrated, partitioned between ethyl acetate and sodium carbonate (sat'd, aq), and transferred to a separation funnel. The layers were separated, and the aqueous portion was then back extracted with EtOAc (1×) and DCM (1×). The organics were combined, dried, filtered, and concentrated. The crude amidine (4.4 g, 80%) was taken on to the key cyclization step without any further purification.

Intermediate-8F:

$^1$H NMR (400 MHz, DMSO-d6) δ 7.98 (d, 1H), 7.91 (d, 1H), 7.38 (s, 1H), 7.35-7.29 (m, 1H), 7.21 (ddd, 1H), 7.10 (ddd, 1H), 6.86 (ddd, 1H), 6.62 (bs, 3H), 5.99 (s, 2H) ppm.

Compound 44

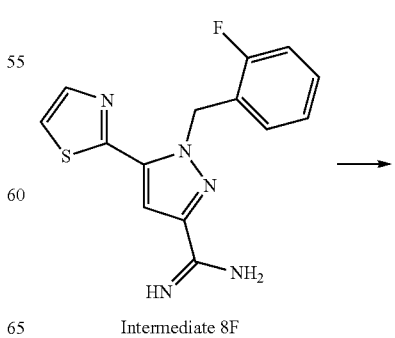

Intermediate 8F

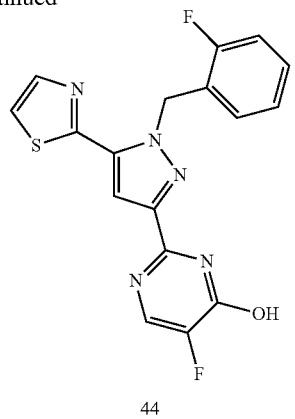

44

A solution of Intermediate 8F and ethyl 3-(dimethylamino)-2-fluoroacrylate (3 equiv) was stirred at 120° C. in ethanol for 4 h then at 80° C. for 10 h. The solvent was removed in vacuo and purification by silica gel chromatography (0-10% 7:1 acetonitrile/methanol in dichloromethane) delivered the desired compound as a white solid (29%).

Compound 44:

$^1$H NMR (400 MHz, DMSO-d$_6$) δ 13.24 (bs, 1H), 8.10 (bs, 1H), 7.97 (d, 1H), 7.92 (d, 1H), 7.51 (s, 1H), 7.32-7.26 (m, 1H), 7.20-7.15 (m, 1H), 7.08 (ddd, 1H), 7.00-6.94 (m, 1H), 6.01 (s, 2H).

Intermediate 8H:

the reaction was heated at 90° C. for 2 h. At this juncture, the reaction mixture was filtered through celite and concentrated. The crude product was added to a 240 g silica gel column and was purified with a gradient of 0% to 40% EtOAc/hexanes to afford the desired product (2.46 g, 20% yield).

Step 2: Amidation:

To a 40 mL vial was added ethyl 1-(2-fluorobenzyl)-5-(oxazol-4-yl)-1H-pyrazole-3-carboxylate (from above, 1.06 g, 3.38 mmol) and sodium cyanide (8.28 mg, 0.169 mmol). Ammonia (7N, 14.47 ml, 101 mmol) in methanol was added, and the solution was heated to 90° C. for 15.5 h. By LCMS, no sm remains at this point. The solvent was removed in vacuo to give an orange solid which was used directly without any further purification or analysis.

Step 3: Dehydration:

To a solution of 1-(2-fluorobenzyl)-5-(oxazol-4-yl)-1H-pyrazole-3-carboxamide (0.967 g, 3.38 mmol) in pyridine (8 mL) at 0° C. was added TFAA (0.954 mL, 6.76 mmol) over the course of 2 min. The brown solution was immediately warmed to RT and stirred for an additional 1.1 hr, at which point LCMS indicated the presence of the desired product (LCMS m/z 269.2 (M+1)). The solution was poured into DCM and water. The layers were separated, and the organics were dried over MgSO$_4$, filtered, and the solvent was removed in vacuo to give the crude product as a brown oil. The crude product was added to a 120 g silica gel column and was purified with a gradient of 0% to 40% EtOAc/hexanes to afford the desired nitrile compound as a light yellow oil (837 mg, 92% yield).

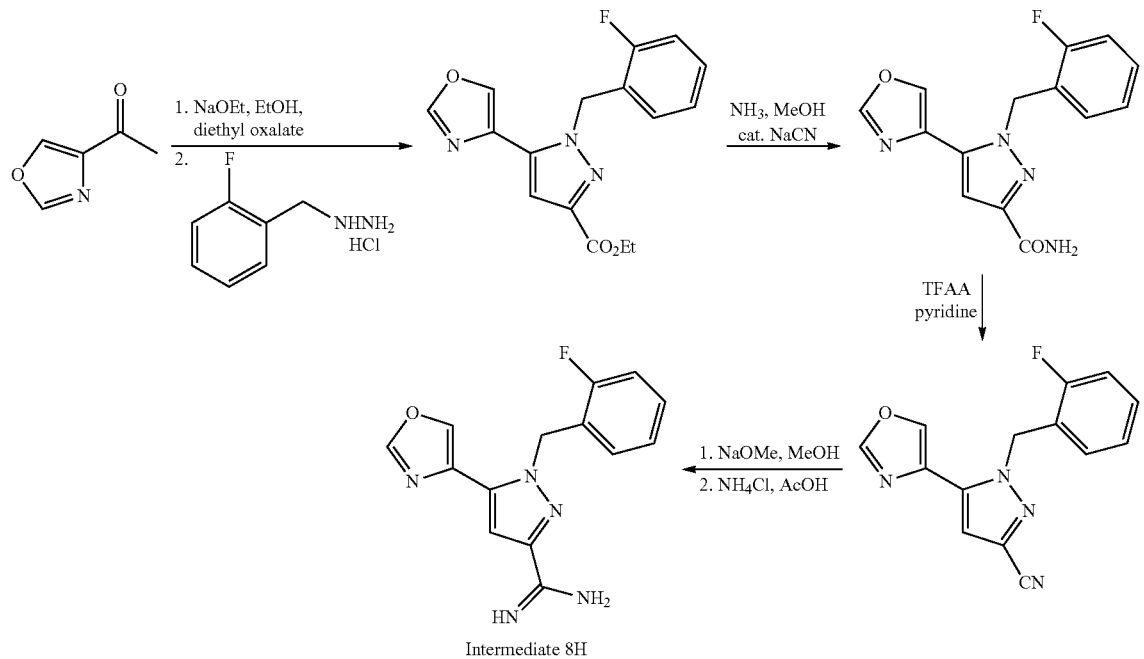

Intermediate 8H

Step 1: Pyrazole Formation:

To an ice cooled solution of sodium ethoxide (2.90 g, 40.5 mmol) in EtOH (193 ml) was added 1-(oxazol-4-yl)ethanone (4.28 g, 38.5 mmol) followed by diethyl oxalate (5.23 ml, 38.5 mmol). The bath was removed and reaction stirred at rt for 4.5 h (see LCMS m/z 210.1 (M−1)). The reaction was then heated at 75° C. for 1.25 h. At this time, (2-fluorobenzyl) hydrazine hydrochloride (6.80 g, 38.5 mmol) was added, and $^1$H NMR (400 MHz, CDCl$_3$) δ 7.98 (d, 1H), 7.86 (d, 1H), 7.31-7.26 (m, 1H), 7.09-7.03 (m, 2H), 6.97 (ddd, 1H), 6.90 (s, 1H), 5.79 (s, 2H) ppm.

Step 4: Amidine Formation:

To a stirred solution of 1-(2-fluorobenzyl)-5-(oxazol-4-yl)-1H-pyrazole-3-carbonitrile (837.2 mg, 3.12 mmol) in methanol (0.126 mL, 3.12 mmol) was added sodium hydride (499 mg, 12.48 mmol) portion-wise over 5 min (gas evolution). After addition of base and gas evolution had ceased, the vial was sealed and heated to 60° C. for 2 h and to 70° C. for 1.5 h. At this point, ammonium chloride (640 mg, 11.97 mmol) was added, followed by acetic acid (0.137 mL, 2.393 mmol) and the reaction mixture was heated to 70° C. for 3 h (confirmation of product by LC/MS: m/z 286.2 (M+1)). The solution was then poured into ethyl acetate and water. The layers were separated, and the aqueous layer was back-extracted with ethyl acetate. The organics were combined, washed with water, dried over MgSO4, filtered, and the solvent was removed in vacuo to give the desired 1-(2-fluorobenzyl)-5-(oxazol-4-yl)-1H-pyrazole-3-carboximidamide (Intermediate 8F, 751.9 mg, 2.64 mmol, 84% yield) as a brown oil, which was directly used without further purification or analysis.

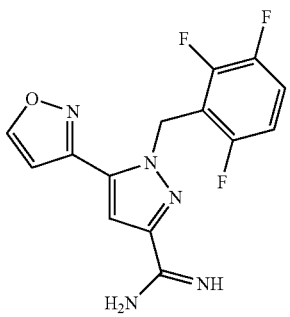

Intermediate-8I

Intermediate-8I was accessed via General Procedure A in 34% yield from 1-(isoxazol-3-yl)ethanone using (2,3,6-trifluorobenzyl)hydrazine hydrochloride in the first step.

Compound 48

Compound 19

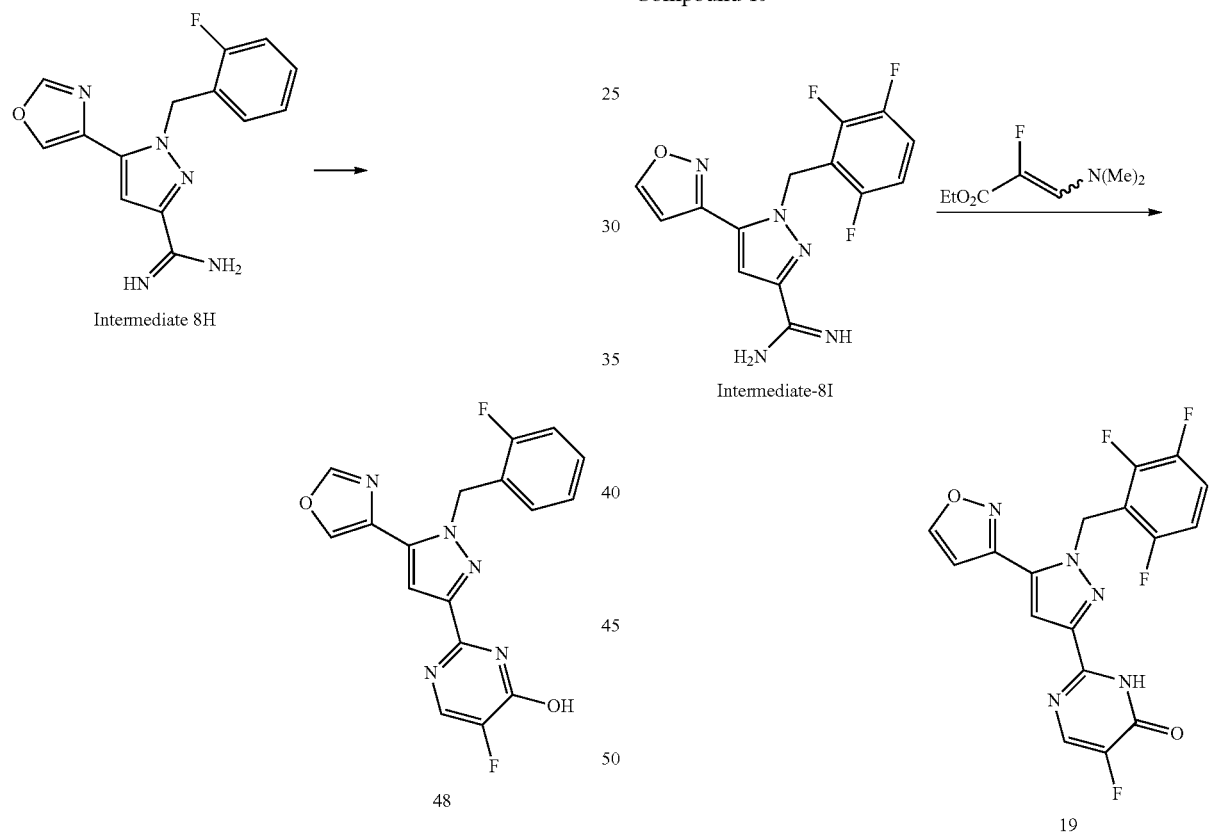

A solution of Intermediate 8H and ethyl 3-(dimethylamino)-2-fluoroacrylate (3 equiv) was stirred at 95° C. for 14 h. The solvent was removed in vacuo and purification by silica gel chromatography (0-10% methanol in dichloromethane) followed by washing with diethyl ether delivered the desired compound as an off-white solid (2%).

Compound 48:
$^1$H NMR (400 MHz, DMSO-d6) δ 13.14 (bs, 1H), 8.67 (s, 1H), 8.58 (d, 1H), 8.10 (bs, 1H), 7.33-7.27 (m, 1H), 7.25 (s, 1H), 7.20-7:15 (m, 1H), 7.09 (ddd, 1H), 5.83 (s, 2H) ppm.

A solution of ethyl 3-(dimethylamino)-2-fluoroacrylate (151 mg, 0.934 mmol), 1,8-diazabicyclo[5.4.0]undec-7-ene (95 mg, 0.62 mmol) and Intermediate-8I (100 mg, 0.311 mmol) in ethanol (2.1 mL) was stirred at 85° C. for 36 hours. Additional ethanol (2 mL) and acrylate (~3 equiv) was added and stirred at 85° C. for an additional 48 hours and then 72 hours at room temperature. The solvent was removed in vacuo and purification by silica gel chromatography (0-5% methanol in dichloromethane) provided impure product. Trituration with diethyl ether (5 mL) provided 5-fluoro-2-(5-(isoxazol-3-yl)-1-(2,3,6-trifluorobenzyl)-1H-pyrazol-3-yl)pyrimidin-4-ol (12 mg, 10% yield) as a white solid.

Compound 19:

¹H-NMR (400 MHz, CDCl₃) δ 10.15 (br s, 1H), 8.56 (d, 1H), 7.88 (d, 1H), 7.21-7.15 (m, 2H), 6.90-6.85 (m, 1H), 6.66 (d, 1H), 5.94 (s, 2H).

Compound 15

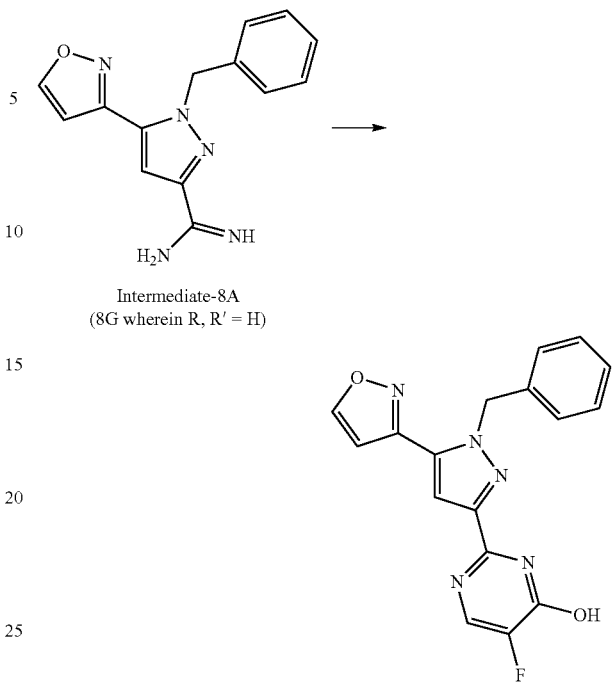

To a solution of Intermediate-8I (107 mg, 0.33 mmol) in pyridine (2 mL) was added a mixture of E- and Z-3-ethoxyacrylonitrile (97 mg, 0.999 mmol). The solution was stirred at 85° C. for 48 hours, and then for another 3 days at room temperature. The solvent was removed in vacuo and purification by silica gel chromatography (0-8% methanol in dichloromethane) provided product Compound 15 (74 mg, 60% yield) as a tan solid.

Compound 15:

¹H-NMR (400 MHz, d₆-DMSO) δ 9.14 (d, 1H), 8.10 (d, 1H), 7.58-7.49 (m, 1H), 7.42 (s, 1H), 7.27 (d, 1H), 7.19-7.15 (m, 1H), 6.94 (s, 2H), 6.35 (d, 1H), 5.94 (s, 2H).

Intermediate-8A

This intermediate (Intermediate 8G wherein R, R'=H) was accessed via General Procedure A in 27% yield from starting 1-(isoxazol-3-yl)ethanone using benzyl hydrazine hydrochloride in the first step.

Intermediate-8A:

¹H NMR (400 MHz, MeOD) δ 8.79 (d, 1H), 7.32-7.20 (m, 6H), 6.81 (d, 1H), 5.86 (s, 2H).

Compound 41

Intermediate-8A (75 mg, 0.281 mmol) and ethyl 3-(dimethylamino)-2-fluoroacrylate (256 mg, 0.842 mmol) were combined and heated neat at 85° C. for 16 hours. An additional 2 equiv of ester was added and the reaction mixture stirred for another 24 hours. The solvent was removed in vacuo and purification of the resulting residue by silica gel chromatography (0-10% methanol in dichloromethane) provided impure solid that was triturated with diethyl ether (5 mL) to give Compound 41 (19 mg 20%) as a pale pink solid.

Compound 41:

¹H-NMR (400 MHz, DMSO-d₆) δ 13.31 (br s, 1H), 9.12 (d, 1H), 8.15 (br s, 1H), 7.62 (s, 1H), 7.34-7.22 (m, 7H), 5.85 (s, 2H).

Intermediate-8B

This intermediate (Intermediate 8G wherein R, R'=F) was accessed starting from Intermediate-5 using General Procedure A in 57% yield for the three final steps.

Intermediate-8B:

¹H NMR (400 MHz, MeOD) δ 8.80 (d, 1H), 7.32 (s, 1H), 7.18 (q, 1H), 7.07-7.02 (m, 1H), 6.87 (d, 1H), 6.74-6.70 (m, 1H), 5.96 (s, 2H).

Compound 1

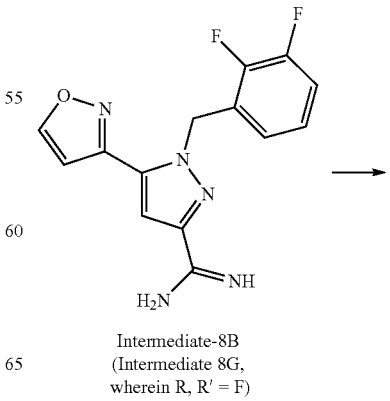

-continued

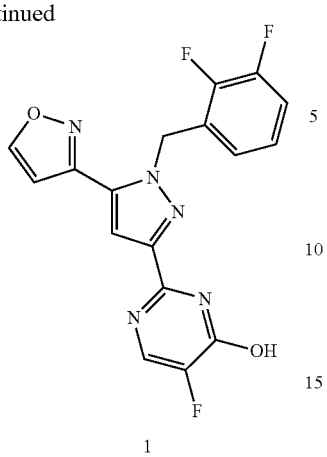

1

Intermediate-8B (165 mg, 0.544 mmol) and ethyl 3-(dimethylamino)-2-fluoroacrylate (263 mg, 1.632 mmol) were heated in ethanol (5 mL) at 85° C. for 44 hours. 1,8-Diazabicycloundec-7-ene (0.164 mL, 1.088 mmol) and additional ethyl 3-(dimethylamino)-2-fluoroacrylate (263 mg, 1.632 mmol) were added and stirring continued at 85° C. for 24 hours. The solvent was removed in vacuo and purification by silica gel chromatography (0-60% ethyl acetate in dichloromethane, followed by 0-5% methanol in dichloromethane) delivered impure product. The semi-pure solid was triturated with diethyl ether, filtered, and washed with a small amount of dichloromethane to remove the orange-colored impurity to deliver Compound 1 (54 mg, 27%) as a white solid.

Compound 1:
$^1$H-NMR (400 MHz, MeOD) δ 8.78 (d, 1H), 8.02 (d, 1H), 7.46 (s, 1H), 7.16 (q, 1H), 7.05-7.00 (m, 1H), 6.91 (d, 1H), 6.73-6.70 (m, 1H), 6.02 (s, 2H).

Compound 8

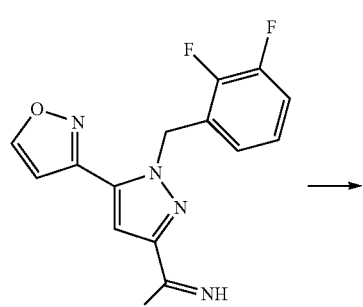

Intermediate-8B

-continued

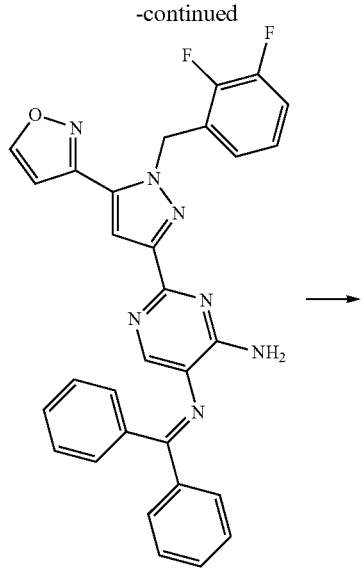

Intermediate-9

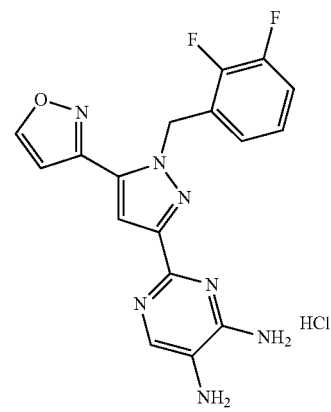

8

Intermediate-8B (300 mg, 0.99 mmol) and 3-(dimethylamino)-2-(diphenylmethyleneamino)acrylonitrile (681 mg, 2.47 mmol) were dissolved in pyridine (5.5 mL). 1,8-Diazabicycloundec-7-ene (300 μl, 2.0 mmol) was added, and the solution was heated to 110° C. for 16 hours. The solvent was removed in vacuum and purification by silica gel chromatography (10-100% ethyl acetate in hexanes) provided Intermediate-9 (96 mg, 18%) as a yellow solid.

To a solution of Intermediate-9 (96 mg, 0.180 mmol) in tetrahydrofuran (1.8 mL) was added aqueous 3N hydrochloric acid (1.4 mL). After stirring for 15 minutes at room temperature, the solvent was removed in vacuo. Diethyl ether (15 mL) was added, and after stirring for 20 minutes, the solids were filtered off to give Compound 8 (60 mg, 82%) as a brown solid.

Compound 8:
$^1$H-NMR (400 MHz, MeOD) δ 8.82 (d, 1H), 7.47 (s, 2H), 7.18 (q, 1H), 7.06-7.01 (m, 1H), 6.90 (d, 1H), 6.79-6.75 (m, 1H), 6.01 (s, 2H).

Compound 37

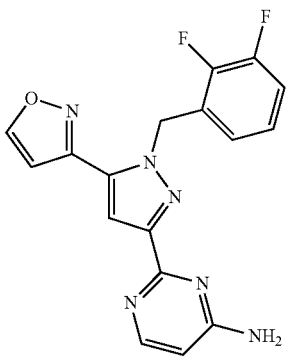

A mixture 1-(2,3-difluorobenzyl)-5-(isoxazol-3-yl)-1H-pyrazole-3-carboximidamide (Intermediate-8B, 600 mg, 1.64 mmol), 3-ethoxyacrylonitrile (0.850 ml, 8.26 mmol, mixture of E and Z), and DBU (0.498, 3.30 mmol) in pyridine (10 mL) was stirred at 110° C. until the reaction was complete by LC/MS analysis. At this point, the reaction mixture was concentrated in vacuo and purified using column chromatography (0-10% MeOH/DCM) to provide the desired product as an off-white solid (40%).

Compound 37:

$^1$H NMR (400 MHz, DMSO-d6) δ 9.10 (d, 1H), 8.13 (d, 1H), 7.53 (s, 1H), 7.41-7.33 (m, 1H), 7.25 (d, 1H), 7.16-7.10 (m, 1H), 6.97 (bs, 2H), 6.72-6.68 (m, 1H), 6.37 (d, 1H), 5.93 (s, 2H) ppm.

Compound 10

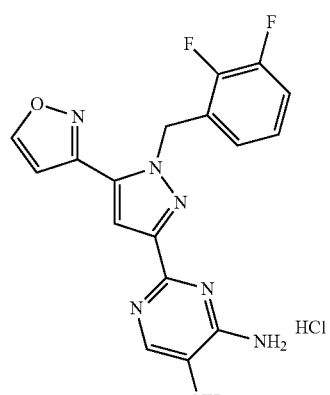

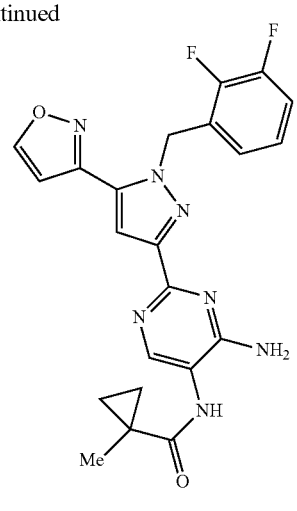

To a solution of 1-methylcyclopropanecarboxylic acid (25 equiv) in dichloromethane was added oxalyl chloride (22.1 equiv) and catalytic N,N-dimethylformamide. Once gas evolution ceased, this crude reaction mixture was added portion-wise to a suspension of Compound 8 (1 equiv) in dichloromethane/pyridine (3:1) until complete consumption of starting material was observed by LS/MS. After an aqueous ammonium chloride and dichloromethane workup, column chromatography (0-10% methanol in dichloromethane) provided the desired compound as a light brown solid (59%).

Compound 10:

$^1$H-NMR (400 MHz, MeOD) δ 8.76 (d, 1H), 8.08 (s, 1H), 7.42 (s, 1H), 7.14 (q, 1H), 7.03-6.98 (m, 1H), 6.88 (d, 1H), 6.66 (t, 1H), 5.98 (s, 2H), 1.48 (s, 3H), 1.25-1.22 (m, 2H), 0.74-0.72 (m, 2H).

Compound 40

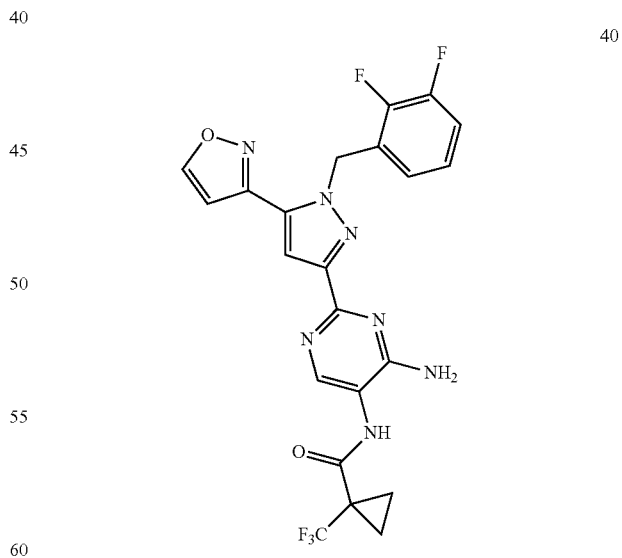

To a solution of 1-(trifluoromethyl)cyclopropanecarboxylic acid (0.159 g, 1.03 mmol) in DCM was added oxalyl chloride (0.081 ml, 0.928 mmol) and catalytic DMF. Once gas evolution ceased, this crude reaction mixture was added portion-wise to a suspension of 2-(1-(2,3-difluorobenzyl)-5-(isoxazol-3-yl)-1H-pyrazol-3-yl)pyrimidine-4,5-diamine hydrochloride (Compound 8, 40 mg, 0.100 mmol) in dichloromethane/pyridine (2 ml/2 ml) until complete consumption of starting material was observed by LS/MS. After an ammonium chloride (saturated aqueous) and dichloromethane workup, column chromatography (0-10% MeOH/DCM) provided the desired product as an off-white solid (36%).
Compound 66:
¹H NMR (400 MHz, DMSO-d6) δ 9.10 (d, 1H), 9.07 (s, 1H), 8.08 (s, 1H), 7.56 (s, 1H), 7.41-7.33 (m, 1H), 7.27 (d, 1H), 7.16-7.10 (m, 1H), 6.92 (bs, 2H), 6.73-6.68 (m, 1H), 5.94 (s, 2H), 1.69-1.64 (m, 2H), 1.32 (dd, 2H) ppm.
Compound 36

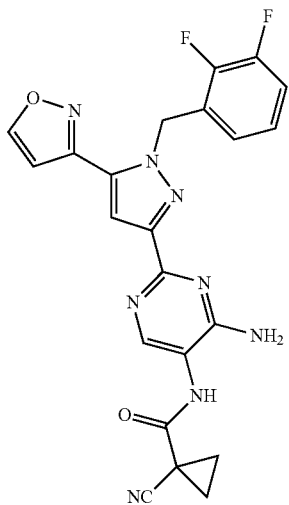

To a solution of 1-cyanocyclopropanecarboxylic acid (0.110 g, 0.986 mmol) in DCM was added oxalyl chloride (0.078 ml, 0.887 mmol) and catalytic DMF. Once gas evolution ceased, this crude reaction mixture was added portionwise to a suspension of 2-(1-(2,3-difluorobenzyl)-5-(isoxazol-3-yl)-1H-pyrazol-3-yl)pyrimidine-4,5-diamine hydrochloride (40 mg, 0.100 mmol) in dichloromethane/pyridine (2 mL/2 mL) until complete consumption of starting material was observed by LS/MS. After an ammonium chloride (saturated aqueous) and dichloromethane workup, column chromatography (0-10% MeOH/DCM) provided the desired product as an off-white solid (24%).
Compound 36:
¹H NMR (400 MHz, DMSO-d6) δ 9.42 (s, 1H), 9.10 (d, 1H), 8.04 (s, 1H), 7.55 (s, 1H), 7.41-7.33 (m, 1H), 7.26 (d, 1H), 7.16-7.09 (m, 1H), 7.04 (bs, 2H), 6.72-6.67 (m, 1H), 5.94 (s, 2H), 1.71-1.65 (m, 4H) ppm.
Compound 80

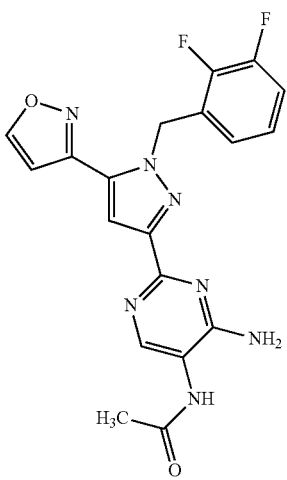

2-(1-(2,3-difluorobenzyl)-5-(isoxazol-3-yl)-1H-pyrazol-3-yl)pyrimidine-4,5-diamine hydrochloride (Compound 8, 50 mg, 0.123 mmol) was charged with acetic acid (2 mL) and resulting solution was heated to 100° C. until complete consumption of SM was noted by LC/MS analysis. At this time, the reaction mixture was concentrated and the crude material was diluted with dichloromethane (50 mL) and neutralized with a saturated solution of sodium carbonate. The layers were separated and the organic portion was dried (sodium sulfate), filtered, and concentrated. The crude material was purified via column chromatography using a 0-10% methanol in DCM gradient to afford the desired product in 40% yield.
Compound 80:
¹H-NMR (400 MHz, DMSO-d₆) δ 9.21 (s, 1H), 9.10 (d, 1H), 8.32 (s, 1H), 7.53 (d, 1H), 7.40-7.33 (m, 1H), 7.26 (dd, 1H), 7.15-7.10 (m, 1H), 6.92 (bs, 2H), 6.69 (t, 1H), 5.93 (s, 2H), 2.06 (s, 3H).
Compound 84

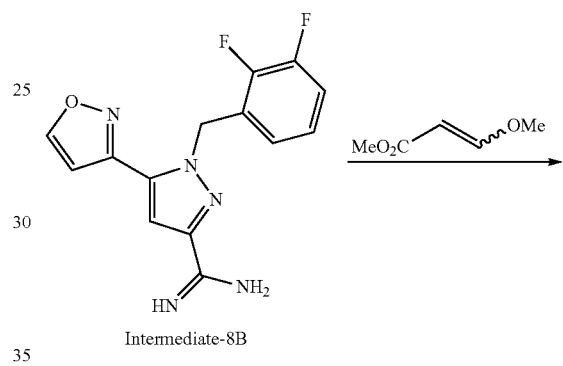

Intermediate-8B

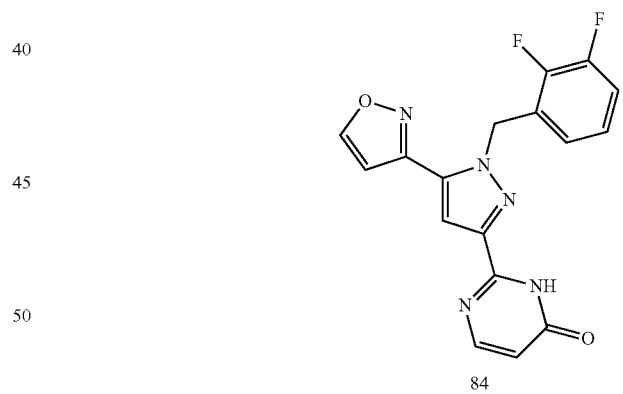

84

A solution of methyl 3-methoxyacrylate (1.2 g, 10.5 mmol), 1,8-diazabicyclo[5.4.0]undec-7-ene (128 mg, 0.838 mmol) and 1-(2,3-difluorobenzyl)-5-(isoxazol-3-yl)-1H-pyrazole-3-carboximidamide (Intermediate-8B, 127 mg, 0.42 mmol) in ethanol was stirred at 90° C. for 1 hour. The solvent was removed in vacuo, and purification by silica gel chromatography (0-10% methanol in dichloromethane) afforded Compound 84 (85% yield).

Compound 84:
¹H-NMR (400 MHz, CD₃OD) δ 8.71 (d, 1H), 7.90 (bs, 1H), 7.41 (s, 1H), 7.12-7.05 (m, 1H), 6.98-6.92 (m, 1H), 6.84 (d, 1H), 6.65 (t, 1H), 6.28 (d, 1H), 5.95 (s, 2H).

Compound 76

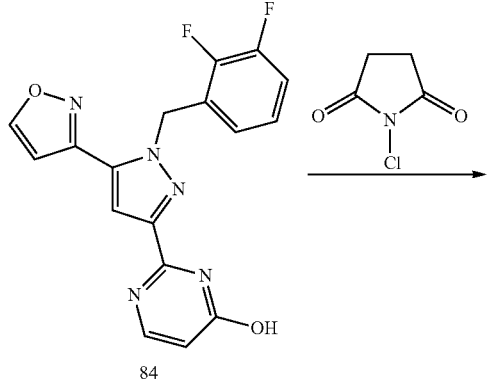

84

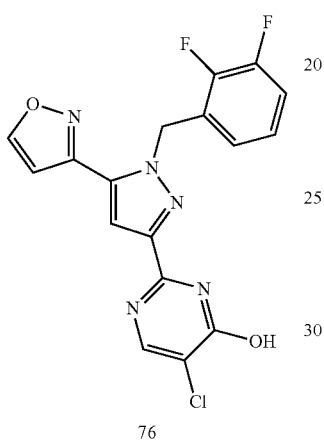

76

To a solution of Compound 84 in DMF (1.6 mL) was added N-chlorosuccinimide (43 mg, 0.32 mmol). The solution was stirred at 70° C. for 2 hours, followed by stirring at 80° C. for 1 hour. The contents were diluted with ethyl acetate (10 mL) and water (10 mL). The layers were separated, and the aqueous layer was further diluted with water (20 mL). The aqueous layer was extracted with ethyl acetate (3×20 mL) and dichloromethane (2×20 mL). The organics were washed with brine (10 mL), dried over MgSO$_4$, filtered, and the solvent was removed in vacuo. Trituration of the resulting solids with diethyl ether (2×5 mL) provided Compound 76 (77 mg, 62% yield) as an off-white solid.

Compound 76:

$^1$H-NMR (400 MHz, DMSO-d$_6$) δ 13.28 (br s, 1H), 9.13 (s, 1H), 8.29 (br s, 1H), 7.70 (s, 1H), 7.43-7.33 (m, 1H), 7.25 (s, 1H), 7.18-7.09 (m, 1H), 6.86 (br s, 1H), 5.95 (s, 2H).

Intermediate-8D

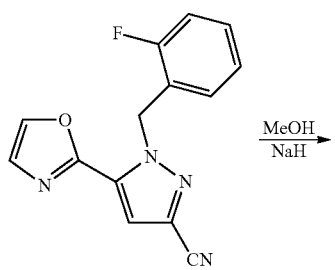

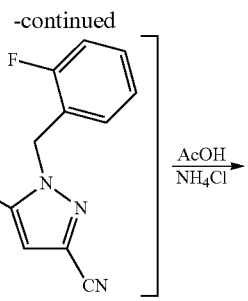

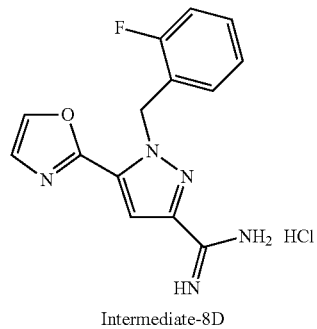

Intermediate-8D

To a stirring solution of 1-(2-fluorobenzyl)-5-(oxazol-2-yl)-1H-pyrazole-3-carbonitrile (1 equiv) in methanol was added sodium hydride (2 equiv). The reaction was stirred at 60° C. for 2 hr. The reaction was then treated with acetic acid (1 equiv) and ammonia hydrochloride (5 equiv) and the temp was raised to 75° C. Once LC/MS analysis showed consumption of starting material (typically 12 hr), a basic aqueous work-up followed by a wash with cold hexanes afforded the resulting desired solid, 11-(2-fluorobenzyl)-5-(oxazol-2-yl)-1H-pyrazole-3-carboximidamide hydrochloride salt (69%). This intermediate was carried forward without any further purification or characterization.

Intermediate-8D:

$^1$H NMR (400 MHz, CDCl$_3$) 6.01-6.06 (m, 5H), 6.89-6.93 (m, 1H), 6.99 7.07 (m, 2H), 7.20-7.30 (m, 3H), 7.70 (s, 1H).

Compound 7

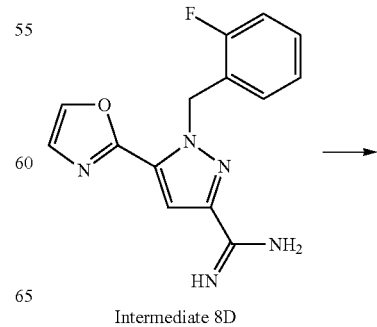

Intermediate 8D

-continued

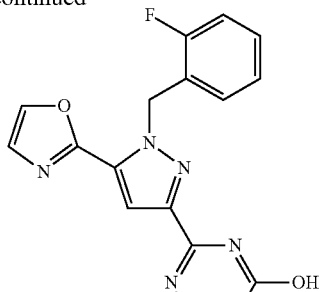

7

A solution of Intermediate 8D (1 equiv) and (E)-ethyl 3-(dimethylamino)-2-(pyridin-2-ylthio)acrylate (4 equiv) was stirred neat at 100° C. for 14 hours. Purification by silica gel chromatography (0-50% 7:1 acetonitrile:methanol in dicloromethane) delivered desired product 2-(1-(2-fluorobenzyl)-5-(oxazol-2-yl)-1H-pyrazol-3-yl)-5-(pyridin-2-ylthio)pyrimidin-4-ol as a solid (3%).

Compound 7:
$^1$H NMR (400 MHz, CDCl$_3$) δ 6.06 (s, 2H) 6.99-7.12 (m, 5H) 7.22 (s, 1H) 7.29 (s, 1H) 7.49-7.55 (m, 2H) 7.76 (s, 1H) 8.34-8.39 (m, 2H).

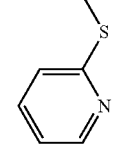

Intermediate 8D

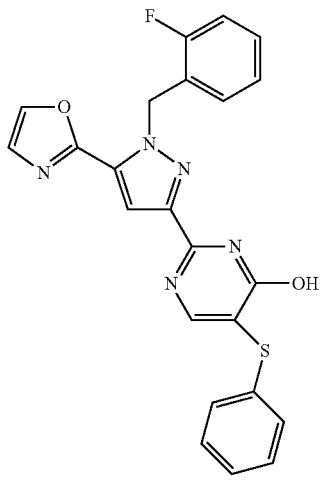

20

Compound 20

A solution of Intermediate 8D (1 equiv) and (E)-ethyl 3-(dimethylamino)-2-(phenylthio)acrylate (4 equiv) was stirred neat at 100° C. for 14 hours. Purification by silica gel chromatography (0-50% 7:1 acetonitrile:methanol in dicloromethane) delivered desired product 2-(1-(2-fluorobenzyl)-5-(oxazol-2-yl)-1H-pyrazol-3-yl)-5-(phenylthio)pyrimidin-4-ol as a solid (16%).

Compound 20:
$^1$H NMR (400 MHz, CDCl$_3$) δ 6.04 (s, 2H) 7.00-7.12 (m, 3H) 7.22-7.29 (m, 3H) 7.31-7.39 (m, 3H) 7.42 (s, 1H) 7.48 (dd, J=7.63, 1.37 Hz, 2H) 7.66 (s, 1H) 7.73 (s, 1H).

Intermediate-00

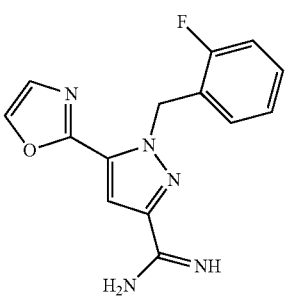

Intermediate-8D

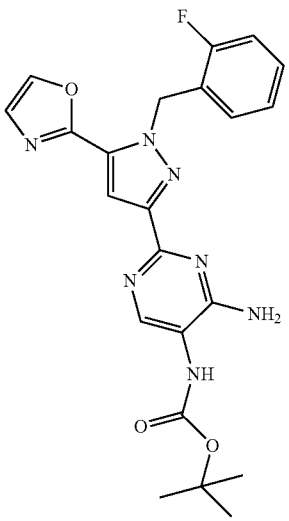

Intermediate-21

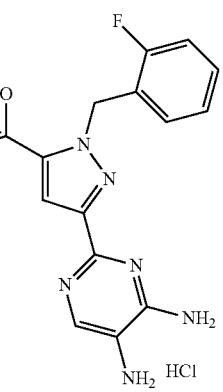

Intermediate-00

A solution of Intermediate-8D (Analogous to Intermediate 8G in General Scheme A, wherein the isoxazole is now an oxazole on the north west and R═F, R'═H) was stirred neat at 110° C. for 14 h. The reaction mixture was purified by silica gel chromatography (0-100% 7:1 acetonitrile:methanol in dichloromethane) to deliver Intermediate-21 as a solid (15.1%).

Intermediate-21:

$^1$H NMR (400 MHz, CDCl$_3$) 8.31 (s, 1H), 7.67 (s, 1H), 7.55 (t, 1H), 7.19 (s, 1H), 7.15 (t, 1H), 6.99 (t, 1H), 6.92 (t, 1H), 6.77 (dt, 1H), 6.69-6.72 (m, 1H), 6.10 (s, 2H), 5.61 (br. s, 2H), 1.44 (s, 9H).

A solution of Intermediate-21 (1 equiv) and 4N HCl (50 equiv) was stirred under ambient conditions for 2 hr. The reaction mixture was concentrated under vacuum and triturated with ethyl ether to afford Intermediate-00 as a solid (88%).

Intermediate-00:

$^1$H NMR (400 MHz, CD$_3$OD) δ 8.06 (s, 1H), 7.55 (s, 1H), 7.46 (s, 1H), 7.37 (s, 1H), 7.28-7.33 (m, 1H), 7.05-7.13 (m, 2H), 6.98-7.01 (tt, 1H), 6.14 (s, 2H).

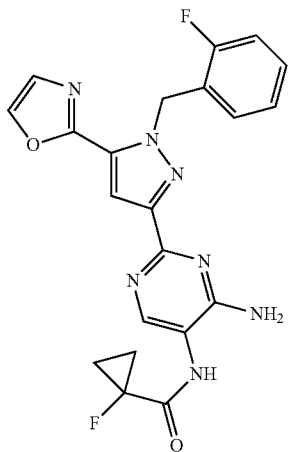

Compound 31

To a solution of 1-fluorocyclopropanecarboxylic acid (12 equiv) in dichloromethane was added oxalyl chloride (10.6 equiv) and catalytic N,N-dimethylformamide. Once gas evolution ceased, this crude reaction mixture was added portionwise to a suspension of 2-(1-(2-fluorobenzyl)-5-(oxazol-2-yl)-1H-pyrazol-3-yl)pyrimidine-4,5-diamine hydro chloride Intermediate-00 (1 equiv) in dichloromethane/pyridine (2:1) until complete consumption of starting material was observed by LS/MS. After an aqueous ammonium chloride and dichloromethane workup, column chromatography (0-5% methanol in dichloromethane) provided the desired compound as a tan solid (75%).

Compound 31:

$^1$H-NMR (400 MHz, MeOD) δ 8.19 (s, 1H), 7.96 (s, 1H), 7.50 (s, 1H), 7.27-7.21 (m, 2H), 7.08-6.99 (m, 2H), 6.86-6.83 (m, 1H), 6.07 (s, 2H), 1.43-1.38 (m, 4H).

Compound 47

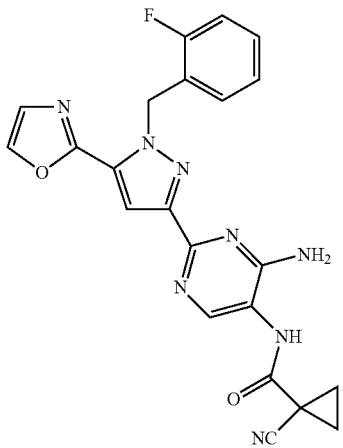

To a solution of 1-cyanocyclopropanecarboxylic acid (10 equiv) in dichloromethane was added oxalyl chloride (9 equiv) and catalytic N,N-dimethylformamide. Once gas evolution ceased, this crude reaction mixture was added portionwise to a suspension of 2-(1-(2-fluorobenzyl)-5-(oxazol-2-yl)-1H-pyrazol-3-yl)pyrimidine-4,5-diamine hydrochloride Intermediate-00 (1 equiv) in dichloromethane/pyridine (2:1) until complete consumption of starting material was observed by LC/MS. After an aqueous ammonium chloride and dichloromethane workup, column chromatography (50-100% ethyl acetate in hexanes) provided the desired product N-(4-amino-2-(1-(2-fluorobenzyl)-5-(oxazol-2-yl)-1H-pyrazol-3-yl)pyrimidin-5-yl)-1-cyanocyclopropanecarboxamide as a solid (13%).

Compound 47:

$^1$H NMR (400 MHz, CDCl$_3$) δ 1.53-1.64 (m, 2H) 1.70-1.84 (m, 2H) 5.35 (s, 2H) 6.06 (s, 2H) 6.73 (t, J=7.43 Hz, 1H) 6.82-7.01 (m, 2H) 7.06-7.12 (m, 1H) 7.14 (s, 1H) 7.52 (s, 1H) 7.62 (s, 1H) 7.98 (s, 1H) 8.25 (s, 1H).

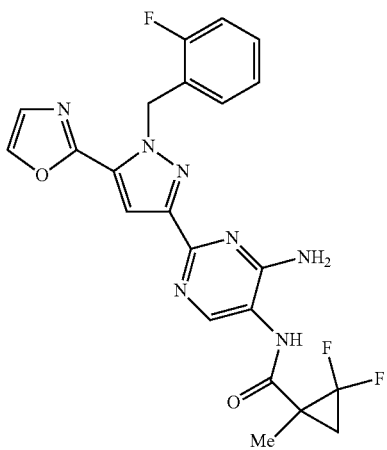

Compound 55

To a solution of 2,2-difluoro-1-methylcyclopropanecarboxylic acid (10 equiv) in dichloromethane was added oxalyl chloride (9 equiv) and catalytic N,N-dimethylformamide. Once gas evolution ceased, this crude reaction mixture was added portion-wise to a suspension of 2-(1-(2-fluorobenzyl)-5-(oxazol-2-yl)-1H-pyrazol-3-yl)pyrimidine-4,5-diamine hydrochloride Intermediate-00 (1 equiv) in dichloromethane/pyridine (2:1) until complete consumption of starting material was observed by LC/MS. After an aqueous ammonium chloride and dichloromethane workup, column chromatography (50-100% ethyl acetate in hexanes) provided Compound 55 (27%).

Compound 55:
$^1$H NMR (400 MHz, CDCl$_3$) δ 1.40 (q, 1H) 2.24-2.40 (m, 1H) 5.30 (br s, 2H) 6.11 (s, 2H) 6.75 (t, 1H) 6.87-7.06 (m, 3H) 7.11-7.21 (m, 3H) 7.46 (br. s., 1H) 7.56 (s, 1H) 7.67 (s, 1H) 8.23 (s, 1H).

Intermediate-8E

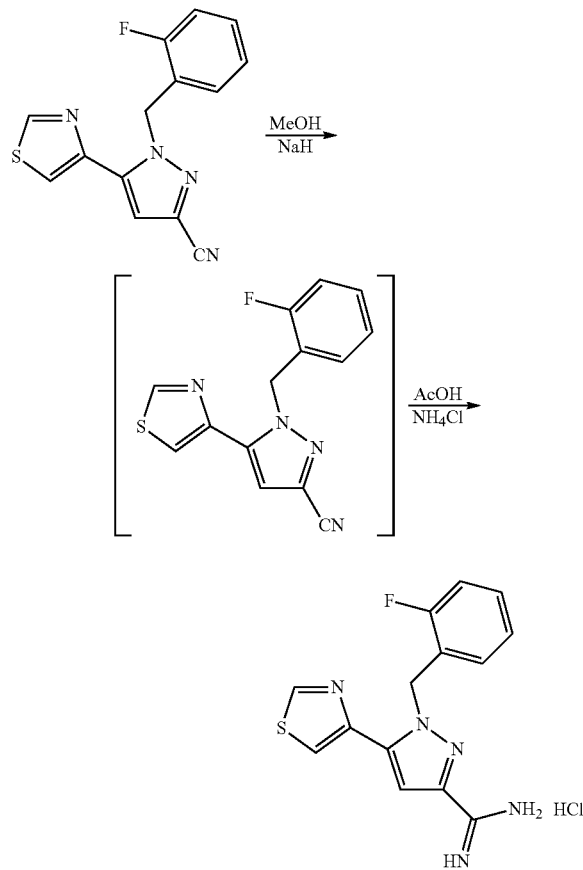

Intermediate-8E

To a stirring solution of 1-(2-fluorobenzyl)-5-(thiazol-4-yl)-1H-pyrazole-3-carbonitrile (1 equiv) in methanol was added sodium hydride (2 equiv). The reaction was stirred at 60° C. for 2 hr. The reaction was then treated with acetic acid (1 equiv) and ammonia hydrochloride (5 equiv) and the temp was raised to 75° C. Once LC/MS analysis showed consumption of starting material (typically 12 hr), a basic aqueous work-up followed by a wash with cold hexanes afforded the resulting desired solid Intermediate-8E, in the form of its HCl salt (1-(2-fluorobenzyl)-5-(thiazol-4-yl)-1H-pyrazole-3-carboximidamide hydrochloride salt (70%). This intermediate was carried forward without any further purification or characterization.

Compound 24

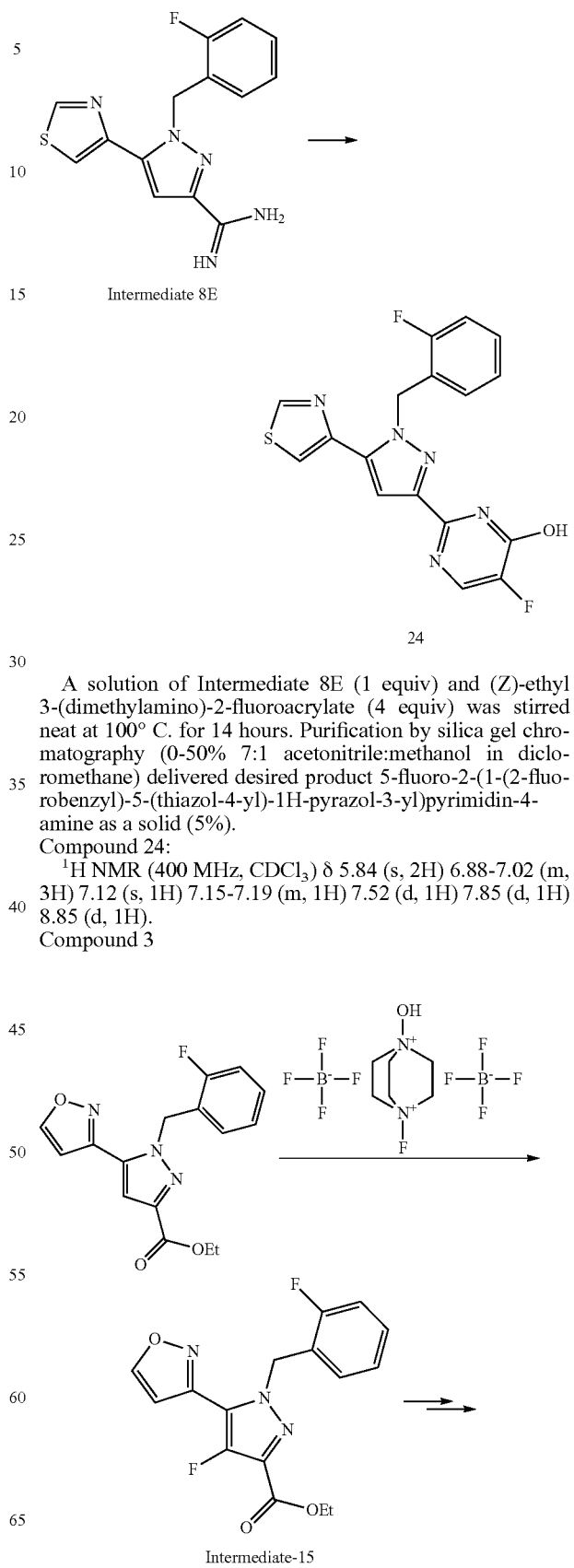

A solution of Intermediate 8E (1 equiv) and (Z)-ethyl 3-(dimethylamino)-2-fluoroacrylate (4 equiv) was stirred neat at 100° C. for 14 hours. Purification by silica gel chromatography (0-50% 7:1 acetonitrile:methanol in dicloromethane) delivered desired product 5-fluoro-2-(1-(2-fluorobenzyl)-5-(thiazol-4-yl)-1H-pyrazol-3-yl)pyrimidin-4-amine as a solid (5%).

Compound 24:
$^1$H NMR (400 MHz, CDCl$_3$) δ 5.84 (s, 2H) 6.88-7.02 (m, 3H) 7.12 (s, 1H) 7.15-7.19 (m, 1H) 7.52 (d, 1H) 7.85 (d, 1H) 8.85 (d, 1H).

Compound 3

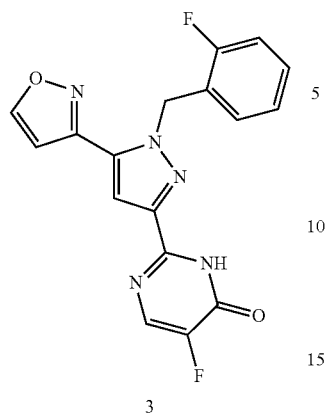

3

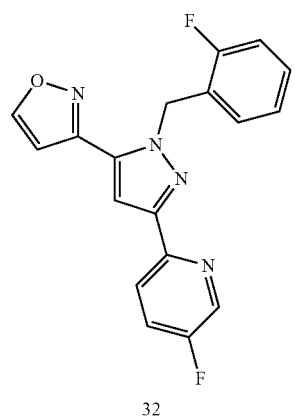

32

Intermediate-15

A solution of ethyl 1-(2-fluorobenzyl)-5-(isoxazol-3-yl)-1H-pyrazole-3-carboxylate (356 mg, 1.13 mmol, prepared as shown in the scheme for the preparation of Intermediate-5C) and 1-fluoro-4-hydroxy-1,4-diazoniabicyclo[2.2.2]octane tetrafluoroborate (2.18 g, 3.39 mmol) in acetonitrile (13 mL) was heated to 75° C. for 24 hours. Additional 1-fluoro-4-hydroxy-1,4-diazoniabicyclo[2.2.2]octane tetrafluoroborate (500 mg) was added and the solution was stirred at 75° C. for another 24 hours. The suspension was diluted with water (100 mL) and dichloromethane (75 mL). The layers were separated and the aqueous layer was extracted with dichloromethane (2×50 mL). The organics were washed with saturated aqueous sodium chloride (50 mL), dried over magnesium sulfate, filtered, and the solvent was removed in vacuo. The crude product was purified by silica gel chromatography (0-50% ethyl acetate in hexanes) to give intermediate Intermediate-15 (100 mg, 27% yield) as a white solid. This compound was carried through under standard conditions (saponification, nitrile formation, amidine formation, pyrimidone formation) to give A as a white solid in 6% yield over 4 steps.

Compound 3:

$^1$H NMR (400 MHz, DMSO) δ 13.43 (br s, 1H), 9.23 (s, 1H), 8.22 (br s, 1H), 7.36-7.33 (m, 1H), 7.24-7.19 (m, 1H), 7.14-7.06 (m, 3H), 5.80 (s, 2H).

Compound 32

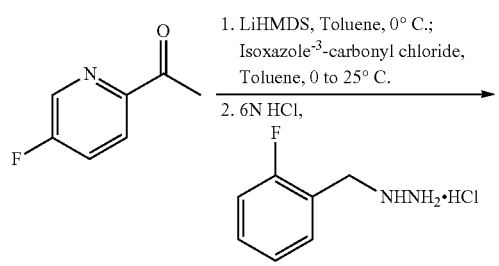

To a cold solution of 1-(5-fluoropyridin-2-yl)ethanone (1 equiv.) in toluene (9.6 ml) at 0° C., was added 1M LiHMDS in toluene (1 equiv.). The mixture was stirred at 0° C. for 5 min. To this mixture, was added a solution of isoxazole-3-carbonyl chloride (1 equiv.) in toluene (4.8 ml). The mixture was removed from the ice bath and stirred at 25° C. for 5 min. To this mixture, were added 6 N HCl (1 equiv.), followed by (2-fluorobenzyl)hydrazine hydrochloride (1 equiv.) and ethanol (5 ml). The mixture was heated to 100° C. for 2 h. The mixture was cooled to 25° C. and concentrated under vacuum to give a thick red oil. The oil was purified by column chromatography (0 to 35% ethyl acetate in hexanes) to give 3-(1-(2-fluorobenzyl)-3-(5-fluoropyridin-2-yl)-1H-pyrazol-5-yl)isoxazole (13% yield) as a clear film and its regioisomer 3-(1-(2-fluorobenzyl)-5-(5-fluoropyridin-2-yl)-1H-pyrazol-3-yl)isoxazole (14% yield) as a white solid.

Compound 32:

$^1$H NMR (400 MHz, CHLOROFORM-d) δ ppm 8.49-8.40 (m, 2H) 7.96-8.07 (m, 1H) 7.37-7.49 (m, 1H) 7.15-7.24 (m, 1H) 6.95-7.13 (m, 2H) 6.84-6.92 (m, 1H) 6.58 (d, 1H) 5.93 (s, 2H).

Compound 33

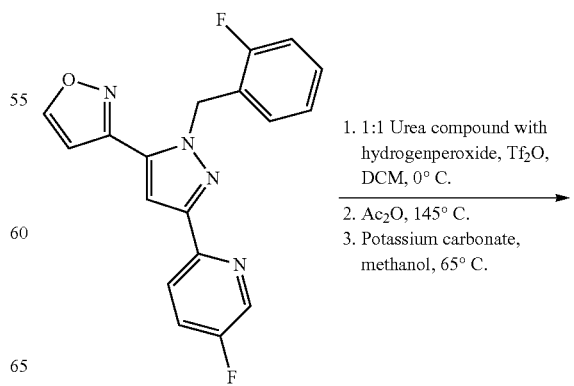

-continued

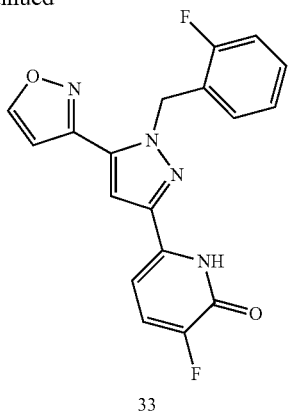

33

To a cold mixture of 3-(1-(2-fluorobenzyl)-3-(5-fluoropyridin-2-yl)-1H-pyrazol-5-yl)isoxazole (1 equiv.) and urea compound with hydrogen peroxide (1:1) (3 equiv.) in DCM (1.7 ml) at 0° C., was added trifluoroacetic anhydride (3 equiv.). The mixture was allowed to warm to 25° C. and stirred for 3 days. The mixture was quenched with saturated solution of sodium bisulfate and extracted with dichloromethane (50 ml×3). The organic layers were combined, filtered and evaporated to give solid. The solid was dissolved in acetic anhydride (1.4 ml) and heated to 145° C. for 4 h. The mixture was cooled to 25° C., diluted with dichloromethane (100 ml) and washed with saturated solution of sodium bicarbonate (50 ml). The organic layer was dried (MgSO$_4$), filtered and evaporated to give an oil. Purification of the oil by column chromatography (0 to 30% ethyl acetate in hexanes) gave 3-fluoro-6-(1-(2-fluorobenzyl)-5-(isoxazol-3-yl)-1H-pyrazol-3-yl)pyridin-2-yl acetate as an yellow oil. The yellow oil was combined with methanol (1.7 ml) and potassium carbonate (1 equiv.). The mixture was heated to 65° C. for 30 min. The mixture was concentrated under vacuum. The resulting residue was diluted with dichloromethane (100 ml) and washed with 1N HCl (30 ml). The organic layer was dried (MgSO$_4$), filtered and evaporated to give a solid. Purification of the solid by column chromatography (0 to 5% methanol in dichloromethane) gave 3-fluoro-6-(1-(2-fluorobenzyl)-5-(isoxazol-3-yl)-1H-pyrazol-3-yl)pyridin-2(1H)-one as a yellow solid (7% overall yield).

Compound 33:

$^1$H NMR (400 MHz, METHANOL-d$_4$) δ ppm 8.74-8.79 (m, 1H) 7.42 (dd, 1H) 7.21-7.33 (m, 2H) 7.01-7.14 (m, 2H) 6.83-6.96 (m, 2H) 6.78 (d, 1H) 5.93 (s, 2H).

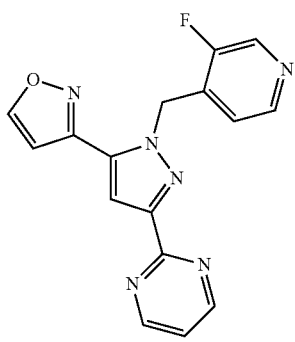

23

Compound 23

To a −78° C. solution of 1-(isoxazol-3-yl)ethanone (54 mg, 0.43 mmol) in tetrahydrofuran (2 mL) was added lithium hexamethyldisilazide (1 M in toluene, 411 μl, 0.411 mmol) in a dropwise manner over the course of 5 min. The solution was immediately warmed to 0° C. for 30 minutes at which point methyl pyrimidine-2-carboxylate (60 mg, 0.43 mmol) was added in a single portion. After stirring for 15 min at 0° C., the solution was warmed to room temperature for 2 hours. Ethanol (2 mL), 3-fluoro-4-(hydrazinylmethyl)pyridine hydrochloride (100 mg, 0.56 mmol), and acetic acid (200 μL) were added and the solution was heated to 70° C. until LCMS indicated consumption of intermediate dione. The solvent was removed in vacuo. Water (50 mL) and dichloromethane (75 mL) were added to the resulting residue. The layers were separated and the aqueous layer was extracted with dichloromethane (2×30 mL). The organics were dried over magnesium sulfate, filtered, and the solvent was removed in vacuo. The crude residue was purified via silica gel chromatography (30-100% hexanes in ethyl acetate) to give compound 23 (26 mg, 19% yield) as a yellow solid.

Compound 23:

$^1$H-NMR (400 MHz, CDCl$_3$) δ 8.82 (d, 2H), 8.45 (d, 1H), 8.41 (s, 1H), 8.20 (d, 1H), 7.49 (s, 1H), 7.24 (t, 1H), 6.69 (t, 1H), 6.63 (d, 1H), 6.06 (s, 2H).

Compound 26

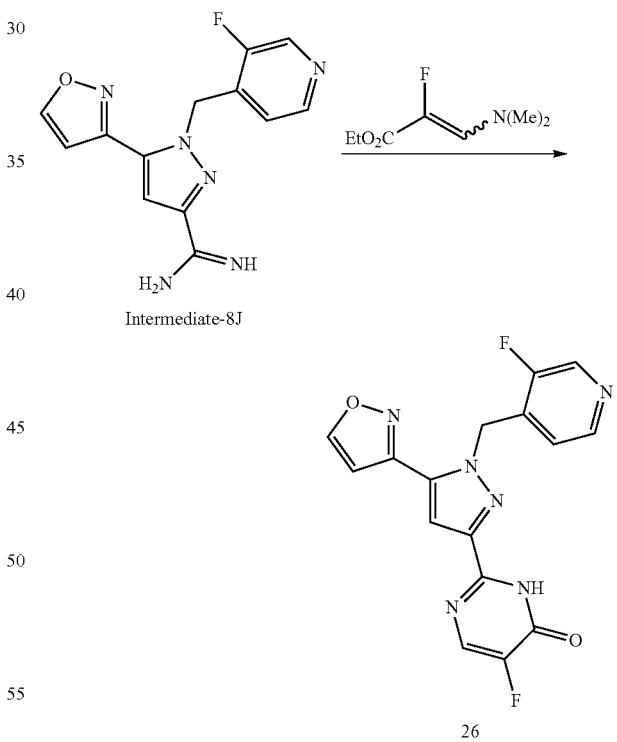

Intermediate Intermediate-8J was prepared via General Procedure A in 14% yield from starting 1-(isoxazol-3-yl)ethanone using 3-fluoro-4-(hydrazinylmethyl)pyridine hydrochloride in the first step. A solution of ethyl 3-(dimethylamino)-2-fluoroacrylate (169 mg, 1.048 mmol) and Intermediate-8J (100 mg, 0.349 mmol) in ethanol (2.3 mL) was stirred at 80° C. for 44 hours. Additional acrylate (3 equiv) was added and the solution was heated to 90° C. for 38 hours. The solvent was removed in vacuo and purification by silica gel chromatography (0-10% methanol in dichloromethane) provided compound 26 (24 mg, 19% yield) as a white solid.

Compound 26:

¹H-NMR (400 MHz, d₆-DMSO) δ 13.28 (br s, 1H), 9.12 (d, 1H), 8.60 (s, 1H), 8.34 (d, 1H), 8.15 (br s, 1H), 7.70 (s, 1H), 7.27 (s, 1H), 6.99-6.96 (m, 1H), 5.98 (s, 2H).

Compound 57

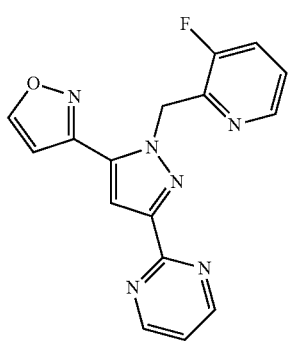

57

To a −78° C. solution of 1-(isoxazol-3-yl)ethanone (46 mg, 0.41 mmol) in tetrahydrofuran (1 mL) was added lithium hexamethyldisilazide (1 M in toluene, 370 μl, 0.37 mmol) in a dropwise manner over the course of 5 minutes. The solution was immediately warmed to 0° C. for 30 minutes at which point methyl pyrimidine-2-carboxylate (49 mg, 0.35 mmol) was added in a single portion. After stirring for 15 minutes at 0° C., the solution was warmed to room temperature for 18 hours. The solvent was removed in vacuo, and residue was diluted with ether (5 mL) and filtered. The resulting solid (72 mg, 0.32 mmol) was re-suspended in ethanol (0.5 mL) with 3-fluoro-2-(hydrazinylmethyl)pyridine dihydrochloride (60 mg, 0.28 mmol). The solution was heated to 40° C. until LCMS indicated consumption of intermediate dione. The solvent was removed in vacuo. The crude residue was purified via silica gel chromatography (3-100% hexanes in ethyl acetate) to give compound 57 (20 mg, 20% yield) as an off-white solid.

Compound-57:

¹H-NMR (400 MHz, CDCl₃) δ 8.81 (d, 2H), 8.43 (d, 1H), 8.21 (d, 1H), 7.49 (s, 1H), 7.35 (dt, 1H), 7.21 (t, 1H), 7.12-7.16 (m, 1H), 6.68 (d, 1H), 6.19 (s, 2H).

Compound 66

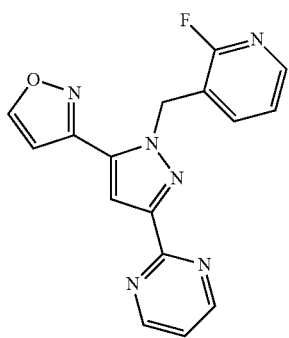

66

To a −78° C. solution of 1-(isoxazol-3-yl)ethanone (60 mg, 0.54 mmol) in tetrahydrofuran (5.4 mL) was added lithium hexamethyldisilazide (1 M in toluene, 486 μl, 0.486 mmol) in a dropwise manner over the course of 5 minutes. The solution was immediately warmed to 0° C. for 30 minutes at which point methyl pyrimidine-2-carboxylate (75 mg, 0.54 mmol) was added in a single portion. After stirring for 15 minutes at 0° C., the solution was warmed to room temperature for 18 hours. The solvent was removed in vacuo, and residue was diluted with ether (5 mL) and filtered. The resulting solid (30 mg, 0.13 mmol) was re-suspended in isopropanol (1.3 mL), and treated with triethylamine (38 μl, 0.27 mmol), trifluoroacetic acid (21 μL, 0.27 mmol), and 3-fluoro-4-(hydrazinylmethyl)pyridine trifluoroacetic acid (192 mg, 0.75 mmol). The solution was heated to 80° C. until LCMS indicated consumption of intermediate dione. The solvent was removed in vacuo. Contents diluted with ethyl acetate (5 mL) and washed with saturated sodium bicarbonate solution (5 mL), water (5 mL), and brine (5 mL). The organics were dried over magnesium sulfate, filtered, and the solvent was removed in vacuo. The crude residue was purified via silica gel chromatography (3-100% hexanes in ethyl acetate, followed by a second purification with 0-60% hexanes in acetone) to give compound A (5.1 mg, 12% yield) as an off-white solid.

Compound-66:

¹H-NMR (400 MHz, CDCl₃) δ 8.84 (d, 2H), 8.48 (d, 1H), 8.08 (d, 1H), 7.49 (s, 1H), 7.23-7.29 (m, 2H), 7.03 (t, 1H), 6.64 (d, 1H), 6.02 (s, 2H).

Compound 67

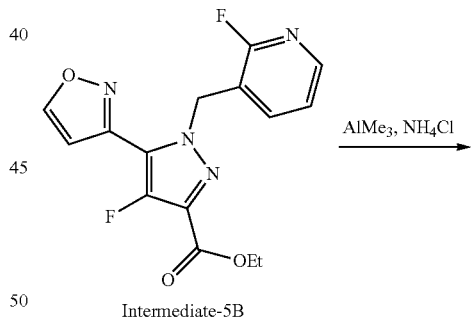

Intermediate-5B

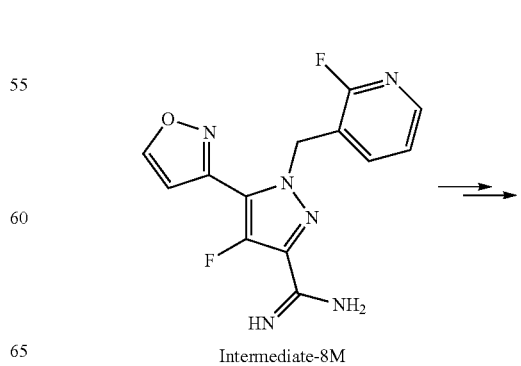

Intermediate-8M

-continued

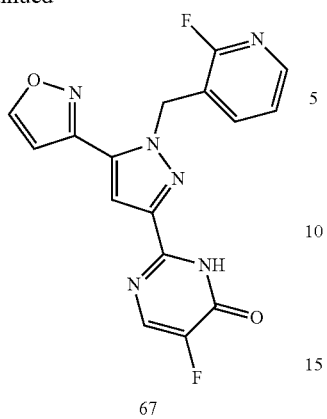

67

To a suspension of ammonium chloride (42 mg, 0.79 mmol) in toluene (1 mL) was added trimethylaluminum (2M in toluene, 395 μL, 0.79 mmol) in a dropwise manner over 5 minutes. The solution was stirred at 23° C. for 10 minutes, at which point ethyl 1-((2-fluoropyridin-3-yl)methyl)-5-(isoxazol-3-yl)-1H-pyrazole-3-carboxylate (Intermediate-5B, 25 mg, 0.08 mmol) was added in 1 portion. The solution was heated to 110° C. until LCMS indicated full consumption of the starting ester. The contents were cooled to 0° C., and quenched with methanol (2 mL). The resulting suspension was allowed to warm to 23° C. while vigorously stirring for 1 hour. Contents filtered, and solvent was removed in vacuo. The resulting white solid (Intermediate-8M) was taken on as is.

A solution of Intermediate-8M (22 mg, 0.077 mmol), ethyl 3-(dimethylamino)-2-fluoroacrylate (74 mg, 0.46 mmol), and DBU (23 μL, 0.15 mmol) in ethanol (1 mL) was heated to 90° C. for 12 hours. The solvent was removed in vacuo and purification by silica gel chromatography (0-20% methanol in dichloromethane) provided compound 67 (5.7 mg, 21% yield) as a white solid.

Compound 67:
$^1$H-NMR (400 MHz, CDCl$_3$) δ 8.55 (d, 1H), 8.18 (d, 1H), 7.93 (d, 1H), 7.53 (t, 1H), 7.28 (s, 1H), 7.16 (t, 1H), 6.64 (d, 1H), 5.91 (s, 2H).

Compound 70

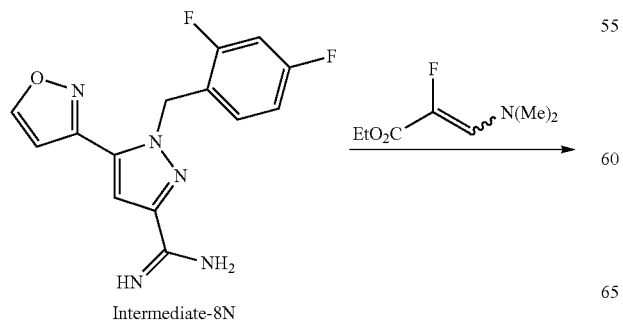

Intermediate-8N

-continued

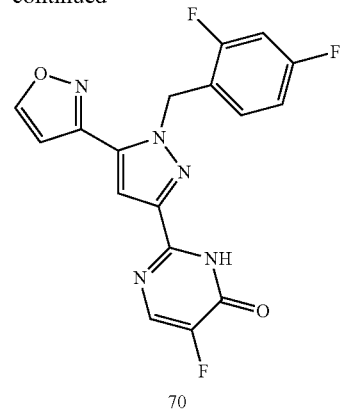

70

Intermediate 8-N was accessed via General Procedure A in 42% yield from 1-(isoxazol-3-yl)ethanone using (2,4-difluorobenzyl)hydrazine hydrochloride in the first step. A solution of ethyl 3-(dimethylamino)-2-fluoroacrylate (90 mg, 0.56 mmol), 1,8-diazabicyclo[5.4.0]undec-7-ene (50 mg, 0.33 mmol) and Intermediate 8-N (50 mg, 0.17 mmol) in ethanol (1.6 mL) was stirred at 90° C. for 19 hours. The solvent was removed in vacuo, and purification by silica gel chromatography (0-40% 7:1=acetonitrile:methanol in dichloromethane) provided Compound 70 (31 mg, 51% yield) as a white solid.

Compound 70:
$^1$H-NMR (400 MHz, DMSO-d$_6$) δ 13.30 (br s, 1H), 9.13 (d, 1H), 8.15 (br s, 1H), 7.63 (s, 1H), 7.32-7.25 (m, 1H), 7.24 (br s, 1H), 7.14 (br s, 1H), 7.03 (td, 1H), 5.87 (s, 2H).

Compound 71

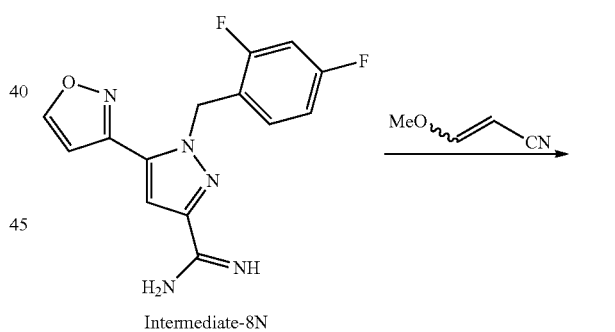

Intermediate-8N

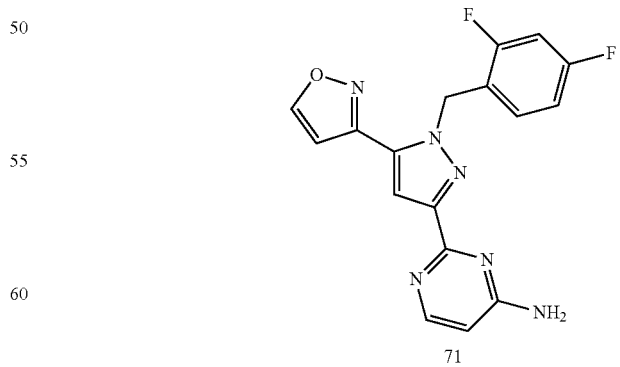

71

To a solution of Intermediate 8-N (50 mg, 0.17 mmol) in pyridine (1 mL) was added a mixture of E- and Z-3-ethoxyacrylonitrile (69 mg, 0.82 mmol) and 1,8-diazabicyclo[5.4.0]

undec-7-ene (50 mg, 0.33 mmol). The solution was stirred at 110° C. for 18 hours. The contents were diluted with ethyl acetate (25 mL), and washed with saturated ammonium chloride solution (5 mL) and brine (10 mL). The organics were dried over MgSO4, filtered, and and the solvent was removed in vacuo. Purification by silica gel chromatography (0-40% 7:1=acetonitrile:methanol in dichloromethane) provided Compound 71 (17 mg, 29% yield) as an off-white solid.

Compound 71:
$^1$H-NMR (400 MHz, DMSO) δ 9.10 (d, 1H), 8.13 (d, 1H), 7.51 (s, 1H), 7.33-7.25 (m, 1H), 7.25 (d, 1H), 6.94-7.06 (m, 4H), 6.37 (d, 1H), 5.85 (s, 2H).

Compound 72

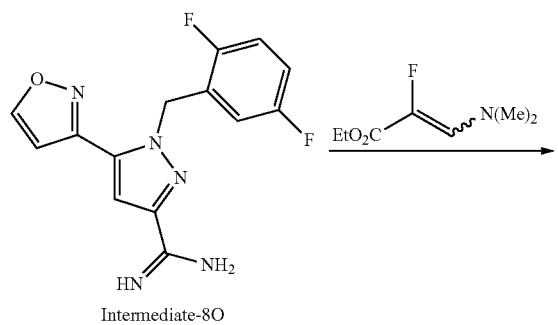

Intermediate-8O

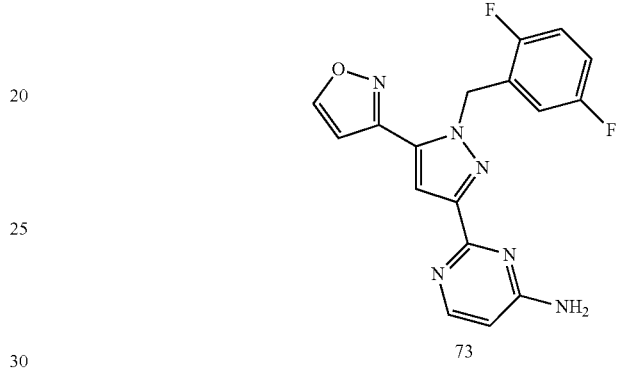

Intermediate 8-O was accessed via General Procedure A in 52% yield from 1-(isoxazol-3-yl)ethanone using (2,5-difluorobenzyl)hydrazine hydrochloride in the first step. A solution of ethyl 3-(dimethylamino)-2-fluoroacrylate (266 mg, 1.65 mmol), 1,8-diazabicyclo[5.4.0]undec-7-ene (100 mg, 0.66 mmol) and Intermediate 8-O (100 mg, 0.33 mmol) in ethanol (1.6 mL) was stirred at 90° C. for 20 hours. The solvent was removed in vacuo, and purification by silica gel chromatography (0-100% 7:1=acetonitrile:methanol in dichloromethane) provided impure product. Trituration with diethyl ether (5 mL) provided Compound 72 (23 mg, 18% yield) as a white solid.

Compound 72:
$^1$H-NMR (400 MHz, DMSO-d$_6$) δ 13.31 (br s, 1H), 9.13 (d, 1H), 8.16 (br s, 1H), 7.64 (s, 1H), 7.30 (td, 1H), 7.26-7.17 (m, 1H), 7.25 (s, 1H), 6.93 (br s, 1H), 5.89 (s, 2H).

Compound 73

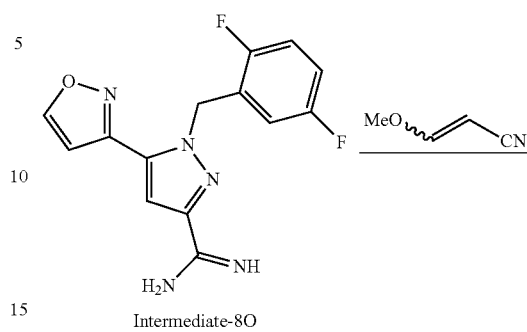

Intermediate-8O

To a solution of Intermediate 8-O (108 mg, 0.36 mmol) in pyridine (1.7 mL) was added a mixture of E- and Z-3-ethoxyacrylonitrile (148 mg, 1.78 mmol) and 1,8-diazabicyclo [5.4.0]undec-7-ene (108 mg, 0.71 mmol). The solution was stirred at 110° C. for 20 hours. The contents were diluted with ethyl acetate (15 mL), and washed with saturated ammonium chloride solution (3 mL) and brine (5 mL). The organics were dried over MgSO4, filtered, and and the solvent was removed in vacuo. Purification by silica gel chromatography (0-40% 7:1=acetonitrile:methanol in dichloromethane) provided impure product. Trituration with diethyl ether (2 mL) provided Compound 73 (50 mg, 34% yield) as a tan solid.

Compound 73:
$^1$H-NMR (400 MHz, DMSO-d$_6$) δ 9.10 (d, 1H), 8.13 (d, 1H), 7.52 (s, 1H), 7.31 (td, 1H), 7.26 (d, 1H), 7.23-7.16 (m, 1H), 6.99 (br s, 2H), 6.65 (ddd, 1H), 6.37 (d, 1H), 5.88 (s, 2H).

Compound 77

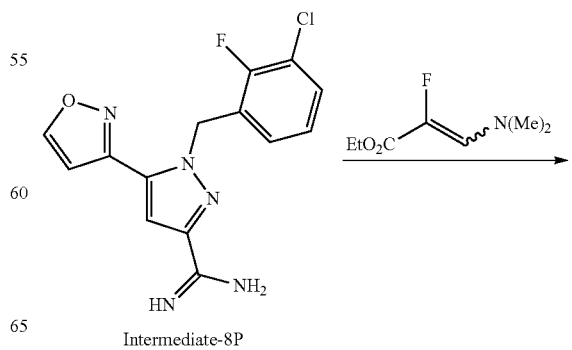

Intermediate-8P

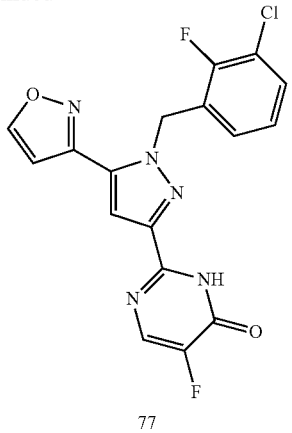

77

Intermediate-8P was accessed via General Procedure A in 45% yield from 1-(isoxazol-3-yl)ethanone using (3-chloro-2-fluorobenzyl)hydrazine hydrochloride in the first step. A solution of ethyl 3-(dimethylamino)-2-fluoroacrylate (267 mg, 1.66 mmol), 1,8-diazabicyclo[5.4.0]undec-7-ene (101 mg, 0.66 mmol) and Intermediate 1-3 (106 mg, 0.33 mmol) in ethanol (1.7 mL) was stirred at 90° C. for 20 hours. Reaction was further treated with additional ethyl 3-(dimethylamino)-2-fluoroacrylate (267 mg, 1.66 mmol), and stirred for another 24 hours. The solvent was removed in vacuo, and purification by silica gel chromatography (0-40% 7:1=acetonitrile:methanol in dichloromethane) provided Compound 77 (49 mg, 38% yield) as a white solid.

Compound 77:

$^1$H-NMR (400 MHz, DMSO-$d_6$) δ 13.23 (br s, 1H), 9.13 (d, 1H), 8.14 (br s, 1H), 7.66 (s, 1H), 7.57-7.49 (m, 1H), 7.25 (s, 1H), 7.16 (t, 1H), 6.98 (t, 1H), 5.94 (s, 2H).

Compound 78

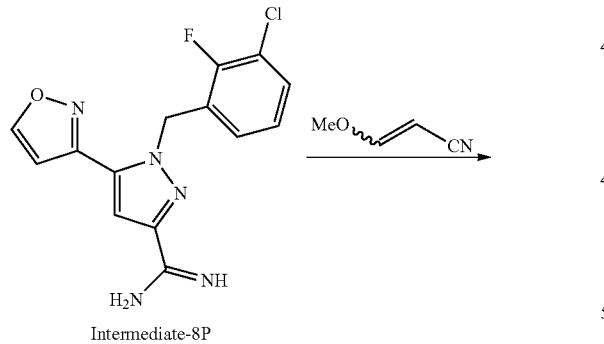

To a solution of Intermediate Intermediate-8P (100 mg, 0.36 mmol) in pyridine (1.6 mL) was added a mixture of E- and Z-3-ethoxyacrylonitrile (152 mg, 1.56 mmol) and 1,8-diazabicyclo[5.4.0]undec-7-ene (95 mg, 0.63 mmol). The solution was stirred at 110° C. for 20 hours. The contents were diluted with ethyl acetate (10 mL), and washed with saturated ammonium chloride solution (3 mL). The aqueous layer was diluted with water (10 mL) and extracted with ethyl acetate (3×10 mL). The organics were washed with brine (10 mL), dried over MgSO4, filtered, and the solvent was removed in vacuo. Purification by silica gel chromatography (0-30% 7:1=acetonitrile:methanol in dichloromethane) provided impure product. Trituration with diethyl ether (2 mL) provided Compound 78 (49 mg, 38% yield) as a tan solid.

Compound 78:

$^1$H-NMR (400 MHz, DMSO-$d_6$) δ 9.10 (d, 1H), 8.13 (d, 1H), 7.56-7.49 (m, 1H), 7.53 (s, 1H), 7.26 (d, 1H), 7.16 (t, 1H), 6.98 (s, 2H), 6.85 (t, 1H), 6.37 (d, 1H), 5.93 (s, 2H).

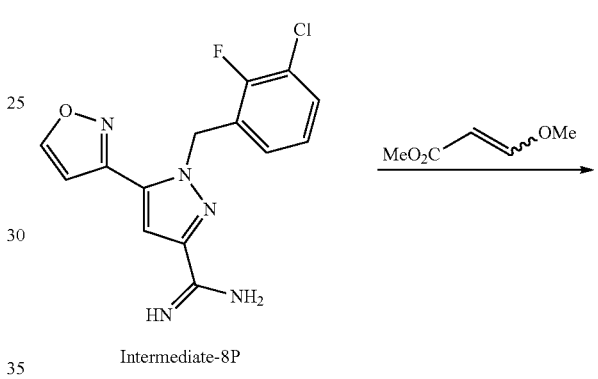

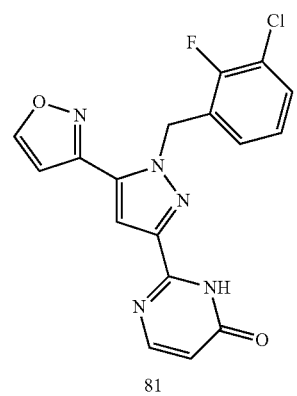

81

Compound 81

A solution of methyl 3-methoxyacrylate (617 mg, 5.32 mmol), 1,8-diazabicyclo[5.4.0]undec-7-ene (162 mg, 1.06 mmol) and Intermediate Intermediate-8P (170 mg, 0.53 mmol) in ethanol (2.7 mL) was stirred at 90° C. for 1 hour. The solvent was removed in vacuo, and purification by silica gel chromatography (0-20% 7:1=acetonitrile:methanol in dichloromethane) provided Compound 81 (98 mg, 47% yield) as a white solid. 1H-NMR (400 MHz, DMSO-$d_6$) δ 12.59 (br s, 1H), 9.13 (d, 1H), 8.03 (br s, 1H), 7.68 (s, 1H), 7.53 (t, 1H), 7.24 (br s, 1H), 7.16 (t, 1H), 7.01 (br s, 1H), 6.35 (br s, 1H), 5.95 (s, 2H).

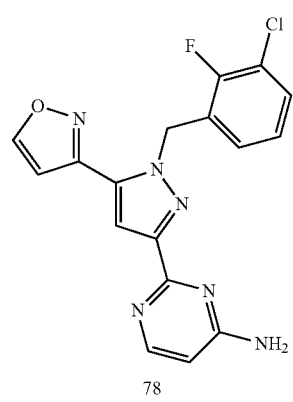

78

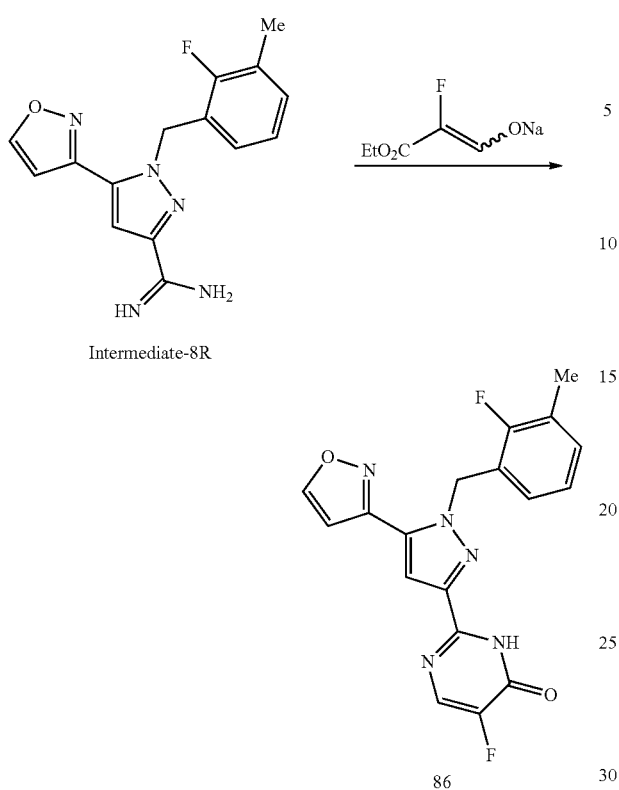

Compound 86

Intermediate-8R was accessed via General Procedure A in 60% yield from 1-(isoxazol-3-yl)ethanone using (2-fluoro-3-methylbenzyl)hydrazine hydrochloride in the first step. A suspension of sodium (E,Z)-3-ethoxy-2-fluoro-3-oxoprop-1-en-1-olate (242 mg, 1.55 mmol) and Intermediate-8R (155 mg, 0.52 mmol) in ethanol (2.6 mL) was stirred at 90° C. for 18 hours. The contents were diluted with ethyl acetate (10 mL) and water (10 mL). The mixture was treated carefully with HCl (1.24 mL, 1.55 mmol, 1.25M solution in ethanol). Layers were separated, and the aqueous layer was extracted with dichloromethane (3×10 mL). The organics were washed with brine (10 mL), dried over MgSO4, filtered, and the solvent was removed in vacuo. Purification by silica gel chromatography (0-30% 7:1=acetonitrile:methanol in dichloromethane) provided Compound 86 (111 mg, 58% yield) as a white solid. 1H-NMR (400 MHz, DMSO-$d_6$) δ 13.26 (br s, 1H), 9.12 (d, 1H), 8.13 (br s, 1H), 7.64 (s, 1H), 7.24 (s, 1H), 7.21 (t, 1H), 7.00 (t, 1H), 6.74 (t, 1H), 5.90 (s, 2H), 2.23 (s, 3H).

Compound 82

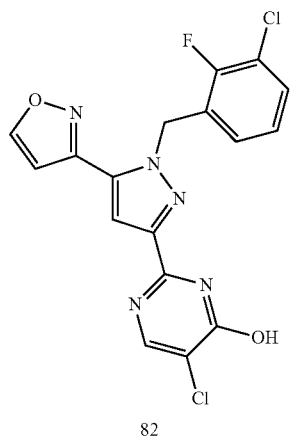

To a solution of Compound 81 (93 mg, 0.25 mmol) in DMF (2.5 mL) was added N-chlorosuccinimide (33 mg, 0.25 mmol). The solution was stirred at 80° C. for 20 hours. The contents were diluted with ethyl acetate (20 mL) and water (20 mL). The layers were separated, and the aqueous layer was further diluted with water (20 mL). The aqueous layer was extracted with ethyl acetate (3×20 mL) and dichloromethane (2×20 mL). The organics were washed with brine (10 mL), dried over MgSO4, filtered, and the solvent was removed in vacuo. Trituration of ther resulting solids with diethyl ether (2×5 mL) provided impure compound. Purification by silica gel chromatography (0-20% 7:1=acetonitrile:methanol in dichloromethane) provided Compound 82 (16 mg, 15% yield) as a white solid.

Compound 82:

1H-NMR (400 MHz, DMSO-$d_6$) δ 13.28 (br s, 1H), 9.13 (d, 1H), 8.31 (br s, 1H), 7.70 (s, 1H), 7.57-7.49 (m, 1H), 7.25 (br s, 1H), 7.17 (t, 1H), 7.02 (br s, 1H), 5.95 (s, 2H).

Compound 68

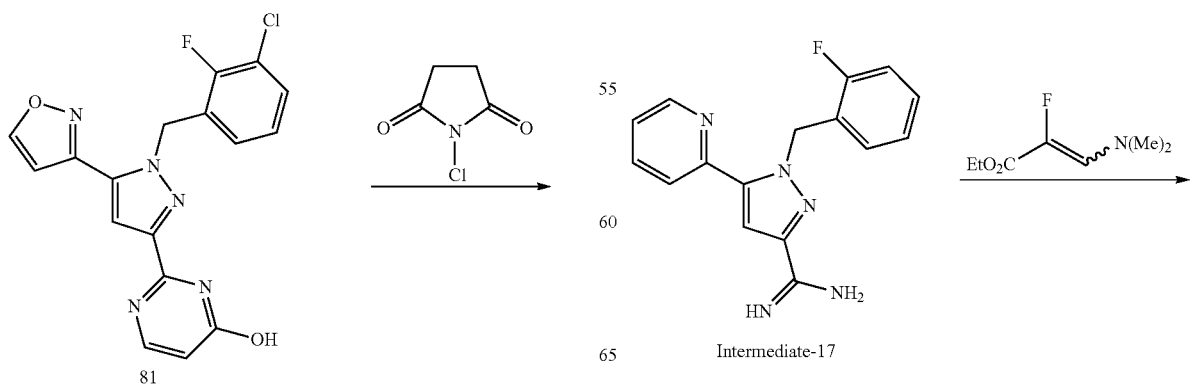

-continued

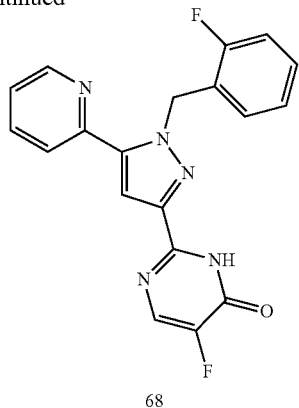

68

A solution of ethyl 3-(dimethylamino)-2-fluoroacrylate (620 mg, 1.92 mmol), 1,8-diazabicyclo[5.4.0]undec-7-ene (98 mg, 0.64 mmol) and 1-(2-fluorobenzyl)-5-(pyridin-2-yl)-1H-pyrazole-3-carboximidamide (Intermediate-17, 189 mg, 0.64 mmol) in ethanol (2 mL) was stirred at 100° C. until complete consumption of starting material was evident by LC/MS analysis. The solvent was removed in vacuo, and purification by silica gel chromatography (0-10% methanol in dichloromethane) afforded Compound 68 (30 mg, 12% yield).

Compound 68;

$^1$H-NMR (400 MHz, DMSO-d$_6$) δ 13.22 (bs, 1H), 8.65 (d, 1H), 8.16 (bs, 1H), 7.95-7.91 (m, 2H), 7.54 (s, 1H), 7.43-7.40 (m, 1H), 7.32-7.26 (m, 1H), 7.16 (t, 1H), 7.08 (dd, 1H), 7.01 (bs, 1H), 6.09 (s, 2H).

Compound 87

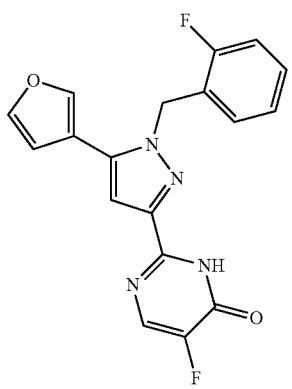

87

This compound was generated exploiting General Procedure A-I from 1-(furan-3-yl)ethanone (1.6 g, 14.53 mmol) in the initial Claisen condensation, and using (2-fluorobenzyl)hydrazine hydrochloride (2.57 g, 14.53 mmol) in the pyrazole formation step (79%, two steps). The ester was then carried on to the corresponding amidine, again, as outlined in General Procedure A-I. The amidine (600 mg, 2.11 mmol) was cyclized via treatment with sodium 3-ethoxy-2-fluoro-3-oxo-prop-1-en-1-olate (989 mg, 6.33 mmol) in ethanol (5.0 mL)—stirring at 90° C. for 1 hour. The solvent was removed in vacuo, and purification by silica gel chromatography (0-100% ethyl acetate in hexanes) provided Compound 87 (400 mg, 54% yield) as a white solid.

Compound 87:

$^1$H-NMR (400 MHz, DMSO-d$_6$) δ 13.08 (bs, 1H), 8.09 (bs, 1H), 8.03 (s, 1H), 7.80 (s, 1H), 7.33 (dd, 1H), 7.20 (dd, 1H), 7.11 (dd, 1H), 7.11 (s, 1H), 6.98-6.90 (m, 1H), 6.79 (s, 1H), 5.57 (s, 2H).

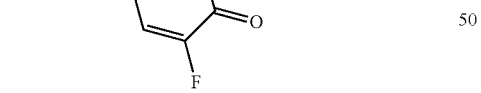

88

Compound 88

Compound 88 was generated via the treatment of known compound, 2-(1-(2,3-difluorobenzyl)-5-(isoxazol-3-yl)-1H-pyrazol-3-yl)pyrimidine-4,5-diamine hydrochloride (100 mg, 0.246 mmol), in a 1:1 DCM/pyridine solution with 4-fluorobenzoyl chloride (dropwise) until complete consumption of SM was noted by LC/MS. Once complete, the solvent was removed in vacuo and the crude material was purified by silica gel chromatography (0-10% methanol in DCM) to provide Compound 88 (42 mg, 35% yield) as a tan solid.

Compound 88:

$^1$H-NMR (400 MHz, CD$_3$OD) δ 8.75 (d, 1H), 8.27 (s, 1H), 8.05 (dd, 2H), 7.44 (d, 1H), 7.24 (dd, 2H), 7.14 (dd, 1H), 7.01 (dd, 1H), 6.88 (d, 1H), 6.66 (dd, 1H), 5.98 (s, 2H).

Compound 90

90

This compound was generated exploiting General Procedure A-I from 1-(furan-2-yl)ethanone (1.5 g, 13.62 mmol) in the initial Claisen condensation, and using (2-fluorobenzyl)hydrazine hydrochloride (2.4 g, 13.62 mmol) in the pyrazole formation step (30%, two steps). The ester was then carried on to the corresponding amidine, again, as outlined in General Procedure A-I. The amidine (878 mg, 3.09 mmol) was cyclized via treatment with ethyl 3-(dimethylamino)-2-fluoroacrylate (1.49 g, 9.27 mmol) and 1,8-diazabicyclo[5.4.0]undec-7-ene (0.466 mL, 3.09 mmol) in ethanol (5.0 mL)—stirring at 90° C. for 16 hours. The solvent was removed in vacuo, and purification by silica gel chromatography (0-100% ethyl acetate in hexanes) provided Compound 90 (178 mg, 16% yield) as a white solid.

Compound 90:
$^1$H-NMR (400 MHz, DMSO-d$_6$) δ 13.10 (bs, 1H), 8.08 (bs, 1H), 7.83-7.81 (m, 1H), 7.32 (dd, 1H), 7.23-7.18 (m, 1H), 7.22 (d, 1H), 7.11 (dd, 1H), 6.98 (dd, 1H), 6.86 (d, 1H), 6.64-6.61 (m, 1H), 5.69 (s, 2H).

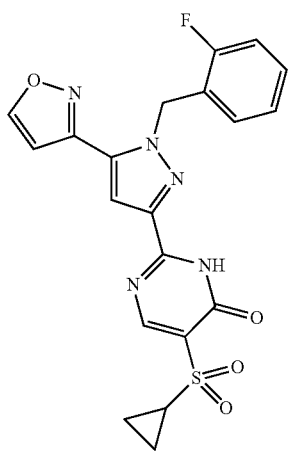

Compound 91

Compound 91

This compound was generated via the cyclization of known intermediate 1-(2-fluorobenzyl)-5-(isoxazol-3-yl)-1H-pyrazole-3-carboximidamide (107 mg, 0.375 mmol) with ethyl 2-(cyclopropylsulfonyl)-3-(dimethylamino)acrylate (464 mg, 1.875 mmol) in the presences of 1,8-diazabicyclo[5.4.0]undec-7-ene (0.057 mL, 0.375 mmol) in ethanol (5.0 mL)—stirring at 90° C. for 16 hours. The solvent was removed in vacuo, and purification by silica gel chromatography (0-10% methanol in DCM) provided Compound 91 (108 mg, 65% yield) as a white solid.

Compound 91:
$^1$H-NMR (400 MHz, DMSO-d$_6$) δ 13.47 (bs, 1H), 9.08 (d, 1H), 8.23 (s, 1H), 7.70 (s, 1H), 7.31 (dd, 1H), 7.24 (d, 1H), 7.19 (dd, 1H), 7.08 (dd, 1H), 6.89 (dd, 1H), 5.91 (s, 2H), 3.10-3.05 (m, 1H), 1.07-0.95 (m, 4H).

Compound 92

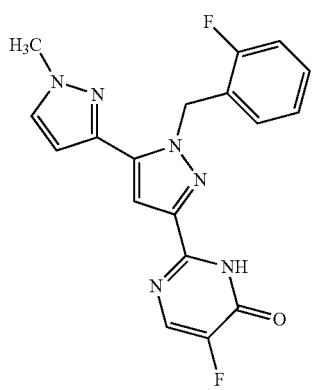

92

This compound was generated exploiting General Procedure A-I from 1-(1-methyl-1H-pyrazol-3-yl)ethanone (1.67 g, 13.45 mmol) in the initial Claisen condensation, and using (2-fluorobenzyl)hydrazine hydrochloride (2.38 g, 13.45 mmol) in the pyrazole formation step (72%, two steps). The ester was then carried on to the corresponding amidine, again, as outlined in General Procedure A-I. The amidine (213 mg, 0.714 mmol) was cyclized via treatment with sodium 3-ethoxy-2-fluoro-3-oxoprop-1-en-1-olate (446 mg, 2.86 mmol) in ethanol (5.0 mL)—stirring at 90° C. for 14 hour. The solvent was removed in vacuo, and purification by silica gel chromatography (0-10% methanol in DCM) provided a mixture of the desired compound and a side-product. The mixture was then subjected to reverse-phase preparative HPLC which afforded Compound 92 (20 mg, 7.6% yield) as a white solid.

Compound 92:
$^1$H-NMR (400 MHz, CD$_3$OD) δ 7.99 (d, 1H), 7.60 (d, 1H), 7.27-7.20 (m, 1H), 7.16 (d, 1H), 7.06 (dd, 1H), 7.01 (dd, 1H), 6.87 (dd, 1H), 6.52-6.50 (m, 1H), 5.93 (s, 2H), 3.89 (s, 3H).

Compound 93

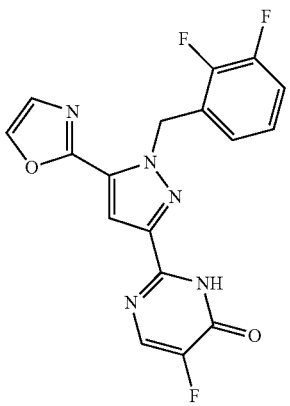

93

This was generated via the cyclization of known intermediate 1-(2,3-difluorobenzyl)-5-(isoxazol-3-yl)-1H-pyrazole-3-carboximidamide (213 mg, 0.702 mmol) with sodium 3-ethoxy-2-fluoro-3-oxoprop-1-en-1-olate (440 mg, 2.81 mmol) in ethanol (5.0 mL)—stirring at 90° C. for 14 hour. The solvent was removed in vacuo, and purification by silica gel chromatography (0-10% methanol in DCM) provided a mixture of the desired compound and a side-product. The mixture was then subjected to reverse-phase preparative HPLC which afforded Compound 93 (15 mg, 7.2% yield) as a white solid.

Compound 93:

¹H-NMR (400 MHz, CD₃OD) δ 8.03 (s, 1H), 8.02 (s, 1H), 7.52 (s, 1H), 7.34 (d, 1H), 7.21-7.14 (m, 1H), 7.06-7.00 (m, 1H), 6.76-6.72 (m, 1H), 6.16 (s, 2H).

Compound 94

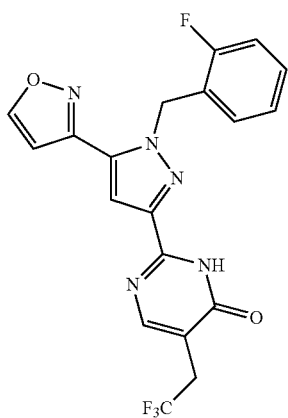

94

This compound was generated via the cyclization of known intermediate 1-(2-fluorobenzyl)-5-(isoxazol-3-yl)-1H-pyrazole-3-carboximidamide (279 mg, 0.978 mmol) with ethyl 4,4,4-trifluoro-2-(hydroxymethylene)butanoate (950 mg, 0.479 mmol) in the presence of 1,8-diazabicyclo[5.4.0]undec-7-ene (0.147 mL, 0.978 mmol) in ethanol (5.0 mL)—stirring at 90° C. for 18 hours. The solvent was removed in vacuo, and purification by silica gel chromatography (0-10% methanol in DCM) provided Compound 94 (70 mg, 17% yield) as a white solid.

Compound 94:

¹H-NMR (400 MHz, DMSO-d₆) δ 12.85 (bs, 1H), 9.09 (d, 1H), 8.06 (bs, 1H), 7.67 (s, 1H), 7.31 (dd, 1H), 7.22-7.17 (m, 2H), 7.08 (dd, 1H), 6.95 (bs, 1H), 5.89 (s, 2H), 3.44 (dd, 2H).

Compound 95

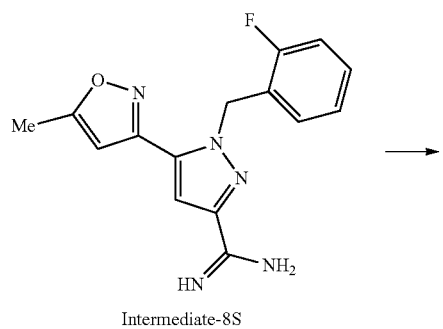

Intermediate-8S

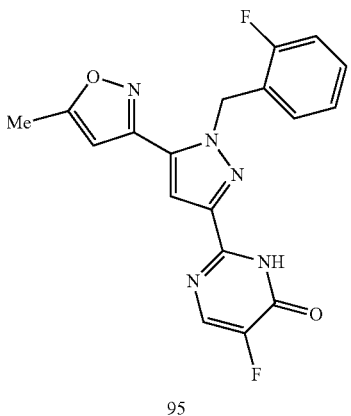

95

Intermediate 8S was synthesized as described in General Procedure A-II starting from 1-(5-methylisoxazol-3-yl)ethanone using 1.5 equivalents of 2-fluorobenzyl hydrazine. A suspension of sodium 3-ethoxy-2-fluoro-3-oxoprop-1-en-1-olate (522 mg, 3.34 mmol) and intermediate-8S (200 mg, 0.668 mmol) was heated to 100° C. for 30 min. The solution was condensed in vacuo and the residue was dissolved in dichloromethane (5 mL) and filtered through celite. Purification via silica gel chromatography (0-5% methanol in dichloromethane) gave material that was further purified via reverse phase HPLC (40-80% acetonitrile w/0.1% TFA in water w/0.1% TFA) to give Compound 95 (8 mg, 3% yield) as a white solid.

Compound 95:

¹H-NMR (400 MHz, CDCl3) δ 7.91 (d, 1H), 7.29-7.25 (m, 1H), 7.17 (s, 1H), 7.08-7.04 (m, 3H), 6.22 (s, 1H), 5.86 (s, 2H), 2.49 (s, 3H).

Compound 96

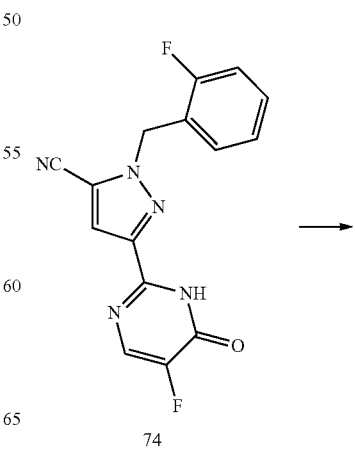

74

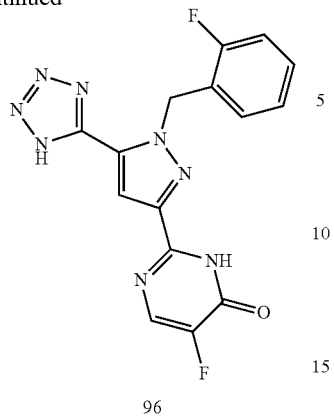

96

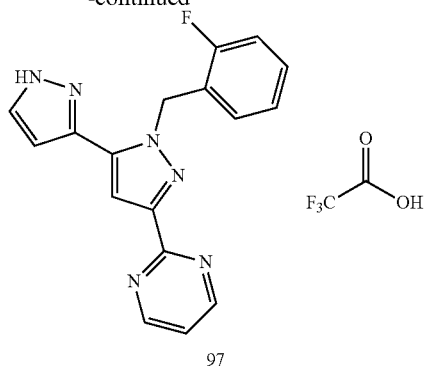

97

A suspension of ammonium chloride (4 mg, 0.08 mmol), sodium azide (5 mg, 0.080 mmol), and Compound 74 (25 mg, 0.080 mmol) was heated to 110° C. in N,N-dimethylformamide (0.4 mL) for 1 hour. The solvent was diluted with ethyl acetate (30 mL) and water (30 mL). The layers were separated and the aqueous layer was extracted with ethyl acetate (2×30 mL). The aqueous layer was acidified to pH~1 and extracted with ethyl acetate (2×30 mL). The organics were dried over magnesium sulfate and filtered. The remaining solid was suspended in diethyl ether (5 mL) and filtered to give Compound 96 (13 mg, 38% yield) as a white solid.

Compound 96:
$^1$H-NMR (400 MHz, DMSO-d6) δ 8.15 (br s, 1H), 7.56 (s, 1H), 7.37-7.32 (m, 1H), 7.24-7.20 (m, 1H), 7.14-7.10 (m, 1H), 7.07-7.03 (m, 1H), 6.03 (s, 2H).

Compound 97

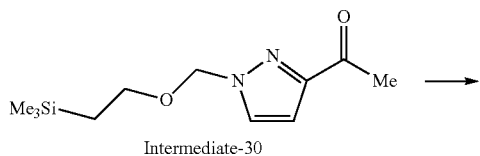

Intermediate-30

To a −78° C. solution of Intermediate-30 (320 mg, 1.33 mmol) in tetrahydrofuran (6.6 mL) was added lithium hexamethylsilazane (1.3 mL, 1.3 mmol, 1M in toluene) dropwise over 5 minutes. Following addition, the solution was immediately warmed to 0° C. for 15 minutes. Methyl pyrimidine-2-carboxylate (220 mg, 1.6 mmol) was then added in a single portion and the solution was warmed to room temperature. After stirring for 30 minutes, ethanol (2 mL), (2-fluorobenzyl)hydrazine hydrochloride (470 mg, 2.66 mmol), and hydrochloric acid (3.1 ml, 4 mmol, 1.25 N in ethanol) were sequentially added. The solution was heated to 70° C. for 14 hours. The solution was poured into ethyl acetate (75 mL) and saturated sodium bicarbonate (75 mL). The layers were separated and the aqueous layer was extracted with ethyl acetate (2×25 mL). The organics were dried over magnesium sulfate, filtered, and the solvent was removed in vacuo. Purification by silica gel chromatography (40-100% ethyl acetate in hexanes) delivered the desired product as an impure mixture. Further purification by reverse phase HPLC (5-75% ACN w/0.1% TFA in Water w/0.1% TFA) gave the TFA salt Compound 97 (23 mg, 4% yield) as a white solid.

Compound 97:
$^1$H-NMR (400 MHz, MeOD) δ 8.89 (d, 2H), 7.72 (d, 1H), 7.49 (t, 1H), 7.37 (s, 1H), 7.28-7.22 (m, 1H), 7.09-6.99 (m, 2H), 6.86 (t, 1H), 6.59 (d, 1H), 5.95 (s, 2H).

Compound 119 (Unregistered Intermediate)

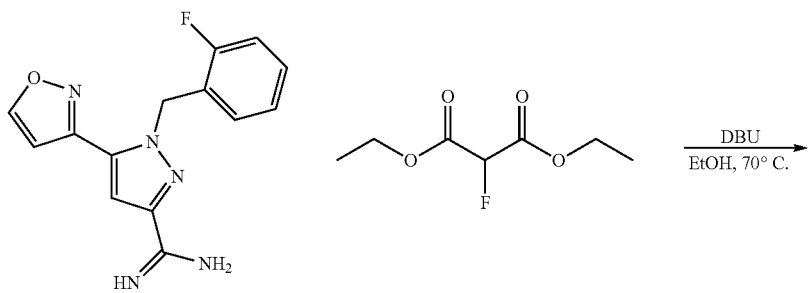

Intermediate-8C

-continued

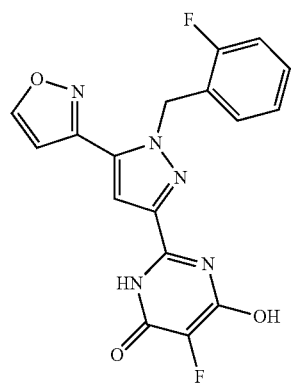

119

A mixture of 1-(2-fluorobenzyl)-5-(isoxazol-3-yl)-1H-pyrazole-3-carboximidamide (Intermediate-8C, 108 mg, 1.0 equiv.), diethyl 2-fluoromalonate (60 μl, 1.0 equiv.) and DBU (57 μl, 1.0 equiv.) in ethanol (1.9 ml) was heated to 70° C. for 24 h. The mixture was concentrated under vacuum to give an oil. The oil was purified by column chromatography (0 to 20% dichloromethane in methanol) to give 5-fluoro-2-(1-(2-fluorobenzyl)-5-(isoxazol-3-yl)-1H-pyrazol-3-yl)-6-hydroxypyrimidin-4(3H)-one (Compound 119, 145 mg, 100% yield) as a white solid.

$^1$H NMR (500 MHz, METHANOL-$d_4$) δ ppm 8.81 (d, 1H) 7.42 (s, 1H) 7.26-7.36 (m, 1H) 7.05-7.18 (m, 2H) 6.97 (t, 1H) 6.92 (d, 1H) 5.97 (s, 2H).

A mixture of 5-fluoro-2-(1-(2-fluorobenzyl)-5-(isoxazol-3-yl)-1H-pyrazol-3-yl)-6-hydroxypyrimidin-4(3H)-one (Compound 119, 145 mg, 1.0 equiv.) and POCl$_3$ (1.5 ml, 40 equiv.) was heated to 70° C. for 24 h. The mixture was concentrated under vacuum to give a white solid. It was diluted in ethyl acetate (100 ml) and washed with water (50 ml). The organic layer was dried, filtered and evaporated to give 3-(3-(4,6-dichloro-5-fluoropyrimidin-2-yl)-1-(2-fluorobenzyl)-1H-pyrazol-5-yl)isoxazole (Compound 117, 61 mg, 38% yield) as a white solid.

$^1$H NMR (500 MHz, CHLOROFORM-d) δ ppm 8.40 (s, 1H) 7.37 (s, 1H) 7.10-7.18 (m, 1H) 6.88-7.00 (m, 2H) 6.76 (t, 1H) 6.53 (d, 1H) 5.96 (s, 2H).

Compound 117 (Unregistered Intermediate)

Compound 116 (462456):

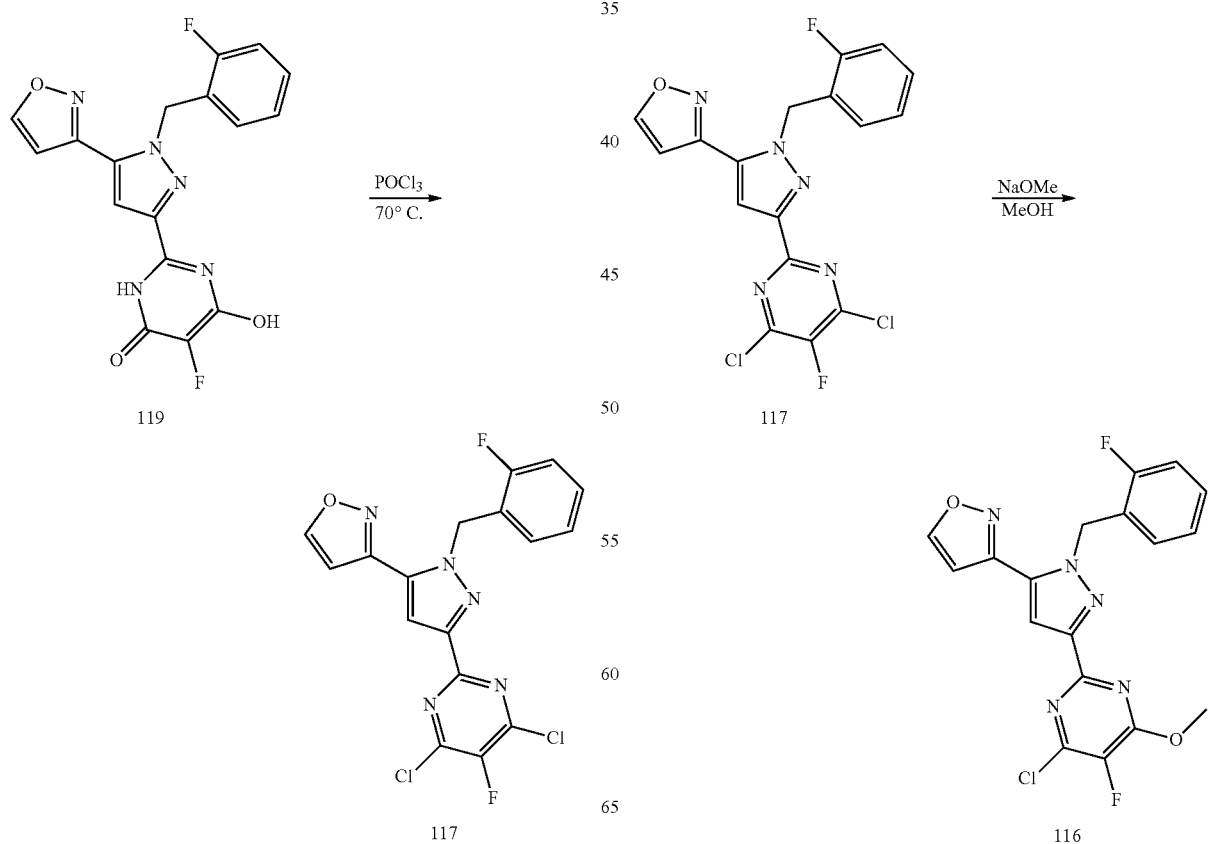

To a suspension of 3-(3-(4,6-dichloro-5-fluoropyrimidin-2-yl)-1-(2-fluorobenzyl)-1H-pyrazol-5-yl)isoxazole (Compound 117, 50 mg, 1.0 equiv.) in methanol (2.5 ml), was added sodium methoxide[0.5 M in methanol] (245 µl, 1.0 equiv.). The mixture was stirred at rt for 4 h. The mixture was treated with HCl (4.0 M in dioxane, 1.0 equiv.). The mixture was concentrated under vacuum. The resulting solid was dissolved in ethyl acetate (100 ml) and washed with brine. The organic layer was dried, filtered and evaporated to give Compound 116 (462456) (42 mg, 85% yield) as a white solid.

$^1$H NMR (500 MHz, METHANOL-d$_4$) δ ppm 8.67 (d, 1H) 7.45 (s, 1H) 7.16-7.21 (m, 1H) 6.97-7.04 (m, 1H) 6.94 (t, 1H) 6.83 (d, 1H) 6.74 (t, 1H) 5.88 (s, 2H) 4.12 (s, 3H).

Compound 120 (Unregistered Intermediate)

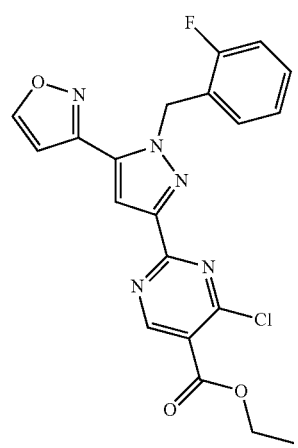

Intermediate-22

1. Hunig's base, H$_2$NNMeBoc, THF, 85° C.

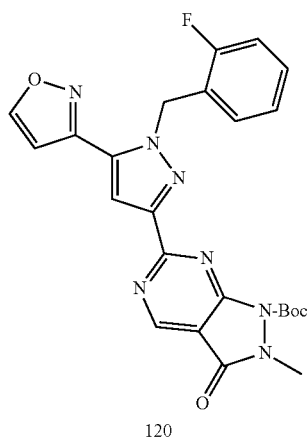

120

A mixture of ethyl 4-chloro-2-(1-(2-fluorobenzyl)-5-(isoxazol-3-yl)-1H-pyrazol-3-yl)pyrimidine-5-carboxylate (Intermediate-22, 80 mg, 1.0 equiv.), Hunig's Base (33 µl, 1.0 equiv.) and tert-butyl 1-methylhydrazinecarboxylate (33 µl, 1.2 equiv.) in THF (1.0 ml) was heated to reflux in a sealed vial for 2 h. The mixture was cooled to rt and concentrated under vacuum to give a white solid. It was rinsed with diethyl ether and dried under vacuum to give ethyl 4-(2-(tert-butoxycarbonyl)-2-methylhydrazinyl)-2-(1-(2-fluorobenzyl)-5-(isoxazol-3-yl)-1H-pyrazol-3-yl)pyrimidine-5-carboxylate (Compound 120, 83 mg, 83% yield) as a white solid.

$^1$H NMR (400 MHz, DMSO-d$_6$) δ ppm 9.84 (d, 1H) 9.13 (d, 1H) 8.93 (s, 1H) 7.47 (s, 1H) 7.28-7.41 (m, 1H) 7.24 (d, 1H) 7.19 (d, 1H) 7.11 (t, 1H) 5.90 (s, 2H) 4.36 (q, 2H) 3.15 (s, 3H) 1.25-1.29 (m, 9H) 1.35 (t, 3H).

Compound 112 (460990)

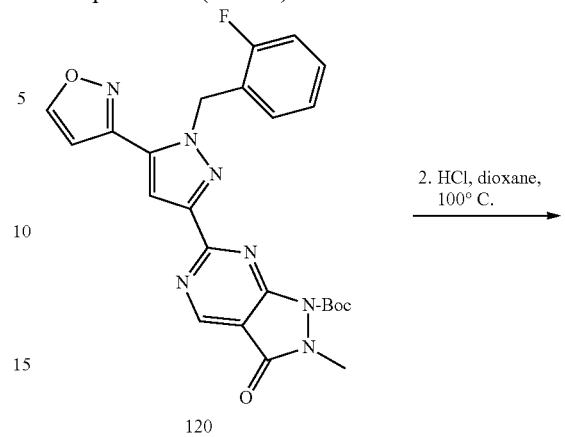

120

2. HCl, dioxane, 100° C.

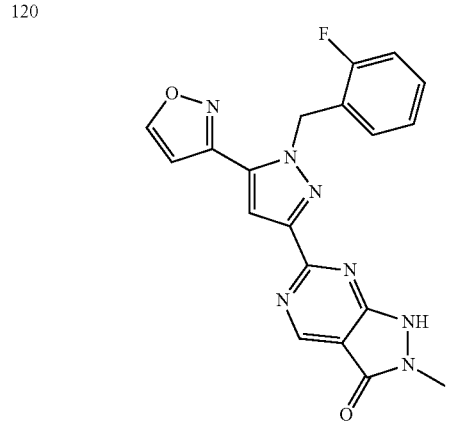

112

A mixture of ethyl 4-(2-(tert-butoxycarbonyl)-2-methylhydrazinyl)-2-(1-(2-fluorobenzyl)-5-(isoxazol-3-yl)-1H-pyrazol-3-yl)pyrimidine-5-carboxylate (Compound 120, 83 mg, 1.0 equiv.) and HCl [4.0 M in dioxane] (94 µl, 20 equiv.) in dioxane (800 µl) was heated to 100° C. for 24 h. The mixture was cooled to rt and rinsed with methanol. The particulate was collected by filtration and dried under vacuum to give Compound 112 (460990) (25.0 mg, 41% yield) as a yellow solid.

$^1$H NMR (400 MHz, DMSO-d$_6$) δ ppm 9.14 (d, 2H) 7.78 (s, 1H) 7.31-7.39 (m, 2H) 7.25 (d, 1H) 7.13 (t, 1H) 6.93 (s, 1H) 5.97 (s, 2H) 3.42 (s, 3H).

Compound 122 (Unregistered Intermediate)

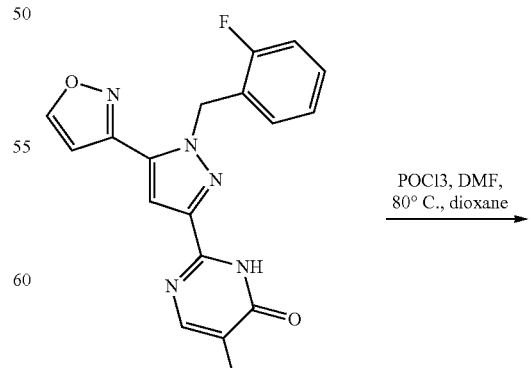

Intermediate-23

POCl3, DMF, 80° C., dioxane

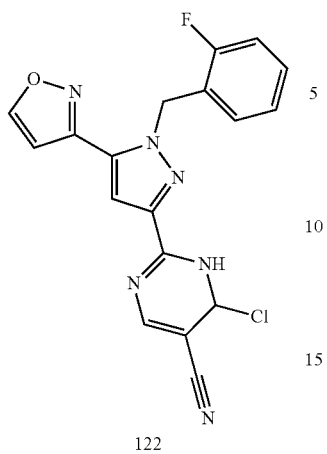

122

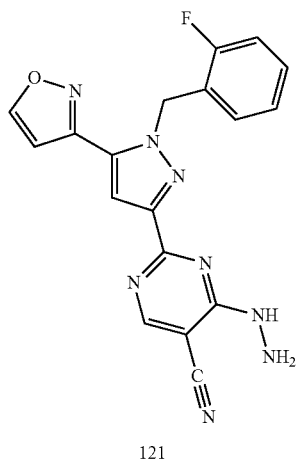

121

To a suspension of 2-(1-(2-fluorobenzyl)-5-(isoxazol-3-yl)-1H-pyrazol-3-yl)-6-oxo-1,6-dihydropyrimidine-5-carbonitrile (Intermediate-23, 279 mg, 1.0 equiv.) in dioxane (4.0 ml), were added phosphoryl trichloride (1.5 ml, 20 equiv.) and a few drops of DMF. The mixture was stirred at 80° C. for 24 h. The mixture was cooled to rt, poured over ice and treated with saturated solution of sodium bicarbonate (100 ml). The mixture was extracted with ethyl acetate (100 ml). The organic layer was dried, filtered and evaporated to give 4-chloro-2-(1-(2-fluorobenzyl)-5-(isoxazol-3-yl)-1H-pyrazol-3-yl)pyrimidine-5-carbonitrile (Compound 122, 293 mg, 100% yield) as a white solid.

$^1$H NMR (400 MHz, CHLOROFORM-d) δ ppm 8.97 (s, 1H) 8.49 (d, 1H) 7.53 (s, 1H) 7.18-7.24 (m, 1H) 6.94-7.07 (m, 2H) 6.82-6.90 (m, 1H) 6.60 (d, 1H) 6.03 (s, 2H).

To a mixture of 4-chloro-2-(1-(2-fluorobenzyl)-5-(isoxazol-3-yl)-1H-pyrazol-3-yl)pyrimidine-5-carbonitrile (Compound 122, 402 mg, 1.0 equiv.) in ethanol (5.3 m) at rt, was added hydrazine hydrate (66 μl, 2.0 equiv.). The mixture was stirred at rt for 1 h and the precipitate was filtered via filtration. It was rinsed with ether and dried under vacuum to give Compound 121 (460928) (286 mg, 72% yield) as a yellow solid.

$^1$H NMR (400 MHz, DMSO-d$_6$) δ ppm 9.64 (br. s., 1H) 9.10 (d, 1H) 8.62 (s, 1H) 7.61 (br. s., 1H) 7.29-7.39 (m, 1H) 7.18-7.27 (m, 2H) 7.10 (t, 1H) 6.85 (t, 1H) 5.91 (s, 2H) 4.84 (br. s., 1H).

Compound 121 (460928)

Compound 118 (460942)

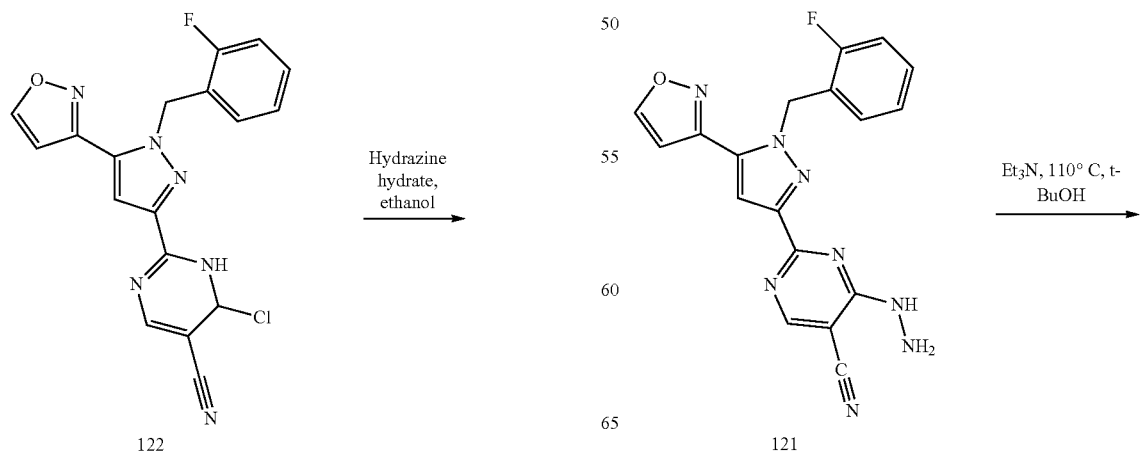

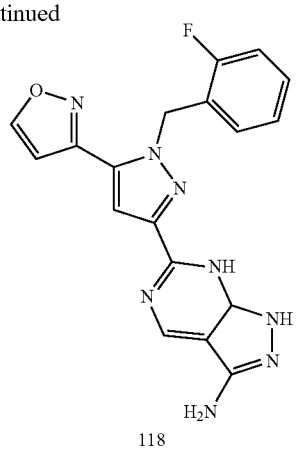

118

A mixture of Compound 121 (286 mg, 1.0 equiv.) and triethylamine (100 µl, 1.0 equiv) in tert-BuOH (15 ml) was heated to 110° C. for 24 h. The mixture was cooled to rt and precipitate was filtered. The precipitate was dried under vacuum to give Compound 118 (460942) (146 mg, 51% yield) as a yellow solid.

$^1$H NMR (400 MHz, DMSO-d$_6$) δ ppm 9.16 (s, 1H) 9.11 (d, 1H) 7.69 (s, 1H) 7.35 (d, 1H) 7.32 (d, 1H) 7.21-7.27 (m, 1H) 7.13 (t, 1H) 6.91-6.98 (m, 1H) 6.05 (s, 2H) 5.94 (s, 2H).

Compound 113 (461031):

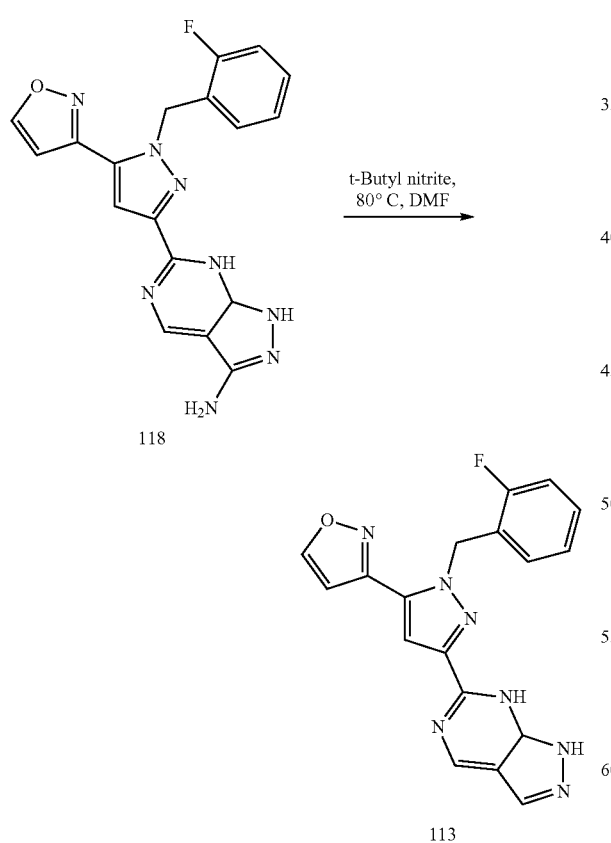

A mixture of Compound 118 (21.7 mg, 1.0 equiv.) and tert-butyl nitrite (69 µl, 10 equiv.) in DMF (300 µl) was heated to 80° C. for 30 min. The precipitate dissolved completely during the course of the reaction. The mixture was diluted in ethyl acetate (100 ml) and washed with water (50 ml). The organic layer was dried, filtered and evaporated to give oil. It was purified by column chromatography (0 to 100% ethyl acetate in hexanes). The concentrated material was rinsed in methanol, collected by filtration and dried under vacuum to give Compound 113 (461031) (1.4 mg, 7% yield) as a white solid.

$^1$H NMR (400 MHz, DMSO-d$_6$) δ ppm 9.40 (s, 1H) 9.13 (d, 1H) 8.38 (s, 1H) 7.75 (s, 1H) 7.32-7.42 (m, 2H) 7.25 (d, 1H) 7.14 (t, 1H) 6.97 (t, 1H) 5.96 (s, 2H).

Compound 114 (461066):

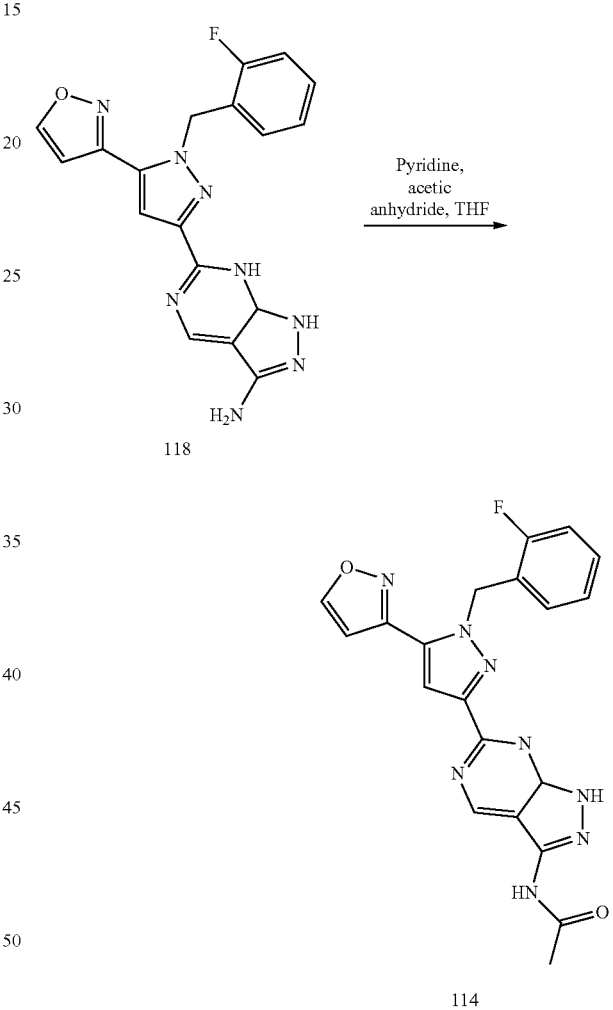

A mixture of Compound 118 (34 mg, 1 equiv.), pyridine (15 µl, 2.0 equiv.) and acetic anhydride (43 µl, 5.0 equiv.) in THF (4.5 ml) was stirred at 80° C. for 1 h. The mixture was diluted in ethyl acetate (50 mL) and washed with 1N HCl. The organic layer was dried, filtered and evaporated to give solid. It was purified by column chromatography (0 to 5% methanol in dichloromethane). The solid obtained was recrystallized from a methanol:chloroform mixture gave the desired Compound 114 (461066) (1.4 mg, 3.7% yield) as a white solid.

$^1$H NMR (400 MHz, DMSO-d$_6$) δ ppm 9.61 (s, 1H) 9.12 (d, 1H) 7.75 (s, 1H) 7.31-7.41 (m, 2H) 7.21-7.28 (m, 1H) 7.13 (t, 1H) 6.93-7.01 (m, 1H) 5.96 (s, 2H) 2.16 (s, 3H).

Compound 115 (462103)

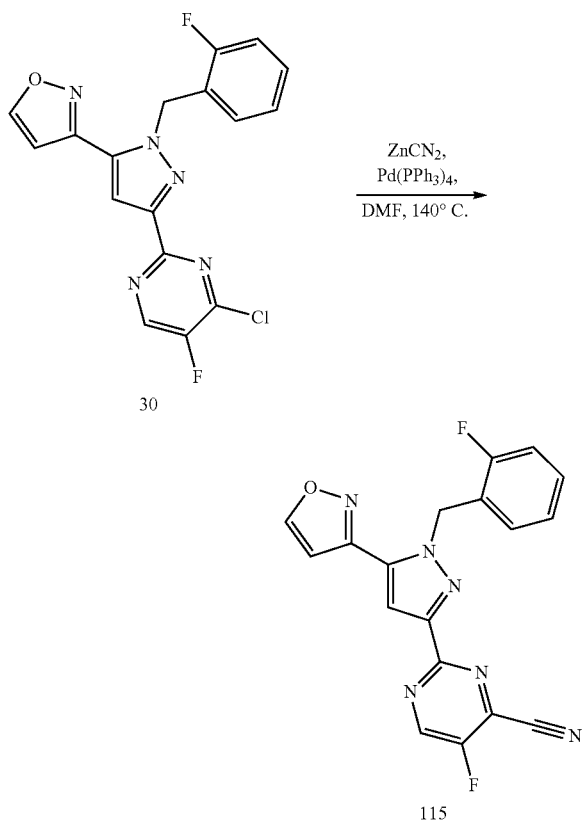

ZnCN₂,
Pd(PPh₃)₄,
—————→
DMF, 140° C.

A mixture of Compound 30 (460424) (100 mg, 1 equiv.), dicyanozinc (16 mg, 0.5 equiv.) and palladium tetrakistriphenylphosphine (31 mg, 0.1 equiv.) in DMF (1.3 ml) was heated to 140° C. in a microwave for 3.5 h. The mixture was diluted in ethyl acetate (100 ml). The organic layer was washed with water (50 ml), dried, filtered and evaporated to give an oil. The oil was purified by column chromatography (0 to 40% ethyl acetate in hexanes) to give Compound 115 (462053) (9.5 mg, 10% yield) as a white solid.

$^1$H NMR (500 MHz, CHLOROFORM-d) δ ppm 8.96 (s, 1H) 8.52 (s, 1H) 7.46-7.51 (m, 1H) 7.22-7.28 (m, 1H) 6.97-7.10 (m, 2H) 6.90 (t, 1H) 6.64 (s, 1H) 6.05 (s, 2H).

Compound 101 (461685)

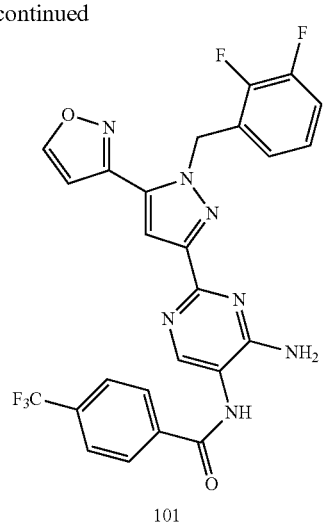

101

To a suspension of Compound 8 (1 equivalent) in dichloromethane and pyridine (2:1 ratio) was added 4-(trifluoromethyl)benzoyl chloride (1 equivalent) dropwise over 3 min. Additional 4-(trifluoromethyl)benzoyl chloride was added until the reaction was complete as indicated by LC/MS. The suspension was poured into saturated aqueous ammonium chloride and dichloromethane. The layers were separated and the aqueous layer was extracted with dichloromethane. The organics were dried over magnesium sulfate, filtered, and the solvent was removed in vacuo. The crude residue was suspended in dichloromethane and diethyl ether (1:1 ratio). The resulting solid was filtered off and washed with diethyl ether to provide Compound 101 (34 mg, 85% yield) as a white solid.

$^1$H-NMR (400 MHz, MeOD) δ 8.79 (m, 1H), 8.33 (s, 1H), 8.20 (d, 2H), 7.86 (d, 2H), 7.47 (s, 1H), 7.17 (q, 1H), 7.06-7.01 (m, 1H), 6.91 (m, 1H), 6.71-6.68 (m, 1H), 6.01 (s, 2H).

Compound 102 (461686)

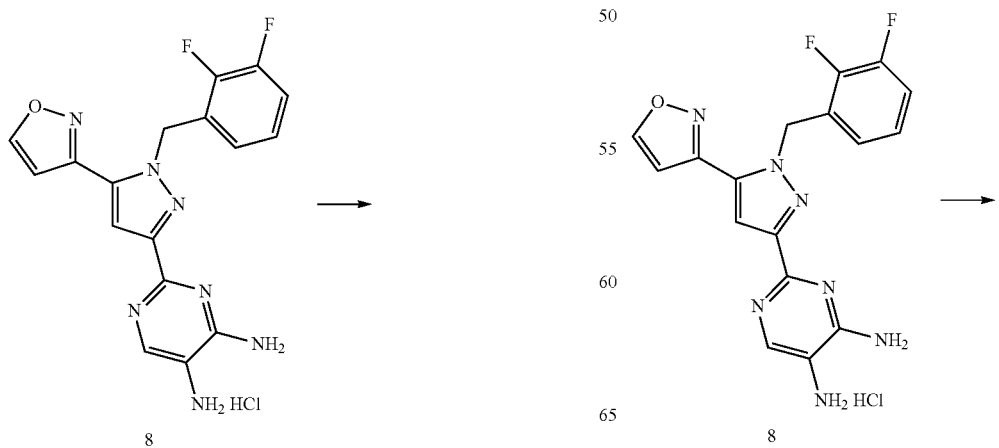

205

-continued

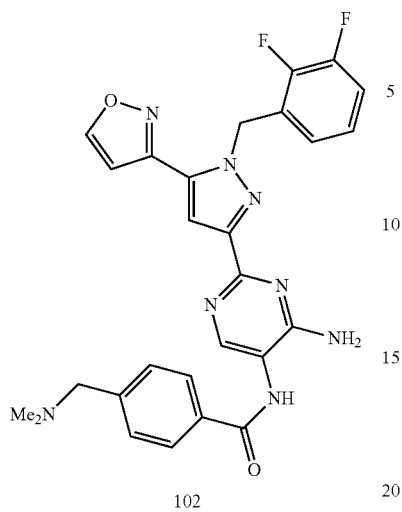

102

To a solution of 4-((dimethylamino)methyl)benzoic acid (8 equivalents) in dichloromethane was added oxalyl dichloride (7.5 equivalents) and a drop of catalytic N,N-dimethylformamide. After 3 hours, the resulting acid chloride was slowly added to Compound 8 (1 equivalent) in dichloromethane and pyridine (2:1 ratio) until starting material was consumed as verified by LC/MS. The solution was diluted with saturated aqueous ammonium chloride solution and dichloromethane. The layers were separated and the aqueous layer was neutralized with saturated aqueous sodium bicarbonate solution. After extracting with dichloromethane, the organics were combined, dried over magnesium sulfate, filtered, and the solvent was removed in vacuo. The residue was brought up in dichloromethane and diethyl ether (1:2.5 ratio) and the resulting solid was filtered and washed with diethyl ether to give Compound 102 (2.6 mg, 16% yield) as a white solid.

$^1$H-NMR (400 MHz, MeOD) δ 8.79 (m, 1H), 8.32 (s, 1H), 8.01 (d, 2H), 7.51 (d, 2H), 7.47 (s, 1H), 7.17 (q, 1H), 7.06-7.01 (m, 1H), 6.91 (m, 1H), 6.71-6.68 (m, 1H), 6.01 (s, 2H), 3.61 (s, 2H), 2.30 (s, 6H).

Compound 103 (461689)

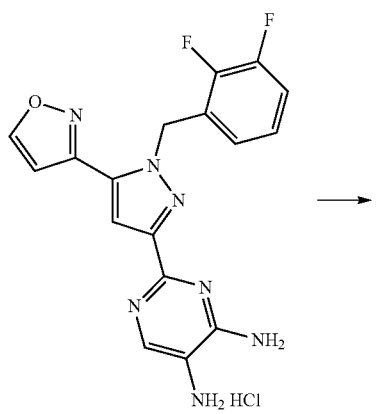

8

206

-continued

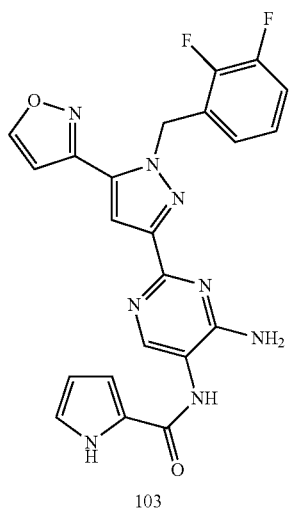

103

To a solution of 1H-pyrrole-2-carboxylic acid (8 equivalents) in dichloromethane was added oxalyl dichloride (7.5 equivalents) and a drop of catalytic N,N-dimethylformamide. After 1.5 hours, the resulting acid chloride was slowly added to Compound 8 (1 equivalent) in dichloromethane and pyridine (2:1 ratio) until starting material was consumed as verified by LC/MS. The solution was diluted with saturated aqueous ammonium chloride solution and dichloromethane. The layers were separated and the aqueous layer was extracted with dichloromethane. The organics were dried over magnesium sulfate, filtered, and the solvent was removed in vacuo. The residue was brought up in dichloromethane and diethyl ether (1:2.5 ratio) and the resulting solid was filtered and washed with diethyl ether to give Compound 103 (9 mg, 79% yield) as a white solid.

$^1$H-NMR (400 MHz, MeOD) δ 8.78 (s, 1H), 8.30 (m, 1H), 8.46 (m, 1H), 7.17 (q, 1H), 7.06-7.01 (m, 2H), 6.91 (s, 1H), 6.71-6.67 (m, 1H), 6.26 (m, 1H), 6.01 (s, 2H).

Compound 104 (461691)

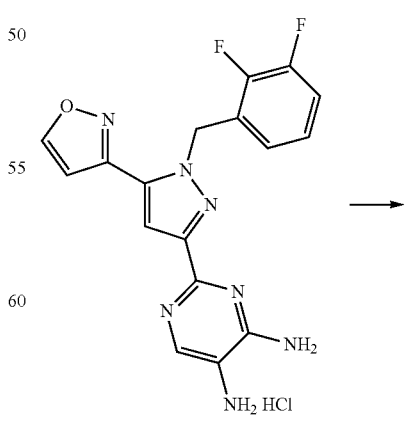

8

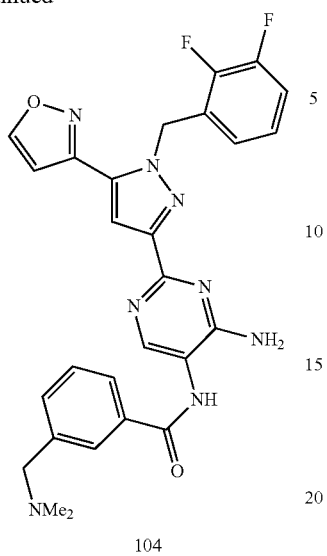

104

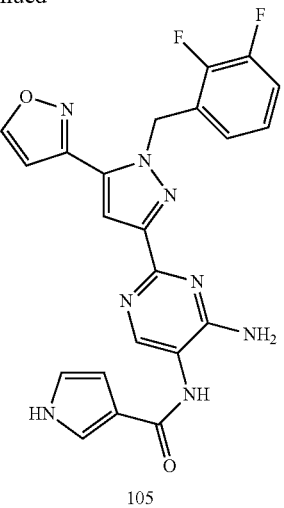

105

To a solution of 3-((dimethylamino)methyl)benzoic acid hydrochloride (8 equivalents) in dichloromethane was added oxalyl dichloride (7.5 equivalents) and a drop of catalytic N,N-dimethylformamide. After 3 hours, the resulting acid chloride was slowly added to Compound 8 (1 equivalent) in dichloromethane and pyridine (2:1 ratio) until starting material was consumed as verified by LC/MS. The solution was diluted with saturated aqueous ammonium chloride solution and dichloromethane. The layers were separated and the aqueous layer was neutralized with saturated aqueous sodium bicarbonate solution. After extracting with dichloromethane, the organics were dried over magnesium sulfate, filtered, and the solvent was removed in vacuo. The residue was brought up in dichloromethane and diethyl ether (3:5 ratio) and the resulting solid was filtered and washed with diethyl ether to give Compound 104 (3 mg, 22% yield) as a white solid.

$^1$H-NMR (400 MHz, MeOD) δ 8.76 (m, 1H), 8.32 (s, 1H), 8.18 (s, 1H), 8.08 (d, 1H), 7.69-7.67 (m, 1H), 7.63-7.59 (m, 1H), 7.45 (s, 1H), 7.15 (q, 1H), 7.02-6.98 (m, 1H), 6.89 (m, 1H), 6.69-6.66 (m, 1H), 5.99 (s, 2H), 4.19 (br s, 2H), 2.72 (s, 6H).

Compound 105 (461707)

To a solution of 1H-pyrrole-3-carboxylic acid (8 equivalents) in dichloromethane was added oxalyl dichloride (7.5 equivalents) and a drop of catalytic N,N-dimethylformamide. After 2 hours, the resulting acid chloride was slowly added to Compound 8 (1 equivalent) in dichloromethane and pyridine (2:1 ratio) until starting material was consumed as verified by LC/MS. The solution was diluted with saturated aqueous ammonium chloride solution and dichloromethane. The layers were separated and the aqueous layer was extracted with dichloromethane. The organics were dried over magnesium sulfate, filtered, and the solvent was removed in vacuo. The residue was brought up in dichloromethane and diethyl ether (4:5 ratio) and the resulting solid was filtered and washed with diethyl ether to give Compound 105 (12 mg, 70% yield) as a light pink solid.

$^1$H-NMR (400 MHz, MeOD) δ 8.78 (m, 1H), 8.28 (s, 1H), 7.54 (m, 1H), 7.46 (s, 1H), 7.17 (q, 1H), 7.06-7.00 (m, 1H), 6.91 (m, 1H), 6.83-6.82 (m, 1H), 6.71-6.67 (m, 2H), 6.00 (s, 2H).

Compound 106 (461766)

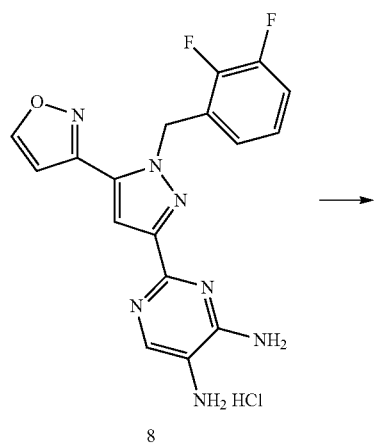

8

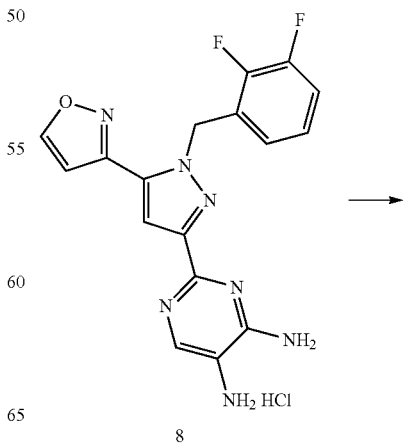

8

-continued

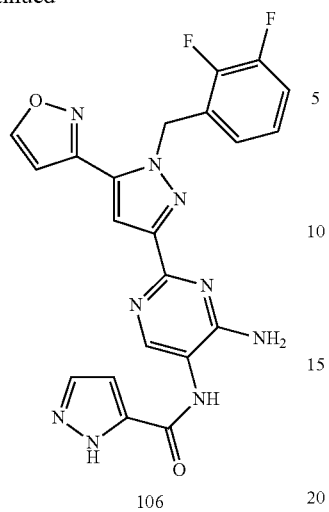

106

-continued

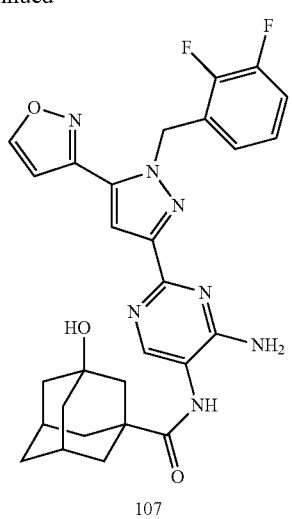

107

To a solution of 1H-pyrazole-5-carboxylic acid (8 equivalents) in dichloromethane was added oxalyl dichloride (7.5 equivalents) and a drop of catalytic N,N-dimethylformamide. After 1 hour, the resulting acid chloride was slowly added to Compound 8 (1 equivalent) in dichloromethane and pyridine (2:1 ratio) until starting material was consumed as verified by LC/MS. The solution was diluted with saturated aqueous ammonium chloride solution and dichloromethane. The layers were separated and the aqueous layer was extracted with dichloromethane. The organics were dried over magnesium sulfate, filtered, and the solvent was removed in vacuo. Purification by silica gel chromatography (0-10% methanol in dichloromethane) provided Compound 106 (4.5 mg, 26% yield) as a pale yellow solid.

$^1$H-NMR (400 MHz, DMSO) δ 13.43 (s, 1H), 9.60 (s, 1H), 9.10 (m, 1H), 8.30 (s, 1H), 7.90 (s, 1H), 7.56 (s, 1H), 7.37 (q, 1H), 7.26 (m, 1H), 7.16-7.12 (m, 1H), 6.89 (br s, 1H), 6.78 (s, 1H), 6.71-6.68 (m, 1H), 5.95 (s, 2H).

To a solution of 3-hydroxyadamantane-1-carboxylic acid (8 equivalents) in dichloromethane was added oxalyl dichloride (7.5 equivalents) and a drop of catalytic N,N-dimethylformamide. After 1 hour, the resulting acid chloride was slowly added to Compound 8 (1 equivalent) in dichloromethane and pyridine (2:1 ratio) until most of the starting material was consumed as verified by LC/MS. The solution was diluted with saturated aqueous ammonium chloride solution and dichloromethane. The layers were separated and the aqueous layer was extracted with dichloromethane. The organics were dried over magnesium sulfate, filtered, and the solvent was removed in vacuo. Purification by silica gel chromatography (0-10% methanol in dichloromethane) provided Compound 107 (3 mg, 22% yield) as a solid.

$^1$H-NMR (400 MHz, MeOD) δ 8.83 (d, 1H), 8.25 (s, 1H), 7.59 (m, 1H), 7.22-7.16 (m, 1H), 7.07-7.02 (m, 1H), 6.92 (m, 1H), 6.82-6.78 (m, 1H), 6.04 (s, 2H), 2.29 (br s, 2H), 1.96-1.88 (m, 6H), 1.74 (br s, 4H).

Compound 107 (461690)

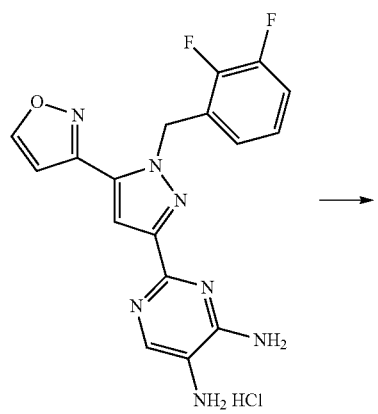

8

Compound 108 (461820)

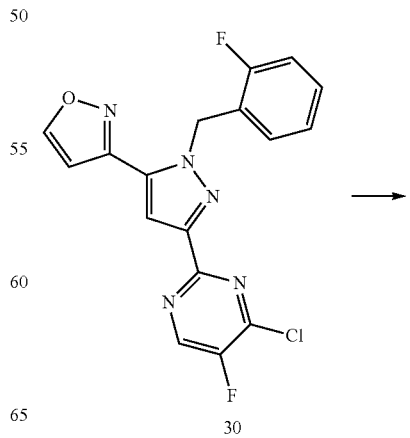

30

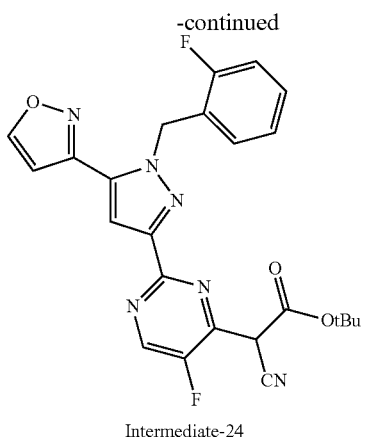

Intermediate-24

To a room temperature solution of tert-butyl 2-cyanoacetate (1.1 equivalents) in tetrahydrofuran was added sodium bis(trimethylsilyl)amide (1.1 equivalents) as a 1M solution in toluene. After stirring for 10 minutes, Compound 30 was added in a single portion and stirred at room temperature for 16 hours. The solution was poured into water and dichloromethane. The layers were separated and the aqueous layer was extracted with dichloromethane. The organics were dried over magnesium sulfate, filtered, and the solvent was removed in vacuo. Purification by silica gel chromatography (0-60% ethyl acetate in hexanes) provided Intermediate-24 (11 mg, 21% yield) as a bright yellow solid.

To a solution of Intermediate-24 (1 equivalent) in dichloromethane was added trifluoroacetic acid (38 equivalents) and the resulting solution was stirred for 60 hours at room temperature. The solvent was removed in vacuo to give Compound 108 (8 mg, quantitative yield) as a brown solid.

$^1$H-NMR (400 MHz, CDCl3) δ 8.73 (m, 1H), 8.51 (m, 1H), 7.48 (s, 1H), 7.25-7.20 (m, 1H), 7.07-6.98 (m, 2H), 6.93-6.89 (m, 1H), 6.65 (m, 1H), 6.03 (s, 2H), 4.08 (s, 2H).

Compound 98 (MM-461958)

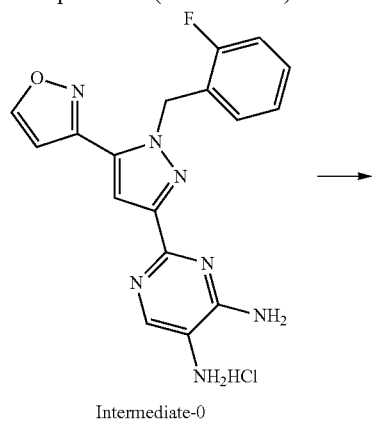

Intermediate-0

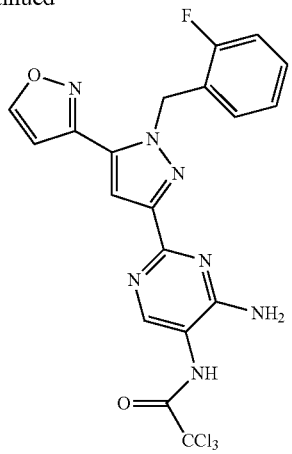

98

A suspension of Intermediate-0 (50 mg, 1 equiv.) in dichloromethane (0.86 mL) and pyridine (0.43 mL) was treated with 2,2,2-trichloroacetyl chloride (38 μl, 2.6 equiv.) at 23° C. The homogeneous mixture was stirred for 15 minutes, then transferred to 1:1 mixture of ethyl acetate and water. The layers were separated, and the organic layer was washed with saturated ammonium chloride solution and brine. The mixture was dried over MgSO4, filtered, and concentrated in vacuo. The crude material was purified via silica gel chromatography utilizing a 0-30% (acetonitrile:methanol=7:1)/dichloromethane gradient to deliver the desired Compound 98 (9 mg, 14%) as a white solid.

$^1$H-NMR (500 MHz, CDCl3) δ 10.38 (s, 1H), 9.09 (d, 1H), 8.14 (s, 1H), 7.59-7.54 (m, 1H), 7.38-7.29 (m, 1H), 7.28-7.19 (m, 2H), 7.12 (t, 1H), 7.01 (br. s., 2H), 6.88 (t, 1H), 5.91 (s, 2H).

Compound 99 (461018)

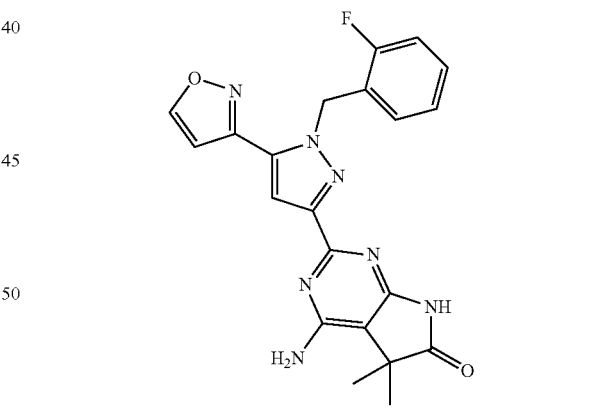

1-(2-Fluorobenzyl)-5-(isoxazol-3-yl)-1H-pyrazole-3-carboximidamide hydrochloride (Intermediate-0, 0.250 g, 0.777 mmol), TEA (0.325 ml, 2.331 mmol), and methyl 3,3-dicyano-2,2-dimethylpropanoate (0.387 g, 2.331 mmol) were stirred as a solution in EtOH (Volume: 2.0 ml) for 3 hours at 100° C. At this time, the reaction was directly concentrated and loaded onto a SiO2 column and purified using a 0-10% MeOH/DCM gradient. Isolated 40 mg (11% yield) of desired product.

$^1$H NMR (400 MHz, DMSO-d6) δ ppm 10.95 (s, 1H), 9.10 (d, 1H), 7.43-7.18 (m, 4H), 7.11 (t, 1H), 6.85 (t, 1H), 6.71 (bs, 2H), 5.88 (s, 2H), 1.40-1.21 (m, 6H).

Compound 100 (461095)

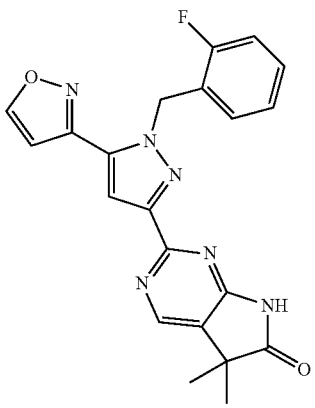

4-amino-2-(1-(2-fluorobenzyl)-5-(isoxazol-3-yl)-1H-pyrazol-3-yl)-5,5-dimethyl-5H-pyrrolo[2,3-d]pyrimidin-6(7H)-one (Compound 99, 0.184 g, 0.439 mmol) was dissolved in DMF (Volume: 1.0 ml) and then charged with tert-butyl nitrite (0.157 ml, 1.316 mmol). After 1 hour at rt, reaction seems to have stalled with fairly low conversion. Heating and additional nitrite did not seem to push reaction. At this point, the DMF was removed and the residue was purified by SiO2 chromatography using a 0-10% MeOH/DCM gradient. At this juncture, the material was not completely clean, therefore an additional purification was done using reverse phase prep HPLC to deliver the desired compound (2 mg, 2% yield).

$^1$H NMR (400 MHz,) δ ppm 8.78-8.58 (m, 1H), 8.38 (s, 1H), 7.47 (s, 1H), 7.27-7.11 (m, 1H), 7.07-6.88 (m, 2H), 6.87-6.65 (m, 2H), 5.91 (s, 2H), 1.38 (s, 6H).

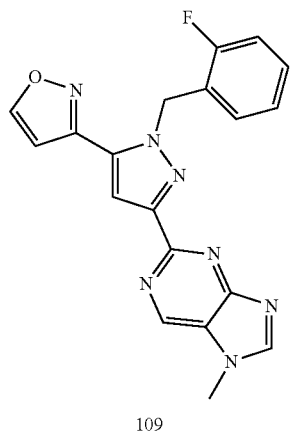

109

Oxalyl chloride (0.08 g, 0.6 mmol) was added to a suspension of chloroacetic acid (0.071 g, 0.75 mmol) in DCM (with trace DMF) at 0° C. and stirred at room temperature for 2 h.

2-(1-(2-fluorobenzyl)-5-(isoxazol-3-yl)-1H-pyrazol-3-yl)-N$^5$-methylpyrimidine-4,5-diamine hydrochloride (Intermediate-25, 0.03 g, 0.075 mmol) was added to the reaction pot, followed by pyridine (0.5 g, 6 mmol) and stirred at room temperature until all starting material was consumed. The reaction was quenched with saturated aqueous NaHCO$_3$, extracted with dichloromethane and purified by flash chromatography to yield Compound 109 (0.017 g, 58%) as a brown solid.

$^1$H NMR (400 MHz, DMSO-d$_6$) δ ppm 9.24 (s, 1H), 9.07-9.15 (m, 1H), 8.66 (s, 1H), 7.75 (s, 1H), 7.30-7.41 (m, 2H), 7.20-7.28 (m, 1H), 7.08-7.18 (m, 1H), 6.93 (t, 1H), 5.95 (s, 2H), 3.99 (s, 3H).

Compound 109 (MM-461139)

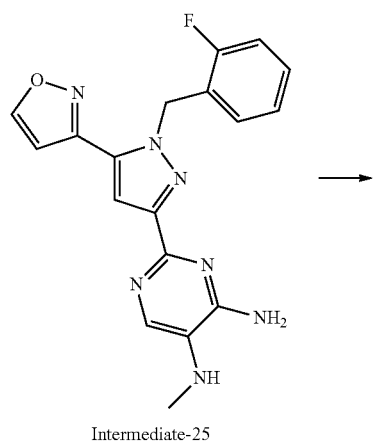

Intermediate-25

Compound 110 (MM-461295)

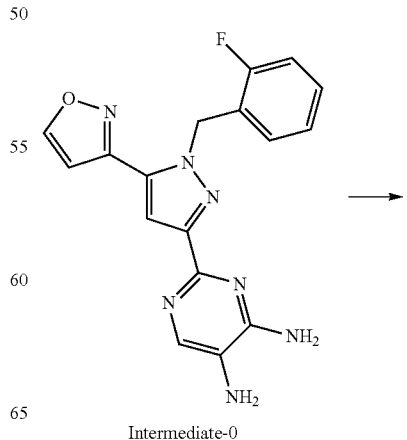

Intermediate-0

-continued

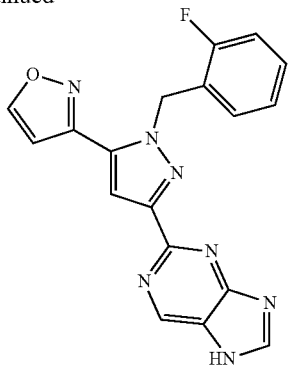

110

2-(1-(2-fluorobenzyl)-5-(isoxazol-3-yl)-1H-pyrazol-3-yl) pyrimidine-4,5-diamine (Intermediate-0, 0.015 g, 0.043 mmol) and triethyl orthoformate (excess) were heated together in DMF/toluene in the microwave at 150° C. for 40 min. The reaction mixture was cooled, diluted with hexanes, and residue filtered to give Compound 110 (0.008 g, 42%) as a brown solid.

$^1$H NMR (400 MHz, DMSO-$d_6$) δ ppm 5.94 (s, 2H) 6.95 (t, 1H) 7.13 (t, 1H) 7.19-7.27 (m, 1H) 7.29-7.39 (m, 2H) 7.68 (s, 1H) 8.60 (s, 1H) 9.11 (s, 1H) 9.19 (s, 1H) 13.53 (br. s., 1H)

Compound 111 (MM-461483)

Intermediate-0

111

2-(1-(2-fluorobenzyl)-5-(isoxazol-3-yl)-1H-pyrazol-3-yl) pyrimidine-4,5-diamine (Intermediate-0, 0.03 g, 0.085 mmol) and 4,4,4-trifluorobutanoyl chloride (0.042 g, 0.25 mmol) were stirred together in dichloromethane at room temperature until all starting material was consumed. The reaction was then quenched with saturated aqueous NaHCO$_3$, extracted with dichloromethane and purified by flash chromatography to yield Compound 111 (0.041 g, 68%) as a tan solid.

$^1$H NMR (400 MHz, methanol-$d_4$) δ ppm 8.72 (s, 1H), 8.23 (s, 1H), 7.94 (s, 1H), 7.38 (s, 1H), 7.17-7.28 (m, 1H), 6.95-7.12 (m, 2H), 6.74-6.86 (m, 2H), 5.92 (s, 2H), 2.90-3.00 (m, 1H), 2.78-2.87 (m, 1H), 2.66-2.76 (m, 2H), 2.65 (br. s., 2H), 2.44-2.63 (m, 2H).

Example 2

Biological Activity Measurement by the sGC-HEK-cGMP Assay (Assay Run with SNP Incubation)

Human embryonic kidney cells (HEK293), endogenously expressing soluble guanylate cyclase (sGC), were used to evaluate the activity of test compounds. Compounds stimulating the sGC receptor should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 μL volume at a density of 1×105 cells/well in a poly-D-lysine coated 96 well flat bottom plate and grown overnight at 37° C. Medium was aspirated and cells were washed with 1× Hank's Buffered Saline Salt Solution (200 μL). Cells were then incubated for 15 minutes at 37° C. with 0.5 mM 3-isobutyl-1-methylxanthine (200 μL). Test article and sodium nitroprusside were then added to the assay mixture (24 each) and incubated at 37° C. for 10 minutes. After the 10 minute incubation, the assay mixture was aspirated and 0.1M HCl (200 μL) was added to the cells. The plate was incubated at 4° C. for 30 minutes in the 0.1M HCl to stop the reaction and lysed the cells. The plates were then centrifuged at 1,200 g for 5 minutes at room temperature. Supernatants were collected and transferred to a new flat bottom 96 well plate for analysis. Vehicle controls were carried out using DMSO (1%). A known sGC stimulator, BAY 41-2272, was used as the positive control. Samples were diluted with an equal volume of 1 M Ammonium Acetate (pH 7) to neutralize samples for better chromatography. A 2× cGMP standard curve was prepared in 0.1 M HCl and then diluted with an equal volume of 1 M Ammonium Acetate, with the following final concentrations in nM: 1024, 512, 256, 128, 64, 32, 16, 8, 4, 2, 1. cGMP concentrations were determined from each sample using the LC/MS conditions (Table 2 below) and calculated standard curve. EC$_{50}$ values were calculated from concentration-response curves generated with GraphPad Prism Software.

The biological activities of some of the compounds of Table I determined with the sGC-HEK assay with SNP incubation are summarized in in Tables 3A, 3B, 3C, 3D, 3E and 3F.

TABLE 2

| (LC/MS experimental conditions) | |
|---|---|
| MS: | Thermo Quantum or Waters LCMS |
| Ion Mode: | ESI$^+$ |
| Scan Type: | MRM |

TABLE 2-continued (LC/MS experimental conditions)

| Compound: | Transition | Dwell Time (msec) | Collision Energy (V) | Tube Lens | Retention Time (min) |
|---|---|---|---|---|---|
| cGMP | 346 > 152 | 100 | 28 | 139 | 1.0 |
| HPLC: | Agilent Technologies 1200 Series with CTC Analytics HTS PAL | | | | |
| Column: | Thermo Hypersil Gold 2.1 × 50 mm 5 micron particle size | | | | |
| Flow Rate: | 400 uL/min | | | | |
| Column Temperature: | RT | | | | |
| Autosampler Temperature: | 6° C. | | | | |
| Injection Volume: | 20 uL | | | | |
| Mobile Phases: | A = 98:2 Water:Acetonitrile + 0.1% Formic Acid | | | | |
| | B = 2:98 Water:Acetonitrile + 0.1% Formic Acid | | | | |

| Gradient: | Time (min) | % A | % B |
|---|---|---|---|
| | 0 | 100 | 0 |
| | 0.3 | 30 | 70 |
| | 2.00 | 30 | 70 |
| | 2.01 | 100 | 0 |
| | 4 | 100 | 0 |

TABLE 3A

Whole cell activity in the HEK assay.

| Compound No. | HEK assay (Percent Emax at 1 μM)* | HEK assay (Percent Emax at 10 μM)* | HEK assay (Percent Emax at 30 μM)* | HEK assay Emax-unconstrained (Percent)** |
|---|---|---|---|---|
| 67 | C | C | C | C |
| 66 | A | A | A | — |
| 60 | E | E | F | F |
| 58 | A | A | B | — |
| 57 | A | A | A | — |
| 56 | E | E | E | E |
| 55 | C | E | G | G |
| 54 | B | C | C | D |
| 53 | C | D | D | E |
| 52 | A | C | C | D |
| 50 | A | A | A | — |
| 49 | A | A | A | — |
| 48 | C | D | E | E |
| 47 | F | F | H | G |
| 46 | A | A | A | — |
| 45 | A | B | B | B |
| 44 | D | D | E | D |
| 43 | B | D | C | D |
| 42 | C | D | D | D |
| 41 | D | F | F | F |
| 40 | E | F | F | F |
| 38 | B | D | E | F |
| 39 | E | G | F | G |
| 35 | E | E | G | F |
| 34 | B | C | C | C |
| 32 | A | A | A | — |
| 31 | C | E | E | F |
| 30 | B | C | D | E |
| 29 | A | C | C | D |
| 28 | D | E | D | E |
| 27 | F | F | F | F |
| 26 | A | A | A | — |
| 25 | C | E | D | E |
| 24 | C | C | C | C |
| 22 | C | E | E | F |
| 21 | D | D | E | E |
| 20 | B | C | C | D |
| 18 | B | C | D | E |
| 17 | A | A | A | — |
| 16 | C | E | D | E |
| 14 | C | D | D | D |
| 13 | E | E | G | F |
| 12 | D | E | E | E |
| 11 | D | D | E | E |
| 10 | F | G | G | G |
| 9 | E | E | E | E |
| 7 | D | E | E | E |
| 6 | C | D | E | E |
| 5 | C | D | E | F |
| 4 | C | D | F | E |
| 1 | D | E | F | E |
| 3 | B | D | E | H |
| 23 | A | A | B | — |
| 19 | C | C | C | C |
| 15 | B | C | C | C |
| 36 | C | D | D | D |
| 37 | A | C | D | F |

TABLE 3B

Whole cell activity in the HEK assay.

| Compound No. | HEK assay (Percent Emax at 1 μM)* | HEK assay (Percent Emax at 10 μM)* | HEK assay (Percent Emax at 30 μM)* | HEK assay Emax-unconstrained (Percent)** |
|---|---|---|---|---|
| 68 | A | C | D | D |
| 69 | D | F | E | F |
| 70 | C | D | D | D |
| 71 | C | D | E | E |
| 72 | C | D | E | D |
| 73 | D | E | E | E |
| 74 | B | C | D | D |
| 75 | B | C | D | D |
| 76 | E | F | F | F |
| 77 | D | F | E | E |
| 78 | D | F | F | F |
| 79 | B | C | D | D |
| 80 | C | D | D | D |
| 81 | C | D | D | D |
| 82 | C | D | B | D |
| 83 | C | E | E | E |
| 84 | C | D | E | E |
| 85 | C | — | C | D |
| 86 | B | — | D | E |
| 87 | — | — | — | D |
| 88 | — | — | — | F |
| 89 | — | — | — | — |
| 90 | — | — | — | D |

*Percent Emax was obtained at three concentrations: 1, 10 and 30 μM. The code for the sGC enzyme activity, expressed as % $E_{max}$ in the presence of 10 μM of SNP (wherein $E_{max}$ = 100% was the activity in the HEK assay obtained with the positive control BAY 41-2272 in the presence of 10 μM SNP) obtained is:
A = 0 to <10%
B = 10 to <20%
C = 20 to <40%
D = 40 to <60
E = 60 or <80%
F = 80 to <100%
G = 100 to <120%
H = 120% or higher
— = not determined
**The term "unconstrained" means that, during analysis of the sGC enzyme activity data, the top portion of the concentration-response curve was not fitted to 100%.
The code for the sGC enzyme activity determined from the 30 μM concentration, expressed as % $E_{max}$ in the presence of 10 μM of SNP (wherein $E_{max}$ = 100% was the activity in the HEK assay obtained with 30 μM of the positive control BAY 41-2272 in the presence of 10 μM SNP) obtained is:

TABLE 3B-continued

Whole cell activity in the HEK assay.

| Compound No. | HEK assay (Percent Emax at 1 μM)* | HEK assay (Percent Emax at 10 μM)* | HEK assay (Percent Emax at 30 μM)* | HEK assay Emax-unconstrained (Percent)** |
|---|---|---|---|---|

A = 0 to <10%
B = 10 to <20%
C = 20 to <40%
D = 40 to <60
E = 60 or <80%
F = 80 to <100%
G = 100 to <120%
H = 120% or higher
— = not determined

TABLE 3C

Whole cell activity in the HEK assay.

| Compound No. | HEK assay (Percent Emax at 1 μM)* | HEK assay (Percent Emax at 10 μM)* | HEK assay (Percent Emax at 30 μM)* | HEK assay Emax-unconstrained (Percent)** |
|---|---|---|---|---|
| 98 | D | F | D | E |
| 99 | D | D | D | D |
| 100 | D | E | E | E |
| 101 | F | F | F | F |
| 102 | C | E | E | E |
| 103 | F | F | G | F |
| 104 | B | D | D | D |
| 105 | D | E | E | E |
| 106 | B | D | E | F |
| 107 | C | D | D | D |
| 109 | A | C | C | D |
| 110 | D | F | E | F |
| 111 | D | E | E | E |
| 112 | A | B | C | E |
| 113 | C | C | C | C |
| 114 | D | E | D | E |
| 115 | B | C | C | C |
| 116 | A | C | C | C |
| 118 | D | E | F | F |

*Percent Emax was obtained at three concentrations: 1, 10 and 30 μM. The code for the sGC enzyme activity, expressed as %$E_{max}$ in the presence of 10 μM of SNP (wherein $E_{max}$ = 100% was the activity in the HEK assay obtained with the positive control BAY 41-2272 in the presence of 10 μM SNP) obtained is:
A = 0 to <10%
B = 10 to <20%
C = 20 to <40%
D = 40 to <60
E = 60 or <80%
F = 80 to <100%
G = 100 to <120%
H = 120% or higher
— = not determined

**The term "unconstrained" means that, during analysis of the sGC enzyme activity data, the top portion of the concentration-response curve was not fitted to 100%.
The code for the sGC enzyme activity determined from the 30 μM concentration, expressed as %$E_{max}$ in the presence of 10 μM of SNP (wherein $E_{max}$ = 100% was the activity in the HEK assay obtained with 30 μM of the positive control BAY 41-2272 in the presence of 10 μM SNP) obtained is:
A = 0 to <10%
B = 10 to <20%
C = 20 to <40%
D = 40 to <60
E = 60 or <80%
F = 80 to <100%
G = 100 to <120%
H = 120% or higher
— = not determined

TABLE 3D

Whole cell activity in the HEK assay.

| Compound No. | HEK assay EC50 (μM)** | HEK assay EC50-unconstrained (μM)*** | HEK MEC-10 (μM)**** |
|---|---|---|---|
| 67 | C | A | B |
| 66 | — | — | — |
| 60 | A | B | C |
| 58 | G | — | E |
| 57 | — | — | — |
| 56 | A | B | B |
| 55 | A | C | C |
| 54 | C | D | D |
| 53 | A | C | C |
| 52 | D | E | D |
| 50 | I | — | — |
| 48 | A | C | C |
| 47 | A | A | B |
| 45 | E | D | E |
| 44 | A | A | C |
| 43 | A | C | C |
| 42 | A | B | C |
| 41 | A | B | B |
| 40 | A | A | C |
| 38 | A | D | D |
| 39 | A | A | A |
| 35 | A | A | A |
| 34 | D | C | D |
| 32 | — | — | — |
| 31 | A | C | C |
| 30 | A | C | D |
| 29 | A | D | E |
| 28 | A | A | B |
| 27 | A | A | B |
| 26 | — | — | — |
| 25 | A | B | C |
| 24 | D | A | B |
| 22 | A | C | D |
| 21 | A | B | C |
| 20 | B | C | C |
| 18 | B | E | C |
| 17 | I | — | — |
| 16 | A | B | C |
| 14 | A | A | B |
| 13 | A | A | B |
| 12 | A | A | B |
| 11 | A | A | B |
| 10 | A | A | A |
| 9 | A | A | B |
| 7 | A | A | B |
| 6 | A | C | C |
| 5 | A | E | C |
| 4 | A | C | C |
| 1 | A | A | B |
| 3 | A | E | D |
| 23 | — | — | E |
| 19 | C | B | D |
| 15 | C | C | D |
| 36 | A | A | D |
| 37 | B | E | C |

**The code for the $EC_{50}$ value obtained in the presence of 10 μM SNP is:
A = 0 to <20 μM
B = 20 to <40 μM
C = 40 to <60 μM
D = 60 to <100 μM
E = 100 to <300 μM
F = 300 to <600 μM
G = 600 to <900 μM
H = 900 to <1,200 μM
I = 1,200 to 7,000 μM

***The term "unconstrained" means that, during analysis of the sGC enzyme activity data, the top portion of the concentration-response curve was not fitted to 100%. The code for the $EC_{50}$ unconstrained value obtained in the presence of 10 μM SNP is:
A = 0.01 to <0.5 μM
B = 0.5 to <1 μM
C = 1 to <5 μM
D = 5 to <10 μM

TABLE 3D-continued

Whole cell activity in the HEK assay.

| Compound No. | HEK assay EC50 (μM)** | HEK assay EC50-unconstrained (μM)*** | HEK MEC-10 (μM)**** |
|---|---|---|---|

E = 10 to 50 μM

****The term "MEC-10" represents the concentration of the test compound that would elicit 10% of the Emax in the presence of 10 μM SNP. The code for the MEC-10 value obtained is:

A = 0.001 to <0.01 μM

B = 0.01 to <0.1 μM

C = 0.1 to <1 μM

D = 1 to <10 μM

E = 10 to 50 μM

TABLE 3E

| Compound No. | HEK assay EC50 (μM)** | HEK assay EC50-unconstrained (μM)*** | HEK MEC-10 (μM)**** |
|---|---|---|---|
| 68 | C | D | D |
| 69 | D | B | A |
| 70 | C | A | C |
| 71 | D | C | C |
| 72 | C | A | B |
| 73 | D | B | C |
| 74 | C | C | C |
| 75 | C | C | C |
| 76 | D | A | B |
| 77 | D | A | C |
| 78 | D | B | B |
| 79 | C | D | D |
| 80 | C | A | C |
| 81 | C | C | C |
| 82 | C | A | B |
| 83 | D | B | C |
| 84 | D | C | B |
| 85 | — | A | — |
| 86 | — | C | — |
| 87 | — | A | — |
| 88 | — | C | — |
| 89 | — | — | — |
| 90 | — | A | — |

**The code for the EC$_{50}$ value obtained in the presence of 10 μM SNP is:

A = 0 to <20 μM

B = 20 to <40 μM

C = 40 to <60 μM

D = 60 to <100 μM

E = 100 to <300 μM

F = 300 to <600 μM

G = 600 to <900 μM

H = 900 to <1,200 μM

I = 1,200 to 7,000 μM

***The term "unconstrained" means that, during analysis of the sGC enzyme activity data, the top portion of the concentration-response curve was not fitted to 100%. The code for the EC$_{50}$ unconstrained value obtained in the presence of 10 μM SNP is:

A = 0.01 to <0.5 μM

B = 0.5 to <1 μM

C = 1 to <5 μM

D = 5 to <10 μM

E = 10 to 50 μM

****The term "MEC-10" represents the concentration of the test compound that would elicit 10% of the Emax in the presence of 10 μM SNP. The code for the MEC-10 value obtained is:

A = 0.001 to <0.01 μM

B = 0.01 to <0.1 μM

C = 0.1 to <1 μM

D = 1 to <10 μM

E = 10 to 50 μM

TABLE 3F

| Compound No. | HEK assay EC50 (μM)** | HEK assay EC50-unconstrained (μM)*** | HEK MEC-10 (μM)**** |
|---|---|---|---|
| 98 | A | A | B |
| 99 | A | A | B |
| 100 | A | B | C |
| 101 | A | A | A |
| 102 | A | C | C |
| 103 | A | A | A |
| 104 | A | C | C |
| 105 | A | B | B |
| 106 | A | D | D |
| 107 | A | C | C |
| 109 | C | E | D |
| 110 | A | C | C |
| 111 | A | A | B |
| 112 | D | E | E |
| 113 | B | A | C |
| 114 | A | A | A |
| 115 | C | C | D |
| 116 | D | — | D |
| 118 | A | B | B |

**The code for the EC$_{50}$ value obtained in the presence of 10 μM SNP is:

A = 0 to <20 μM

B = 20 to <40 μM

C = 40 to <60 μM

D = 60 to <100 μM

E = 100 to <300 μM

F = 300 to <600 μM

G = 600 to <900 μM

H = 900 to <1,200 μM

I = 1,200 to 7,000 μM

***The term "unconstrained" means that, during analysis of the sGC enzyme activity data, the top portion of the concentration-response curve was not fitted to 100%. The code for the EC$_{50}$ unconstrained value obtained in the presence of 10 μM SNP is:

A = 0.01 to <0.5 μM

B = 0.5 to <1 μM

C = 1 to <5 μM

D = 5 to <10 μM

E = 10 to 50 μM

****The term "MEC-10" represents the concentration of the test compound that would elicit 10% of the Emax in the presence of 10 μM SNP. The code for the MEC-10 value obtained is:

A = 0.001 to <0.01 μM

B = 0.01 to <0.1 μM

C = 0.1 to <1 μM

D = 1 to <10 μM

E = 10 to 50 μM

Example 3A

Biological Activity Measurements by the Purified Human sGC Enzyme Activity Assay Human soluble guanylate cyclase enzyme (hsGC) obtained from Enzo Inc. (P/N: ALX-201-177) was used to evaluate the activity of test compounds. The assay reactions contained 0.1 M Tris (pH 8.0), 0.5 mg/mL BSA (pH 8.0), 2 mM DTT, 2 mM MgCl$_2$, 300 μM GTP, 1 mM 3-isobutyl-1-methylxanthine (IBMX) and 5 ng human soluble guanylate cyclase enzyme. Test compounds in DMSO were then added (2 μL, 10 or 30 μM final concentration) and incubated (200 μL, 96-well plate format) at 37° C. for 30 minutes. The controls were carried out using 2 μL DMSO. After the 30 minute incubation, the reaction was stopped with the addition of 200 μL of cold methanol. The plate was then centrifuged at 3,200 rpm for 10 minutes at room temperature. Supernatants (200 μL) were collected and transferred to a new 96 well plate for analysis.

An 8 point cGMP (Sigma-Aldrich P/N: G6129) standard curve was prepared in assay buffer ranging from 0.156-20 μM. Samples for the cGMP standard curve were then diluted with an equal volume of methanol resulting in final cGMP concentrations of 0.078-10 μM.

cGMP concentrations in all samples were determined using LC/MS/MS analysis, using the conditions listed in Table 4 below. The cGMP standard curve was generated using GraphPad Prism Software.

Calculations: Specific Activity was determined by the amount of cGMP formed (nmoles) per mg of sGC per min. Enzyme "fold-change" was calculated by dividing Specific Activity for test compounds by Specific Activity of DMSO controls.

TABLE 4

LC/MS/MS method for detection of cGMP

Inlet Method:

| | |
|---|---|
| HPLC: | Waters Acquity |
| Column: | Thermo Hypersile Gold PFP, 2.1 × 30 mm, 3 μm |
| Guard Column: | Thermo Hypersile Gold, 2.1 × 10 mm |
| Column Temp: | 25° C. |
| Flow Rate: | 0.4 mL/min |
| Auto sampler: | Acquity; 6° C. |
| Injection Volume: | 10 uL |
| Mobile Phases: | A = 0.1% Acetic Acid (v/v) in 100% water |
| | B = 0.1% Acetic Acid (v/v) in 100 methanol |

| Gradient: | Time (min) | % A | % B | Curve |
|---|---|---|---|---|
| | 0 | 95 | 5 | 6 |
| | 0.5 | 95 | 5 | 6 |
| | 0.6 | 10 | 90 | 6 |
| | 2.0 | 10 | 90 | 6 |
| | 2.1 | 95 | 5 | 6 |
| | 4 | (end) | | |
| | MS File: cGMP.exp | | | |

| | |
|---|---|
| Mass Spectrum: | Waters Quattro micro |
| Ionization: | ES+ |
| Source, Desolvation: | 150° C., 450° C. |

MS Function: MRM

| Compound | Transition | Dwell (sec) | Cone (V) | Collision Energy (eV) |
|---|---|---|---|---|
| cGMP | 346 > 152 | 0.1 | 35 | 20 |

Example 3B

Biological Measurement by the Purified Human sGC Enzyme Synergy Performed in the Presence of Sodium Nitroprusside (SNP), a Nitric Oxide Donor Enzyme assays were performed as described above, but was done in the absence or presence of 1 μM sodium nitroprusside (SNP). Data for selected compounds of Table I is summarized in Tables 5A, 5B and 5C below.

TABLE 5A

Enzyme Data With or Without SNP.*

| Compound No. | Enzyme Activity (increase at 30 μM without SNP)* | Enzyme Activity (increase at 30 μM with SNP)* |
|---|---|---|
| 67 | A | B |
| 66 | A | A |
| 60 | B | D |
| 58 | A | B |
| 57 | A | A |
| 56 | C | D |
| 55 | C | F |
| 54 | A | C |
| 53 | C | E |
| 52 | B | D |
| 51 | A | A |
| 45 | A | B |
| 44 | B | D |
| 43 | B | D |
| 42 | B | D |
| 41 | C | D |
| 40 | C | D |
| 38 | B | C |
| 39 | D | E |
| 35 | D | E |
| 34 | B | D |
| 32 | — | — |
| 31 | B | D |
| 29 | B | D |
| 28 | C | D |
| 27 | D | D |
| 26 | A | A |

*The compounds were tested at a concentration of 30 μM in the absence or presence of 1 μM SNP. The code for the fold increase in enzyme activity is:
A = no increase to <2 fold increase
B = 2 to <5 fold increase
C = 5 to <10 fold increase
D = 10 or <20 fold increase
E = 20 to 30 fold increase
F = >30 fold increase

TABLE 5B

Enzyme Data With or Without SNP.*

| Compound No. | Enzyme Activity (increase at 30 μM without SNP)* | Enzyme Activity (increase at 30 μM with SNP)* |
|---|---|---|
| 79 | B | D |
| 78 | C | E |
| 77 | C | E |
| 76 | D | E |
| 75 | B | C |
| 74 | B | C |
| 73 | D | D |
| 72 | D | D |
| 71 | A | D |
| 70 | C | D |
| 69 | B | D |
| 68 | A | C |
| 80 | D | E |
| 81 | C | D |
| 84 | C | D |
| 85 | C | E |
| 86 | C | D |
| 87 | D | E |
| 88 | F | E |

*The compounds were tested at a concentration of 30 μM in the absence or presence of 1 μM SNP. The code for the fold increase in enzyme activity is:
A = no increase to <2 fold increase
B = 2 to <5 fold increase
C = 5 to <10 fold increase
D = 10 or <20 fold increase
E = 20 to 30 fold increase
F = >30 fold increase

TABLE 5C

Enzyme Data With or Without SNP.*

| Compound No. | Enzyme Activity (increase at 30 µM without SNP)* | Enzyme Activity (increase at 30 µM with SNP)* |
|---|---|---|
| 99 | D | D |
| 100 | D | F |
| 109 | B | B |
| 110 | D | D |
| 112 | A | B |
| 113 | C | D |
| 114 | D | E |
| 118 | C | E |

*The compounds were tested at a concentration of 30 µM in the absence or presence of 1 µM SNP. The code for the fold increase in enzyme activity is:
A = no increase to <2 fold increase
B = 2 to <5 fold increase
C = 5 to <10 fold increase
D = 10 or <20 fold increase
E = 20 to 30 fold increase
F = >30 fold increase Example 4

Biological Activity Measurement by the Thoracic Aortic Rings Assay

Thoracic aortic rings were dissected from anesthetized (isoflurane) male Sprague-Dawley rats weighing 275-299 g. Tissues were immediately transferred to ice-cold Krebs-Henseleit solution, which had been aerated with 95% $O_2$ and 5% $CO_2$ for 30 minutes. Following removal of connective tissue, aortic sections were cut into 4 rings (~2 mm each) and suspended on 2 L-shaped hooks, with one hook fixed at the bottom of the tissue bath (Schuler Organ Bath, Harvard Apparatus) and the other connected to a force transducer (F30 Force Transducer, Harvard Apparatus). Baths contained Krebs Henseleit solution (10 mL) heated to 37° C. and aerated with 95% $O_2$ and 5% $CO_2$. Rings were brought to an initial tension of 0.3-0.5 g and gradually raised to a resting tension of 1.0 g over 60 minutes. Rings were rinsed with Krebs Henseleit solution (heated to 37° C. and aerated with 95% 02 and 5% CO2) at 15 minute intervals until a stable baseline was obtained. Rings were considered to be stable after a resting tension of 1.0 g was maintained (for approximately 10 minutes) without need for adjustment. Rings were then contracted with 100 ng/mL phenylephrine by adding 100 uL of a 10 µg/mL phenylephrine stock solution. Tissues achieving a stable contraction were then treated in a cumulative, dose dependent manner with test compounds prepared in dimethylsulfoxide (DMSO). In some cases, tissues were rinsed three times over a 5 minute period with Krebs-Heinseleit's solution (heated to 37° C. and aerated with 95% 02 and 5% CO2), allowed to stabilize at baseline, and then used for characterization of other test articles or DMSO effects. All data were collected using the HSE-ACAD software provided by Harvard Apparatus. Percent relaxation effects were calculated in Microsoft Excel using the recorded tension value of 100 ng/mL phenylephrine treatment as 0% inhibition and treatment with 100 µM 3-isobutyl-1-methylxanthine as 100% inhibition. $EC_{50}$ values were calculated from concentration-response curves generated with GraphPad Prism Software.

Example 5

Biological Activity Measurement by the Thoracic Aortic Rings Assay

As an alternative thoracic aortic rings assay, the procedure of Example 11 a was used except that percent relaxation effects were calculated in Microsoft Excel using the recorded tension value of 100 ng/mL phenylephrine treatment as 0% inhibition and, after washing the tissue with buffer, the original resting tension of the tissue was used as 100% inhibition.

The biological data for some of a compound of Table I, in comparison with the known compound, BAY 41-2272, as the reference compound, determined by the thoracic aorta ring assay of Example 5 are presented in Table 6 below.

TABLE 6

Thoracic Aortic Ring Assay Results.

| Compound No. | Aortic Ring Percent Relaxation at 1 µM* | Aortic Ring Percent Relaxation at 3 µM* | Aortic Ring Percent Relaxation at 10 µM* | Aortic Ring EC50 (µM)** |
|---|---|---|---|---|
| 47 | E | F | G | A |
| 40 | G | G | G | A |
| 35 | G | H | H | A |
| 27 | F | G | G | A |
| 10 | G | G | G | A |
| 1 | F | G | G | A |

*The compounds were tested at a concentration of 1, 3 or 10 µM to obtain data using the method described in Example 15. The code for the percent relaxation of the aotic ring is:
A = 0 to <10%
B = 10 to <20%
C = 20 to <40%
D = 40 to <60%
E = 60 or <80%
F = 80 to <100%
G = 100 to <120%
H = higher than 120%
**The code for the $EC_{50}$ value obtained is:
A = 0 to <2 µM
B = 2 to <4 µM
C = 4 to <8 µM
D = 8 to <12 µM A number of embodiments have been described. Nevertheless, it will be understood that various modifications may be made without departing from the spirit and scope of the invention.

Example 6

Animal Models Descriptions

Lamb Model of Pulmonary Hemodynamics Using Inhaled sGC Stimulator ("Inhaled Agonists of Soluble Guanylate Cyclase Induce Selective Pulmonary Vasodilation", Oleg V. et al, American J of Resp and Critical Care Medicine, Vol 176, 2007, p 1138)

It is possible to test whether inhalation of novel dry-powder microparticle formulations containing sGC stimulators would produce selective pulmonary vasodilation in lambs with acute pulmonary hypertension by following a published procedure. It is also possible to evaluate the combined administration of the microparticles of sGC stimulator and inhaled nitric oxide (iNO) in this system. Finally, it is possible to examine whether inhaling microparticles of an sGC stimulator would produce pulmonary vasodilation when the response to iNO (inducible nitric oxide synthase) is impaired.

Protocol: In awake, spontaneously breathing lambs instrumented with vascular catheters and a tracheostomy tube, U-46619 is infused intravenously to increase mean pulmonary arterial pressure to 35 mm Hg Inhalation of microparticles composed of either BAY 41-2272, BAY 41-8543, or BAY 58-2667 and excipients (dipalmitoylphosphatidylcholine, albumin, lactose) produced dose dependent pulmonary vasodilation and increased transpulmonary cGMP release without significant effect on mean arterial pressure Inhalation of microparticles containing BAY 41-8543 or BAY 58-2667 increased systemic arterial oxygenation. The magnitude and duration of pulmonary vasodilation induced by iNO were augmented after inhaling BAY 41-8543 microparticles. Intravenous administration of 1H-[1,2,4]oxadiazolo[4,3-a]quinoxalin-1-one (ODQ), which oxidizes the prosthetic heme group of sGC, markedly reduced the pulmonary vasodilator effect of iNO. In contrast, pulmonary vasodilation and transpulmonary cGMP release induced by inhaling BAY 58-2667 microparticles were greatly enhanced after treatment with ODQ. Thus, inhalation of microparticles containing agonists of sGC may provide an effective novel treatment for patients with pulmonary hypertension, particularly when responsiveness to iNO is impaired by oxidation of sGC. Note: BAY 41-2272, BAY 41-8543 are sGC stimulators whereas BAY 58-2667 is an sGC activator.

Electrical Field Stimulated Guinea Pig Tracheal Smooth Muscle In Vitro (Ex Vivo) Model for the Assessment of Bronchodilation.

It is possible to assess the bronchodilating effects of sGC stimulators by using the system described below. This system allowed us to determine potency, efficacy and duration of action of several sGC stimulators, as well as to assess potential side effects such as blood pressure, or heart rate changes.

Animals: Guinea pig, Dunkin Hartley, male, Full barrier-bred and certified free of specific micro-organisms on receipt 525-609 g on the experimental day, Harlan UK Ltd. Guinea pigs were housed in a group of 4 in solid-bottomed cages with Gold Flake bedding in a controlled environment (airflow, temperature and humidity). Food (FD1, Special Diet Services) and water were provided ad libitum.

Guinea Pig Tracheal Smooth Muscle Contraction in Response to EFS. Assessment of Compound Potency and Efficacy:

On each experimental day, a guinea pig was killed by exposure to a rising concentration of CO2 and the trachea removed. The trachea was cleaned of extraneous tissue and cut open longitudinally in a line opposite the muscle, opened out and cut into strips 2-3 cartilage rings wide. A cotton loop was attached to one end of each tracheal strip and a length of cotton to the other end. Tracheal strips were then suspended between two platinum electrodes, using tissue holders, in a Myobath system (World Precision Instruments Stevenage, UK). The loop was attached over the hook at the bottom of the tissue holder and the other end attached to the arm of a FORT10 force transducer (World Precision Instruments Stevenage, UK) ensuring that the tissue was positioned between the two platinum electrodes. The whole assembly was then lowered into a 10 ml tissue bath containing modified Kreb's-Henseleit buffer, at 37° C., bubbled with Carbogen. A 1 g tension was applied to each piece of tissue and the tissue washed, followed by a 1 hour stabilization period. Once the tissues had been allowed to stabilize, the apparatus for electrical field stimulation was set to deliver a stimulation of frequency 80 Hz pulse width 0.1 ms, with a gated, uni-polar pulse, every 2 minutes using a DS8000 8 channel digital stimulator (World Precision Instruments Stevenage, UK). A voltage response curve was carried out on each tracheal strip at 2, 4, 6, 7, 8, 10, 12 V and a sub-maximal voltage then selected to apply to each tissue during the remainder of the experiment. Guinea pig tracheal smooth muscle (GPTSM) contraction was induced using sub-maximal Electrical Field Stimulation (EFS) (It is also possible to induce contraction by using a spasmogen substance, such as methacholine or histamine as described in Coleman et al.*). Compounds were dissolved in 100% DMSO at 3×10-2M and aliquots stored at −200 C. A separate aliquot was used for each experiment. Tissues were washed with Kreb's buffer and stimulated using the previously determined sub-maximal voltage for 1 hour to establish a stable baseline contraction prior to assessment of compound activity.

A cumulative dose response curve (DRC) to each test substance was then performed and changes in smooth muscle contraction measured. The effect of each test substance in each experiment was expressed as a percentage inhibition of the baseline contraction, normalized to the relevant vehicle controls. The experiment was performed three times, using tissue from three different animals. The data from all three experiments was pooled, the DRC plotted, and the test substance potency and efficacy determined. The potency of Ipratropium bromide was assessed alongside the test compounds and the IC50 determined to be 0.86 nM (95% Cl, 0.78-0.94), in agreement with data previously produced in the system.

*"Novel and Versatile Superfusion System. Its use in the Evaluation of Some Spasmogenic and Spasmolytic Agents Using Guinea pig isolated Tracheal Smooth Muscle.", R. A. Coleman et al., J. Pharmacol. Methods, 21, 71-86, 1989.

The invention claimed is:

1. A compound depicted below, or a pharmaceutically acceptable salt thereof:

Compound 1

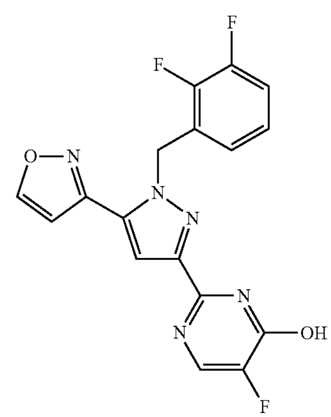

Compound 2

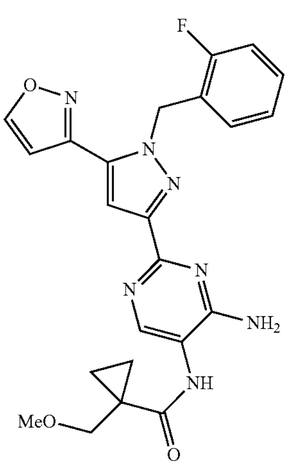

Compound 3
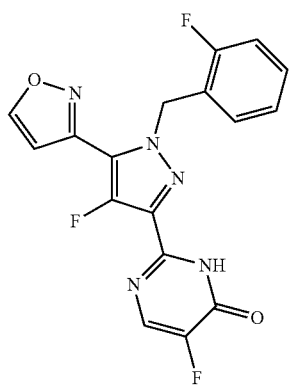
Compound 4
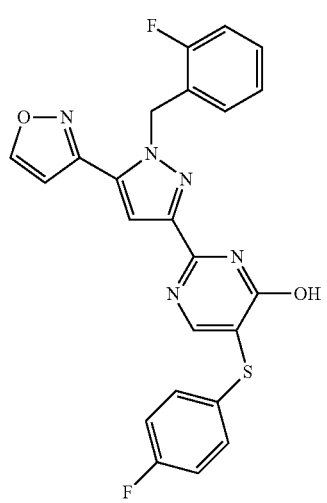
Compound 5
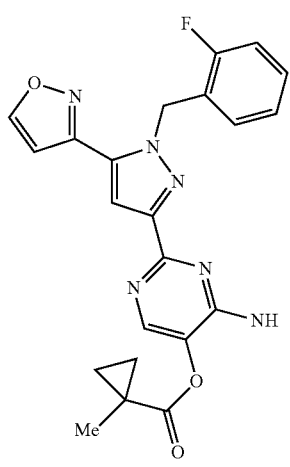
Compound 6
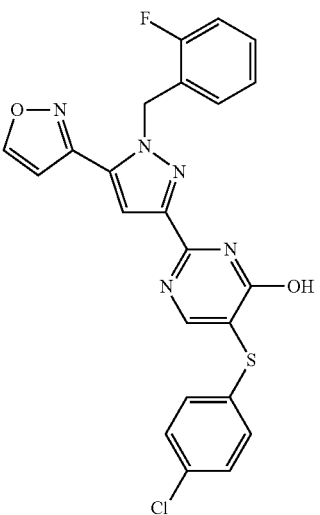
Compound 7
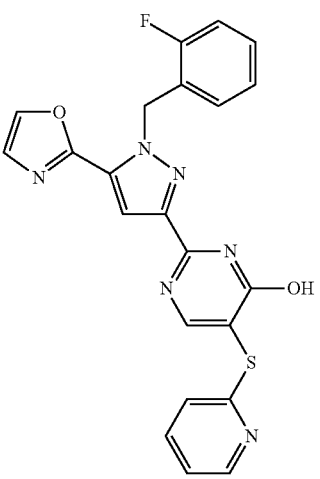
Compound 8
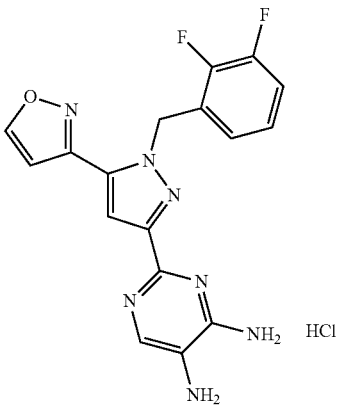

-continued
Compound 9
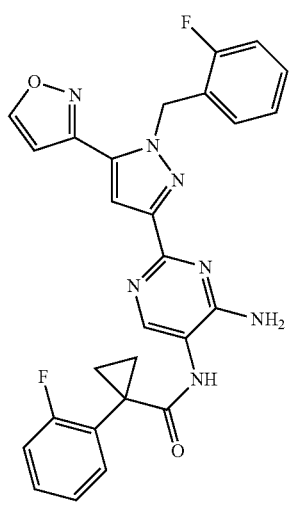
Compound 10
Compound 11
Compound 12
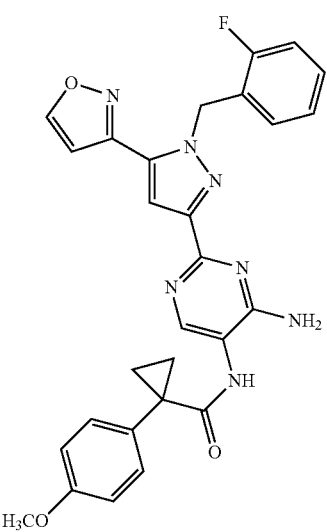
Compound 13
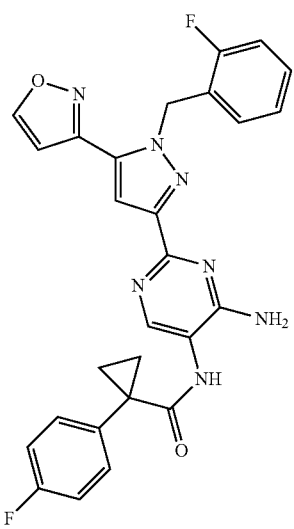
Compound 14
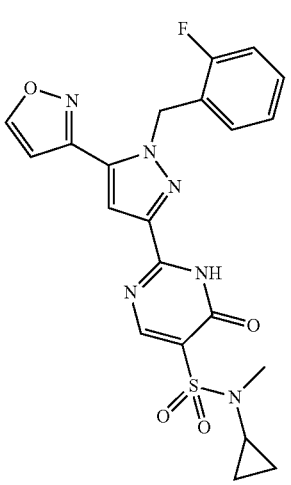 [SMILES: CN(C1CC1)S(=O)(=O)c1cnc(-c2cc(-c3ccon3)n(Cc3ccccc3F)n2)[nH]c1=O]

Compound 15
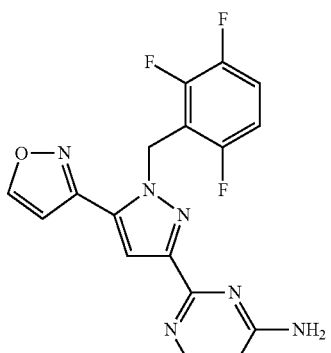
Compound 16
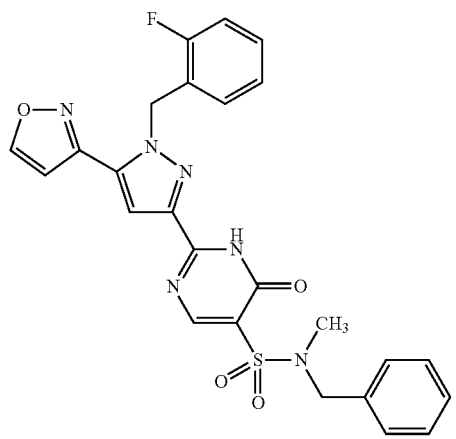
Compound 17
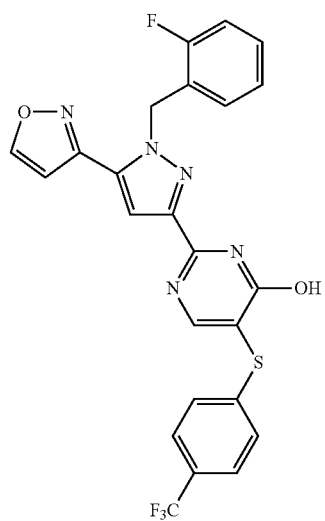 [SMILES: Oc1nc(-c2cc(-c3ccon3)n(Cc3ccccc3F)n2)ncc1Sc1ccc(C(F)(F)F)cc1]
Compound 18
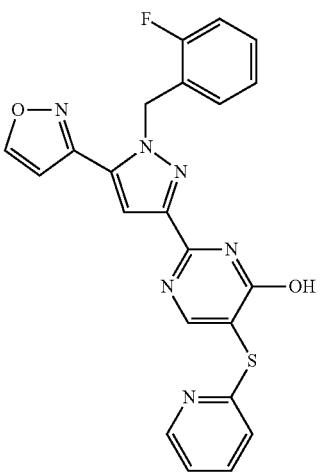 [SMILES: Oc1nc(-c2cc(-c3ccon3)n(Cc3ccccc3F)n2)ncc1Sc1ccccn1]
Compound 19
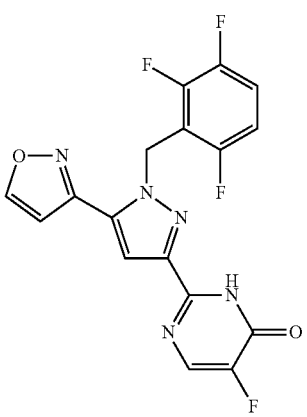 [SMILES: O=c1[nH]c(-c2cc(-c3ccon3)n(Cc3c(F)ccc(F)c3F)n2)ncc1F]
Compound 20
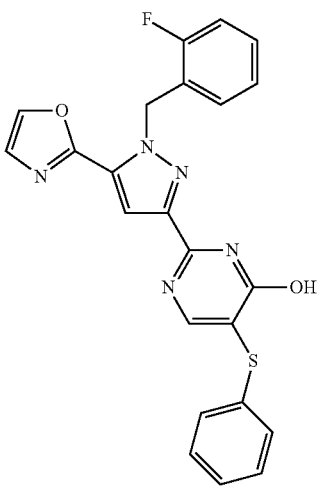 [SMILES: Oc1nc(-c2cc(-c3ncco3)n(Cc3ccccc3F)n2)ncc1Sc1ccccc1]

235
-continued
Compound 21
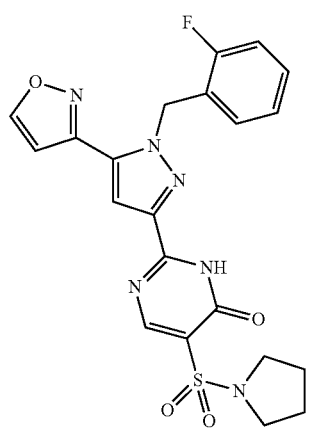
Compound 22
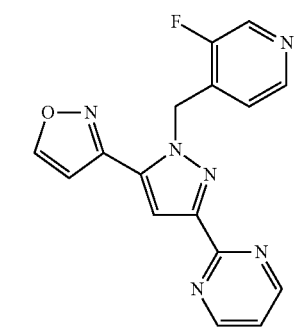 [SMILES: Fc1cnccc1Cn1nc(-c2ncccn2)cc1-c1ccon1]
Compound 23
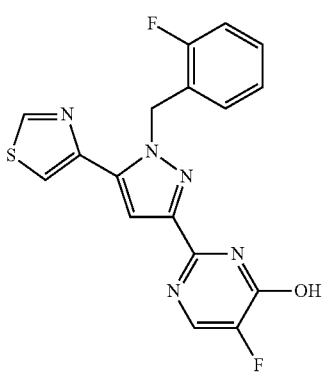 [SMILES: Oc1nc(-c2cc(-c3cscn3)n(Cc3ccccc3F)n2)ncc1F]
Compound 24
236
-continued
Compound 25
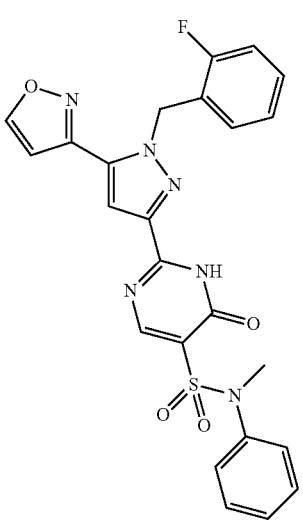 [SMILES: CN(c1ccccc1)S(=O)(=O)c1cnc(-c2cc(-c3ccon3)n(Cc3ccccc3F)n2)[nH]c1=O]
Compound 26
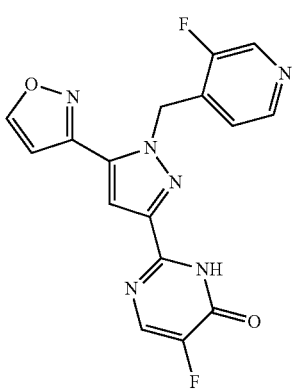 [SMILES: O=c1[nH]c(-c2cc(-c3ccon3)n(Cc3ccncc3F)n2)ncc1F]
Compound 27
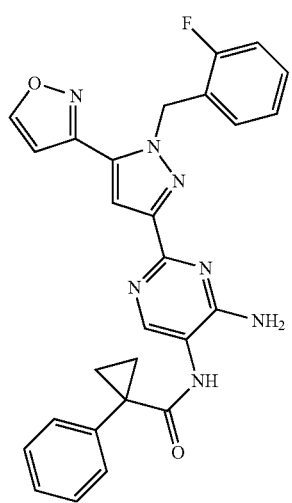 [SMILES: Nc1nc(-c2cc(-c3ccon3)n(Cc3ccccc3F)n2)ncc1NC(=O)C1(c2ccccc2)CC1]

237
-continued
Compound 28
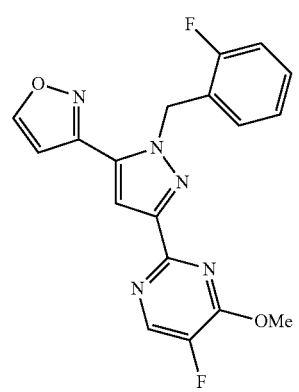
Compound 29
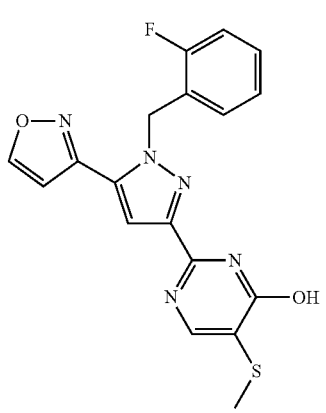 [SMILES: CSc1cnc(-c2cc(-c3ccon3)n(Cc3ccccc3F)n2)nc1O]
Compound 30
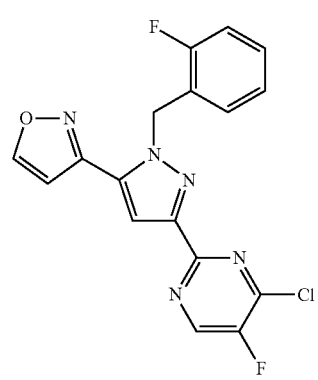 [SMILES: Fc1ccccc1Cn1nc(-c2ncc(F)c(Cl)n2)cc1-c1ccon1]
Compound 31
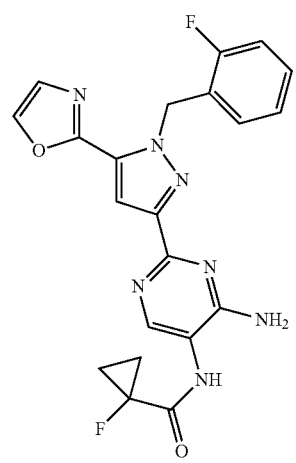 [SMILES: Nc1nc(-c2cc(-c3ncco3)n(Cc3ccccc3F)n2)ncc1NC(=O)C1(F)CC1]
238
-continued
Compound 32
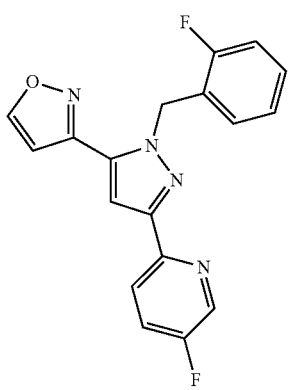 [SMILES: Fc1ccc(-c2cc(-c3ccon3)n(Cc3ccccc3F)n2)nc1]
Compound 33
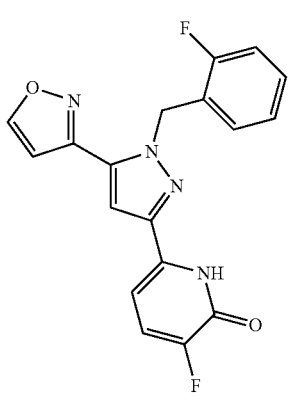 [SMILES: O=c1[nH]c(-c2cc(-c3ccon3)n(Cc3ccccc3F)n2)ccc1F]
Compound 34
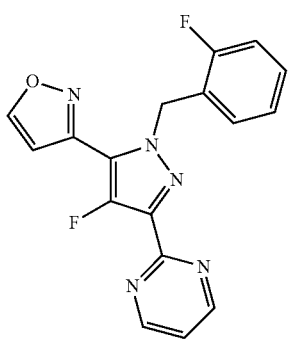 [SMILES: Fc1ccccc1Cn1nc(-c2ncccn2)c(F)c1-c1ccon1]
Compound 35
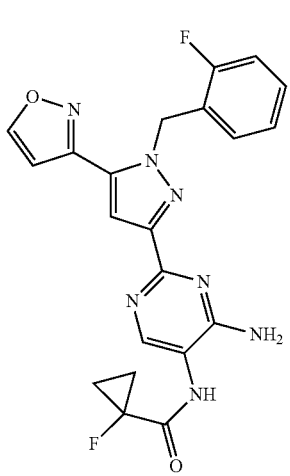 [SMILES: Nc1nc(-c2cc(-c3ccon3)n(Cc3ccccc3F)n2)ncc1NC(=O)C1(F)CC1]

Compound 36
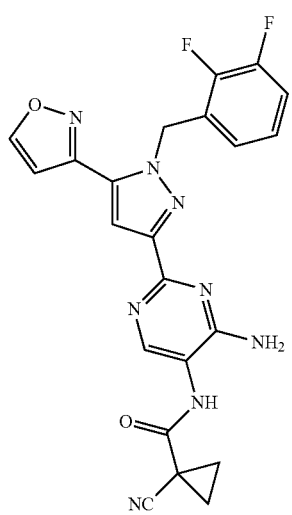 [SMILES: N#CC1(C(=O)Nc2cnc(-c3cc(-c4ccon4)n(Cc4cccc(F)c4F)n3)nc2N)CC1]
Compound 37
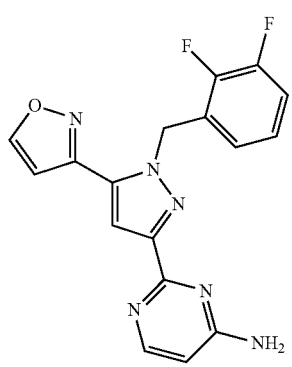 [SMILES: Nc1ccnc(-c2cc(-c3ccon3)n(Cc3cccc(F)c3F)n2)n1]
Compound 38
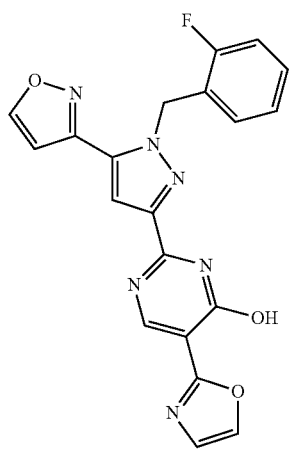 [SMILES: Oc1nc(-c2cc(-c3ccon3)n(Cc3ccccc3F)n2)ncc1-c1ncco1]
Compound 39
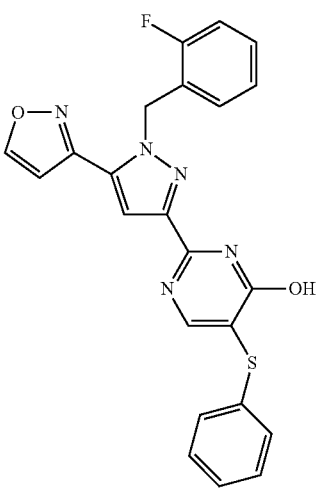 [SMILES: Oc1nc(-c2cc(-c3ccon3)n(Cc3ccccc3F)n2)ncc1Sc1ccccc1]
Compound 40
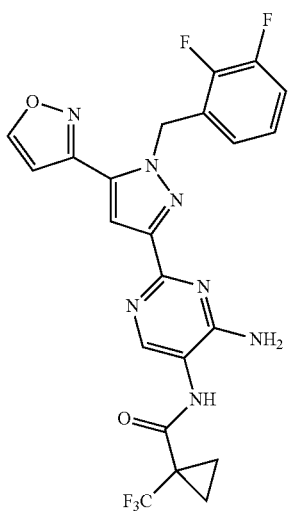 [SMILES: Nc1nc(-c2cc(-c3ccon3)n(Cc3cccc(F)c3F)n2)ncc1NC(=O)C1(C(F)(F)F)CC1]
Compound 41
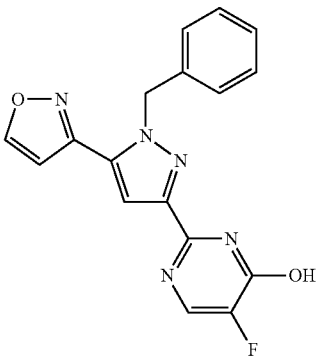 [SMILES: Oc1nc(-c2cc(-c3ccon3)n(Cc3ccccc3)n2)ncc1F]

Compound 42
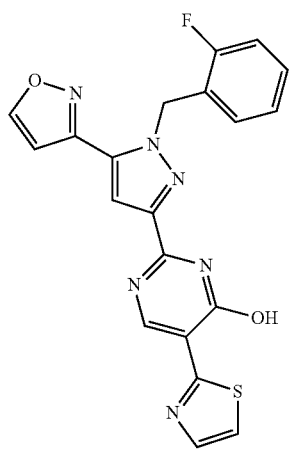 [SMILES: Oc1nc(-c2cc(-c3ccon3)n(Cc3ccccc3F)n2)ncc1-c1nccs1]
Compound 43
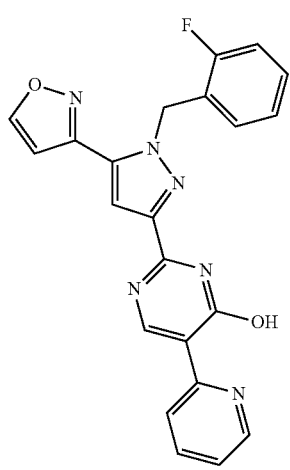 [SMILES: Oc1nc(-c2cc(-c3ccon3)n(Cc3ccccc3F)n2)ncc1-c1ccccn1]
Compound 44
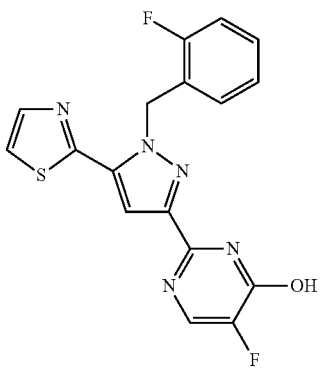 [SMILES: Oc1nc(-c2cc(-c3nccs3)n(Cc3ccccc3F)n2)ncc1F]
Compound 45
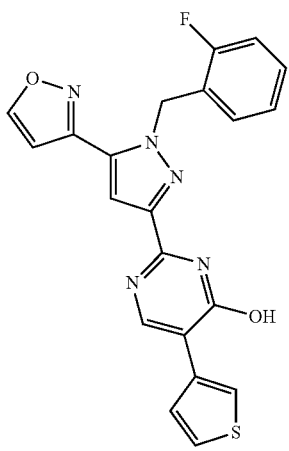 [SMILES: Oc1nc(-c2cc(-c3ccon3)n(Cc3ccccc3F)n2)ncc1-c1ccsc1]
Compound 46
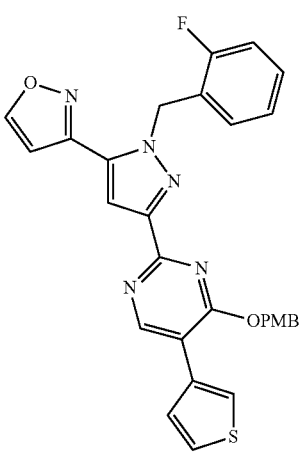
Compound 47
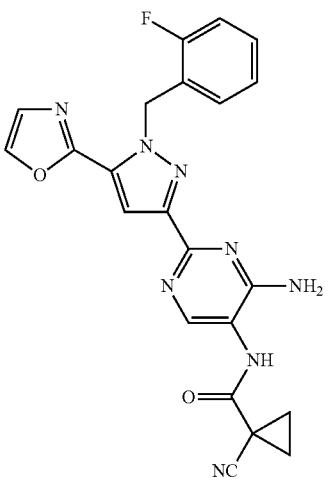

Compound 48
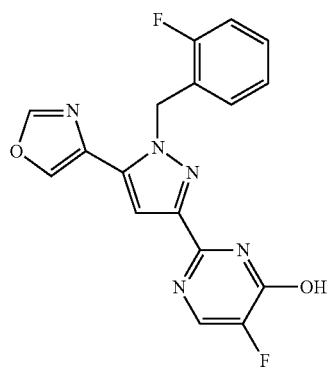 [SMILES: Oc1nc(-c2cc(-c3cocn3)n(Cc3ccccc3F)n2)ncc1F]
Compound 49
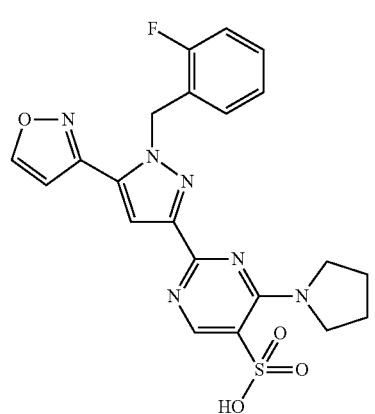 [SMILES: O=S(=O)(O)c1cnc(-c2cc(-c3ccon3)n(Cc3ccccc3F)n2)nc1N1CCCC1]
Compound 50
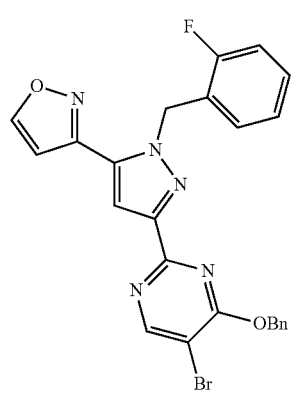 [SMILES: Fc1ccccc1Cn1nc(-c2ncc(Br)c(OCc3ccccc3)n2)cc1-c1ccon1]
Compound 51
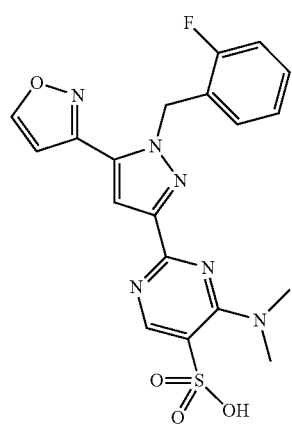
Compound 52
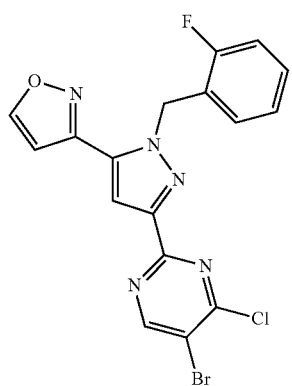 [SMILES: Fc1ccccc1Cn1nc(-c2ncc(Br)c(Cl)n2)cc1-c1ccon1]
Compound 53
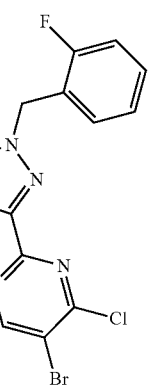
Compound 54
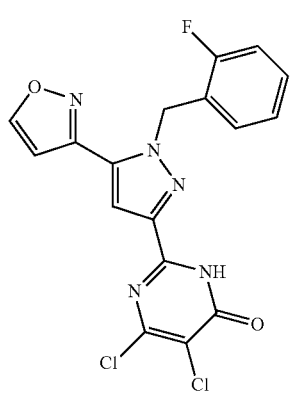 [SMILES: O=c1[nH]c(-c2cc(-c3ccon3)n(Cc3ccccc3F)n2)nc(Cl)c1Cl]
Compound 56
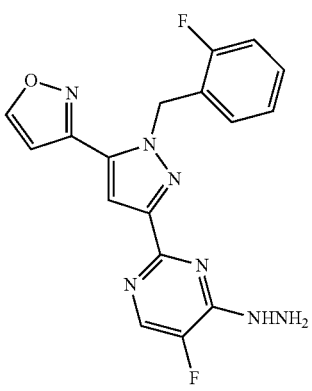 [SMILES: NNc1nc(-c2cc(-c3ccon3)n(Cc3ccccc3F)n2)ncc1F]

Compound 57
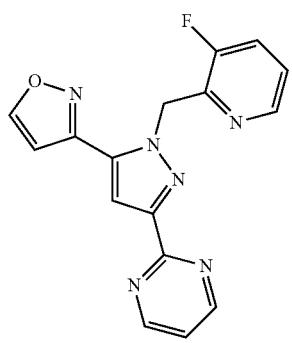 [SMILES: Fc1cccnc1Cn1nc(-c2ncccn2)cc1-c1ccon1]
Compound 58
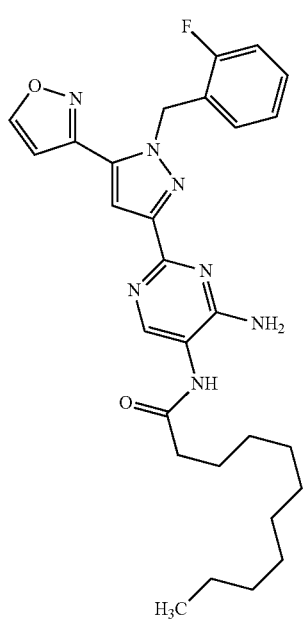 [SMILES: CCCCCCCCCCC(=O)Nc1cnc(-c2cc(-c3ccon3)n(Cc3ccccc3F)n2)nc1N]
Compound 59
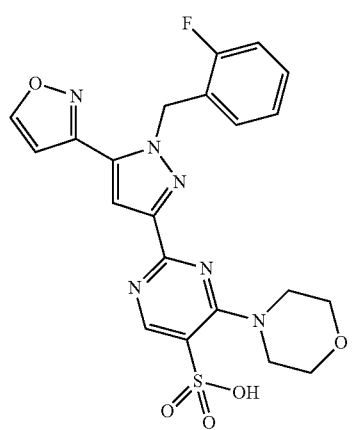
Compound 61
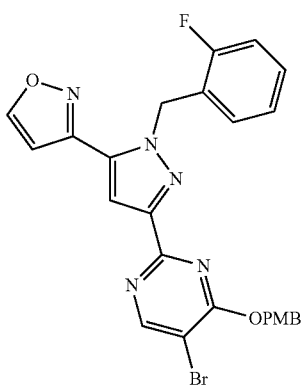
Compound 62
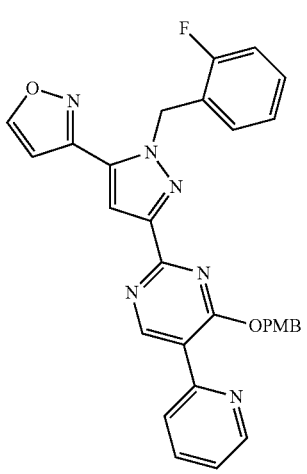
Compound 63
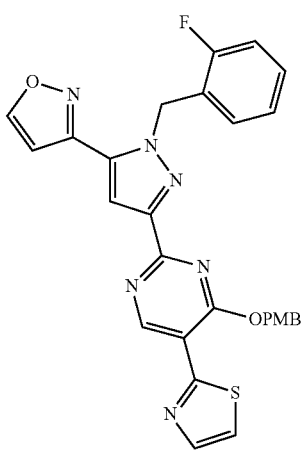

Compound 64
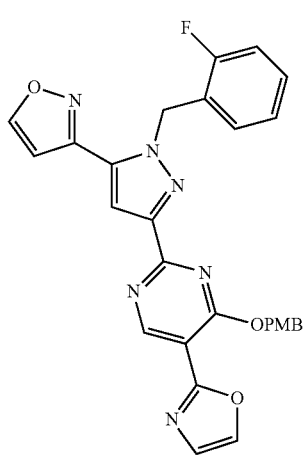
Compound 65
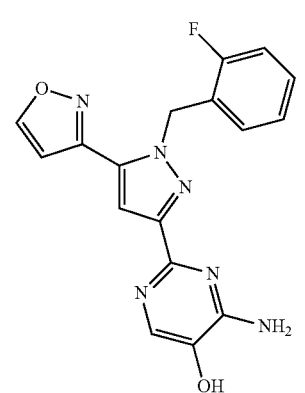 [SMILES: Nc1nc(-c2cc(-c3ccon3)n(Cc3ccccc3F)n2)ncc1O]
Compound 66
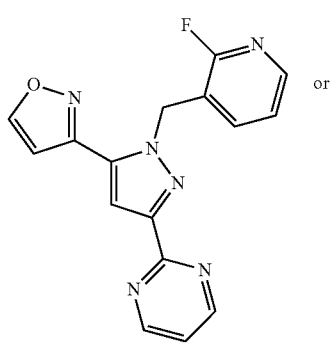
or
Compound 67
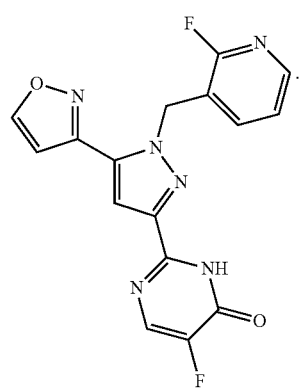
2. A pharmaceutical composition comprising at least one compound of claim 1, or a pharmaceutically acceptable salt thereof, and at least one pharmaceutically acceptable excipient.
3. A compound depicted below, or a pharmaceutically acceptable salt thereof:
Compound 68
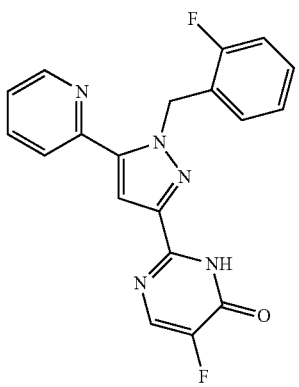 [SMILES: O=c1[nH]c(-c2cc(-c3ccccn3)n(Cc3ccccc3F)n2)ncc1F]
Compound 69
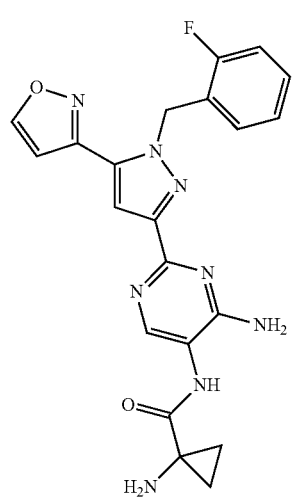 [SMILES: Nc1nc(-c2cc(-c3ccon3)n(Cc3ccccc3F)n2)ncc1NC(=O)C1(N)CC1]
Compound 70
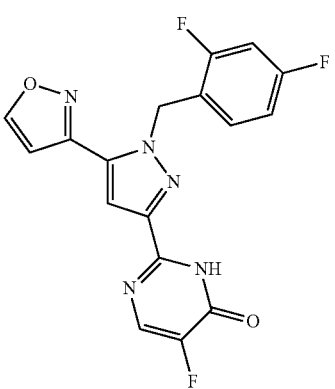 [SMILES: O=c1[nH]c(-c2cc(-c3ccon3)n(Cc3ccc(F)cc3F)n2)ncc1F]

Compound 71
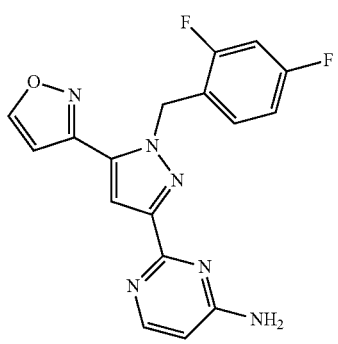 [SMILES: Nc1ccnc(-c2cc(-c3ccon3)n(Cc3ccc(F)cc3F)n2)n1]
Compound 72
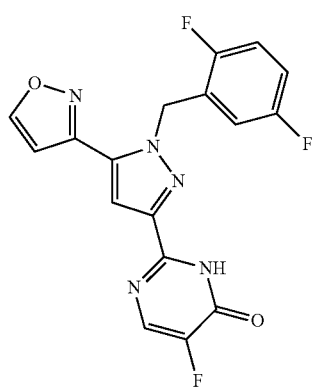 [SMILES: O=c1[nH]c(-c2cc(-c3ccon3)n(Cc3cc(F)ccc3F)n2)ncc1F]
Compound 73
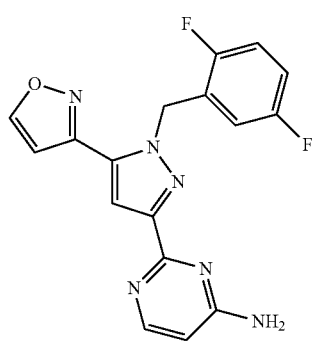 [SMILES: Nc1ccnc(-c2cc(-c3ccon3)n(Cc3cc(F)ccc3F)n2)n1]
Compound 74
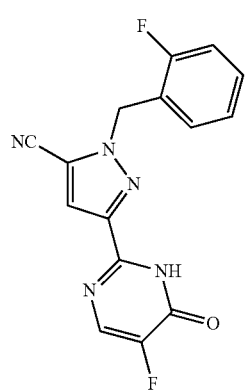 [SMILES: N#Cc1cc(-c2ncc(F)c(=O)[nH]2)nn1Cc1ccccc1F]
Compound 75
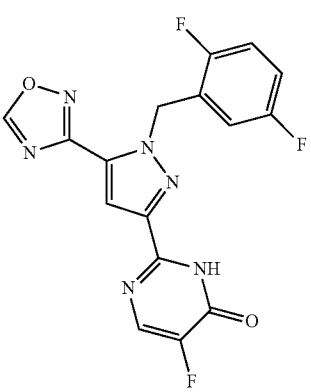 [SMILES: O=c1[nH]c(-c2cc(-c3ncon3)n(Cc3cc(F)ccc3F)n2)ncc1F]
Compound 76
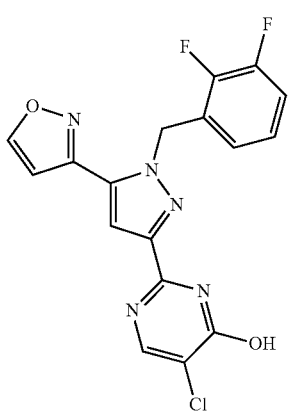 [SMILES: Oc1nc(-c2cc(-c3ccon3)n(Cc3cccc(F)c3F)n2)ncc1Cl]
Compound 77
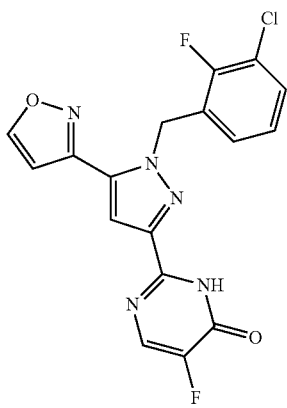 [SMILES: O=c1[nH]c(-c2cc(-c3ccon3)n(Cc3cccc(Cl)c3F)n2)ncc1F]
Compound 78
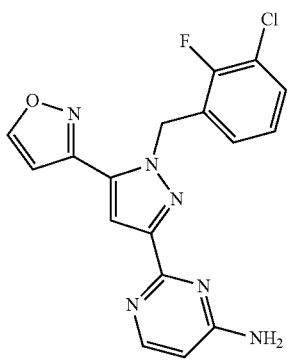 [SMILES: Nc1ccnc(-c2cc(-c3ccon3)n(Cc3cccc(Cl)c3F)n2)n1]

Compound 79
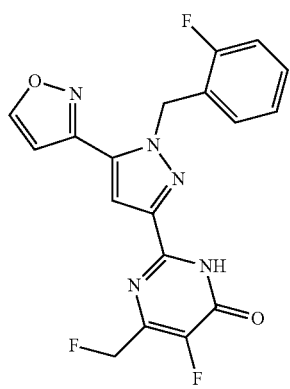 [SMILES: O=c1[nH]c(-c2cc(-c3ccon3)n(Cc3ccccc3F)n2)nc(CF)c1F]
Compound 80
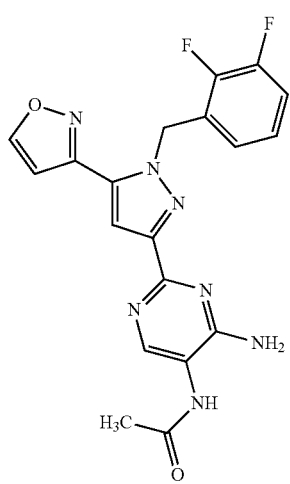 [SMILES: CC(=O)Nc1cnc(-c2cc(-c3ccon3)n(Cc3cccc(F)c3F)n2)nc1N]
Compound 81
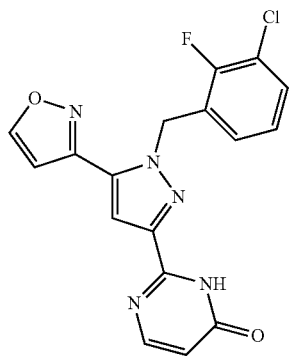 [SMILES: O=c1ccnc(-c2cc(-c3ccon3)n(Cc3cccc(Cl)c3F)n2)[nH]1]
Compound 82
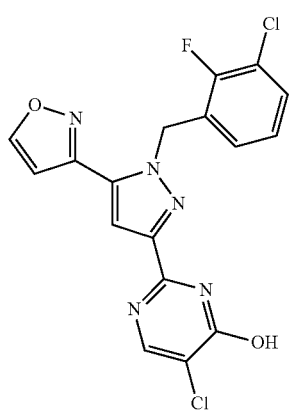 [SMILES: Oc1nc(-c2cc(-c3ccon3)n(Cc3cccc(Cl)c3F)n2)ncc1Cl]
Compound 83
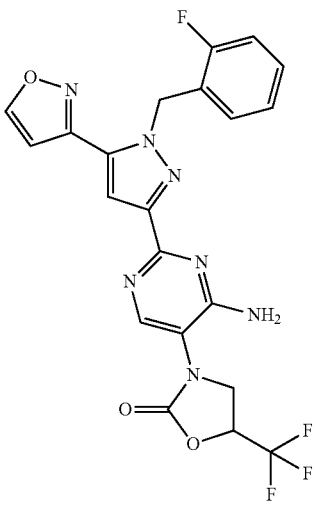
Compound 84
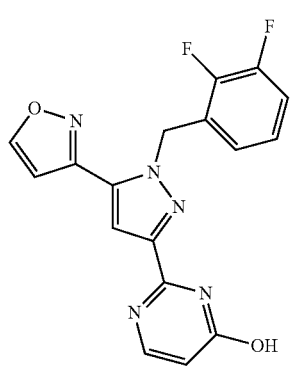 [SMILES: Oc1ccnc(-c2cc(-c3ccon3)n(Cc3cccc(F)c3F)n2)n1]
Compound 85
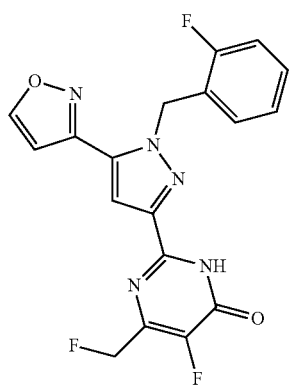

Compound 86
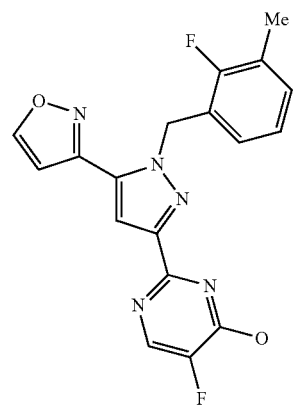 [SMILES: Cc1cccc(Cn2nc(-c3ncc(F)c(O)n3)cc2-c2ccon2)c1F]
Compound 87
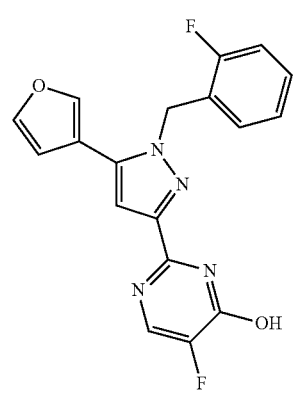 [SMILES: Oc1nc(-c2cc(-c3ccoc3)n(Cc3ccccc3F)n2)ncc1F]
Compound 88
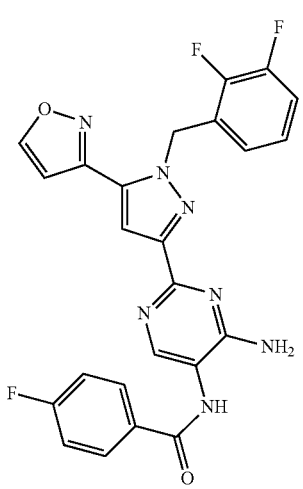
Compound 89
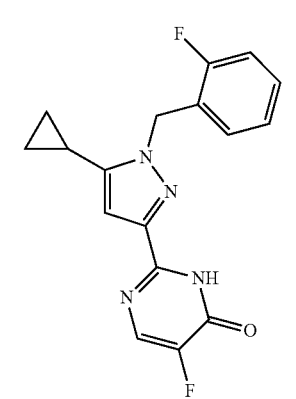 [SMILES: O=c1[nH]c(-c2cc(C3CC3)n(Cc3ccccc3F)n2)ncc1F]
Compound 90
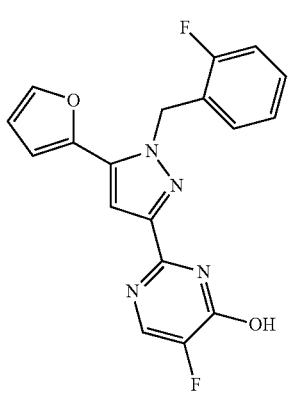 [SMILES: Oc1nc(-c2cc(-c3ccco3)n(Cc3ccccc3F)n2)ncc1F]
Compound 91
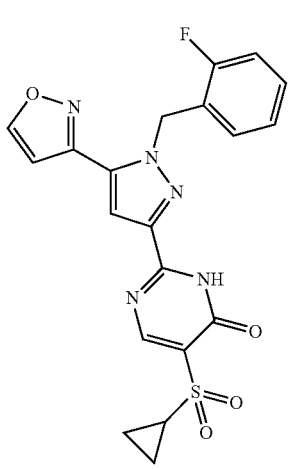
Compound 92
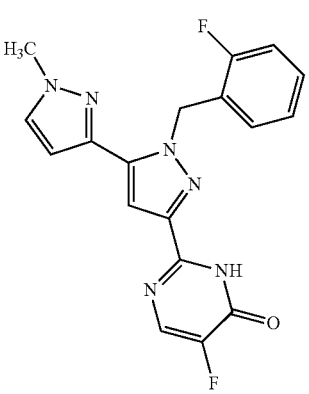 [SMILES: Cn1ccc(-c2cc(-c3ncc(F)c(=O)[nH]3)nn2Cc2ccccc2F)n1]
Compound 93
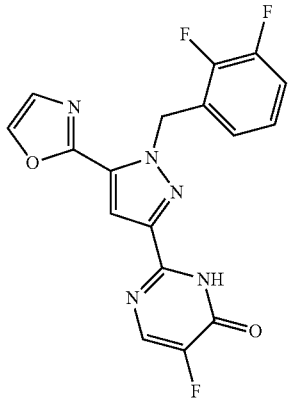 [SMILES: O=c1[nH]c(-c2cc(-c3ncco3)n(Cc3cccc(F)c3F)n2)ncc1F]

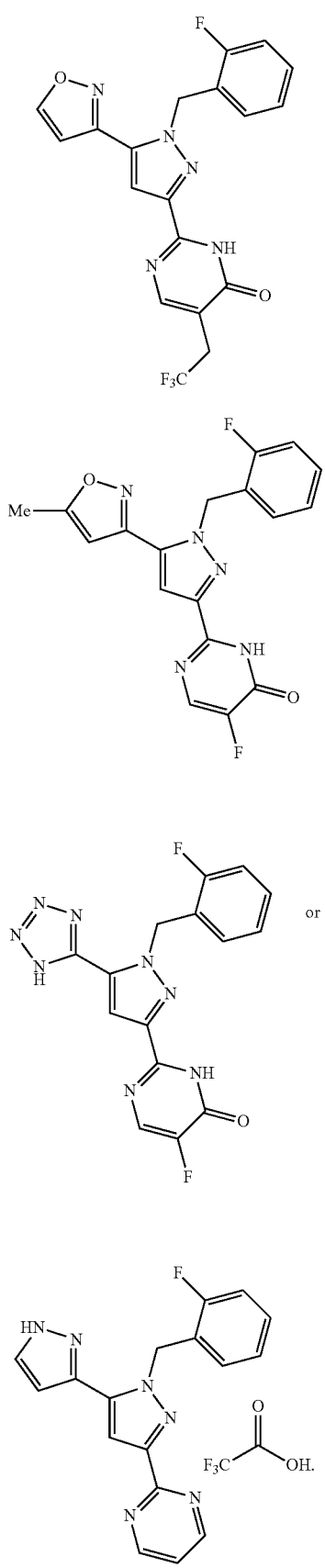
4. A compound depicted below, or a pharmaceutically acceptable salt thereof:

Compound 101
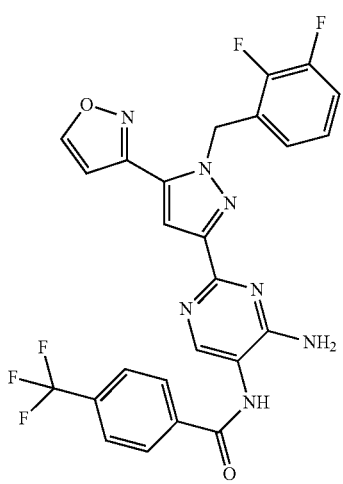 [SMILES: Nc1nc(-c2cc(-c3ccon3)n(Cc3cccc(F)c3F)n2)ncc1NC(=O)c1ccc(C(F)(F)F)cc1]
Compound 104
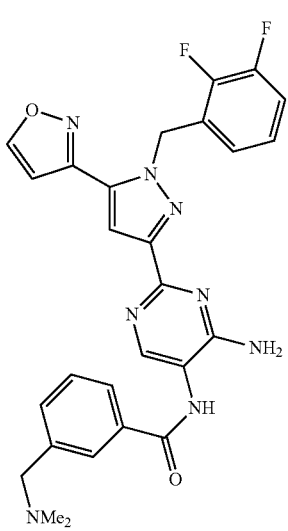
Compound 102
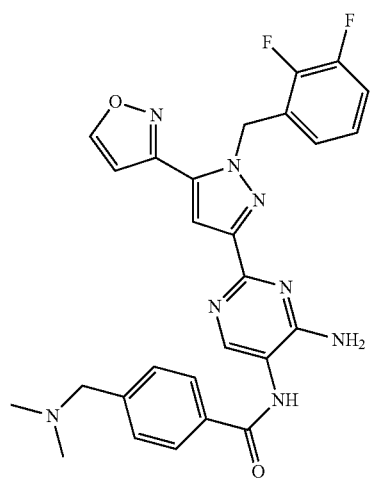 [SMILES: CN(C)Cc1ccc(C(=O)Nc2cnc(-c3cc(-c4ccon4)n(Cc4cccc(F)c4F)n3)nc2N)cc1]
Compound 105
Compound 103
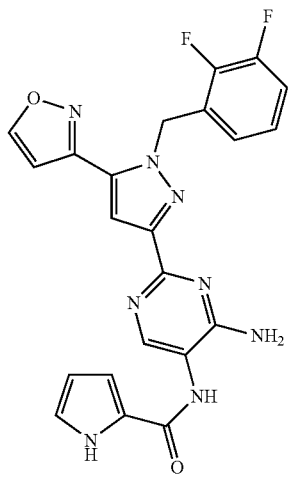 [SMILES: Nc1nc(-c2cc(-c3ccon3)n(Cc3cccc(F)c3F)n2)ncc1NC(=O)c1ccc[nH]1]
Compound 106
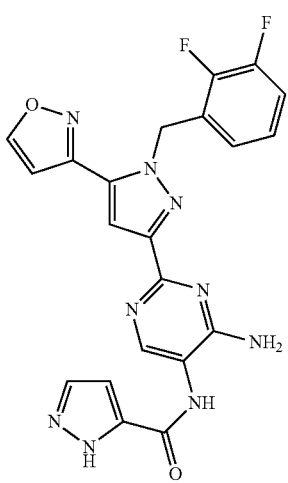 [SMILES: Nc1nc(-c2cc(-c3ccon3)n(Cc3cccc(F)c3F)n2)ncc1NC(=O)c1ccn[nH]1]

Compound 107
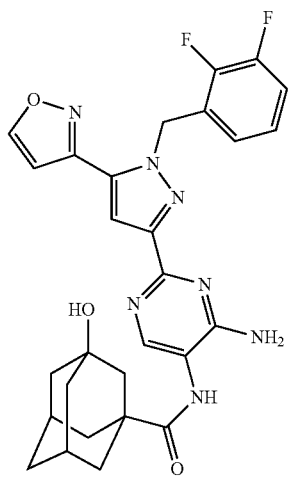 [SMILES: Nc1nc(-c2cc(-c3ccon3)n(Cc3cccc(F)c3F)n2)ncc1NC(=O)C12CC3CC(CC(O)(C3)C1)C2]
Compound 108
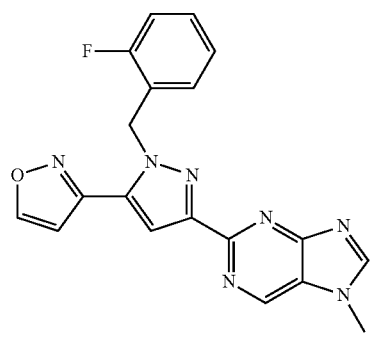 [SMILES: Cn1cnc2nc(-c3cc(-c4ccon4)n(Cc4ccccc4F)n3)ncc21]
Compound 109
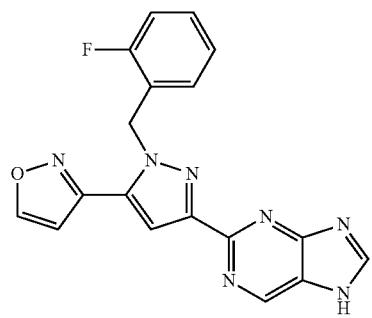 [SMILES: Fc1ccccc1Cn1nc(-c2ncc3[nH]cnc3n2)cc1-c1ccon1]
Compound 110
Compound 111
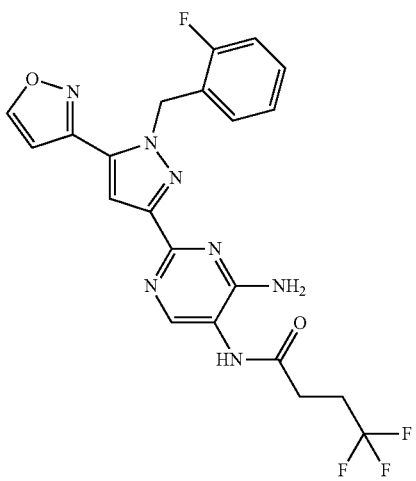
Compound 112
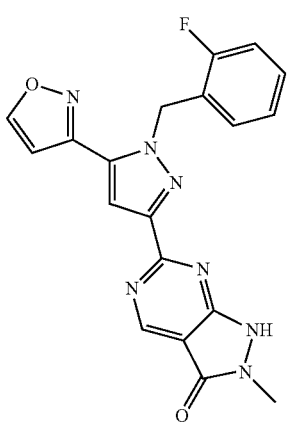
Compound 113
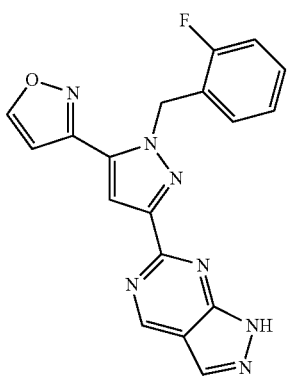 [SMILES: Fc1ccccc1Cn1nc(-c2ncc3cn[nH]c3n2)cc1-c1ccon1]

Compound 114
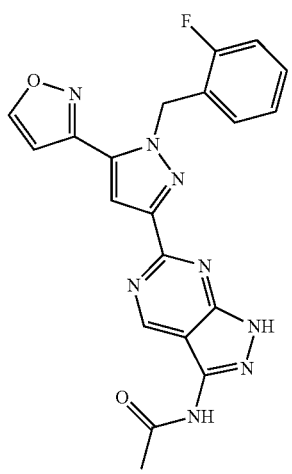 [SMILES: CC(=O)Nc1n[nH]c2nc(-c3cc(-c4ccon4)n(Cc4ccccc4F)n3)ncc12]
Compound 115
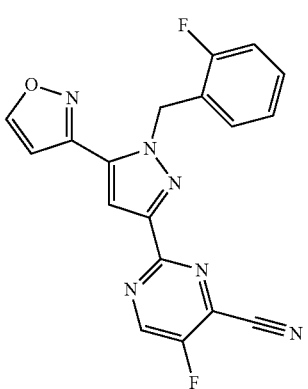 [SMILES: N#Cc1nc(-c2cc(-c3ccon3)n(Cc3ccccc3F)n2)ncc1F]
Compound 116
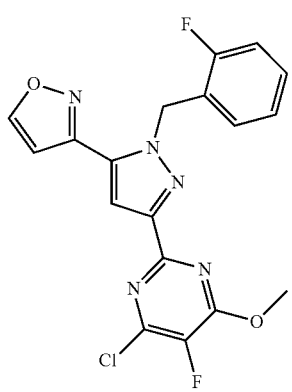 [SMILES: COc1nc(-c2cc(-c3ccon3)n(Cc3ccccc3F)n2)nc(Cl)c1F]
Compound 117
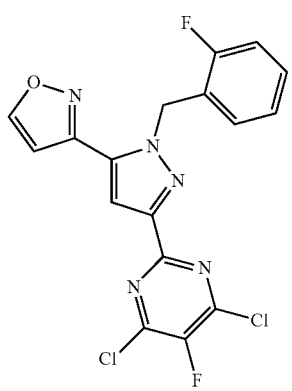 [SMILES: Fc1ccccc1Cn1nc(-c2nc(Cl)c(F)c(Cl)n2)cc1-c1ccon1]
Compound 118
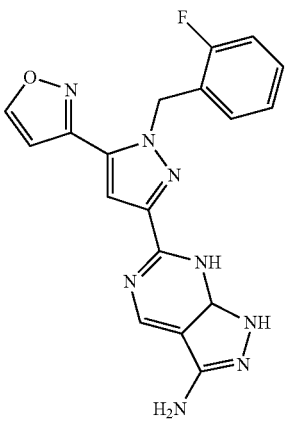 [SMILES: NC1=NNC2NC(c3cc(-c4ccon4)n(Cc4ccccc4F)n3)=NC=C12]
Compound 119
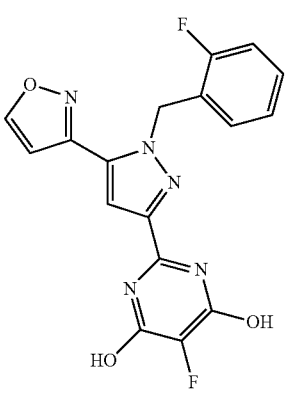 [SMILES: Oc1nc(-c2cc(-c3ccon3)n(Cc3ccccc3F)n2)nc(O)c1F]
Compound 120
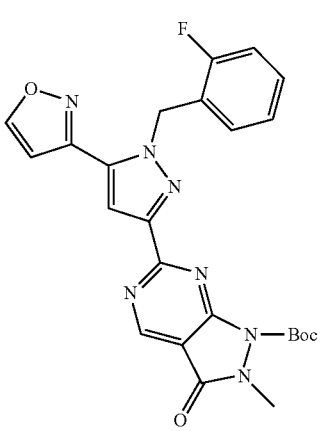 [SMILES: Cn1c(=O)c2cnc(-c3cc(-c4ccon4)n(Cc4ccccc4F)n3)nc2n1C(=O)OC(C)(C)C]
Compound 121 or
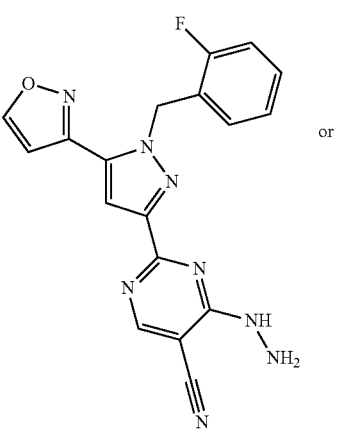

Compound 122

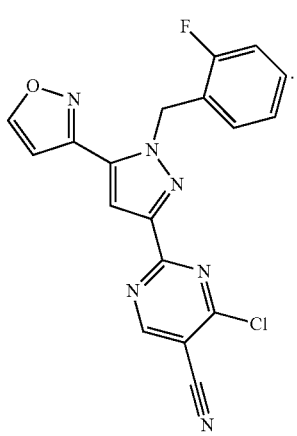

5. A pharmaceutical composition comprising at least one compound of claim 3, or a pharmaceutically acceptable salt thereof, and at least one pharmaceutically acceptable excipient.

6. A pharmaceutical composition comprising at least one compound of claim 4, or a pharmaceutically acceptable salt thereof, and at least one pharmaceutically acceptable excipient.

* * * * *